(12) United States Patent
Anderson et al.

(10) Patent No.: US 10,963,417 B2
(45) Date of Patent: Mar. 30, 2021

(54) SYSTEMS AND METHODS FOR MANAGING DIABETES CARE DATA

(71) Applicant: ABBOTT DIABETES CARE INC., Alameda, CA (US)

(72) Inventors: Carolyn Anderson, Dublin, CA (US); Thomas W. Love, Monticello, FL (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 655 days.

(21) Appl. No.: 14/960,027

(22) Filed: Dec. 4, 2015

(65) Prior Publication Data

US 2016/0085714 A1    Mar. 24, 2016

Related U.S. Application Data

(63) Continuation of application No. 11/146,897, filed on Jun. 6, 2005, now abandoned.
(Continued)

(51) Int. Cl.
*G06F 13/42* (2006.01)
*G16H 15/00* (2018.01)
(Continued)

(52) U.S. Cl.
CPC ........ *G06F 13/4282* (2013.01); *G06F 13/102* (2013.01); *G06F 13/20* (2013.01);
(Continued)

(58) Field of Classification Search
CPC ............... G06F 13/4282; G06F 19/324; G06F 19/3481; G06F 13/102; G06F 13/20;
(Continued)

(56) References Cited

U.S. PATENT DOCUMENTS 3,581,062 A    5/1971 Aston
3,926,760 A    12/1975 Allen et al.
(Continued)

FOREIGN PATENT DOCUMENTS

CA    2396613    3/2008
EP    0098592    1/1984
(Continued)

OTHER PUBLICATIONS

Benrdt, D. J., et al., "Introduction to the Minitrack: Databases, Data Warehousing, and Data Mining in Health Care," System Sciences, Proceedings of 33rd Annual Hawaii International Conference, Jan. 4-7, 2000, pp. 1588.
(Continued)

*Primary Examiner* — Robert A Sorey
*Assistant Examiner* — Kimberly A. Sass
(74) *Attorney, Agent, or Firm* — One LLP

(57) ABSTRACT

A host-client data sharing system manages diabetes care data. A host database, preferably web or internet based, is implemented for storing diabetes care data relating to multiple diabetics. A client or local database stores the diabetes care data relating to multiple diabetics on a personal appliance such as a PC, or a portable or handheld microprocessor-based computing device. The host database uses multiple servers for handling client interactions with the system.

6 Claims, 157 Drawing Sheets

Related U.S. Application Data

(60) Provisional application No. 60/577,064, filed on Jun. 4, 2004.

(51) Int. Cl.
*G16H 10/60* (2018.01)
*G06F 13/10* (2006.01)
*G06F 13/20* (2006.01)
*G06F 13/40* (2006.01)

(52) U.S. Cl.
CPC ......... *G06F 13/4068* (2013.01); *G16H 10/60* (2018.01); *G16H 15/00* (2018.01)

(58) Field of Classification Search
CPC .... G06F 13/4068; G06Q 50/22; G16H 15/00; G16H 10/60; G16H 70/60
See application file for complete search history.

(56) References Cited

U.S. PATENT DOCUMENTS

| | | |
|---|---|---|
| 3,949,388 A | 4/1976 | Fuller |
| 3,956,701 A | 5/1976 | James, Jr. et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,432,360 A | 2/1984 | Mumford et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,558,139 A | 12/1985 | Hagenmaier et al. |
| 4,559,037 A | 12/1985 | Franetzki et al. |
| 4,619,793 A | 10/1986 | Lee |
| 4,619,995 A | 10/1986 | Hayes |
| 4,635,836 A | 1/1987 | Mooney et al. |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,741,074 A | 5/1988 | Budano, II et al. |
| 4,749,985 A | 6/1988 | Corsberg |
| 4,757,022 A | 7/1988 | Shults et al. |
| 4,759,828 A | 7/1988 | Young et al. |
| 4,777,953 A | 10/1988 | Ash et al. |
| 4,779,618 A | 10/1988 | Mund et al. |
| 4,803,625 A | 2/1989 | Fu et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,016,326 A | 5/1991 | Goldenberg |
| 5,019,974 A | 5/1991 | Beckers |
| 5,050,612 A | 9/1991 | Matsumura |
| 5,054,170 A | 10/1991 | Otrusina |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,127,404 A | 7/1992 | Wyborny et al. |
| 5,165,407 A | 11/1992 | Wilson et al. |
| 5,216,597 A | 6/1993 | Beckers |
| 5,228,449 A | 7/1993 | Christ et al. |
| 5,246,867 A | 9/1993 | Lakowicz et al. |
| 5,251,126 A | 10/1993 | Kahn et al. |
| 5,261,583 A | 11/1993 | Long et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,276,628 A | 1/1994 | Schneirderhan |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,319,543 A | 6/1994 | Wilhelm |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,349,852 A | 9/1994 | Kamen et al. |
| 5,356,786 A | 10/1994 | Heller et al. |
| 5,360,404 A | 11/1994 | Novacek et al. |
| 5,360,446 A | 11/1994 | Kennedy |
| 5,372,427 A | 12/1994 | Padovani et al. |
| 5,376,070 A | 12/1994 | Purvis et al. |
| 5,379,238 A | 1/1995 | Stark |
| 5,385,282 A | 1/1995 | Chen |
| 5,390,671 A | 2/1995 | Lord et al. |
| 5,391,250 A | 2/1995 | Cheney, II et al. |
| 5,394,877 A | 3/1995 | Orr et al. |
| 5,402,780 A | 4/1995 | Faasse, Jr. |
| 5,408,999 A | 4/1995 | Singh et al. |
| 5,411,647 A | 5/1995 | Johnson et al. |
| 5,425,868 A | 6/1995 | Pedersen |
| 5,426,825 A | 6/1995 | Soren et al. |
| 5,431,160 A | 7/1995 | Wilkins |
| 5,431,921 A | 7/1995 | Thombre |
| 5,437,024 A | 7/1995 | French |
| 5,452,829 A | 9/1995 | King et al. |
| 5,462,645 A | 10/1995 | Albery et al. |
| 5,471,382 A * | 11/1995 | Tallman ................ G06F 19/325 600/300 |
| 5,472,317 A | 12/1995 | Field et al. |
| 5,489,414 A | 2/1996 | Schreiber et al. |
| 5,492,117 A | 2/1996 | Eisenberg et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,526,844 A | 6/1996 | Kamen et al. |
| 5,528,770 A | 6/1996 | Castilla et al. |
| 5,531,878 A | 7/1996 | Vadgama et al. |
| 5,532,686 A | 7/1996 | Utbas et al. |
| 5,533,389 A | 7/1996 | Kamen et al. |
| 5,542,024 A | 7/1996 | Balint |
| 5,544,044 A | 8/1996 | Leatherman |
| 5,561,852 A * | 10/1996 | Heeschen ......... H04W 74/0841 455/509 |
| 5,562,713 A | 10/1996 | Silvian |
| 5,563,042 A | 10/1996 | Phillips et al. |
| 5,568,806 A | 10/1996 | Cheney, II et al. |
| 5,569,186 A | 10/1996 | Lord et al. |
| 5,558,638 A | 11/1996 | Evers et al. |
| 5,582,184 A | 12/1996 | Erickson et al. |
| 5,586,553 A | 12/1996 | Halili et al. |
| 5,593,852 A | 1/1997 | Heller et al. |
| 5,594,637 A | 1/1997 | Eisenberg et al. |
| 5,597,102 A | 1/1997 | Saarikko et al. |
| 5,601,435 A | 2/1997 | Quy |
| 5,609,575 A | 3/1997 | Larson et al. |
| 5,613,236 A | 3/1997 | Tajima et al. |
| 5,620,120 A | 4/1997 | Tien |
| 5,622,296 A | 4/1997 | Pirhonen et al. |
| 5,626,630 A | 5/1997 | Markowitz et al. |
| 5,628,310 A | 5/1997 | Rao et al. |

(56) References Cited

U.S. PATENT DOCUMENTS

| | | |
|---|---|---|
| 5,628,324 A | 5/1997 | Sarbach |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,665,065 A | 9/1997 | Colman et al. |
| 5,665,222 A | 9/1997 | Heller et al. |
| 5,673,322 A | 9/1997 | Pepe et al. |
| 5,678,571 A | 10/1997 | Brown |
| 5,683,407 A | 11/1997 | Jolly et al. |
| 5,683,432 A | 11/1997 | Goedeke et al. |
| 5,691,486 A | 11/1997 | Behringer |
| 5,696,686 A | 12/1997 | Sanka et al. |
| 5,707,502 A | 1/1998 | McCaffrey et al. |
| 5,711,001 A | 1/1998 | Bussan et al. |
| 5,711,861 A | 1/1998 | Ward et al. |
| 5,719,667 A | 2/1998 | Miers |
| 5,724,030 A | 3/1998 | Urbas et al. |
| 5,730,342 A | 3/1998 | Tien |
| 5,733,259 A | 3/1998 | Valcke et al. |
| D393,313 S | 4/1998 | Meisner et al. |
| 5,735,285 A | 4/1998 | Albert et al. |
| 5,741,289 A | 4/1998 | Jolly et al. |
| 5,745,308 A | 4/1998 | Spangenberg |
| 5,749,907 A | 5/1998 | Mann |
| 5,771,891 A | 6/1998 | Gozani |
| 5,772,586 A | 6/1998 | Heinonen et al. |
| 5,772,963 A | 6/1998 | Cantatore et al. |
| 5,782,611 A | 7/1998 | Neftel et al. |
| 5,788,927 A | 8/1998 | Farrell et al. |
| 5,791,344 A | 8/1998 | Schulman et al. |
| 5,792,204 A | 8/1998 | Snell |
| 5,804,047 A | 9/1998 | Karube et al. |
| 5,820,551 A | 10/1998 | Hill et al. |
| 5,822,715 A | 10/1998 | Worthington et al. |
| 5,800,473 A | 11/1998 | Faisandier |
| 5,833,603 A | 11/1998 | Kovacs et al. |
| 5,843,692 A | 12/1998 | Phillips et al. |
| 5,844,685 A | 12/1998 | Gontin |
| 5,848,137 A | 12/1998 | Hsiao |
| 5,861,019 A | 1/1999 | Sun et al. |
| 5,872,627 A | 2/1999 | Miers |
| 5,875,186 A | 2/1999 | Belanger et al. |
| 5,883,378 A | 3/1999 | Irish et al. |
| 5,891,049 A | 4/1999 | Cyrus et al. |
| 5,897,493 A | 4/1999 | Brown |
| 5,899,855 A | 5/1999 | Brown |
| 5,906,031 A | 5/1999 | Jensen |
| 5,907,796 A | 5/1999 | Matchett et al. |
| 5,908,599 A | 6/1999 | Behringer et al. |
| 5,912,114 A | 6/1999 | Hutchinson et al. |
| 5,913,310 A | 6/1999 | Brown |
| 5,916,501 A | 6/1999 | Hehl |
| 5,918,603 A | 7/1999 | Brown |
| 5,925,021 A | 7/1999 | Castellano et al. |
| 5,933,136 A | 8/1999 | Brown |
| 5,934,885 A | 8/1999 | Farrell et al. |
| 5,935,224 A | 8/1999 | Svancarek et al. |
| 5,936,986 A | 8/1999 | Cantatore et al. |
| 5,939,583 A | 8/1999 | Kluender et al. |
| 5,940,802 A | 8/1999 | Hildebrand et al. |
| 5,942,979 A | 8/1999 | Luppino |
| 5,951,300 A | 9/1999 | Brown |
| 5,951,485 A | 9/1999 | Cyrus et al. |
| 5,953,681 A | 9/1999 | Cantatore et al. |
| 5,956,501 A | 9/1999 | Brown |
| 5,957,854 A | 9/1999 | Besson et al. |
| 5,960,403 A | 9/1999 | Brown |
| 5,961,451 A | 10/1999 | Reber et al. |
| 5,964,993 A | 10/1999 | Blubaugh, Jr. et al. |
| 5,965,380 A | 10/1999 | Heller et al. |
| 5,968,760 A | 10/1999 | Phillips |
| 5,968,764 A | 10/1999 | Knowles et al. |
| 5,971,922 A | 10/1999 | Arita et al. |
| 5,972,199 A | 10/1999 | Heller et al. |
| 5,972,680 A | 10/1999 | Knowles et al. |
| 5,973,842 A | 10/1999 | Spangenberg |
| 5,988,577 A | 11/1999 | Phillips et al. |
| 5,994,295 A | 11/1999 | Khoo et al. |
| 5,995,860 A | 11/1999 | Sun et al. |
| 5,997,475 A | 12/1999 | Bortz |
| 5,997,476 A | 12/1999 | Brown |
| 5,999,857 A | 12/1999 | Weijand et al. |
| 6,001,067 A | 12/1999 | Shults et al. |
| 6,014,629 A | 1/2000 | Debruin-Ashton |
| 6,022,315 A | 2/2000 | Iliff |
| 6,024,699 A | 2/2000 | Surwit et al. |
| 6,028,413 A | 2/2000 | Brockman |
| 6,032,064 A | 2/2000 | Devlin et al. |
| 6,032,337 A | 3/2000 | Rankin, Jr. et al. |
| 6,042,249 A | 3/2000 | Spangenberg |
| 6,048,900 A | 4/2000 | Connell et al. |
| 6,049,727 A | 4/2000 | Crothall |
| 6,071,391 A | 6/2000 | Gotoh et al. |
| 6,083,248 A | 7/2000 | Thompson |
| 6,083,710 A | 7/2000 | Heller et al. |
| 6,088,608 A | 7/2000 | Schulman et al. |
| 6,088,618 A | 7/2000 | Kerver |
| 6,091,976 A | 7/2000 | Pfeiffer et al. |
| 6,091,987 A | 7/2000 | Thompson |
| 6,093,172 A | 7/2000 | Funderburk et al. |
| 6,101,478 A | 8/2000 | Brown |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,125,513 A | 10/2000 | Cheraso et al. |
| 6,128,620 A | 10/2000 | Pissanos et al. |
| 6,130,623 A | 10/2000 | MacLellan et al. |
| 6,134,461 A | 10/2000 | Say et al. |
| 6,139,494 A | 10/2000 | Cairnes |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,150,951 A | 11/2000 | Olejniczak |
| 6,151,586 A | 11/2000 | Brown |
| 6,159,147 A | 12/2000 | Lichter et al. |
| 6,161,095 A | 12/2000 | Brown |
| 6,162,611 A | 12/2000 | Heller et al. |
| 6,167,362 A | 12/2000 | Brown et al. |
| 6,168,563 B1 | 1/2001 | Brown |
| 6,175,752 B1 | 1/2001 | Say et al. |
| 6,177,940 B1 | 1/2001 | Bond et al. |
| 6,186,145 B1 | 2/2001 | Brown |
| 6,188,648 B1 | 2/2001 | Olsen |
| 6,190,324 B1 | 2/2001 | Kieval et al. |
| 6,200,265 B1 | 3/2001 | Walsh et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,233,301 B1 | 5/2001 | Robergeau |
| 6,233,471 B1 | 5/2001 | Berner et al. |
| 6,233,539 B1 | 5/2001 | Broan |
| 6,238,337 B1 | 5/2001 | Kambhatla et al. |
| 6,240,393 B1 | 5/2001 | Brown |
| 6,242,463 B1 | 6/2001 | Reitberg |
| 6,243,606 B1 | 6/2001 | Mann et al. |
| 6,248,065 B1 | 6/2001 | Brown |
| 6,248,067 B1 | 6/2001 | Causey, III et al. |
| 6,249,705 B1 | 6/2001 | Snell |
| 6,259,950 B1 | 7/2001 | Mann et al. |
| 6,263,244 B1 | 7/2001 | Mann et al. |
| 6,268,162 B1 | 7/2001 | Phillips et al. |
| 6,269,276 B1 | 7/2001 | Akhavan et al. |
| 6,270,455 B1 | 8/2001 | Brown |
| 6,275,717 B1 | 8/2001 | Gross et al. |
| 6,283,348 B1 | 9/2001 | Wang |
| 6,283,761 B1 | 9/2001 | Joao |
| 6,284,478 B1 | 9/2001 | Heller et al. |

(56) References Cited

U.S. PATENT DOCUMENTS

| | | | |
|---|---|---|---|
| 6,285,377 | B1 | 9/2001 | Greenbaum et al. |
| 6,285,908 | B1 | 9/2001 | Mann et al. |
| 6,291,200 | B1 | 9/2001 | LeJeune et al. |
| 6,293,925 | B1 | 9/2001 | Safabash et al. |
| 6,294,997 | B1 | 9/2001 | Paratore et al. |
| 6,295,506 | B1 | 9/2001 | Heinonen et al. |
| 6,299,757 | B1 | 10/2001 | Feldman et al. |
| 6,306,104 | B1 | 10/2001 | Cunningham et al. |
| 6,309,884 | B1 | 10/2001 | Cooper et al. |
| 6,311,089 | B1 | 10/2001 | Mann et al. |
| 6,322,504 | B1 | 11/2001 | Kirshner |
| 6,327,501 | B1 | 12/2001 | Levine et al. |
| 6,329,161 | B1 | 12/2001 | Heller et al. |
| 6,330,426 | B2 | 12/2001 | Brown et al. |
| 6,338,790 | B1 | 1/2002 | Feldman et al. |
| 6,348,640 | B1 | 2/2002 | Navot et al. |
| 6,352,505 | B1 | 3/2002 | Bortz |
| 6,359,270 | B1 | 3/2002 | Bridson |
| 6,359,444 | B1 | 3/2002 | Grimes |
| 6,360,888 | B1 | 3/2002 | McIvor et al. |
| 6,366,794 | B1 | 4/2002 | Moussy et al. |
| 6,368,273 | B1 | 4/2002 | Brown |
| 6,375,469 | B1 | 4/2002 | Brown |
| 6,377,828 | B1 | 4/2002 | Chaiken et al. |
| 6,377,894 | B1 | 4/2002 | Deweese et al. |
| 6,379,301 | B1 | 4/2002 | Worthington et al. |
| 6,381,577 | B1 | 4/2002 | Brown |
| 6,387,048 | B1 | 5/2002 | Schulman et al. |
| 6,496,416 | B1 | 5/2002 | Kuusela et al. |
| 6,400,974 | B1 | 6/2002 | Lesho |
| 6,405,066 | B1 | 6/2002 | Essenpreis et al. |
| 6,410,792 | B1 | 6/2002 | Connell et al. |
| 6,413,393 | B1 | 7/2002 | Van Antwerp et al. |
| 6,416,471 | B1 | 7/2002 | Kumar et al. |
| 6,418,346 | B1 | 7/2002 | Nelson et al. |
| 6,424,847 | B1 | 7/2002 | Mastrototaro et al. |
| 6,426,504 | B1 | 7/2002 | Finarov |
| 6,427,088 | B1 | 7/2002 | Bowman, IV et al. |
| 6,428,475 | B1 | 8/2002 | Shen |
| 6,434,429 | B1 | 8/2002 | Kraus et al. |
| 6,438,229 | B1 | 8/2002 | Overy et al. |
| 6,440,068 | B1 | 8/2002 | Brown et al. |
| 6,442,432 | B2 | 8/2002 | Lee |
| 6,443,340 | B1 | 9/2002 | Chung et al. |
| 6,454,708 | B1 | 9/2002 | Ferguson et al. |
| 6,461,496 | B1 | 10/2002 | Feldman et al. |
| 6,470,215 | B1 | 10/2002 | Kraus et al. |
| 6,470,320 | B1 | 10/2002 | Hildebrand et al. |
| 6,470,535 | B1 | 10/2002 | Mayne et al. |
| 6,477,424 | B1 | 11/2002 | Thompson et al. |
| 6,478,736 | B1 | 11/2002 | Mault |
| 6,484,046 | B1 | 11/2002 | Say et al. |
| 6,485,461 | B1 | 11/2002 | Mason et al. |
| 6,489,133 | B2 | 12/2002 | Phillips et al. |
| 6,490,487 | B1 | 12/2002 | Kraus et al. |
| 6,493,069 | B1 | 12/2002 | Nagashimada et al. |
| 6,496,729 | B2 | 12/2002 | Thompson |
| 6,497,655 | B1 | 12/2002 | Lindberg et al. |
| 6,498,043 | B1 | 12/2002 | Schulman et al. |
| 6,503,381 | B1 | 1/2003 | Gotoh et al. |
| 6,512,942 | B1 | 1/2003 | Burdette et al. |
| 6,514,460 | B1 | 2/2003 | Fendrock |
| 6,514,718 | B2 | 2/2003 | Heller et al. |
| 6,518,069 | B1 | 2/2003 | Otvos et al. |
| 6,520,326 | B2 | 2/2003 | Mclvor et al. |
| 6,525,330 | B2 | 2/2003 | Paolini et al. |
| 6,529,841 | B2 | 4/2003 | Cocking et al. |
| 6,540,672 | B1 | 4/2003 | Simonsen et al. |
| 6,540,891 | B1 | 4/2003 | Stewart et al. |
| 6,541,266 | B2 | 4/2003 | Modzelewski et al. |
| 6,544,212 | B2 | 4/2003 | Galley et al. |
| 6,549,796 | B2 | 4/2003 | Sohrab |
| 6,551,276 | B1 | 4/2003 | Mann et al. |
| 6,551,494 | B1 | 4/2003 | Heller et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,975 | B1 | 5/2003 | Pool et al. |
| 6,561,978 | B1 | 5/2003 | Conn et al. |
| 6,562,001 | B2 | 5/2003 | Lebel et al. |
| 6,562,625 | B2 | 5/2003 | Modzelewski et al. |
| 6,564,105 | B2 | 5/2003 | Starkweather et al. |
| 6,565,509 | B1 | 5/2003 | Say et al. |
| 6,571,128 | B2 | 5/2003 | Lebel et al. |
| 6,572,542 | B1 | 6/2003 | Houben et al. |
| 6,574,510 | B2 | 6/2003 | Von Arx et al. |
| 6,576,101 | B1 | 6/2003 | Heller et al. |
| 6,577,899 | B2 | 6/2003 | Lebel et al. |
| 6,579,231 | B1 | 6/2003 | Phipps |
| 6,579,690 | B1 | 6/2003 | Bonnecaze et al. |
| 6,579,888 | B2 | 6/2003 | Reitberg |
| 6,582,365 | B1 | 6/2003 | Hines et al. |
| 6,582,366 | B1 | 6/2003 | Porumbescu |
| 6,583,108 | B1 | 6/2003 | Tamburini et al. |
| 6,584,335 | B1 | 6/2003 | Haar et al. |
| 6,585,644 | B2 | 7/2003 | Lebel et al. |
| 6,589,229 | B1 | 7/2003 | Connelley et al. |
| 6,591,125 | B1 | 7/2003 | Buse et al. |
| 6,592,745 | B1 | 7/2003 | Feldman et al. |
| 6,594,523 | B1 | 7/2003 | Levine |
| 6,595,919 | B2 | 7/2003 | Berner et al. |
| 6,599,250 | B2 | 7/2003 | Webb et al. |
| 6,600,997 | B2 | 7/2003 | Deweese et al. |
| 6,602,191 | B2 | 8/2003 | Quy |
| 6,602,469 | B1 | 8/2003 | Maus et al. |
| 6,604,050 | B2 | 8/2003 | Trippel et al. |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,609,032 | B1 | 8/2003 | Woods et al. |
| 6,610,012 | B2 | 8/2003 | Mault |
| 6,613,942 | B1 | 9/2003 | Ling et al. |
| 6,616,819 | B1 | 9/2003 | Liamos et al. |
| 6,618,622 | B1 | 9/2003 | Mann et al. |
| 6,618,934 | B1 | 9/2003 | Feldman et al. |
| 6,633,772 | B2 | 10/2003 | Ford et al. |
| 6,635,014 | B2 | 10/2003 | Starkweather et al. |
| 6,635,167 | B1 | 10/2003 | Batman et al. |
| 6,641,353 | B2 | 11/2003 | Oliver |
| 6,641,533 | B2 | 11/2003 | Causey, III et al. |
| 6,644,322 | B2 | 11/2003 | Webb |
| 6,645,142 | B2 | 11/2003 | Braig et al. |
| 6,648,821 | B2 | 11/2003 | Lebel et al. |
| 6,654,625 | B1 | 11/2003 | Say et al. |
| 6,656,114 | B1 | 12/2003 | Poulsen et al. |
| 6,656,158 | B2 | 12/2003 | Mahoney et al. |
| 6,656,159 | B2 | 12/2003 | Flaherty |
| 6,658,396 | B1 | 12/2003 | Tang et al. |
| 6,658,456 | B1 | 12/2003 | Shimoosawa |
| 6,659,948 | B2 | 12/2003 | Lebel et al. |
| 6,665,909 | B2 | 12/2003 | Collins et al. |
| 6,668,196 | B1 | 12/2003 | Villegas et al. |
| 6,669,669 | B2 | 12/2003 | Flaherty et al. |
| 6,675,030 | B2 | 1/2004 | Ciurczak et al. |
| 6,675,044 | B2 | 1/2004 | Chen |
| 6,676,816 | B2 | 1/2004 | Mao et al. |
| 6,687,546 | B2 | 2/2004 | Lebel et al. |
| 6,689,056 | B1 | 2/2004 | Kilcoyne et al. |
| 6,692,457 | B2 | 2/2004 | Flaherty |
| 6,694,191 | B2 | 2/2004 | Starkweather et al. |
| 6,695,860 | B1 | 2/2004 | Ward et al. |
| 6,698,269 | B2 | 3/2004 | Baber et al. |
| 6,699,218 | B2 | 3/2004 | Flaherty et al. |
| 6,702,857 | B2 | 3/2004 | Brauker et al. |
| 6,723,046 | B2 | 4/2004 | Litchenstein et al. |
| 6,723,072 | B2 | 4/2004 | Flaherty et al. |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,733,619 | B2 | 5/2004 | Finarov |
| 6,735,183 | B2 | 5/2004 | O-Toole et al. |
| 6,736,957 | B1 | 5/2004 | Forrow et al. |

(56) References Cited

U.S. PATENT DOCUMENTS

| | | |
|---|---|---|
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,744,350 B2 | 6/2004 | Blomquist |
| 6,746,582 B2 | 6/2004 | Heller et al. |
| 6,748,250 B1 | 6/2004 | Berman et al. |
| 6,749,587 B2 | 6/2004 | Flaherty |
| 6,749,740 B2 | 6/2004 | Liamos et al. |
| 6,752,299 B2 | 6/2004 | Shetler et al. |
| 6,758,810 B2 | 7/2004 | Lebel et al. |
| 6,764,581 B1 | 7/2004 | Forrow et al. |
| 6,766,198 B1 | 7/2004 | Snell |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,772,026 B2 | 8/2004 | Bradbury et al. |
| 6,773,671 B1 | 8/2004 | Lewis et al. |
| 6,781,522 B2 | 8/2004 | Sleva et al. |
| 6,786,405 B2 | 9/2004 | Wiedenhoefer |
| 6,789,195 B1 | 9/2004 | Prihoda et al. |
| 6,790,178 B1 | 9/2004 | Mault et al. |
| 6,791,686 B1 | 9/2004 | Finarov |
| 6,793,632 B2 | 9/2004 | Sohrab |
| 6,802,810 B2 | 10/2004 | Ciarniello et al. |
| 6,804,558 B2 | 10/2004 | Haller et al. |
| 6,804,656 B1 | 10/2004 | Rosenfeld et al. |
| 6,809,653 B1 | 10/2004 | Mann et al. |
| 6,810,290 B2 | 10/2004 | Lebel et al. |
| 6,811,516 B1 | 11/2004 | Dugan |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,814,845 B2 | 11/2004 | Wilson et al. |
| 6,820,235 B1 | 11/2004 | Bleicher et al. |
| 6,821,483 B2 | 11/2004 | Phillips et al. |
| 6,825,933 B2 | 11/2004 | Roberts et al. |
| 6,830,558 B2 | 12/2004 | Flaherty et al. |
| 6,835,381 B1 | 12/2004 | Friedrich et al. |
| 6,847,451 B2 | 1/2005 | Pugh |
| 6,849,237 B2 | 2/2005 | Housefield et al. |
| 6,850,790 B2 | 2/2005 | Berner et al. |
| 6,852,104 B2 | 2/2005 | Blomquist |
| 6,856,928 B2 | 2/2005 | Harmon |
| 6,858,401 B2 | 2/2005 | Phillips et al. |
| 6,862,465 B2 | 3/2005 | Shults et al. |
| 6,862,466 B2 | 3/2005 | Ackerman |
| 6,865,515 B2 | 3/2005 | Fox et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,913,174 B1 | 7/2005 | Harvey et al. |
| 6,916,159 B2 | 7/2005 | Rush et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,936,007 B2 | 8/2005 | Quy |
| 6,939,310 B2 | 9/2005 | Matzinger et al. |
| 6,940,403 B2 | 9/2005 | Kail, IV |
| 6,941,163 B2 | 9/2005 | Ford et al. |
| 6,942,518 B2 | 9/2005 | Liamos et al. |
| 6,943,787 B2 | 9/2005 | Webb |
| 6,946,299 B2 | 9/2005 | Neel et al. |
| 6,950,708 B2 | 9/2005 | Bowman, IV et al. |
| 6,954,673 B2 | 10/2005 | Von Arx et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,961,448 B2 | 11/2005 | Nichols et al. |
| 6,964,871 B2 | 11/2005 | Bell et al. |
| 6,968,294 B2 | 11/2005 | Gutta et al. |
| 6,968,375 B1 | 11/2005 | Brown |
| 6,971,274 B2 | 12/2005 | Olin |
| 6,974,328 B2 | 12/2005 | Aspe et al. |
| 6,974,437 B2 | 12/2005 | Lebel et al. |
| 6,975,893 B2 | 12/2005 | Say et al. |
| 6,976,958 B2 | 12/2005 | Quy |
| 6,978,182 B2 | 12/2005 | Mazar et al. |
| 6,978,517 B2 | 12/2005 | Collins et al. |
| 6,980,958 B1 | 12/2005 | Surwit et al. |
| 6,980,999 B1 | 12/2005 | Grana |
| 6,984,307 B2 | 1/2006 | Zweig |
| 6,985,088 B2 | 1/2006 | Goetz et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,816 B2 | 2/2006 | Van Bentem |
| 7,003,336 B2 | 2/2006 | Holker et al. |
| 7,003,340 B2 | 2/2006 | Say et al. |
| 7,003,341 B2 | 2/2006 | Say et al. |
| 7,003,335 B2 | 3/2006 | Morris et al. |
| 7,009,511 B2 | 3/2006 | Mazar et al. |
| 7,011,425 B2 | 3/2006 | Morris et al. |
| 7,011,630 B2 | 3/2006 | Desai et al. |
| 7,018,360 B2 | 3/2006 | Flaherty et al. |
| 7,018,568 B2 | 3/2006 | Tierney |
| 7,019,123 B2 | 3/2006 | Tamburini et al. |
| 7,020,508 B2 | 3/2006 | Stivoric et al. |
| 7,020,515 B2 | 3/2006 | Graindorge |
| 7,022,072 B2 | 4/2006 | Fox et al. |
| 7,023,359 B2 | 4/2006 | Goetz et al. |
| 7,024,236 B2 | 4/2006 | Ford et al. |
| 7,024,245 B2 | 4/2006 | Lebel et al. |
| 7,025,774 B2 | 4/2006 | Freeman et al. |
| 7,027,931 B1 | 4/2006 | Jones et al. |
| 7,029,444 B2 | 4/2006 | Shin et al. |
| 7,029,455 B2 | 4/2006 | Flaherty |
| 7,039,810 B1 | 5/2006 | Nichols |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,049,962 B2 | 5/2006 | Atherton et al. |
| 7,050,855 B2 | 5/2006 | Zeijlemaker et al. |
| 7,052,251 B2 | 5/2006 | Nason et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,069,085 B2 | 6/2006 | Cao et al. |
| 7,070,564 B2 | 7/2006 | Matzinger et al. |
| 7,072,725 B2 | 7/2006 | Bristol et al. |
| 7,074,307 B2 | 7/2006 | Simpson et al. |
| 7,076,520 B2 | 7/2006 | Nelson et al. |
| 7,077,806 B2 | 7/2006 | Ackerman et al. |
| 7,081,195 B2 | 7/2006 | Simpson et al. |
| 7,082,334 B2 | 7/2006 | Boute et al. |
| 7,089,049 B2 | 8/2006 | Kerver et al. |
| 7,092,891 B2 | 8/2006 | Maus et al. |
| 7,098,803 B2 | 8/2006 | Mann et al. |
| 7,103,414 B1 | 9/2006 | Poore et al. |
| 7,103,578 B2 | 9/2006 | Beck et al. |
| 7,107,547 B2 | 9/2006 | Cule et al. |
| 7,108,778 B2 | 9/2006 | Simpson et al. |
| 7,110,803 B2 | 9/2006 | Shults et al. |
| 7,113,172 B2 | 9/2006 | Hohl et al. |
| 7,113,821 B1 | 9/2006 | Sun et al. |
| 7,118,667 B2 | 10/2006 | Lee |
| 7,125,382 B2 | 10/2006 | Zhou et al. |
| 7,127,299 B2 | 10/2006 | Nelson et al. |
| 7,129,744 B2 | 10/2006 | Madurawe |
| 7,134,999 B2 | 11/2006 | Brauker et al. |
| 7,136,689 B2 | 11/2006 | Shults et al. |
| 7,137,951 B2 | 11/2006 | Pilarski |
| 7,137,964 B2 | 11/2006 | Flaherty |
| 7,141,548 B2 | 11/2006 | Johansen et al. |
| 7,144,384 B2 | 12/2006 | Gorman et al. |
| 7,149,773 B2 | 12/2006 | Haller et al. |

(56) References Cited

U.S. PATENT DOCUMENTS

| | | |
|---|---|---|
| 7,150,975 B2 | 12/2006 | Tamada et al. |
| 7,155,290 B2 | 12/2006 | Von Arx et al. |
| 7,156,655 B2 | 1/2007 | Sachdeva et al. |
| 7,156,808 B2 | 1/2007 | Quy |
| 7,156,809 B2 | 1/2007 | Quy |
| 7,160,251 B2 | 1/2007 | Neel et al. |
| 7,167,818 B2 | 1/2007 | Brown |
| 7,171,274 B2 | 1/2007 | Starkweather et al. |
| 7,172,890 B2 | 2/2007 | Shao et al. |
| 7,173,005 B2 | 2/2007 | Pillutla et al. |
| 7,179,226 B2 | 2/2007 | Crothall et al. |
| 7,181,505 B2 | 2/2007 | Haller et al. |
| 7,183,068 B2 | 2/2007 | Bursen et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,202,854 B2 | 4/2007 | Hohl et al. |
| 7,203,549 B2 | 4/2007 | Schommer et al. |
| 7,204,823 B2 | 4/2007 | Estes et al. |
| 7,207,974 B2 | 4/2007 | Safabash et al. |
| 7,225,535 B2 | 6/2007 | Feldman et al. |
| 7,226,278 B2 | 6/2007 | Nason et al. |
| 7,226,978 B2 | 6/2007 | Tapsak et al. |
| 7,228,163 B2 | 6/2007 | Ackerman |
| 7,228,182 B2 | 6/2007 | Healy et al. |
| 7,229,288 B2 | 6/2007 | Stuart et al. |
| 7,231,263 B2 | 6/2007 | Choi |
| 7,232,451 B2 | 6/2007 | Boecker et al. |
| 7,234,937 B2 | 6/2007 | Sachdeva et al. |
| 7,236,826 B2 | 6/2007 | Lindh et al. |
| 7,237,712 B2 | 7/2007 | DeRocco et al. |
| 7,245,117 B1 | 7/2007 | Joy et al. |
| 7,255,748 B2 | 8/2007 | Finarov |
| 7,258,673 B2 | 8/2007 | Racchini et al. |
| 7,259,681 B2 | 8/2007 | Kwoen |
| 7,261,690 B2 | 8/2007 | Teller et al. |
| 7,261,691 B1 | 8/2007 | Asomani |
| 7,267,651 B2 | 9/2007 | Nelson |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,282,029 B1 | 10/2007 | Poulsen et al. |
| 7,288,736 B2 | 10/2007 | Schilden |
| 7,295,867 B2 | 11/2007 | Berner et al. |
| 7,295,988 B1 | 11/2007 | Reeves |
| 7,299,082 B2 | 11/2007 | Feldman et al. |
| 7,303,549 B2 | 12/2007 | Flaherty et al. |
| 7,306,562 B1 | 12/2007 | Baykal |
| 7,310,544 B2 | 12/2007 | Brister et al. |
| 7,310,651 B2 | 12/2007 | Dave et al. |
| 7,318,816 B2 | 1/2008 | Bobroff et al. |
| 7,319,107 B2 | 1/2008 | Eisinger et al. |
| 7,323,296 B2 | 1/2008 | Ma et al. |
| 7,324,012 B2 | 1/2008 | Mann et al. |
| 7,324,850 B2 | 1/2008 | Persen et al. |
| 7,324,949 B2 | 1/2008 | Bristol |
| 7,325,076 B1 | 1/2008 | Morrison et al. |
| 7,335,294 B2 | 2/2008 | Heller et al. |
| 7,347,836 B2 | 3/2008 | Peterson et al. |
| 7,348,500 B2 | 3/2008 | Zhou |
| 7,349,947 B1 | 3/2008 | Slage et al. |
| 7,353,179 B2 | 4/2008 | Ott et al. |
| 7,354,420 B2 | 4/2008 | Steil et al. |
| 7,358,238 B2 | 4/2008 | Andersen et al. |
| 7,361,143 B2 | 4/2008 | Kichhoff et al. |
| 7,364,592 B2 | 4/2008 | Carr-Brendel et al. |
| 7,366,556 B2 | 4/2008 | Brister et al. |
| 7,347,819 B2 | 5/2008 | Lebel et al. |
| 7,378,494 B2 | 5/2008 | Froland et al. |
| 7,379,765 B2 | 5/2008 | Petisce et al. |
| 7,384,397 B2 | 6/2008 | Zhang et al. |
| 7,384,967 B2 | 6/2008 | Polisetti et al. |
| 7,387,010 B2 | 6/2008 | Sunshine et al. |
| 7,390,484 B2 | 6/2008 | Fraser et al. |
| 7,395,117 B2 | 7/2008 | Mazer et al. |
| 7,395,216 B2 | 7/2008 | Rosenfeld et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,403,814 B2 | 7/2008 | Cox et al. |
| 7,404,796 B2 | 7/2008 | Ginsberg |
| 7,419,573 B2 | 9/2008 | Gundel |
| 7,424,318 B2 | 9/2008 | Brister et al. |
| 7,429,255 B2 | 9/2008 | Thompson |
| 7,433,827 B2 | 10/2008 | Rosenfeld et al. |
| 7,436,532 B2 | 10/2008 | Tsujimoto |
| 7,445,152 B2 | 11/2008 | Golabek, Jr. et al. |
| 7,447,596 B2 | 11/2008 | Kawatahara et al. |
| 7,448,996 B2 | 11/2008 | Khanuja et al. |
| 7,454,359 B2 | 11/2008 | Rosenfeld et al. |
| 7,460,898 B2 | 12/2008 | Brister et al. |
| 7,463,930 B2 | 12/2008 | Housworth et al. |
| 7,464,041 B2 | 12/2008 | Merkin et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,476,827 B1 | 1/2009 | Bhullar et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,504,233 B2 | 3/2009 | Hellerstein |
| 7,515,060 B2 | 4/2009 | Blomquist |
| 7,516,847 B2 | 4/2009 | Henning |
| 7,517,664 B2 | 4/2009 | Shoa et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,539,532 B2 | 5/2009 | Tran |
| 7,539,533 B2 | 5/2009 | Tran |
| 7,541,373 B2 | 6/2009 | Polisetti et al. |
| 7,545,272 B2 | 6/2009 | Goodnow et al. |
| 7,547,281 B2 | 6/2009 | Hayes et al. |
| 7,551,175 B2 | 6/2009 | Sakanishi et al. |
| 7,551,301 B2 | 6/2009 | Yamaguchi et al. |
| 7,552,101 B2 | 6/2009 | Bleines |
| 7,563,232 B2 | 7/2009 | Freeman et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,575,457 B2 | 8/2009 | Micinski |
| 7,580,334 B2 | 8/2009 | Kadowaki et al. |
| 7,583,578 B2 | 9/2009 | Kadowaki et al. |
| 7,583,990 B2 | 9/2009 | Goode, Jr. et al. |
| 7,590,462 B2 | 9/2009 | Brauker et al. |
| 7,591,801 B2 | 9/2009 | Brauker et al. |
| 7,593,952 B2 | 9/2009 | Soll et al. |
| 7,595,647 B2 | 9/2009 | Kroh et al. |
| 7,595,902 B2 | 9/2009 | Yamaguchi et al. |
| 7,599,726 B2 | 10/2009 | Goode, Jr. et al. |
| 7,600,022 B2 | 10/2009 | Takamine |
| 7,602,310 B2 | 10/2009 | Mann et al. |
| 7,604,178 B2 | 10/2009 | Stewart |
| 7,604,593 B2 | 10/2009 | Parris et al. |
| 7,608,940 B2 | 10/2009 | Osawa |
| 7,613,491 B2 | 11/2009 | Boock et al. |
| 7,613,620 B2 | 11/2009 | Salwan |
| 7,615,007 B2 | 11/2009 | Shults et al. |
| 7,618,369 B2 | 11/2009 | Hayter et al. |
| 7,632,228 B2 | 12/2009 | Brauker et al. |
| 7,634,315 B2 | 12/2009 | Cholette |
| 7,637,868 B2 | 12/2009 | Saint et al. |
| 7,640,048 B2 | 12/2009 | Dobbles et al. |
| 7,643,969 B2 | 1/2010 | Soto et al. |
| 7,647,237 B2 | 1/2010 | Malave et al. |
| 7,651,489 B2 | 1/2010 | Estes et al. |
| 7,651,596 B2 | 1/2010 | Petisce et al. |
| 7,651,845 B2 | 1/2010 | Doyle, III et al. |
| 7,654,127 B2 | 2/2010 | Krulevitch et al. |
| 7,654,956 B2 | 2/2010 | Brister et al. |
| 7,657,297 B2 | 2/2010 | Simpson et al. |
| 7,657,442 B2 | 2/2010 | Merkin |
| 7,659,823 B1 | 2/2010 | Killian et al. |

(56) References Cited

U.S. PATENT DOCUMENTS

| | | |
|---|---|---|
| 7,668,596 B2 | 2/2010 | Von Arx et al. |
| 7,678,811 B2 | 3/2010 | Dumas et al. |
| 7,679,789 B2 | 3/2010 | Fukuda |
| 7,685,000 B1 | 3/2010 | Petit et al. |
| 7,697,152 B2 | 4/2010 | Hisatomi et al. |
| 7,698,117 B2 | 4/2010 | Usuka et al. |
| 7,699,775 B2 | 4/2010 | Desai et al. |
| 7,701,353 B1 | 4/2010 | Moreno |
| 7,705,653 B2 | 4/2010 | Schell |
| 7,705,980 B2 | 4/2010 | Smous et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,722,536 B2 | 5/2010 | Goodnow et al. |
| 7,741,734 B2 | 6/2010 | Joannopoulos et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,779,332 B2 | 8/2010 | Karr et al. |
| 7,780,827 B1 | 8/2010 | Bhullar et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,873,299 B2 | 1/2011 | Berner et al. |
| 7,882,611 B2 | 2/2011 | Shah et al. |
| 7,883,464 B2 | 2/2011 | Stafford |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,460 B2 | 3/2011 | Melker et al. |
| 7,916,013 B2 | 3/2011 | Stevenson |
| 7,920,907 B2 | 4/2011 | McGarraugh et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,976,466 B2 | 7/2011 | Ward et al. |
| 7,999,674 B2 | 8/2011 | Kamen |
| 8,010,174 B2 | 8/2011 | Goode et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,180,423 B2 | 5/2012 | Mang et al. |
| 8,373,544 B2 | 2/2013 | Pitt-Pladdy |
| 8,512,243 B2 | 8/2013 | Stafford |
| 8,515,518 B2 | 8/2013 | Ouyang et al. |
| 8,545,403 B2 | 10/2013 | Peyser et al. |
| 8,585,591 B2 | 11/2013 | Sloan et al. |
| 8,602,991 B2 | 12/2013 | Stafford |
| 8,617,071 B2 | 12/2013 | Say et al. |
| 8,622,903 B2 | 1/2014 | Jin et al. |
| 8,628,498 B2 | 1/2014 | Safabash et al. |
| 8,652,043 B2 | 2/2014 | Drucker et al. |
| 8,684,930 B2 | 4/2014 | Feldman et al. |
| 8,692,655 B2 | 4/2014 | Zimman et al. |
| 8,771,183 B2 | 7/2014 | Sloan |
| 8,797,163 B2 | 8/2014 | Finkenzeller |
| 8,961,413 B2 | 2/2015 | Teller et al. |
| 9,014,774 B2 | 4/2015 | Mao et al. |
| 9,031,630 B2 | 5/2015 | Hoss et al. |
| 9,060,805 B2 | 6/2015 | Goodnow et al. |
| 9,066,697 B2 | 6/2015 | Peyser et al. |
| 2001/0011224 A1 | 8/2001 | Brown |
| 2001/0037060 A1 | 11/2001 | Thompson et al. |
| 2001/0039504 A1 | 11/2001 | Linberg et al. |
| 2001/0054217 A1 | 12/2001 | Wang |
| 2002/0019022 A1 | 2/2002 | Dunn et al. |
| 2002/0092611 A1 | 2/2002 | Ackerman |
| 2002/0029157 A1* | 3/2002 | Marchosky ......... G06F 19/3418 705/3 |
| 2002/0049617 A1 | 4/2002 | Lencki et al. |
| 2002/0054320 A1 | 5/2002 | Ogino |
| 2002/0055855 A1 | 5/2002 | Cule et al. |
| 2002/0072784 A1 | 6/2002 | Sheppard et al. |
| 2002/0072858 A1 | 6/2002 | Cheng |
| 2002/0082850 A1 | 6/2002 | Panelli |
| 2002/0103499 A1 | 8/2002 | Perez et al. |
| 2002/0106709 A1 | 8/2002 | Potts et al. |
| 2002/0107476 A1 | 8/2002 | Mann et al. |
| 2002/0111832 A1 | 8/2002 | Judge |
| 2002/0128594 A1 | 9/2002 | Das et al. |
| 2002/0169635 A1 | 11/2002 | Shillingburg |
| 2002/0170148 A1 | 11/2002 | Mayne et al. |
| 2002/0183693 A1* | 12/2002 | Peterson ............ A61M 5/14228 604/151 |
| 2002/0188424 A1 | 12/2002 | Grinstein et al. |
| 2002/0788748 | 12/2002 | Blackwell et al. |
| 2003/0004403 A1 | 1/2003 | Drinan et al. |
| 2003/0011646 A1* | 1/2003 | Levine ................. G16H 40/20 715/848 |
| 2003/0023317 A1 | 1/2003 | Brauker et al. |
| 2003/0023461 A1 | 1/2003 | Quintanilla et al. |
| 2003/0032077 A1 | 2/2003 | Itoh et al. |
| 2003/0032867 A1 | 2/2003 | Ceothall et al. |
| 2003/0032874 A1 | 2/2003 | Rhodes et al. |
| 2003/0038047 A1 | 2/2003 | Sleva et al. |
| 2003/0040661 A1 | 2/2003 | Abraham et al. |
| 2003/0040821 A1 | 2/2003 | Case |
| 2003/0047575 A1 | 3/2003 | Enkerlin et al. |
| 2003/0053665 A1 | 3/2003 | Hamid |
| 2003/0055679 A1 | 3/2003 | Soli et al. |
| 2003/0058245 A1 | 3/2003 | Brazhnik et al. |
| 2003/0060692 A1 | 3/2003 | Ruchti et al. |
| 2003/0063524 A1 | 4/2003 | Niemiec et al. |
| 2003/0064751 A1 | 4/2003 | Charlier et al. |
| 2003/0065308 A1 | 4/2003 | Lebel et al. |
| 2003/0065534 A1 | 4/2003 | McCartney |
| 2003/0069753 A1 | 4/2003 | Brown |
| 2003/0078481 A1 | 4/2003 | McIvor et al. |
| 2003/0088238 A1 | 5/2003 | Poulsen et al. |
| 2003/0097279 A1 | 5/2003 | deLusignan et al. |
| 2003/0100821 A1 | 5/2003 | Heller et al. |
| 2003/0106917 A1 | 6/2003 | Shetler et al. |
| 2003/0110059 A1 | 6/2003 | Janas et al. |
| 2003/0120516 A1 | 6/2003 | Perednia |

(56) References Cited

U.S. PATENT DOCUMENTS

| | | | |
|---|---|---|---|
| 2003/0125612 A1* | 7/2003 | Fox | A61B 5/14532 600/347 |
| 2003/0158707 A1 | 8/2003 | Doi | |
| 2003/0158754 A1 | 8/2003 | Elkind | |
| 2003/0160683 A1* | 8/2003 | Blomquist | A61M 5/142 340/309.16 |
| 2003/0163351 A1 | 8/2003 | Brown et al. | |
| 2003/0176933 A1 | 9/2003 | Lebel et al. | |
| 2003/0187338 A1 | 10/2003 | Say et al. | |
| 2003/0199739 A1 | 10/2003 | Gordon et al. | |
| 2003/0199790 A1 | 10/2003 | Boecker et al. | |
| 2003/0208110 A1 | 11/2003 | Mault et al. | |
| 2003/0208113 A1 | 11/2003 | Mault et al. | |
| 2003/0212379 A1 | 11/2003 | Bylund et al. | |
| 2003/0216630 A1 | 11/2003 | Jersey-Willuhn et al. | |
| 2003/0217966 A1 | 11/2003 | Tapsak et al. | |
| 2003/0225324 A1 | 12/2003 | Anderson et al. | |
| 2003/0229514 A2 | 12/2003 | Brown | |
| 2003/0231552 A1 | 12/2003 | Markart | |
| 2003/0233257 A1 | 12/2003 | Matian et al. | |
| 2003/0236738 A1 | 12/2003 | Lange et al. | |
| 2004/0010207 A1 | 1/2004 | Flaherty et al. | |
| 2004/0011671 A1 | 1/2004 | Shults et al. | |
| 2004/0014069 A1 | 1/2004 | Cohen et al. | |
| 2004/0034289 A1 | 2/2004 | Teller et al. | |
| 2004/0035897 A1 | 2/2004 | Salentine et al. | |
| 2004/0039298 A1 | 2/2004 | Abreu | |
| 2004/0040840 A1 | 3/2004 | Mao et al. | |
| 2004/0041749 A1 | 3/2004 | Dixon | |
| 2004/0044548 A1 | 3/2004 | Marshall et al. | |
| 2004/0054263 A1 | 3/2004 | Moerman et al. | |
| 2004/0056055 A1 | 3/2004 | Folmer | |
| 2004/0059201 A1 | 3/2004 | Ginsberg | |
| 2004/0063435 A1 | 4/2004 | Sakamoto et al. | |
| 2004/0064068 A1 | 4/2004 | DeNuzzio et al. | |
| 2004/0073266 A1 | 4/2004 | Haefner et al. | |
| 2004/0078215 A1 | 4/2004 | Dahlin et al. | |
| 2004/0106858 A1 | 6/2004 | Say et al. | |
| 2004/0122353 A1 | 6/2004 | Shahmirian et al. | |
| 2004/0133164 A1 | 7/2004 | Funderburk et al. | |
| 2004/0133440 A1* | 7/2004 | Carolan | G06Q 10/10 705/38 |
| 2004/0133462 A1 | 7/2004 | Smith et al. | |
| 2004/0135684 A1 | 7/2004 | Steinthal et al. | |
| 2004/0138588 A1 | 7/2004 | Saikley et al. | |
| 2004/0146909 A1 | 7/2004 | Duong et al. | |
| 2004/0152622 A1 | 8/2004 | Keith et al. | |
| 2004/0152961 A1 | 8/2004 | Carlson et al. | |
| 2004/0155079 A1 | 8/2004 | Shetler et al. | |
| 2004/0165211 A1 | 8/2004 | Herrmann et al. | |
| 2004/0167801 A1 | 8/2004 | Say et al. | |
| 2004/0171921 A1 | 9/2004 | Say et al. | |
| 2004/0172284 A1 | 9/2004 | Sullivan et al. | |
| 2004/0172307 A1 | 9/2004 | Gruber | |
| 2004/0176672 A1 | 9/2004 | Silver et al. | |
| 2004/0176913 A1 | 9/2004 | Kawatahara et al. | |
| 2004/0186362 A1 | 9/2004 | Brauker et al. | |
| 2004/0186365 A1 | 9/2004 | Jin et al. | |
| 2004/0193090 A1 | 9/2004 | Lebel et al. | |
| 2004/0195284 A1 | 10/2004 | Iitsuka | |
| 2004/0197846 A1 | 10/2004 | Hockersmith et al. | |
| 2004/0199059 A1 | 10/2004 | Brauker et al. | |
| 2004/0199409 A1 | 10/2004 | Brown | |
| 2004/0200867 A1 | 10/2004 | Chee | |
| 2004/0204687 A1 | 10/2004 | Mogensen et al. | |
| 2004/0204863 A1 | 10/2004 | Kim et al. | |
| 2004/0204868 A1 | 10/2004 | Maynard et al. | |
| 2004/0210458 A1 | 10/2004 | Evans et al. | |
| 2004/0232180 A1 | 11/2004 | Badillo | |
| 2004/0254433 A1 | 12/2004 | Bandis et al. | |
| 2004/0254434 A1 | 12/2004 | Goodnow et al. | |
| 2004/0260155 A1 | 12/2004 | Ciarniello et al. | |
| 2004/0260478 A1 | 12/2004 | Schwamm | |
| 2004/0267300 A1 | 12/2004 | Mace | |
| 2005/0003470 A1 | 1/2005 | Nelson et al. | |
| 2005/0004439 A1 | 1/2005 | Shin et al. | |
| 2005/0004494 A1 | 1/2005 | Perez et al. | |
| 2005/0022274 A1 | 1/2005 | Campbell et al. | |
| 2005/0023137 A1 | 2/2005 | Bhullar et al. | |
| 2005/0031689 A1 | 2/2005 | Shults et al. | |
| 2005/0038680 A1 | 2/2005 | McMahon | |
| 2005/0043598 A1 | 2/2005 | Goode, Jr. et al. | |
| 2005/0045685 A1 | 3/2005 | Goode, Jr. et al. | |
| 2005/0048194 A1 | 3/2005 | Sesto | |
| 2005/0049179 A1 | 3/2005 | Davidson et al. | |
| 2005/0055243 A1 | 3/2005 | Shmulewitz | |
| 2005/0059873 A1 | 3/2005 | Arndt et al. | |
| 2005/0065555 A1 | 3/2005 | Er | |
| 2005/0071752 A1 | 3/2005 | Marlatt | |
| 2005/0086074 A1* | 4/2005 | Punzak | G06Q 10/10 705/2 |
| 2005/0090607 A1 | 4/2005 | Tapsak et al. | |
| 2005/0092791 A1 | 5/2005 | Labarca et al. | |
| 2005/0096511 A1 | 5/2005 | Fox et al. | |
| 2005/0096512 A1 | 5/2005 | Fox et al. | |
| 2005/0112169 A1 | 5/2005 | Brauke et al. | |
| 2005/0113653 A1 | 5/2005 | Fox et al. | |
| 2005/0114068 A1 | 5/2005 | Chey et al. | |
| 2005/0116683 A1 | 6/2005 | Cheng et al. | |
| 2005/0121322 A1 | 6/2005 | Say et al. | |
| 2005/0131311 A1 | 6/2005 | Leuthardt et al. | |
| 2005/0137530 A1 | 6/2005 | Campbell et al. | |
| 2005/0143635 A1 | 6/2005 | Kamath et al. | |
| 2005/0154271 A1 | 7/2005 | Rasdal et al. | |
| 2005/0171512 A1 | 8/2005 | Flaherty | |
| 2005/0176136 A1 | 8/2005 | Burd et al. | |
| 2005/0177398 A1 | 8/2005 | Watanabe et al. | |
| 2005/0182366 A1 | 8/2005 | Vogt et al. | |
| 2005/0187720 A1 | 8/2005 | Goode, Jr. et al. | |
| 2005/0192557 A1 | 9/2005 | Brauker et al. | |
| 2005/0195930 A1 | 9/2005 | Spital et al. | |
| 2005/0199494 A1 | 9/2005 | Say et al. | |
| 2005/0203360 A1 | 9/2005 | Brauker et al. | |
| 2005/0203461 A1 | 9/2005 | Flaherty et al. | |
| 2005/0203707 A1 | 9/2005 | Tsutsui et al. | |
| 2005/0238507 A1 | 10/2005 | Dilanni et al. | |
| 2005/0239156 A1 | 10/2005 | Drucker et al. | |
| 2005/0241957 A1 | 11/2005 | Mao et al. | |
| 2005/0245795 A1 | 11/2005 | Goode, Jr. et al. | |
| 2005/0245799 A1 | 11/2005 | Brauker et al. | |
| 2005/0245839 A1 | 11/2005 | Stivoric et al. | |
| 2005/0256417 A1 | 11/2005 | Rischell et al. | |
| 2005/0260174 A1 | 11/2005 | Fraser et al. | |
| 2005/0261558 A1 | 11/2005 | Eaton et al. | |
| 2005/0271996 A1 | 11/2005 | Sporbert et al. | |
| 2005/0267780 A1 | 12/2005 | Ray et al. | |
| 2005/0277164 A1 | 12/2005 | Drucker et al. | |
| 2005/0281234 A1 | 12/2005 | Kawamura et al. | |
| 2005/0281706 A1 | 12/2005 | Funke et al. | |
| 2005/0283386 A1 | 12/2005 | Powers et al. | |
| 2005/0287620 A1 | 12/2005 | Heller et al. | |
| 2005/0288571 A1 | 12/2005 | Perkins et al. | |
| 2006/0001538 A1 | 1/2006 | Kraft et al. | |
| 2006/0001551 A1 | 1/2006 | Kraft et al. | |
| 2006/0004270 A1 | 1/2006 | Bedard et al. | |
| 2006/0004603 A1 | 1/2006 | Peterka et al. | |
| 2006/0004607 A1 | 1/2006 | Marshall et al. | |
| 2006/0006141 A1 | 1/2006 | Ufer et al. | |
| 2006/0010098 A1 | 1/2006 | Goodnow et al. | |
| 2006/0015020 A1 | 1/2006 | Neale et al. | |
| 2006/0016700 A1 | 1/2006 | Brister et al. | |
| 2006/0019327 A1 | 1/2006 | Brister et al. | |
| 2006/0020186 A1 | 1/2006 | Brister et al. | |
| 2006/0020187 A1 | 1/2006 | Brister et al. | |
| 2006/0020188 A1 | 1/2006 | Kamath et al. | |
| 2006/0020189 A1 | 1/2006 | Brister et al. | |
| 2006/0020190 A1 | 1/2006 | Kamath et al. | |
| 2006/0020191 A1 | 1/2006 | Brister et al. | |
| 2006/0020192 A1 | 1/2006 | Brister et al. | |
| 2006/0029177 A1 | 2/2006 | Cranford, Jr. et al. | |
| 2006/0031094 A1 | 2/2006 | Cohen et al. | |
| 2006/0036134 A1 | 2/2006 | Tarassenko et al. | |
| 2006/0036139 A1 | 2/2006 | Briste r et al. | |
| 2006/0036140 A1 | 2/2006 | Brister et al. | |

(56) References Cited

U.S. PATENT DOCUMENTS

| | | |
|---|---|---|
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0051738 A1 | 3/2006 | Zweig |
| 2006/0058612 A1 | 3/2006 | Dave et al. |
| 2006/0058626 A1 | 3/2006 | Weiss et al. |
| 2006/0063135 A1 | 3/2006 | Mehl |
| 2006/0079740 A1 | 4/2006 | Silver et al. |
| 2006/0094952 A1 | 5/2006 | Ma et al. |
| 2006/0095225 A1 | 5/2006 | Harmon et al. |
| 2006/0115790 A1 | 6/2006 | Alon et al. |
| 2006/0129328 A1 | 6/2006 | Leo et al. |
| 2006/0143041 A1 | 6/2006 | Tipirneni |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0167718 A1 | 7/2006 | Tischer |
| 2006/0173260 A1 | 8/2006 | Gaoni et al. |
| 2006/0173444 A1 | 8/2006 | Choy et al. |
| 2006/0178633 A1 | 8/2006 | Garibotto et al. |
| 2006/0183985 A1 | 8/2006 | Brister et al. |
| 2006/0189863 A1 | 8/2006 | Peyser et al. |
| 2006/0202805 A1 | 9/2006 | Schulman et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0235009 A1 | 10/2006 | Glickman et al. |
| 2006/0240549 A1 | 10/2006 | Minton |
| 2006/0241969 A1 | 10/2006 | Wilhide et al. |
| 2006/0244465 A1 | 11/2006 | Kroh et al. |
| 2006/0247710 A1 | 11/2006 | Goetz et al. |
| 2006/0272652 A1 | 12/2006 | Stocker et al. |
| 2006/0282290 A1 | 12/2006 | Flaherty et al. |
| 2006/0287691 A1 | 12/2006 | Drew |
| 2007/0007237 A1 | 1/2007 | Lorsch |
| 2007/0010950 A1 | 1/2007 | Abensour et al. |
| 2007/0012324 A1 | 1/2007 | Nirkondar et al. |
| 2007/0016381 A1 | 1/2007 | Kamath et al. |
| 2007/0016449 A1 | 1/2007 | Cohen et al. |
| 2007/0027381 A1 | 2/2007 | Stafford |
| 2007/0033074 A1 | 2/2007 | Nitzan et al. |
| 2007/0033114 A1 | 2/2007 | Minor |
| 2007/0041626 A1 | 2/2007 | Weiss et al. |
| 2007/0055799 A1 | 3/2007 | Koehler et al. |
| 2007/0060814 A1 | 3/2007 | Stafford |
| 2007/0060979 A1 | 3/2007 | Strother et al. |
| 2007/0061170 A1 | 3/2007 | Lorsch et al. |
| 2007/0066873 A1 | 3/2007 | Kamath et al. |
| 2007/0066956 A1 | 3/2007 | Finkel |
| 2007/0067000 A1 | 3/2007 | Strother et al. |
| 2007/0071681 A1 | 3/2007 | Gadkar et al. |
| 2007/0073129 A1 | 3/2007 | Shah et al. |
| 2007/0074043 A1 | 3/2007 | Lacey |
| 2007/0078321 A1 | 4/2007 | Mazza et al. |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0096715 A1 | 5/2007 | Joy et al. |
| 2007/0100215 A1 | 5/2007 | Powers et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173698 A1 | 7/2007 | Kivela et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0185390 A1 | 8/2007 | Perkins et al. |
| 2007/0191701 A1 | 8/2007 | Feldman et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0219432 A1 | 9/2007 | Thompson |
| 2007/0219480 A1 | 9/2007 | Kamen et al. |
| 2007/0219597 A1 | 9/2007 | Kamen et al. |
| 2007/0228071 A1 | 10/2007 | Kamen et al. |
| 2007/0231846 A1 | 10/2007 | Cosentino et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0253021 A1 | 11/2007 | Mehta et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0293932 A1 | 12/2007 | Zilla et al. |
| 2008/0004904 A1 | 1/2008 | Tran |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0026338 A1 | 1/2008 | Cinader |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058626 A1 | 3/2008 | Miyata et al. |
| 2008/0058678 A1 | 3/2008 | Miyata et al. |
| 2008/0062891 A1 | 3/2008 | Van der Merwe et al. |
| 2008/0063948 A1 | 3/2008 | O'Brien |
| 2008/0064937 A1 | 3/2008 | McGarraugh et al. |
| 2008/0064943 A1 | 3/2008 | Talbot et al. |
| 2008/0065236 A1 | 3/2008 | Bristol |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus et al. |
| 2008/0073993 A1 | 3/2008 | Sortore et al. |
| 2008/0077433 A1 | 3/2008 | Kasprisin et al. |
| 2008/0078567 A1 | 4/2008 | Miller et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0105479 A1 | 5/2008 | Lei |
| 2008/0105748 A1 | 5/2008 | Lei |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0125636 A1 | 5/2008 | Ward et al. |
| 2008/0126882 A1 | 5/2008 | Fulton et al. |
| 2008/0127052 A1 | 5/2008 | Rostoker |
| 2008/0129465 A1 | 6/2008 | Rao |
| 2008/0139910 A1 | 6/2008 | Mastrototaro et al. |
| 2008/0145277 A1 | 6/2008 | Wohland |
| 2008/0154513 A1 | 6/2008 | Kovatchev et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0183500 A1 | 7/2008 | Banigan |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |

(56) References Cited

U.S. PATENT DOCUMENTS

| | | |
|---|---|---|
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0235469 A1 | 9/2008 | Drew |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269723 A1 | 10/2008 | Mastrototaro et al. |
| 2008/0275313 A1 | 11/2008 | Brister et al. |
| 2008/0281167 A1 | 11/2008 | Soderberg et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006133 A1 | 1/2009 | Weinert et al. |
| 2009/0012377 A1 | 1/2009 | Jennewine et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0018779 A1 | 1/2009 | Cohen et al. |
| 2009/0030294 A1 | 1/2009 | Petisce et al. |
| 2009/0030733 A1 | 1/2009 | Cohen et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048501 A1 | 2/2009 | Goodnow |
| 2009/0048503 A1 | 2/2009 | Dalal et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069744 A1 | 3/2009 | Goodnow |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0085873 A1 | 4/2009 | Betts et al. |
| 2009/0088427 A1 | 4/2009 | Clickman et al. |
| 2009/0099436 A1 | 4/2009 | Brister et al. |
| 2009/0105554 A1 | 4/2009 | Stahman et al. |
| 2009/0105560 A1 | 4/2009 | Solomon |
| 2009/0105636 A1 | 4/2009 | Hayter et al. |
| 2009/0112478 A1 | 4/2009 | Mueller, Jr. et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149717 A1 | 6/2009 | Brauer et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0187351 A1 | 7/2009 | Orr et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0221880 A1 | 9/2009 | Soderberg et al. |
| 2009/0224773 A1 | 9/2009 | Joy et al. |
| 2009/0224837 A1 | 9/2009 | Joy et al. |
| 2009/0227876 A1 | 9/2009 | Tran et al. |
| 2009/0227877 A1 | 9/2009 | Tran et al. |
| 2009/0228304 A1 | 9/2009 | Ciarniello et al. |
| 2009/0234200 A1 | 9/2009 | Husheer |
| 2009/0240120 A1 | 9/2009 | Mensinger et al. |
| 2009/0240127 A1 | 9/2009 | Ray |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0253973 A1 | 10/2009 | Bashan et al. |
| 2009/0258790 A1 | 10/2009 | Cohen et al. |
| 2009/0267765 A1 | 10/2009 | Greene et al. |
| 2009/0269315 A1 | 10/2009 | Fraser et al. |
| 2009/0273353 A1 | 11/2009 | Kroh et al. |
| 2009/0278553 A1 | 11/2009 | Kroh et al. |
| 2009/0281519 A1 | 11/2009 | Rao et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |

(56) References Cited

U.S. PATENT DOCUMENTS

| | | |
|---|---|---|
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0088199 A1 | 4/2010 | Tipirneni |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0146300 A1 | 6/2010 | Brown |
| 2010/0152554 A1 | 6/2010 | Steine et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168546 A1 | 7/2010 | Kamath et al. |
| 2010/0168547 A1 | 7/2010 | Kamath et al. |
| 2010/0168645 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179399 A1 | 7/2010 | Goode et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0190435 A1 | 7/2010 | Cook et al. |
| 2010/0191082 A1 | 7/2010 | Brister et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0312176 A1 | 12/2010 | Lauer et al. |
| 2011/0004276 A1 | 1/2011 | Blair et al. |
| 2011/0046977 A1 | 2/2011 | Goodnow et al. |
| 2011/0145172 A1 | 6/2011 | Petisce et al. |
| 2011/0148905 A1 | 6/2011 | Simmons et al. |
| 2011/0152637 A1 | 6/2011 | Kateraas et al. |
| 2011/0257895 A1 | 10/2011 | Brauker et al. |
| 2012/0190989 A1 | 7/2012 | Kaiser et al. |
| 2014/0184423 A1* | 7/2014 | Mensinger ............ A61B 5/0004 340/870.09 |

FOREIGN PATENT DOCUMENTS

| | | |
|---|---|---|
| EP | 0127958 | 12/1984 |
| EP | 0320109 | 6/1989 |
| EP | 0390390 | 10/1990 |
| EP | 0396788 | 11/1990 |
| EP | 1669020 | 6/2006 |
| EP | 1729128 | 12/2006 |
| WO | WO-2000/059370 | 10/2000 |
| WO | WO-2000/072181 | 11/2000 |
| WO | WO-2000/075814 | 12/2000 |
| WO | WO-2001/052935 | 7/2001 |
| WO | WO-2001/054753 | 8/2001 |
| WO | WO-2002/041231 | 5/2002 |
| WO | WO-2003/082091 | 10/2003 |
| WO | WO-2005/040793 | 5/2005 |
| WO | WO-2008/001366 | 1/2008 |

OTHER PUBLICATIONS

Travenol Laboratories, Inc., An Introduction of "Eugly," Book 1, 1985, pp. 1-22.
Canadian Patent Application No. CA-2,572,455, Examiner's Report dated Jun. 13, 2012.
Canadian Patent Application No. CA-2,858,901, Examiner's Report dated Jan. 25, 2016.
European Patent Application No. EP-05756627.5, Supplementary European Search Report dated Dec. 4, 2009.
European Patent Application No. EP-05756627.5, Office Action dated Jun. 24, 200.
European Patent Application No. EP-05756627.5, Decision to Refuse the Application dated Dec. 12, 2013.
European Patent Application No. EP-05756627.5, Decision to Refuse the Application dated Dec. 7, 2012.
European Patent Application No. EP-05756627.5, Examination Report dated Jun. 7, 2013.
European Patent Application No. EP-05756627.5, Official Communication dated Jun. 13, 2012.
PCT Application No. PCT/US2005/020044, International Preliminary Report on Patentability dated Dec. 20, 2006.
PCT Application No. PCT/US2008/054165, International Preliminary Report on Patentability and Written Opinion of the International Searching Authority dated Aug. 27, 2009.
PCT Application No. PCT/US2008/054165, International Search Report and Written Opinion of the International Searching Authority dated Jun. 5, 2008.
PCT Application No. PCT/US2008/067791, International Search Report and Written Opinion of the International Searching Authority dated Sep. 29, 2008.
PCT Application No. PCT/US2008/067791, International Search Report on Patentability and Written Opinion of the International Searching Authority dated Jan. 7, 2010.

* cited by examiner

Initial User Setup

Application Mode

Select whether you want to run the program as a Home User or Health Care Professional:

◉ Home User   ○ Health Care Professional ← 22

20 ↗

User Identification

Before using the FreeStyle CoPilot Health Management System, you must provide your Name and a User ID and Password.

First Name: [ ]
Last Name: [ ]
E-Mail Address: [ ]
User ID*: [ ]
Password*: [ ]
Confirm Password*: [ ]

24 ↗

*User ID and Password are case-sensitive and must be at least 5 characters long.

[ OK ]  [ Cancel ]  [ ? Help ]

Profile for: Marlon Tucker

File  Edit  Help

User Information | Health Profile | Data Entry Preferences | Glucose Targets | Options

Exercise Preferences

| Type | Duration | Intensity |
|---|---|---|
| Swim | | |
| Aerobics | | |
| Jog | | |
| Run | | |
| Swim | | |
| Weights | | |
| Walk | | |
| Bike | | |
| Other | | |

| Insulin Name | Dosage (units) | Type |
|---|---|---|
| | 0.00 | |

Medication Preferences

| Medication | Dosage | # of Pills |
|---|---|---|
| | | |

Rights...  OK  Cancel  Apply  ? Help

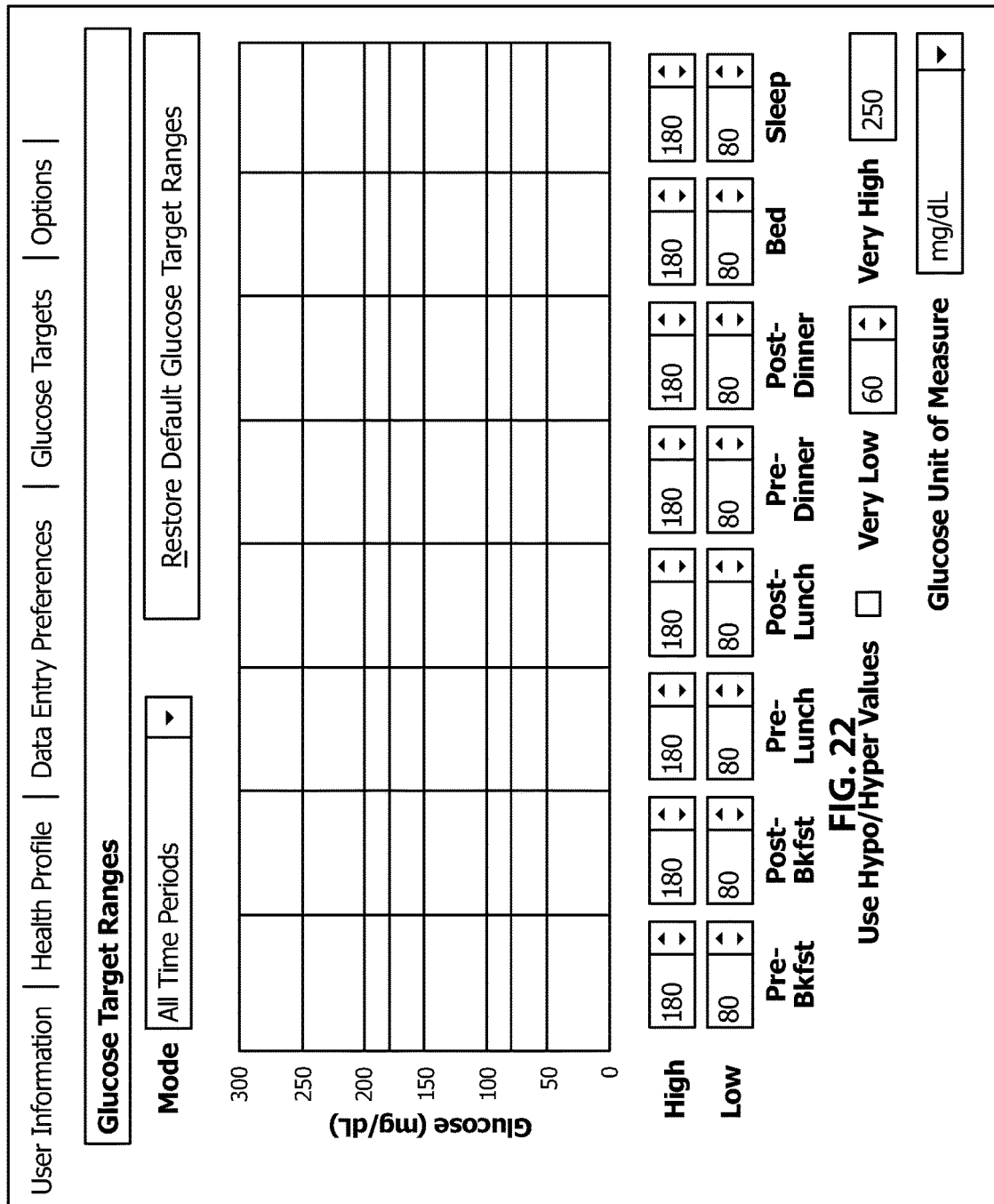

Profile for: Marlon Tucker

File

| Last | First | MI | ID |
|---|---|---|---|
| Administrator | System | | Admin |
| Tucker | Marlon | | mtucker |
| Tucker | Linda | | ltucker |

FIG. 30

Profile for:

File  Edit  Help

Contact Information

HCP ID*           Host Account

Title             HCP Type

First        MI        Last*

Facility**

Address 1

Address 2

Address 3

City              State/Province

Country           Zip/Postal Code

Email

Phone   Type              Phone Number

Click here to add a new Phone

No data to display

*Denotes a required field / ** Required to Synchronize

Help

Apply

Cancel

| Use Hypo/Hyper Values ☑ | Very Low | 60 | Very High | 250 |
| --- | --- | --- | --- | --- |
| | Glucose Unit of Measure | mg/dL | | |

FIG. 45

| Glucose Unit of Measure | mg/dL ▼ |
| --- | --- |
| | mg/dL |
| | mmol/L |

FIG. 46

HCP Profile for: Dr. Jeremy Sloane

File  Edit  Help

User Information | Glucose Targets | Options

Data Entry Options
- ☑ Insulin
- ☑ Meals
- ☑ Exercise
- ☑ State Of Health
- ☑ Medications
- ☑ Exams
- ☑ Lab Results
- ☑ Ketones

Program Options
- ☐ Confirm on Exit
- ☑ Show Tool Bar
- ☑ Show Tool Tips
- ☐ Show Button Captions
- ☑ Show Status Bar

Report Options
Default Report Type: Glucose Modal ▼
Default Report Date Range: Last 2 Weeks ▼

Include Statistics Summary With Each Report Print Out ☐

Favorite Report Options
Print Favorite Reports after device upload ☐

Favorite Reports

| ✓ | Report | Date Range |
|---|---|---|
| ☐ | Diary List | Last 2 Weeks |
| ☐ | Glucose Modal Day | Last 2 Weeks |
| ☐ | Glucose Line | Last 2 Weeks |
| ☐ | Glucose Average | Last 2 Weeks |
| ☐ | Glucose Histogram | Last 2 Weeks |
| ☐ | Glucose Pie Chart | Last 2 Weeks |
| ☐ | Logbook | Last 2 Weeks |
| ☐ | Lab & Exam Record | Last 2 Weeks |
| ☐ | Statistics | Last 2 Weeks |
| ☐ | Daily Combination | Last 2 Weeks |
| ☐ | Weekly Pump | Last 2 Weeks |

[Rights...]  [OK]  [Cancel]  [Apply]  [? Help]

| Last | First | MI | ID | Authorization Level | | | |
|---|---|---|---|---|---|---|---|
| Tucker | Marlon | | mtucker | ○ None | ○ Read Only | ⦿ Full | ○ Owner |

HCP List

| Last | First | MI | ID |
|---|---|---|---|
| Administrator | System | | Admin |
| Andrews | David | | dandrews |
| Crawford | Mary | | mcrawford |
| Meyer | Samuel | | smeyer |
| Sloane | Jeremy | | jsloane |
| Thatcher | Rhonda | | rthatcher |

FIG. 57

Cable Setup Diagram

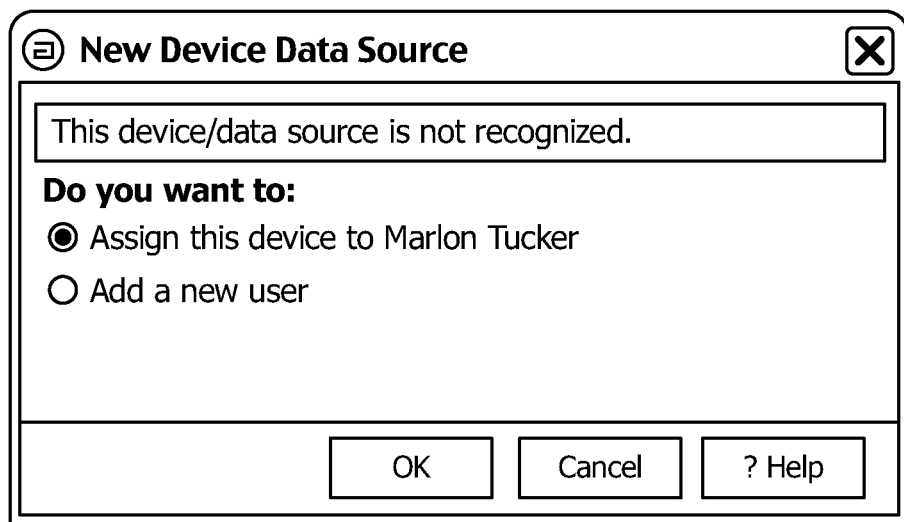
FIG. 72
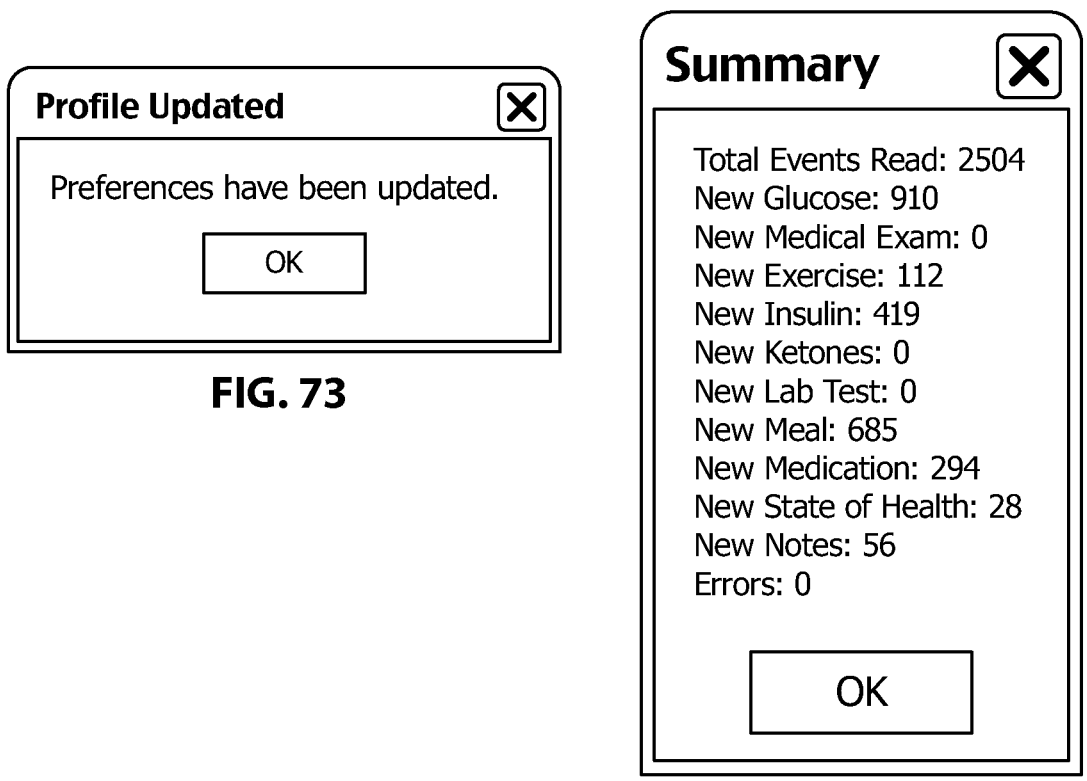
FIG. 73
FIG. 74

Data Entry

Glucose Reading

Date: 9/10/2004  Time: 2:26 PM  Time Period: Post-Lunch — 98

Glucose Value (mg/dL) — 100

Sample Site — 102

Hours Since Last Meal — 104

Calibration Code — 106

Control Reading ☐ — 108

Data Source: Manual

Comment

OK   Cancel   Apply   ? Help

Data Entry

Menu

G | 🍎 | 😊 | ⚕ | K | A

Meal

Date: 10/3/2004  Time: 11:11 AM  Meal: Lunch

| Food Item | Svgs | Carbs (g) | Total Carbs (g) |
|---|---|---|---|
| Milk, 1/2% (1 cup) | 1 | 11 | 11 |
| 8" while cake with whip cream (Chuck E. Cheese) (1 slice) | 1 | 26 | 26 |
| Albacore tuna sandwich, light, small (Schlotzsky's) (1 serving) | 1 | 50 | 50 |
|  |  |  | 76.00 |

Use Only Favorite Foods ☐

Comment

OK | Cancel | Apply | ? Help

FIG. 79

Data Entry

Menu

*G* | 🥤 | 🍎 | ☎ | 🙂 | ⚕ | Ƴ | 🧪 | K | 📄

Exercise

Date 9/10/2004    Time 03:03 PM    Time Period Post-Lunch

| ☑ | Type | Duration | Intensity |
|---|---|---|---|
|  | Click here to add a new row | | |
| ☑ | Aerobics | 0:30 | Low |

Check the check box to include an entry ☑

Comment

[ OK ]  [ Cancel ]  [ Apply ]  [ ? Help ]

Customize Data Entry Lists

Lists

Customizing Lists for: Marlon Tucker

Select List to Customize: Test Types ▼

| | Item | Hide | |
|---|---|---|---|
| | Click here to add a new row | | |
| | Ketones (Blood) | ☐ | |
| | Ketones (Urinary) | ☐ | |
| | LDH | ☐ | |
| | Microalbumin | ☐ | |
| | Proteinuria | ☐ | |
| | PSA | ☐ | |
| | Pulse | ☐ | |
| | Serum theophylline level | ☐ | |
| | T4 | ☐ | |
| | T4 (free) | ☐ | |

[ OK ]  [ Cancel ]  [ Apply ]  [ ? Help ]

FIG. 93

Customize Data Entry Lists

Lists

Customizing Lists for: Marlon Tucker

Select List to Customize: | Exam Types ▼

| | Item | Hide |
|---|---|---|
| | Click here to add a new row | |
| | Cardiologist | ☐ |
| | Educator | ☐ |
| | Endocrinologist | ☐ |
| | Exercise Consultant | ☐ |
| | Eye | ☐ |
| | Family Planning | ☐ |
| | Foot | ☐ |
| | Kidney specialist | ☐ |
| | Nutritionist | ☐ |
| | Other Physician | ☐ |

[ OK ]  [ Cancel ]  [ Apply ]  [ ? Help ]

Report Configuration

Data Filter | Miscellaneous

| Event Types | Time Periods | Week Days |
|---|---|---|
| ☑ Glucose | ☑ Pre-Breakfast | ☑ Sunday |
| ☑ Insulin | ☑ Post-Breakfast | ☑ Monday |
| ☑ Carbohydrates | ☑ Pre-Lunch | ☑ Tuesday |
| ☑ Exercise | ☑ Post-Lunch | ☑ Wednesday |
| ☑ Medications | ☑ Pre-Dinner | ☑ Thursday |
| ☑ State of Health | ☑ Post-Dinner | ☑ Friday |
| ☑ Lab Results | ☑ Bed | ☑ Saturday |
| ☑ Exams | ☑ Sleep | |
| ☑ Ketones | | |
| ☑ Notes | | |

Reset  OK  Cancel  Apply  ? Help

FIG. 110

FreeStyle CoPilot Health Management System - Home Version

File  DataEntry  Reports  UserProfile  References  Host  Help

FreeStyleCoPILOT
Health Management System

Select User: Marlon Tucker

Custom Dates  ▶  5/5/2004  ⇧  7/4/2004  ▶

Glucose Modal Day | Glucose Average | Glucose Line | Glucose Pie | Lab & Exam Record | Statistics | Diary List

Diary List
5/4/2004-5/1/2004

| Type | Date | Time | Time Period | Value | Description | Other Info | Comment |
|---|---|---|---|---|---|---|---|
| 🐃 | 5/17/2004 | 11:09 PM | Snack | 15 grams | 1 Svg (15 g) - N/A | | |
| G | 5/17/2004 | 11:08 PM | Bed | 142 (mg/dL) | | | |
| ∿ | 5/17/2004 | 07:08 PM | Post-Dinner | 2 | Prandin Dosage: | | |
| 🐃 | 5/17/2004 | 06:08 PM | Dinner | 45 grams | 1 Svg (45 g) - N/A | | |
| G | 5/17/2004 | 06:08 PM | Post-Dinner | 169 (mg/dL) | | | |
| ∿ | 5/17/2004 | 02:26 PM | Post-Lunch 2 | | Prandin Dosage: | | |
| 🐃 | 5/17/2004 | 02:07 PM | Lunch | 40 grams | 1 Svg (40 g) - N/A | | Late lunch after church |

CoPilot.cpd

FIG. 113

Logbook Report
4/1/2004-5/1/2004

| Date | Breakfast | | | | Lunch | | | |
|---|---|---|---|---|---|---|---|---|
| | Units/Type | 🍴 (g) | G Pre (mg/dL) | G Post (mg/dL) | Units/Type | 🍴 (g) | G Pre (mg/dL) | G Post (mg/dL) |
| 5/1/2004 | | | 188 | | | | | |
| 4/30/2004 | | 35 | 161 | | | 50 | 112 | |
| 4/29/2004 | | 50 | 110 | | | 35 | 144 | |
| 4/28/2004 | Dr.Appt ate bf at 11am | 30 | 201 | | | 45 | 271 | |
| 4/27/2004 | Small BF | 50 | 183 | | | 45 | 188 | |
| 4/26/2004 | 5.00(H) | 46 | 110 | 350 | 5.00(H) | 60 | 82 | 180 |
| 4/25/2004 | 5.00(H) | 40 | 100 | 170 | 3.00(H) | 60 | 220 | |
| 4/24/2004 | 4.00(H) | | 98 | 240 | 4.00(H) | 55 | 140 | 200 |
| | | | | | | | 190 | |

FIG. 124

FreeStyle CoPilot Health Management System - HCP Version

File  DataEntry  Reports  UserProfile  References  Host  Help

Select HCP: Dr. Jeremy Sloane ▼  8/29/2004 ▼  9/11/2004 ▼  Select Patient: John Doe ▼

FreeStyleCoPILOT
Health Management System

Last 2 Weeks | Weekly Pump | Daily Combination | Lab & Exam Record | Glucose Histogram | Glucose Average | Statistics

Lab & Exam Record
9/12/2002-9/11/2004

Type of Diabetes: Type 1  Year Diagnosed: 1966  Gender: Male
Height: 5'10"  Age: 47  Weight: 173

| Lab Tests | Value | Reference Range | Date |
|---|---|---|---|
| A1C | 11.5 | | 12/2/2002 |
| A1C | 11.1 | | 3/15/2003 |
| A1C | 10.7 | | 5/7/2003 |
| A1C | 10.8 | | 8/30/2003 |
| A1C | 10.5 | | 12/2/2003 |
| A1C | 10.1 | | 3/15/2004 |
| A1C | 10.8 | | 5/30/2004 |
| A1C | 9.5 | | 8/30/2004 |
| A1C | 9.7 | | 8/31/2004 |
| Cholesterol HDL | 45 | | 8/30/2004 |
| Cholesterol HDL | 45 | | 8/30/2004 |
| Cholesterol LDL | 98 | | 8/30/2004 |
| Cholesterol LDL | 98 | | 8/30/2003 |
| Cholesterol Total | 143 | | 8/30/2004 |
| Cholesterol Total | 143 | | 8/30/2004 |
| Weight | 250 | | 8/30/2003 | sample.cpd

FIG. 125

FreeStyleCoPILOT
Health Management System

Lab & Exam Record
9/12/2002-9/11/2004

| Exam Type | Examined By | Date | Comment |
|---|---|---|---|
| Eye | Dr. Cynthia Farrell | 8/30/2003 | Healthy, normal retina. No problem. |
| Eye | Dr. Cynthia Farrell | 8/30/2004 | Healthy, normal retina. No problem. |
| Foot | Dr. Chuck Podosa | 12/1/2002 | Normal. No cuts, redness, or blisters. |
| Foot | Dr. Chuck Podosa | 3/16/2003 | Normal. No cuts, redness, or blisters. |
| Foot | Self | 5/8/2003 | Normal. No cuts, redness, or blisters. |
| Foot | Self | 8/30/2003 | Normal. No cuts, redness, or blisters. |
| Foot | Self | 12/3/2003 | Normal. No cuts, redness, or blisters. |
| Foot | Self | 3/16/2004 | Normal. No cuts, redness, or blisters. |
| Foot | Self | 5/8/2004 | Normal. No cuts, redness, or blisters. |
| Foot | Dr. Chuck Podosa | 8/30/2004 | Normal. No cuts, redness, or blisters. |

FIG. 126

FreeStyleCoPilot
Health Management System

Statistics Report
4/1/2004–5/1/2004

| G Glucose Statistics (mg/dL) | Breakfast | | Lunch | | Dinner | | Bed & Sleep | | Total/Summary |
|---|---|---|---|---|---|---|---|---|---|
| | Pre | Post | Pre | Post | Pre | Post | Bed | Sleep | |
| #Readings | 31 | 10 | 27 | 10 | 27 | 2 | 31 | 4 | 142 |
| #Days w/Readings | 31 | 10 | 27 | 10 | 27 | 2 | 31 | 4 | 31 |
| Avg. # Readings/day | 1.0 | 0.3 | 0.9 | 0.3 | 0.9 | 0.1 | 1.0 | 0.1 | 4.6 |
| Highest | 201 | 350 | 380 | 330 | 310 | 169 | 297 | 130 | 380 |
| Lowest | 55 | 150 | 82 | 112 | 105 | 169 | 65 | 110 | 55 |
| Average | 129 | 240 | 196 | 208 | 153 | 169 | 166 | 120 | 168 |
| Standard Deviation | 52 | 74 | 75 | 71 | 49 | N/A | 67 | 10 | 70 |
| Above % | 29 | 60 | 63 | 60 | 7 | 0 | 32 | 0 | 35 |
| Within% | 45 | 40 | 37 | 40 | 93 | 100 | 62 | 100 | 58 |
| Below% | 26 | 0 | 0 | 0 | 0 | 0 | 6 | 0 | 7 |

FIG. 128

FreeStyleCoPilot™
Health Management System

File  DataEntry  Reports  UserProfile  References  Host  Help

Select User: Marlon Tucker

Custom Dates  4/1/2004  5/1/2004

Diary List | Glucose Modal Day | Glucose Line | Glucose Average | Glucose Histogram | Glucose Pie | Logbook | Lab & Exam Record | Statistics

Statistics Report
4/1/2004 - 5/1/2004

| Insulin Statistics (Units) | Breakfast | | Lunch | | Dinner | | Bed & Sleep | | Total/Summary |
|---|---|---|---|---|---|---|---|---|---|
| | Pre | Post | Pre | Post | Pre | Post | Bed | Sleep | |
| Avg./day. Glargine | 4.29 | | | | | | 14.43 | | 14.43 |
| Avg./day. Humalog | 4.29 | | 4.43 | | 8.86 | | 1.00 | | 5.43 |
| Avg./day. Total Insulin | | | 4.43 | | 8.86 | | 11.44 | | 7.53 |

| Carbs Statistics (Grams) | Breakfast | Lunch | Dinner | Bed & Sleep | Total/Summary |
|---|---|---|---|---|---|
| Avg./day. Carbohydrates | 41.2 | 49.1 | 66.6 | 16.3 | 164.4 |

CoPilot.cpd

FIG. 129

| Custom Dates ▼ | ⇐ | 8/3/2004 ▼ | 8/3/2004 ▼ | ⇒ |

FIG. 130

| Custom Dates ▼ | ⇐ | 7/8/2004 ▼ | 8/3/2004 ▼ | ⇒ |

FIG. 133

Insulin Adjustment Table

Insulin Sensitivity 50

Glucose Start Value (mg/dL) 50

| Low Glucose Value | High Glucose Value | Insulin Dosage Amount |
|---|---|---|
| 150 | 200 | 1 |
| 201 | 251 | 2 |
| 252 | 302 | 3 |
| 303 | 353 | 4 |
| 354 | 404 | 5 |
| 405 | 455 | 6 |
| 456 | 506 | 7 |
| 507 | 557 | 8 |

Print     OK     ? Help

Prescribed Plan

Prescribed Plan for: Marlon Tucker

| Type | Item | Bkfst | Lunch | Dinner | Bed | Snack |
|---|---|---|---|---|---|---|
| | Ratio | Click here to add a new row | | | | |
| | Sensitivity | | | | | |
| | Carbohydrates (grams) | | | | | |

Comments

| Print | Reset | | OK | Cancel | Apply | ? Help |

FIG. 142

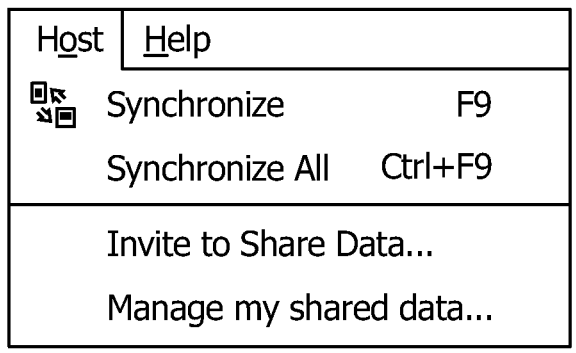
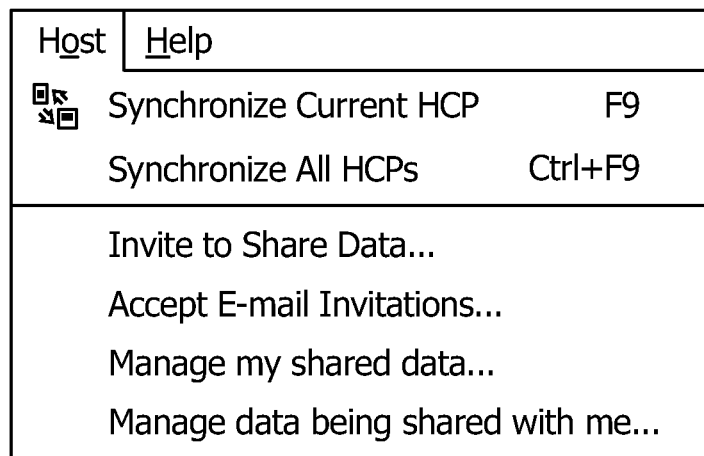
FIG. 143

FIG. 145

Invite HCP to Share Data

Step 1: Invite to Share Data

This feature assists you in inviting an HCP to access your data. After you specify the HCP to whom you wish to grant this access, they will be sent an invitation message identifying you and giving instructions on how to accept the invitation, if they choose to do so.

Select the appropriate option below and click NEXT.

● Search Host HCP Database to find an HCP from the list of existing accounts

○ Enter the Host HCP Account Number given to you by your HCP

○ Send an email invitation to an HCP who does not have an existing account

FIG. 149

@ Invite HCP to Share Data

Step 2: Find an HCP from the list of existing accounts

Indicate the location of your HCP and click SEARCH. Then select the desired HCP on the list. Click NEXT to continue.

| CA ▼ | | Search |

| ▼ HCP Name | ▼ Facility | ▼ Address |

⇦ Previous | Next ⇧ | Cancel | ? Help

FIG. 150

Invite HCP to Share Data

Step 3: Assign Access Level for selected HCP

Specify the Access Level that you wish to assign (You may change this level at any time)

⦿ Read Only Access

○ Full Access (Read and Enter Data)

After assigning and Access Level, click SUBMIT. A message will be sent to the HCP advising them of your wish that they have access to your data.

You will be notified by a message on your Main Menu screen when the HCP has accepted your invitation. Be sure to Synchronize regularly to the Host Server to keep current with your messages.

Note: If you receive no messages confirming acceptance by the HCP within a reasonable period of time, you should follow-up with the HCP yourself as the system will not generate repeat invitation messages.

[ ? Help ]

[ Cancel ]

[ ⇦ Previous ]   [ Submit ⇨ ]

FIG. 151

Invite HCP to Share Data

Step 1: Invite to Share Data

This feature assists you in inviting an HCP to access your data. After you specify the HCP to whom you wish to grant this access, they will be sent an invitation message identifying you and giving instructions on how to accept the invitation, if they choose to do so.

Select the appropriate option below and click NEXT.

○ Search Host HCP Database to find an HCP from the list of existing accounts

⦿ Enter the Host HCP Account Number given to you by your HCP

○ Send an email invitation to an HCP who does not have an existing account

FIG. 153

Invite HCP to Share Data

Step 2: Enter the Host HCP Account Number

Enter the Host Account Number and click SEARCH. The database will then be searched and the desired HCP will be listed. Click NEXT to continue.

HCP Account#  [      ]  [ Search ]

Verify result then click "Next" to continue

Search Result
123694
Dr. Jeremy Sloane

[ ⇦ Previous ]  [ Next ⇧ ]  [ Cancel ]  [ ? Help ]

FIG. 154

Invite HCP to Share Data

Step 3: Assign Access Level for selected HCP

Specify the Access Level that you wish to assign (You may change this level at any time)

○ Read Only Access

⦿ Full Access (Read and Enter Data)

After assigning and Access Level, click SUBMIT. A message will be sent to the HCP advising them of your wish that they have access to your data.

You will be notified by a message on your Main Menu screen when the HCP has accepted your invitation. Be sure to Synchronize regularly to the Host Server to keep current with your messages.

Note: If you receive no messages confirming acceptance by the HCP within a reasonable period of time, you should follow-up with the HCP yourself as the system will not generate repeat invitation messages.

[ ⇦ Previous ]  [ Submit ⇧ ]  [ Cancel ]  [ ? Help ]

FIG. 155

| Messages From CoPilot Host | | |
|---|---|---|
| Date | From | Subject |
| 11/7/2004 | Millard Fillmore | Attention: Access Authorization has been granted to you |
| An invitation to share data on the FreeStyle CoPilot Health Management System has been sent to you by Dwayne White.... | | |

FIG. 157

Invite HCP to Share Data

Step 1: Invite to Share Data

This feature assists you in inviting an HCP to access your data. After you specify the HCP to whom you wish to grant this access, they will be sent an invitation message identifying you and giving instructions on how to accept the invitation, if they choose to do so.

Select the appropriate option below and click NEXT.

○ Search Host HCP Database to find an HCP from the list of existing accounts

○ Enter the Host HCP Account Number given to you by your HCP

⦿ Send an email invitation to an HCP who does not have an existing account

[Previous] [Next] [Cancel] [? Help]

FIG. 159

Invite HCP to Share Data

Step 2: Send an e-mail invitation to an HCP who does not have an account

Enter the name and e-mail address of the HCP whom you wish to invite. Then click NEXT to continue.

Name: Dr. Mary Crawford

E-mail Address: mcrawford@anynet.net

[Previous] [Next] [Cancel] [? Help]

FIG. 160

Invite HCP to Share Data

Step 3: Assign Access Level for selected HCP

Specify the Access Level that you wish to assign (You may change this level at any time)

● Read Only Access

○ Full Access (Read and Enter Data)

After assigning and Access Level, click SUBMIT. A message will be sent to the HCP advising them of your wish that they have access to your data.

You will be notified by a message on your Main Menu screen when the HCP has accepted your invitation. Be sure to Synchronize regularly to the Host Server to keep current with your messages.

Note: If you receive no messages confirming acceptance by the HCP within a reasonable period of time, you should follow-up with the HCP yourself as the system will not generate repeat invitation messages.

[Previous]  [Submit ⇧]  [Cancel]  [? Help]

FIG. 161

Invitation Code: A_Guw5I5dnOKaQbAsvhASx

Manage my shared data

Parties Authorized by: Anita Bryant

| Access Level | First Name | Last Name | City | State |
|---|---|---|---|---|
| READ_ONLY   123885 | William | Reade | Anyplace | AK |

Grant NO Access | Grant Read Only Access | Grant Full Access | Close

FIG. 169

SYSTEMS AND METHODS FOR MANAGING DIABETES CARE DATA

PRIORITY

The present application is a continuation of U.S. patent application Ser. No. 11/146,897, filed Jun. 6, 2005, which claims the benefit of U.S. Provisional Application No. 60/577,064, filed Jun. 4, 2004, both of which are incorporated herein by reference in their entirety for all purposes.

FIELD OF THE INVENTION

The invention relates to diabetes care data management, and particularly to a host-client architecture for communicating, managing and analyzing the data and for generating versatile reports.

SUMMARY OF THE INVENTION

The invention provides a host-client data sharing system for managing diabetes care data. A host database, preferably web or internet based, is implemented for storing diabetes care data relating to multiple diabetics. A client or local database stores the diabetes care data relating to multiple diabetics on a personal appliance such as a PC, or a portable or handheld microprocessor-based computing device. The host database uses multiple servers for handling client interactions with the system. A host based data warehouse component is used for storing, searching and/or analyzing, customer information and health data stored on the host database for the population of multiple diabetics using the Host. The host-based data warehouse component applies security mechanisms to protect access to the data stored on the host server. The data mining terminal runs an analytical data processing application and has access to the data warehouse.

A browser-accessible or client-resident graphics rendering component provides a graphical user interface (GUI) that includes a patient selection component permitting uploading data to or calling data from, the database, or both, relating to a particular diabetic of the multiple diabetics. The GUI further includes diabetes care device and health care professional (HCP) selection components, and report configuration components for generating customized reports of selected diabetics, HCPs, data ranges, data types or categories and other criteria.

Population analysis reporting or generation of reports on a population of multiple diabetics is permitted with the report generation component. These reports are allowed to base the data analysis on multiple selection criteria. These data elements may be applied in a selected combination and may use a selected number of selection criteria, such as patient profile information, demographic information, selected data event types, a range of values for a given selection criteria, dates, or other data filters or elements. The report may then be ordered using a selected column or field in the resulting report. Multiple Filter/search criteria may be stored together or individually, and then selectively applied and turned off in the resulting display. A pattern recognition component for the resulting display uses the GUI (color or other highlighting) to draw the user's attention to determining whether patterns of interest exist within the data and for indicating any recognized patterns.

Diabetes related health information may be overlayed in a particular form of report. In a weekly Pump Report, a combination of insulin data (which may be derived from an insulin pump) is provided in a weekly format summarizing each day in a one week period where the GUI is divided left to right by day with vertical demarcation, and containing data analysis statistics that include insulin information, glucose information and/or carbohydrate information, among other data types described herein, summarized in each day's column. In a daily combination report, a combination of Glucose, insulin and/or carbohydrate data, or other data type, may be provided in an hourly format summarizing one full day, where the GUI is divided left to right by hour with vertical demarcation, and containing data analysis statistics that include insulin information, glucose information and carbohydrate information summarized into each hour's column. For each report, whether it be monthly, weekly, daily or another selected temporal duration, the report may include graphical charts or pictures or text-based analytical information, or a combination of these. The statistics and analytical information shown can be adjusted for pump users and non pump users depending on the insulin data type.

The system provides an ability to track a large number of health and demographic elements on a same report. These may include glucose, insulin, meals, exercise, state of health, medication, medical exam, lab result, ketones, or combinations thereof. These elements may be displayed in a graphical or text based (charts) or in a tabular form. Reports may be filtered, grouped or sorted by any of the fields associated with these events. Multiple criteria may be applied to a single patient's data or multiple patients' data.

The system provides a data sharing feature including a synchronization architecture by which a diabetic client may share data useful in management of the diabetic condition with selected health care professionals. This architecture may be implemented through an Internet-based synchronizing server. The system can handle incrementally added or modified data that is synchronized to the internet-based server. This feature saves having to copy a full database each time a synchronization operation is requested. A security process assures that data is shared only as authorized by the original user and is accepted by the sharing health care professional.

The system provides for storing packets of new or modified data on the Internet-based synchronizing server. The system of stored packets of new or modified data can be organized into a database for meaningful viewing and analysis of the contained data. A diabetic client may maintain data useful in management of the diabetic condition in two or more physically separate locations and/or computers and by which this data may be synchronized to be identical on the multiple locations and/or computers.

Data protection is provided by which a diabetic client may store back-up copies of data useful in management of the diabetic condition in a remote, protected internet server location.

Local area networking provides a mechanism by which multiple client computers may store and retrieve data useful in management of diabetes from a single server database in a local area networking environment.

Synchronizing internet computer scalability is provided for distributing stored synchronizing diabetes management data across multiple server computers in order to scale the capacity of the system. A client database is also synchronized within the system. Traffic to the multiple servers is managed for storing synchronizing diabetes management data that balances the load more or less equally among the various multiple available servers.

A host email system permits the host to send email messages notifying host users of upgrades, or other health or product information or upgrades. A user may also upload from a compatible device and immediately or subsequently print out any or all of the available reports (or specific multiple reports) in a desired date range (date ranges apply specifically to each report) with any personal printing preferences specified. In one embodiment, a user profile may be created first, while selection of report generation and printing preferences may be manually applied or automatically selected based on past history or other default criteria.

DETAILED DESCRIPTION OF THE PREFERRED EMBODIMENTS

Figure 1:
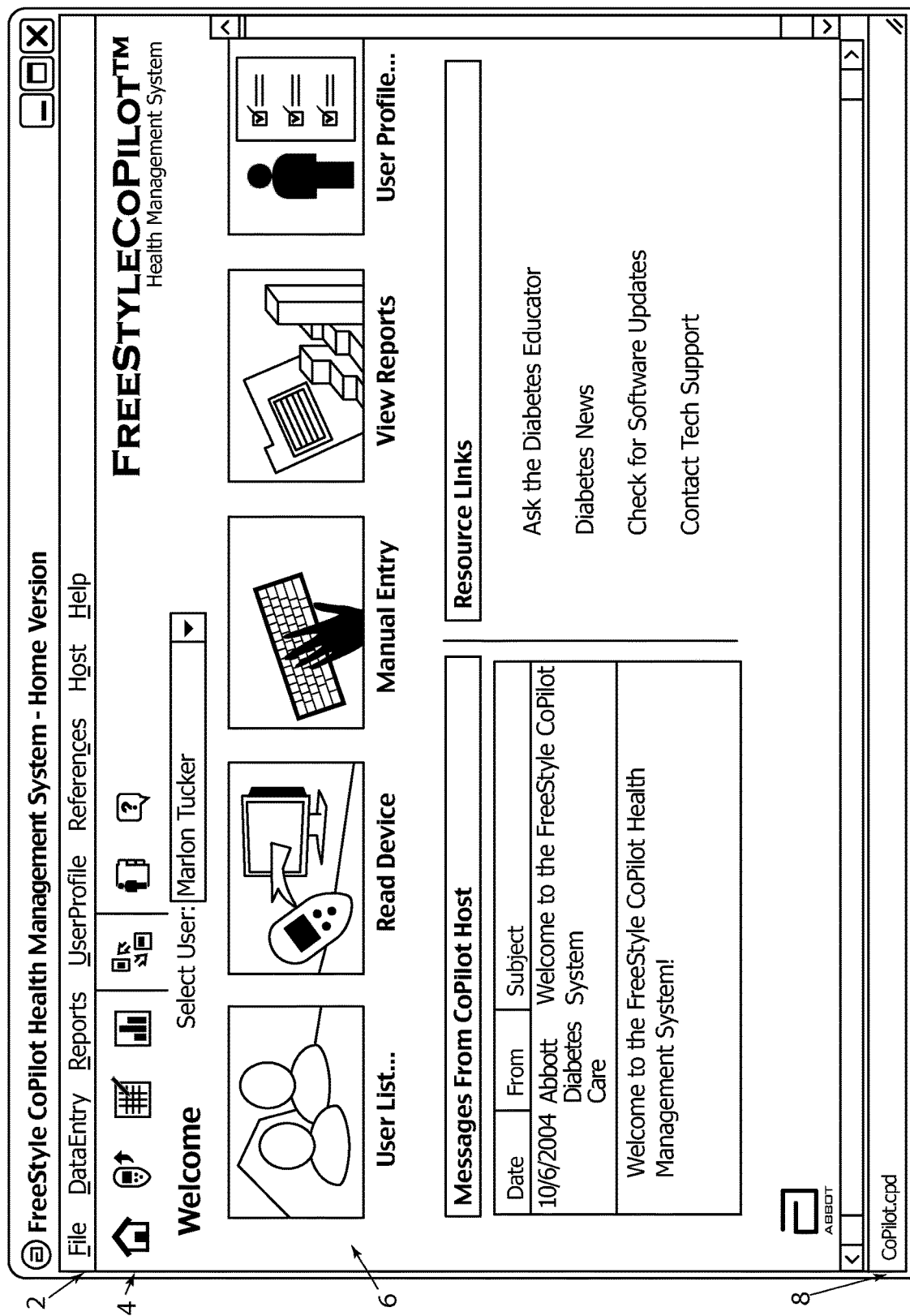
FIG. 1. Home Page
FIG. 2. Application Installation Screen
FIG. 3. Installation Destination Screen
FIG. 4. Select Program Manager Group Screen
FIG. 5. Start Installation Screen
FIG. 6. Finish Screen
FIG. 7. Location of Start Button (PC Desktop) and Programs List
FIG. 8. Initial User Setup Screen
FIG. 9. Home Page
FIG. 10. HCP Version: Select HCP and Select Patient Fields
FIG. 11. File Drop-Down Box: System Settings
FIG. 12. System Settings Screen
FIG. 13. Logon to System Screen
FIG. 14. Home Page: UserProfile Drop-Down Box
FIG. 15. User Information Screen
FIG. 16. Health Profile Screen
FIG. 17. Condition Drop-Down Box
FIG. 18. Date Diagnosed Drop-Down Calendar
FIG. 19. Data Entry Preferences Screen
FIG. 20. Glucose Target Ranges Screen: Standard Mode
FIG. 21. Glucose Targets Mode Drop-Down Box
FIGS. 22A-B. Pre/Post Meal Mode with Hypo/Hyper Checked (A); All Time Periods Mode (B)
FIG. 23. Hypo/Hyper Values Check Box
FIG. 24. Time Periods
FIG. 25. Time Period Error Message
FIG. 26. Glucose Unit of Measure Drop-Down Box
FIG. 27. Options Screen
FIG. 28. User Rights Screen
FIG. 29. File Drop-Down Box: Add User
FIG. 30. User List Screen
FIG. 31. Error Message
FIG. 32. Home: UserProfile Drop-Down Box
FIG. 33. User Rights Screen
FIG. 34. File Menu Drop-Down Box: Add HCP
FIG. 35. HCP Profile Screen
FIG. 36. HCP Type Drop-Down Box
FIG. 37. UserProfile Drop-Down Box: HCP List
FIG. 38. HCP List Screen
FIG. 39. HCP Home Page
FIG. 40. HCP: UserProfile Drop-Down Box
FIG. 41. HCP User Information Screen
FIG. 42. Glucose Target Ranges Screen: Standard Mode
FIG. 43. Glucose Targets Mode Drop-Down Box
FIG. 44. Pre/Post Meal Mode with Hypo/Hyper Checked (left); All Time Periods Mode (right)
FIG. 45. Hypo/Hyper Values Check Box
FIG. 46. Glucose Unit of Measure Drop-Down Box
FIG. 47. HCP Profile Options Screen
FIG. 48. User Rights Screen
FIG. 49. HCP: UserProfile Drop-Down Box
FIG. 50. Patient List Screen
FIG. 51. Patient Profile Screen
FIG. 52. Patient List Screen
FIG. 53. Patient List Screen
FIG. 54. Assign Patients Drop-Down Box
FIG. 55. Authorization Levels
FIG. 56. HCP: File Drop-Down Box
FIG. 57. HCP List Screen
FIG. 58. Reassign Local Patients Message
FIG. 59. User Rights Screen
FIG. 60. Cable Connection Example
FIG. 61. Home Page with Select User Drop-Down List
FIG. 62. DataEntry Drop-Down List: Device Setup
FIG. 63. Device Setup Screen
FIG. 64. Device Setup Screen with Details
FIG. 65. DataEntry Drop-Down List: Read Device
FIG. 66. Assign Device Screen
FIG. 67. Summary Window
FIG. 68. DataEntry Drop-Down List: Undo Last Upload
FIG. 69. DataEntry Drop-Down List: Read Tracker
FIG. 70. Read Tracker Screen: HotSync Prompt
FIG. 71. HotSync Progress Screen
FIG. 72. Assign Device Screen
FIG. 73. Profile Updated Screen
FIG. 74. Upload Summary Screen
FIG. 75. Reports Drop-Down List: Diary List
FIG. 76. Glucose Reading Data Entry Screen
FIG. 77. Insulin Data Entry Screen
FIG. 78. Meal Data Entry Screen
FIG. 79. Multi-item Meal with Total Carbs Shown
FIG. 80. Exercise Data Entry Screen
FIG. 81. State of Health Data Entry Screen
FIG. 82. Medication Data Entry Screen
FIG. 83. Medical Exam Data Entry Screen
FIG. 84. Lab Test Result Data Entry Screen
FIG. 85. Ketones (Blood) Data Entry Screen
FIG. 86. Sample Site Drop-Down Box
FIG. 87. Notes Data Entry Screen
FIG. 88. DataEntry Drop-Down Box: Customize Data Entry Lists
FIG. 89. Select List to Customize Drop-Down List
FIG. 90. Exercise Types
FIG. 91. Food List
FIG. 92. Insulin Names List
FIG. 93. Test Types List
FIG. 94. Medications List
FIG. 95. Exam Types List
FIG. 96. DataEntry Drop-Down Box and Import Drop-Down Box
FIG. 97. File Browser Window: Select Database to Import
FIG. 98. Import Drop-Down Box: Activate FreeStyle CoPilot I Data
FIG. 99. Import Drop-Down List: Import Events From File
FIG. 100. File Browser Window
FIG. 101. Reports Drop-Down Box
FIG. 102. Diary List: Date Adjustment
FIG. 103. File Browser Window
FIG. 104. Reports Window: Glucose Modal Day Report (Default Report)
FIG. 105. Reports Drop-Down Box
FIG. 106. Glucose Line Report Active with Several Other Open Reports
FIG. 107. Reports Toolbar (Date Range)
FIG. 108. Print Drop-Down Box
FIG. 109. User Profile Screen with Options Tab Active
FIG. 110. Report Configuration Screen: Data Filter Tab FIG. 111. Report Configuration Screen: Miscellaneous Tab
FIG. 112. Black-and-White Display: Distinctive Patterns (Screen Detail)
FIG. 113. Diary List
FIG. 114. Reports: Right-Click Pop-Up Menu
FIG. 115. Customization List
FIG. 116. Glucose Modal Day Report (Dotted Line Linking Readings for Apr. 3, 2004)
FIG. 117. Glucose Line Report (Show Line Is Activated)
FIG. 118. Pop-up Menu: Glucose Line Report
FIG. 119. Glucose Average Report: By Meal
FIG. 120. Glucose Average Report: By Day
FIG. 121. Glucose Histogram Report
FIG. 122. Glucose Pie Chart Report: Total Readings Pie Chart
FIG. 123. Glucose Pie Chart Report: Ten Summary Pie Charts
FIG. 124. Logbook Report
FIG. 125. Lab & Exam Record Report: Lab Record
FIG. 126. Lab & Exam Record Report: Exam Record
FIG. 127. Lab & Exam Record Report: A1C History
FIG. 128. Statistics Report: Glucose Statistics
FIG. 129. Statistics Report: Insulin and Carbs Statistics Tables
FIG. 130. Date Field for Selecting Date
FIG. 131. Daily Combination View Report: Glucose Line and Carbohydrates Graphs
FIG. 132. Daily Combination View Report: Insulin Summary and Data Table
FIG. 133. Date Field for Selecting Date
FIG. 134. Weekly Pump View Report: Bar Graph
FIG. 135. Weekly Pump View Report: Pie Charts and Glucose Statistics Table
FIG. 136. HCP Group Analysis Report
FIG. 137. Pop-Up Window
FIG. 138. Customization List
FIG. 139. Filter Builder Screen
FIG. 140. References Drop-Down Box
FIG. 141. Insulin Adjustment Table
FIG. 142. Prescribed Plan
FIG. 143. Home User: Host Drop-Down Box (left); HCP User: Host Drop-Down Box (right)
FIG. 144. First Time Synchronization Screen
FIG. 145. Host Account Number
FIG. 146. Synchronization Summary Screen
FIG. 147. Confirmation Message From the Host
FIG. 148. Invite to Share Data (Home User Screen, left; HCP User Screen, right)
FIG. 149. Invite HCP to Share Data Screen
FIG. 150. Find HCP from Existing Accounts Screen
FIG. 151. Assign Access Level Screen
FIG. 152. Process Complete Screen
FIG. 153. Invite HCP to Share Data Screen
FIG. 154. Enter Host HCP Account Number Screen
FIG. 155. Assign Access Level Screen
FIG. 156. Process Complete Screen
FIG. 157. Messages from CoPilot Host Window
FIG. 158. Invitation to Share Data (from Host)
FIG. 159. Invite HCP to Share Data Screen
FIG. 160. E-mail Invitation to HCP with No Host Account
FIG. 161. Assign Access Level
FIG. 162. Process Complete Screen
FIG. 163. E-mail Invitation to Register and Share Data
FIG. 164. Invitation Code Example
FIG. 165. HCP: Host Drop-Down List
FIG. 166. Accept Invitation Screen
FIG. 167. Synchronization Screen
FIG. 168. Home User: Host Drop-Down Box
FIG. 169. Manage My Shared Data Screen
FIG. 170. HCP User: Host Drop-Down Box
FIG. 171. Manage Data Being Shared With Me Screen
FIG. 172. Changed Access Level Message
FIG. 173. File Drop-Down Box: Database Maintenance Submenu
FIG. 174. Archive Event Data Screen
FIG. 175. File Browser Window: Save Archive Data
FIG. 176. File Browser: Location of Archived Data File (*.xml)
FIG. 177. DataEntry Drop-Down Box: Import Submenu
FIG. 178. Importing Screen
FIG. 179. File Browser: Select Backup Location
FIG. 180. Restore Log
FIG. 181. File Browser: Restore Log
FIG. 182. Help Drop-Down List
FIG. 183. Help Screen
FIG. 184. Help: Index Tab
FIG. 185. Help: Search Tab
FIG. 186. Help Drop-Down Box
FIG. 187. Customer Service Contact Information Screen

A system in accordance with a preferred embodiment is referred to as the FreeStyle CoPilot™ Health Management System (also referred to as the FreeStyle CoPilot System or the System), and is a personal computer (PC or portable or handheld appliance)-based software application that permits people with diabetes, their healthcare team, and caregivers to upload data preferably from FreeStyle™ and Precision Xtra™ blood glucose monitoring systems (and generally to several other commercially available blood glucose meters and insulin pumps) into the FreeStyle CoPilot application.

The FreeStyle CoPilot System provides graphs and other software tools for people with diabetes and their healthcare professionals (HCPs) to help evaluate and analyze glucose readings, carbohydrate intake, insulin dosage, and other diabetes-related factors uploaded from devices or manually entered into the System. The System can help identify trends that can be used to educate persons with diabetes to improve their glucose control.

Common terms that have additional special meanings within the FreeStyle CoPilot System are capitalized to distinguish their special usage (for example, Diary as opposed to a written diary). System-specific screen, control, commands, and function names (for example, Home page, the Apply button) are also capitalized throughout. The specific usages of these terms within the system of the preferred embodiment is intended to be added to their ordinary meanings and usages to enlarge the scopes of these terms in the context of the invention, and not to limit them.

The FreeStyle CoPilot Health Management System provides an accessory to a blood glucose monitoring system such as the FreeStyle and Precision Xtra blood glucose monitoring systems and other commercially available blood glucose meters and insulin pumps. The FreeStyle CoPilot Health Management System may be used in home and clinical settings to upload data from these devices to a patient's or healthcare professional's computer where the data may be saved, displayed in a number of formats, printed, or exported to an authorized user. The FreeStyle CoPilot System is an aid to people with diabetes and healthcare professionals in the review, analysis, and evaluation of historical blood glucose test results, insulin dosages, and carbohydrate intake data to support an effective diabetes management program. The System may be used in home and healthcare professional settings to manage diabetes factors, such as insulin dosage, carbohydrate intake, and exercise.

There are two primary users contemplated for the System: home users (people with diabetes or their caregivers), and HCP users (healthcare professionals). A home version of the software for a person with diabetes or the caregiver of a person with diabetes may permit recording information for them such as glucose, insulin, meals, exercise and/or other data types described herein. A HCP version of the software is for managing health data provided to a HCP by one or more patients with diabetes. HCP can mean an individual healthcare professional (such as physician, nurse educator, or other diabetes healthcare team member), a group or entity (such as a clinic), or even case managers, medical directors, and other managed care professionals, if authorized by the person with diabetes. The System may be used to monitor the health status of the patients they manage.

The System is a personal computer (PC) or personal computing appliance software application that enables users to upload, store, and/or analyze glucose readings and other important information for diabetes management. This information can be used by people with diabetes, their healthcare professionals (HCPs), and caregivers.

After installing the System on a PC or PC appliance, glucose data can be uploaded or copied from a compatible glucose meter, or data can be typed in from a keyboard, or imported from a file. One can maintain a record of his or her glucose, carbohydrates, insulin, exercise, state of health, doctor visits, medications, blood ketones, and/or laboratory results. One may enter as much or as little information as desired.

The System analyzes the data and displays it in simple, clear reports (graphs and tables). The reports can be viewed on the computer screen or on the display of the computing appliance or they can be printed out (black-and-white or color). One can also automatically print one or more reports that are selected to be printed or displayed once each data is uploaded from a particular device.

The System further allows data sharing securely over the Internet with selected HCPs. The System further promotes teamwork for effective diabetes health management. The System encourages people with diabetes to stick to lifestyle recommendations and medication plans. It can help them and their HCPs to identify trends in health or care.

The System preferably utilizes a personal computing desktop, portable or handheld appliance with 400 megahertz (MHz) or higher processor clock speed recommended. The system preferably includes either an internet connection or a compact disc (CD-ROM) drive or other digital storage device interface. Random access memory (RAM) of 64 megabytes (MB) or more is recommended, while available hard disk space of 30 MB is used for running the program. Microsoft® Windows 98 SE, 2000, NT, ME, or XP operating systems are preferred. A monitor with 1024×768 or higher resolution is preferred. A standard keyboard and mouse are also preferred, or other input device that may be utilized with a particular personal computing appliance.

A few optional accessories that can be useful in combination with the System include a serial port, available 9-pin EIA-232 (also known as RS-232 or V.24) or appropriate adapter for a universal serial bus (USB) for glucose meter connection, a Windows-compatible printer for printing copies of reports, a Windows-compatible fax software and drivers for faxing reports, an email application for e-mailing reports, data cables for uploading from compatible devices, and a HotSync® cradle for uploading data from a PDA-type diabetes management system.

The System is preferably available as a download from a web site such as the FreeStyle CoPilot website (www.freestylecopilot.com), and/or on a CD purchased through a website or customer care center.

Using the System, a diabetic or HCP can read (upload) or export data from devices such as glucose meters and insulin pumps. These devices can be connected to the System by serial port or USB.

Graphical User Interface

Display screens of the System preferably have a consistently similar look and structure. Common screen icons are preferably organized on a Home page, such as that illustrated in FIG. 1, with the main user activities highlighted. The screen shot illustrated at FIG. 1 includes a main menu bar 2, a small icons bar 4, large buttons 6, and name of open database 8.

Tabs on the main menu bar 2 enable access to program activities. The small icons 4 and large buttons 6 represent a subset of the program activities including commonly used activities. Clicking on a tab of the main menu bar 2, a small icon 4, or a large button 6 opens a corresponding screen. The Home page is described in more detail below with reference to FIG. 9.

The System can be a stand-alone product operated by itself on a user's PC and can serve as a self-management tool for the collection and analysis of diabetes-related data. The System can also be used by HCPs in an office or clinic. The System can also operate in a LAN environment. In this case, a central database is preferably installed on the LAN server, wherein each computer in the network can access and review this central database.

For users who want to communicate and share data remotely, the System has a Host server on the internet that acts as a processing, storage, and routing center for the files of users who choose to use these communication and data access capabilities. A user may choose to synchronize with the Host via internet access from a PC or other capable desktop, portable or handheld appliance (hereinafter simply referred to as PC). The communication can occur between people with diabetes and their HCPs or among HCPs.

Users (Home and HCP) can share data by synchronizing. Synchronization allows each user to update and match the data they track. The process includes sending data from a PC to a Host server. The Host server acts as the central database for the System. When a user synchronizes the client System with the Host server, diabetes data, notes, comments, new entries, and edits entered into the client System are mirrored on the Host server and client PC. Each party sharing data preferably synchronizes regularly with the Host server to stay current.

Figure 2:
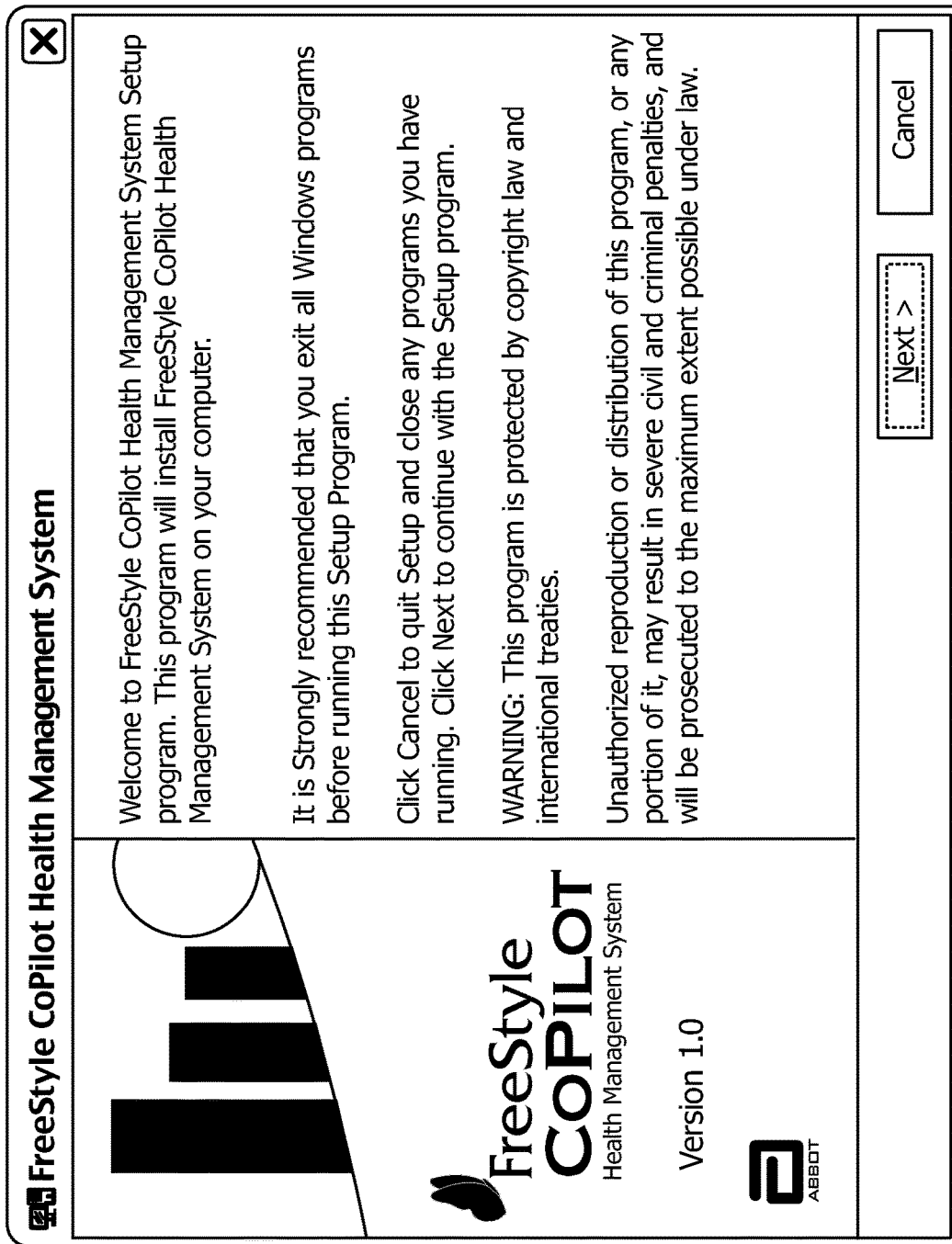

The System software can be installed by downloading the program from the Internet, or installing the program from a CD or other digital storage device. FIG. 2 illustrates a screen shot of an application installation screen.

Figure 3:
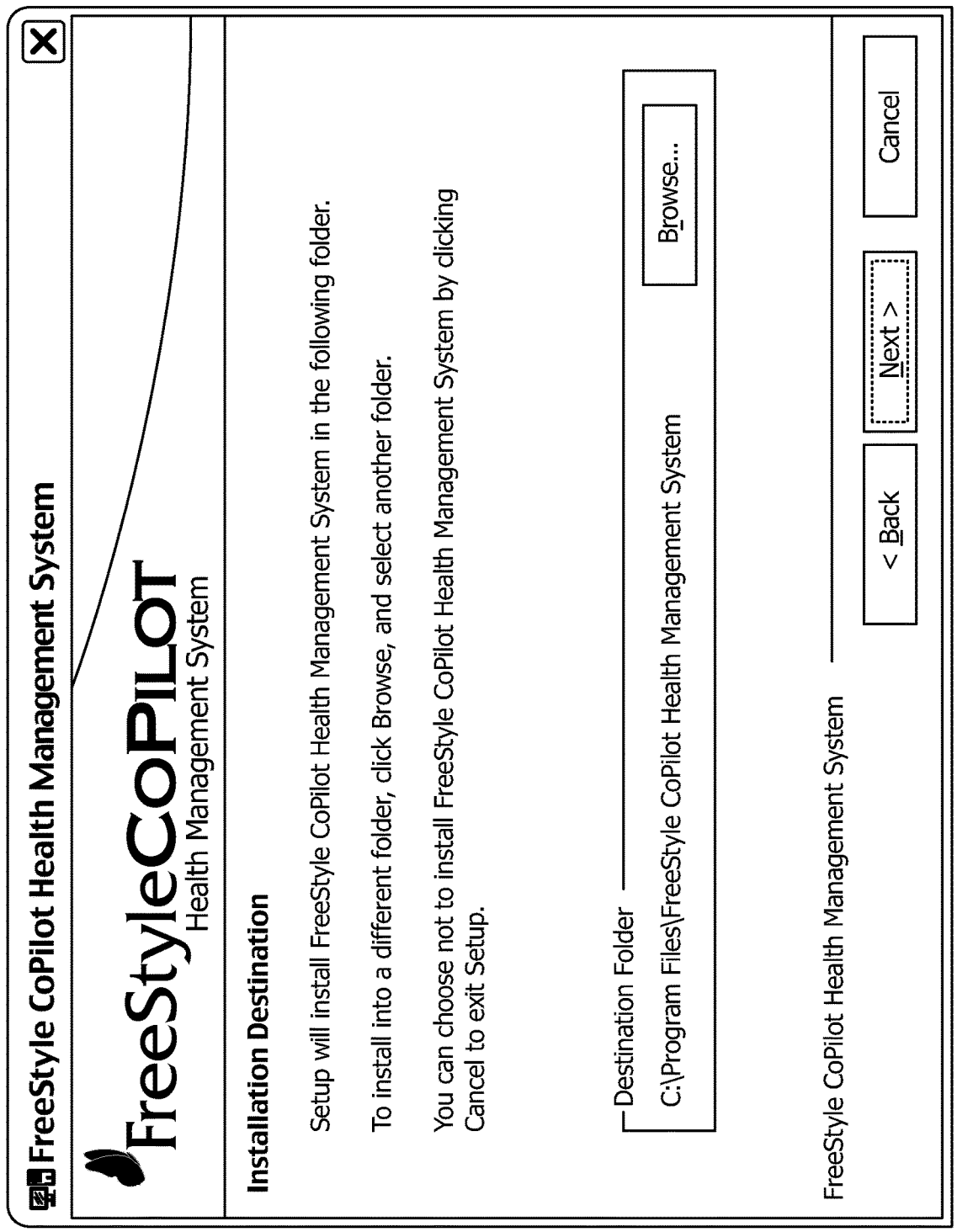
Figure 4:
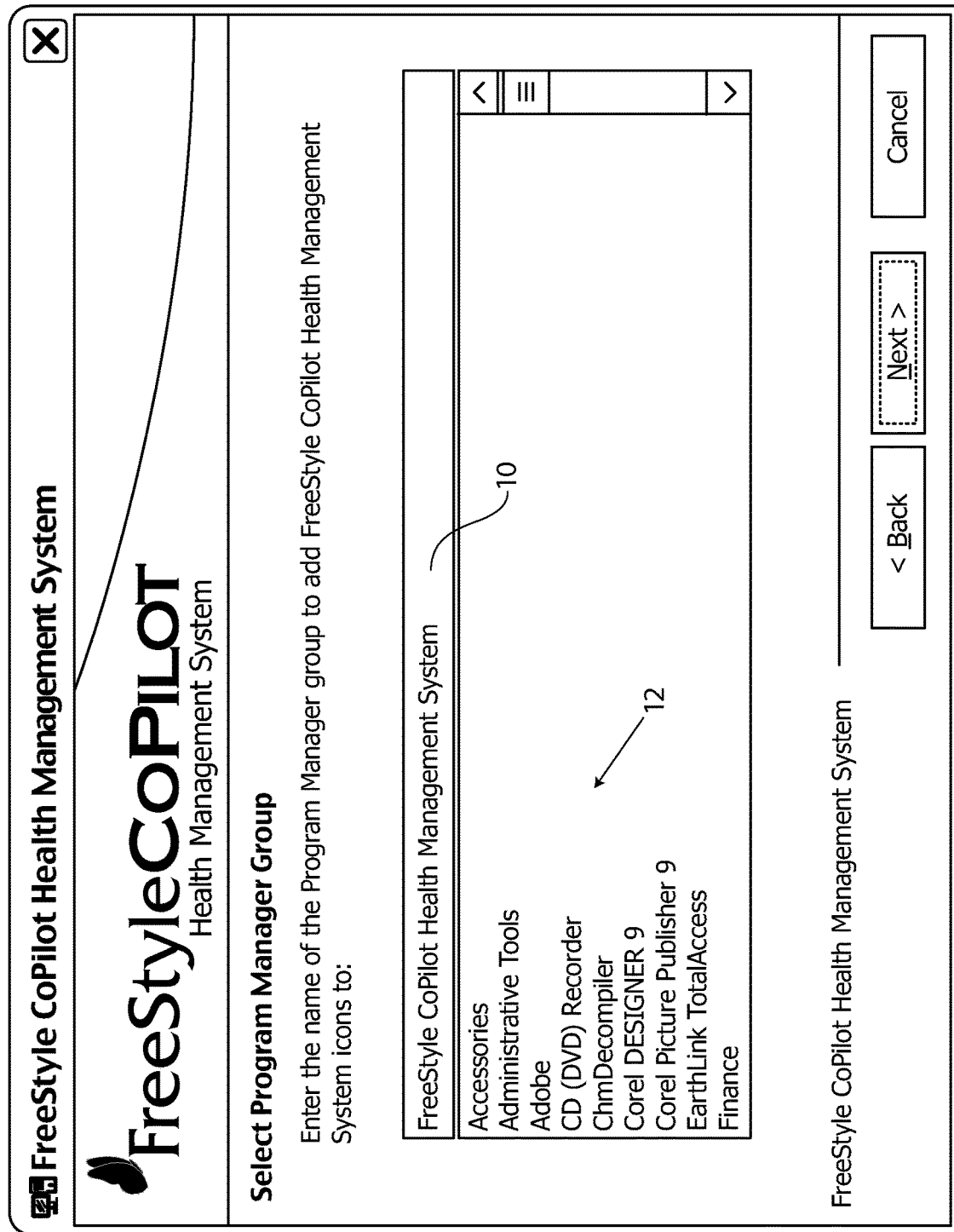
Figure 5:
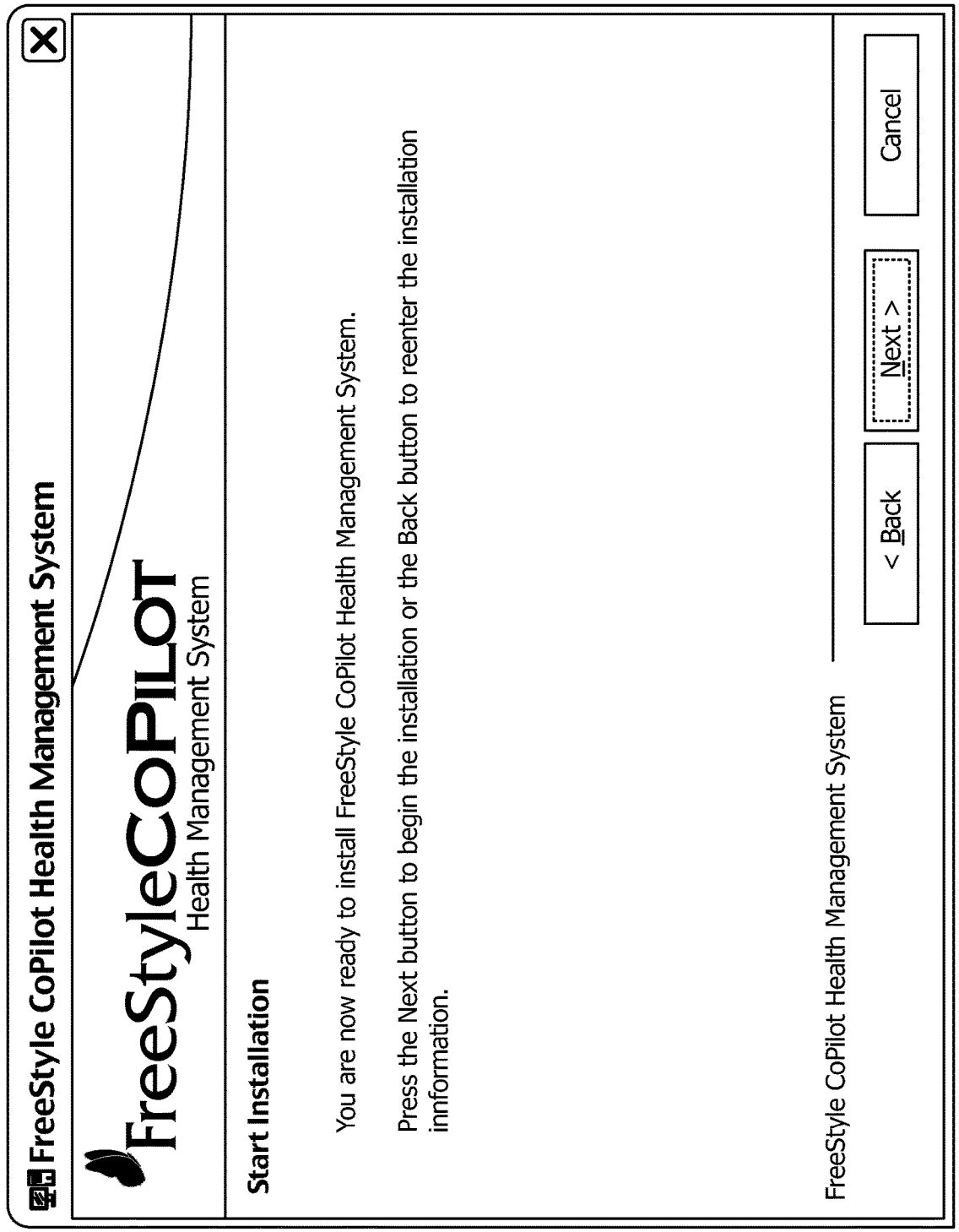
Figure 6:
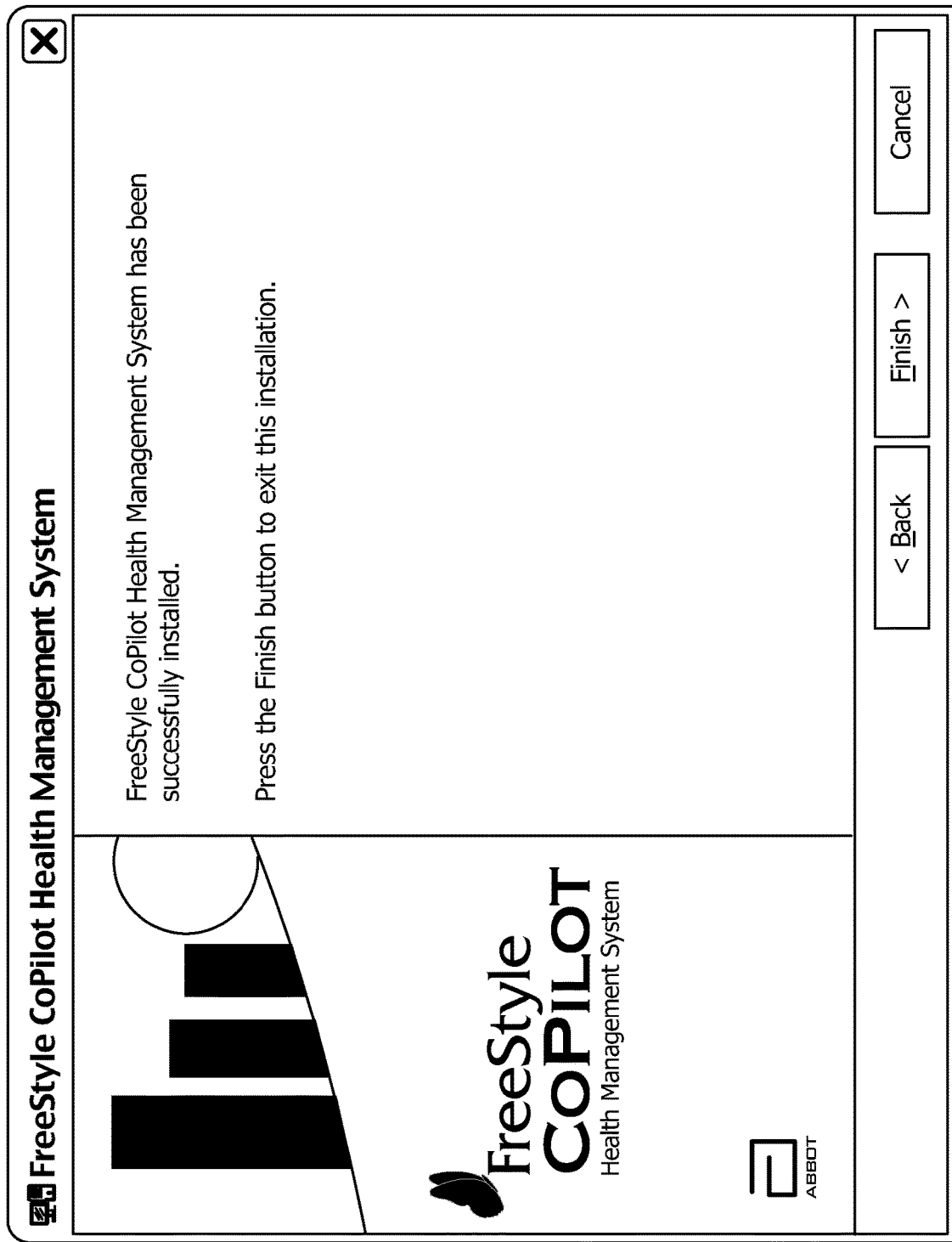

FIG. 3 illustrates an installation destination screen. A user may install the System on a selected device. If installing the program on a local area network (LAN), synchronizing with a network administrator is preferred. At a select program manager group screen, such as that illustrated at FIG. 4, a suggested program manager group 10 or another selected from a scroll-down list 12, may be selected. A start installation screen such as that illustrated at FIG. 5 permits the software to be installed. If the installation is successful in fully installing the System, a final setup screen then displays, such as that illustrated at FIG. 6. A System icon will now appear on the PC desktop, and System program and user guides are added to the PC's Programs list.

Figure 7:
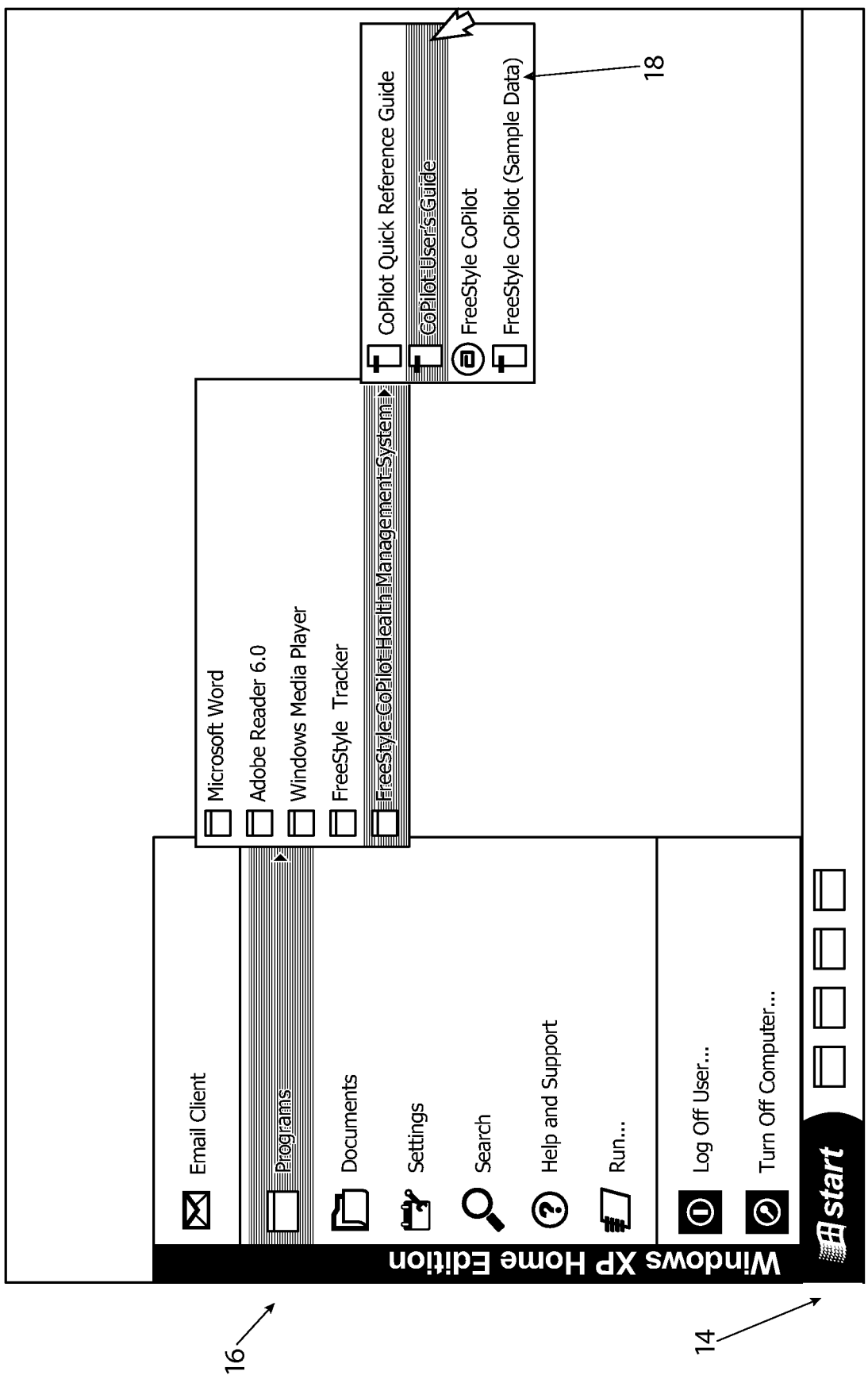

FIG. 7 illustrates location of Start Button 14 (PC Desktop) and Programs List 16 within Windows™. The system program files and guides menu options 18 can be accessed this way.

A User Profile can now be set up, as described in more detail below. Setting up a User Profile allows a diabetic to take full advantage of advantageous features of the System. The process begins with an initial user set up screen, such as that illustrated at FIG. 8, if this is the first time a user is running the program. The user may select Home User 20 if he or she is a person with diabetes, or Health Care Professional 22 if he or she is a HCP. Personal identification information including a password is then input in a user identification section 24. After filling in the Initial User Setup information, this screen is not utilized again, and instead a home page, such as that illustrated at FIG. 9, will display when the System program is run.

Home Page

From the Home page, a diabetic or HCP can access multiple advantageous features of the System, either by clicking a small icon 4 or a large button 6, or by selecting a tab on the main menu bar 2.

Figure 9:
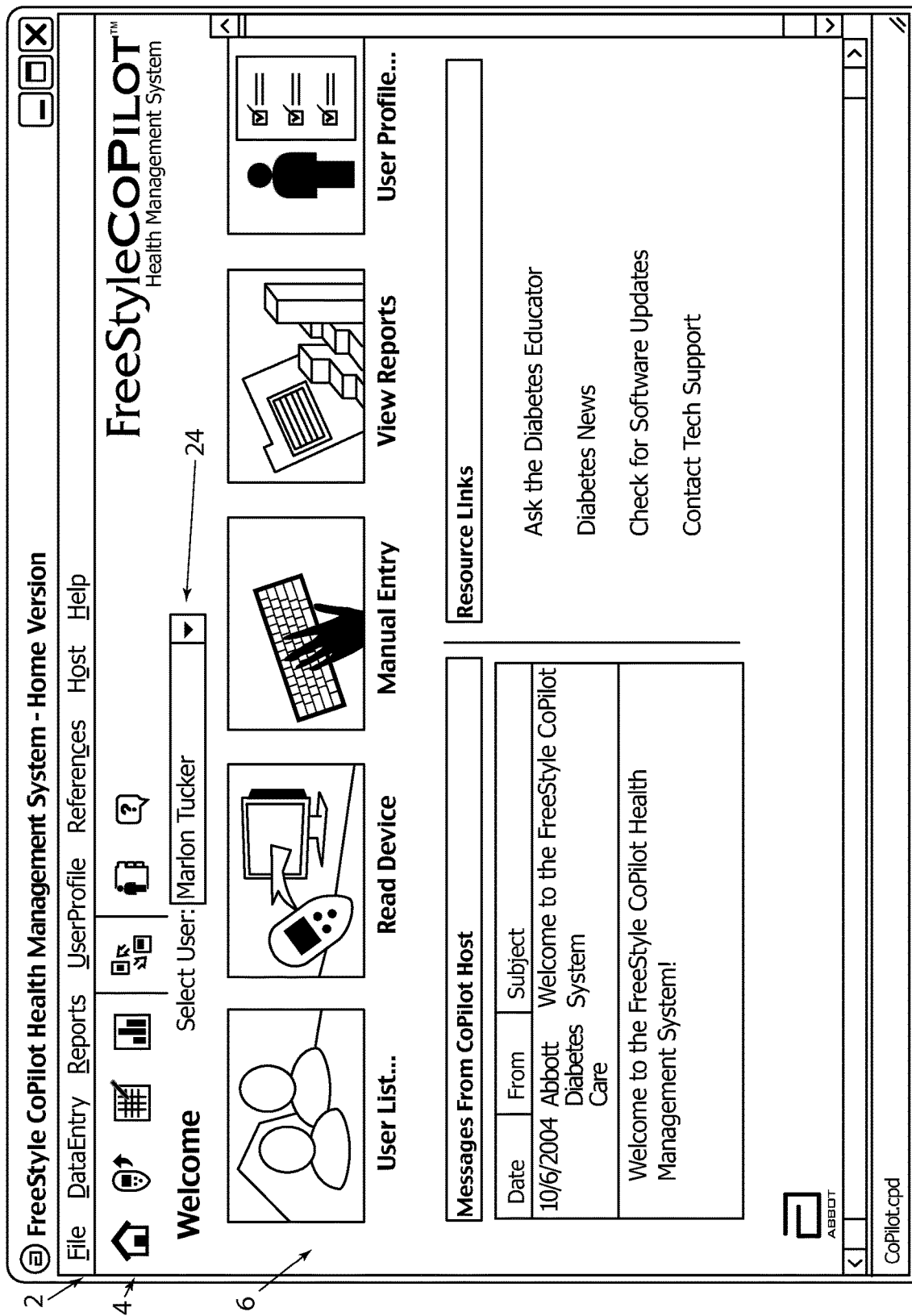
Figure 10:
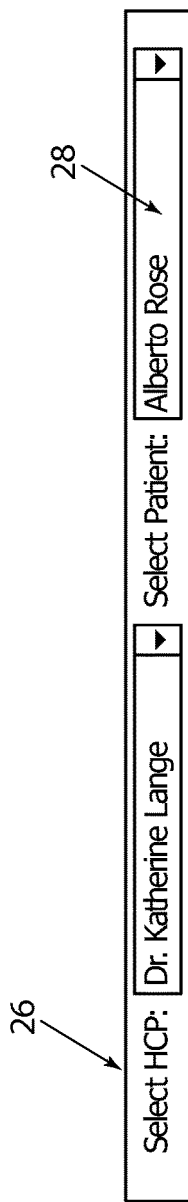

A select user field 24 is illustrated in FIG. 9. The name of the active user is displayed in the Select User field 24. The select user filed 24 includes a drop-down list of multiple persons each having a User Profile in the System. Referring to FIG. 10, in a HCP version, there is a Select HCP field 26 and a Select Patient field 28.

The small icons 4 provide access to program functions. From left to right in FIG. 9, preferred small icons 4 include: a go to home page icon, a read data from a meter icon, a manually enter data icon, a view reports icon, a synchronize with host icon, and edit current user's profile or edit current patient's profile icon, and a show context help icon.

The Large Buttons 6 provide quick access to main program functions. From left to right in FIG. 9, preferred large icons 6 include: a User List or patient list icon a Read Device icon, a Manual Entry icon, a View Reports icon, and a User Profile or Patient Profile icon.

When the client is synchronized with the Host computer via the Internet, messages are preferably sent from the Host that may include information about data sharing, healthcare management, and updates to the System.

A Resource Links section provides options to take a user directly to resources available at the System website. These may include Ask the Diabetes Educator, Diabetes News, Check for Software Updates and Contact Tech Support. Contact tech support is preferably an email support option that, upon clicking, will result in a pop-up window either informing the user that a "local mail client" is not available or will supply the user with the e-mail address for Customer Service/Tech Support.

Figure 11:
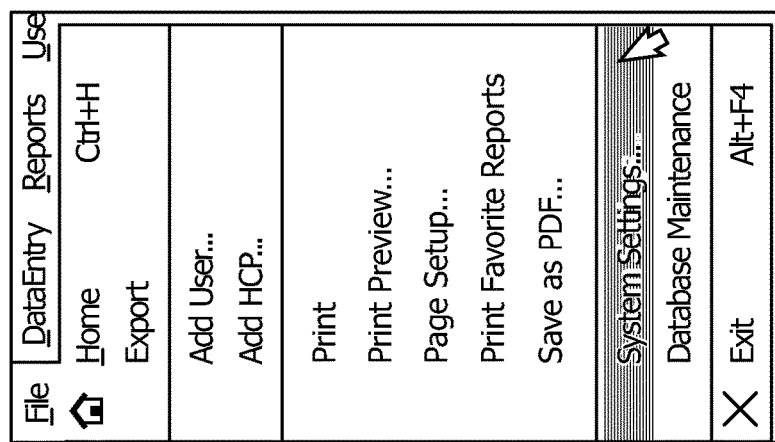
Figure 12:
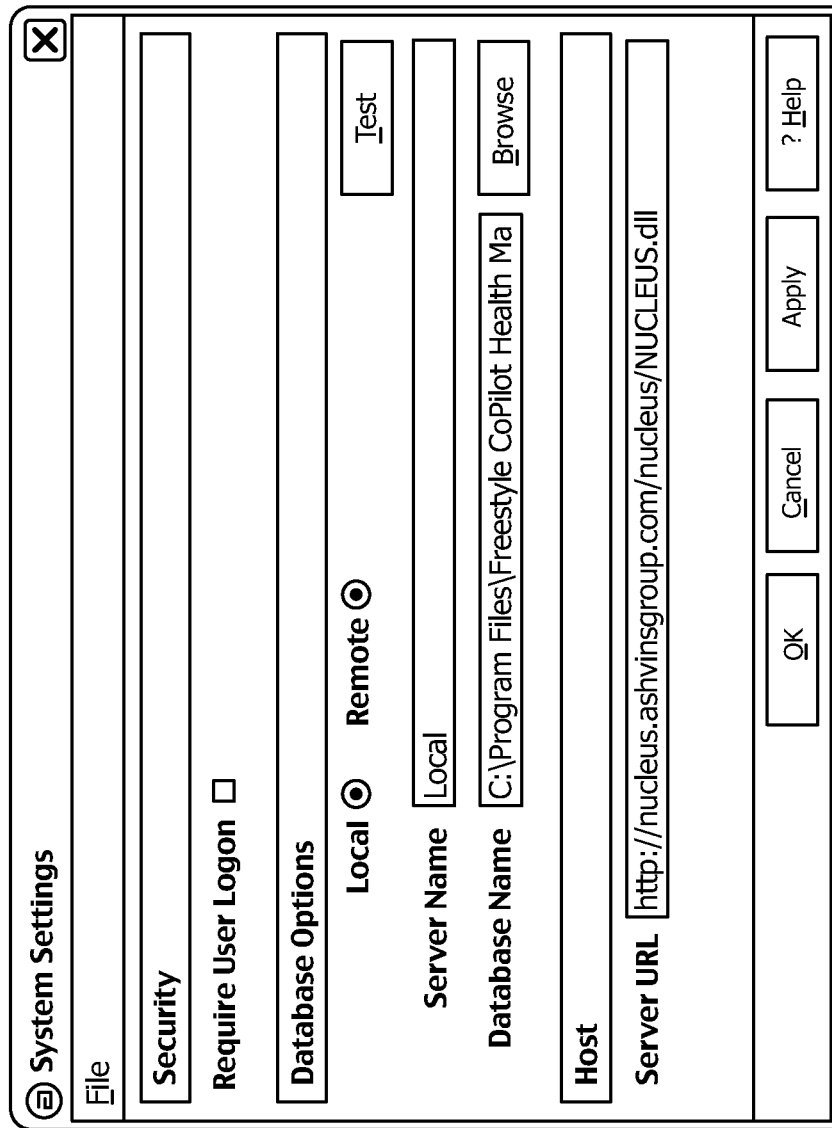
Figure 13:
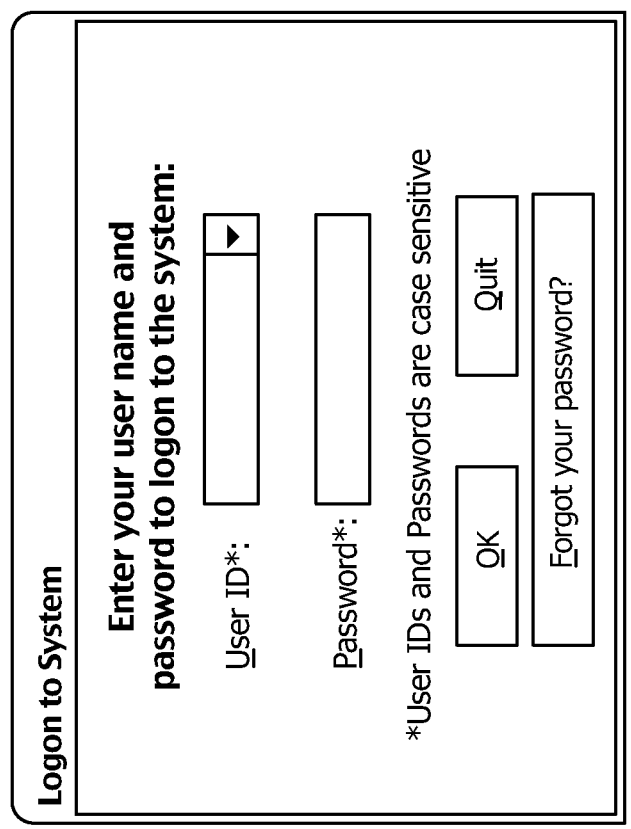

A Turning On Password Protection option is for users desiring to protect their data (and their privacy) by requiring the entry of a User ID and Password each time they start the System or each time they select a different user in the Select User field (Home version) or the Select HCP field (HCP version). To turn on password protection, on the Home page, a user may select System Settings from the File drop-down box (see FIG. 11). If System Settings is grayed out, then a user does not have the User Rights to turn on password protection. If a user does have User Rights, then the System Settings screen displays (see FIG. 12). When the box to Require User Logon is checked, then password protection is turned on and the first screen will be a Logon to System screen (see FIG. 13). This screen will also display when changing users in the Select User field (Home version) or in the Select HCP field (HCP version). The home page will appear upon typing in or otherwise inserting a User ID and Password.

For a home user to take advantage of many features of the program, a user should set up a Home User Profile. This allows the user and HCP, if selected, to enter data and create reports to monitor trends in the health or care of the diabetic user.

Figure 14:
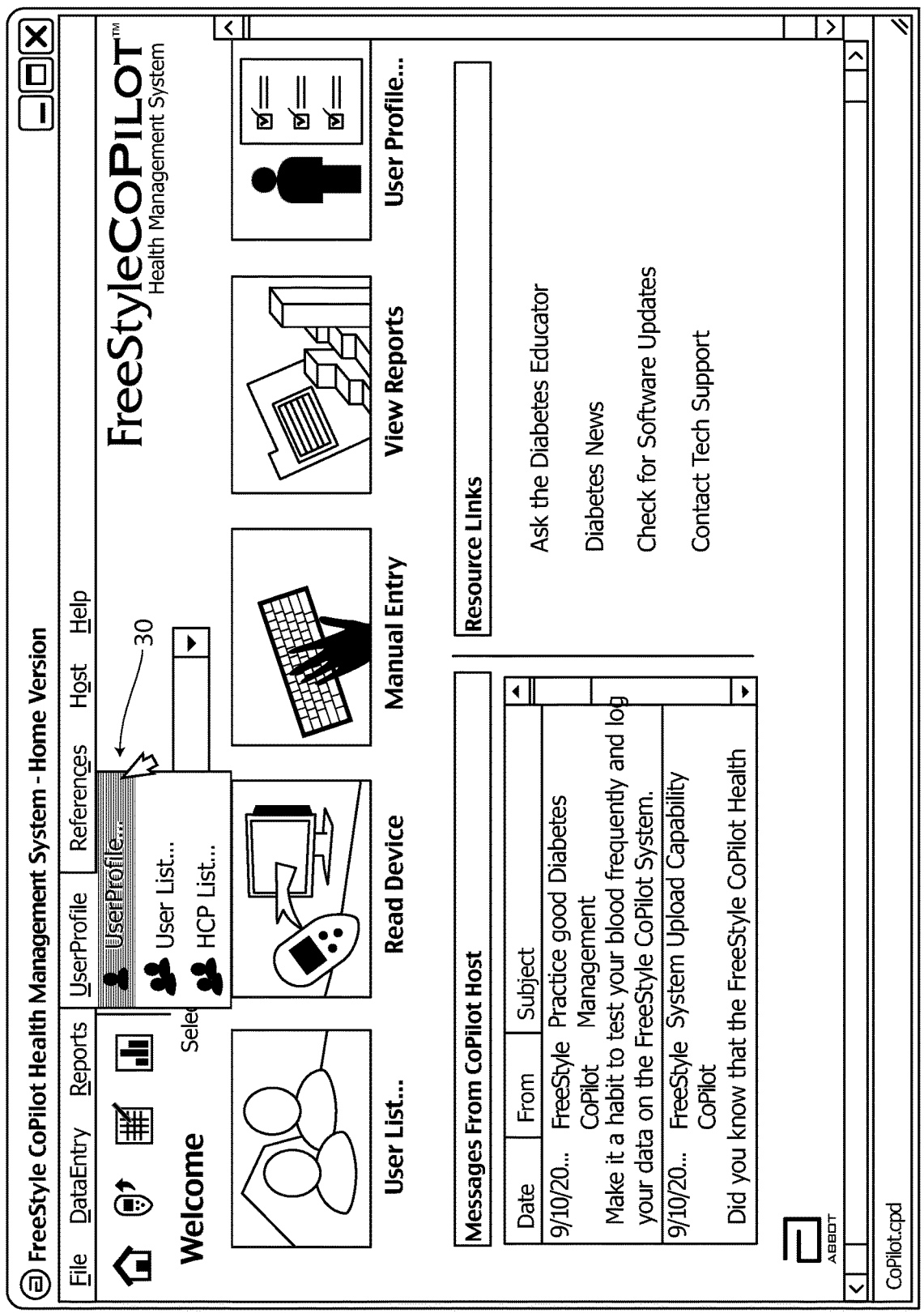

FIG. 14 illustrates a home page having a UserProfile tab on the main menu bar 2 selected and expanded. The User Profile button of the large icon bar 6 may also be clicked. Either way, User Profile may be now selected from the drop-down box 30 or other menu expansion architecture.

Figure 15:
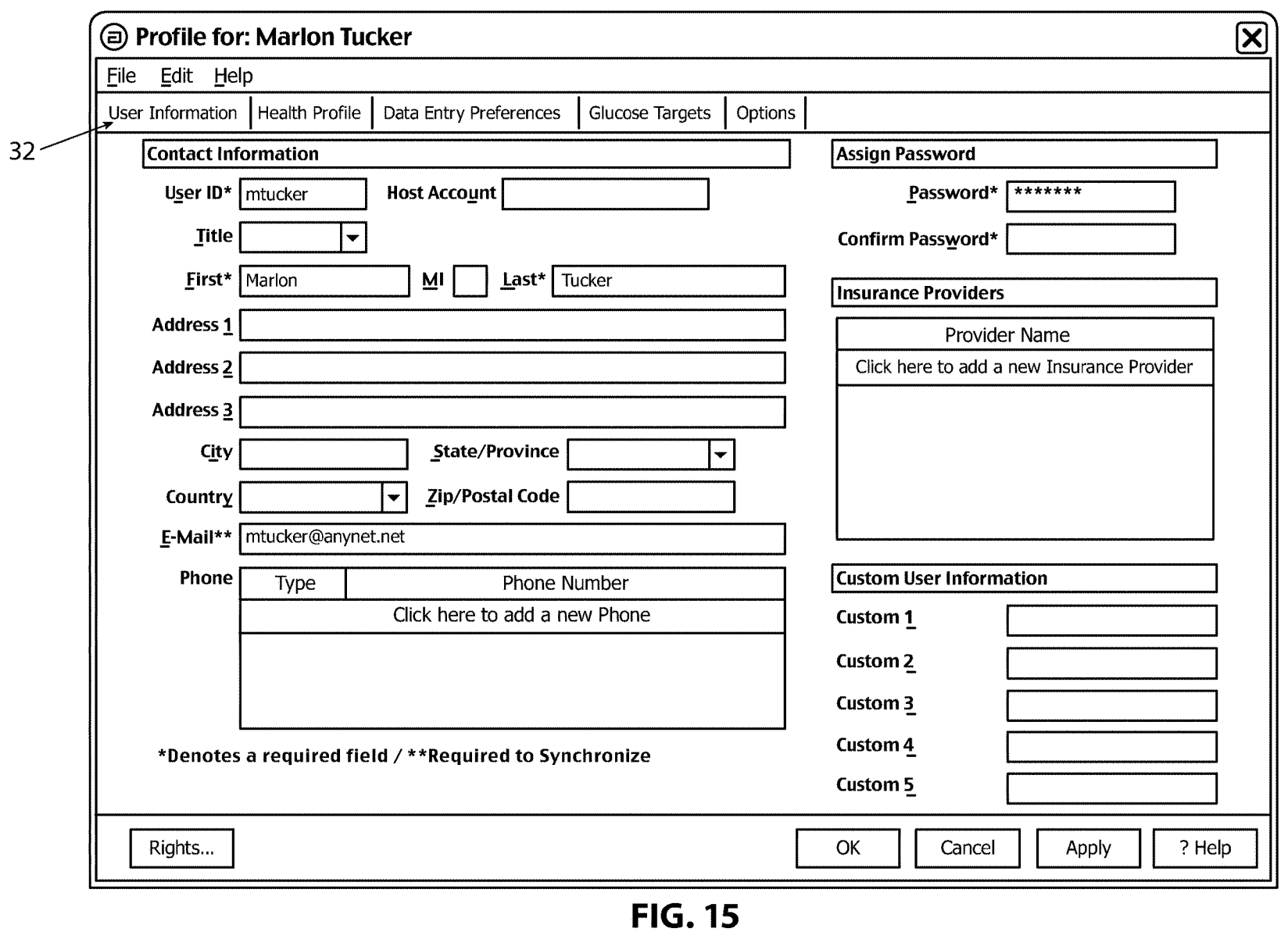
Figure 16:
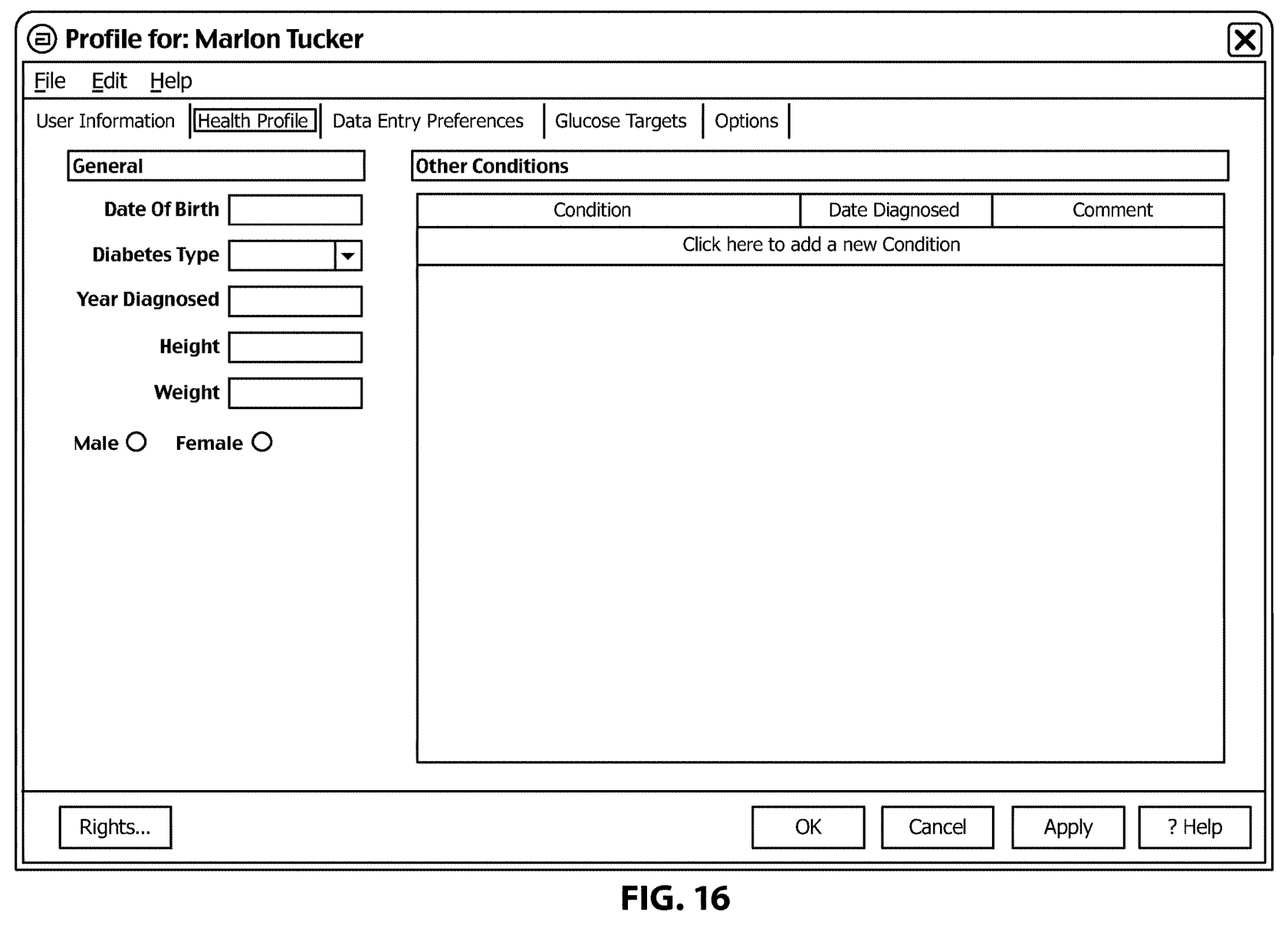
Figure 17:
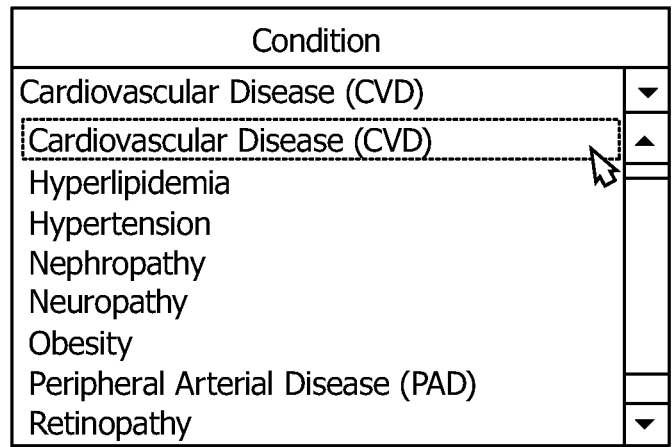

A Profile For screen is illustrated in FIG. 15. In the screen display of FIG. 15, the User Information tab 32 is selected. A user may provide whatever information that he or she wishes to, except that fields marked with an asterisk (*) or double-asterisk (**) will be required fields. Information can be added by selecting items from drop-down boxes or by typing in words and numbers. A Health Profile tab is illustrated at FIG. 16. When a Condition column arrow is clicked, a drop-down box is displayed such as that illustrated at FIG. 17. The user can select any of the conditions listed that apply to him or her, or type in a new condition that will be added to the list.

Figure 18:
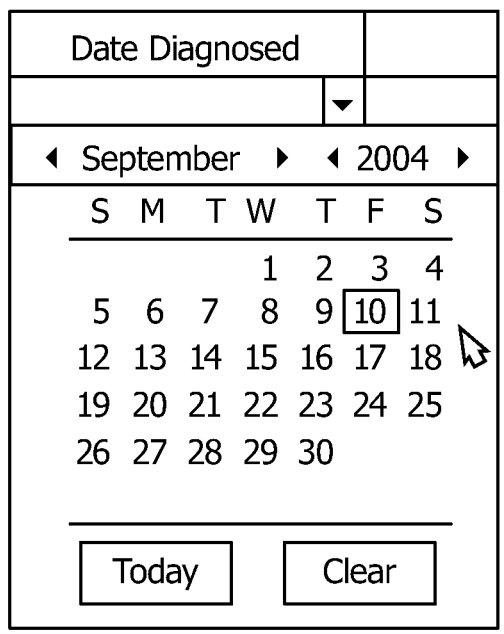

A screen shot such as that illustrated at FIG. 18 will appear when the arrow on a Date Diagnosed column is clicked. The screen shot of FIG. 18 is preferably a basic calendar. The arrows may be used to select the date this condition was diagnosed.

FIG. 19 illustrates a Data Entry Preferences screen that can be used to save time in manually entering data by setting up Data Entry Preferences. For example, if a user regularly takes a certain type of insulin at a particular dose, the user can enter it here. The same is true for regular exercise routines and other medications the user may take. Information entered here will then be automatically listed when manual entries are made. To enter user preferences, the user selects a Data Entry Preferences tab and fills in Exercise Preferences (type, duration, intensity); Insulin Preferences (insulin name, dosage, type); and/or Medication Preferences (medication name, dosage, number of pills). Each column heading preferably has a drop-down box. A user can select one of the listed entries or type in a new entry that will be added to the list.

Figure 20:
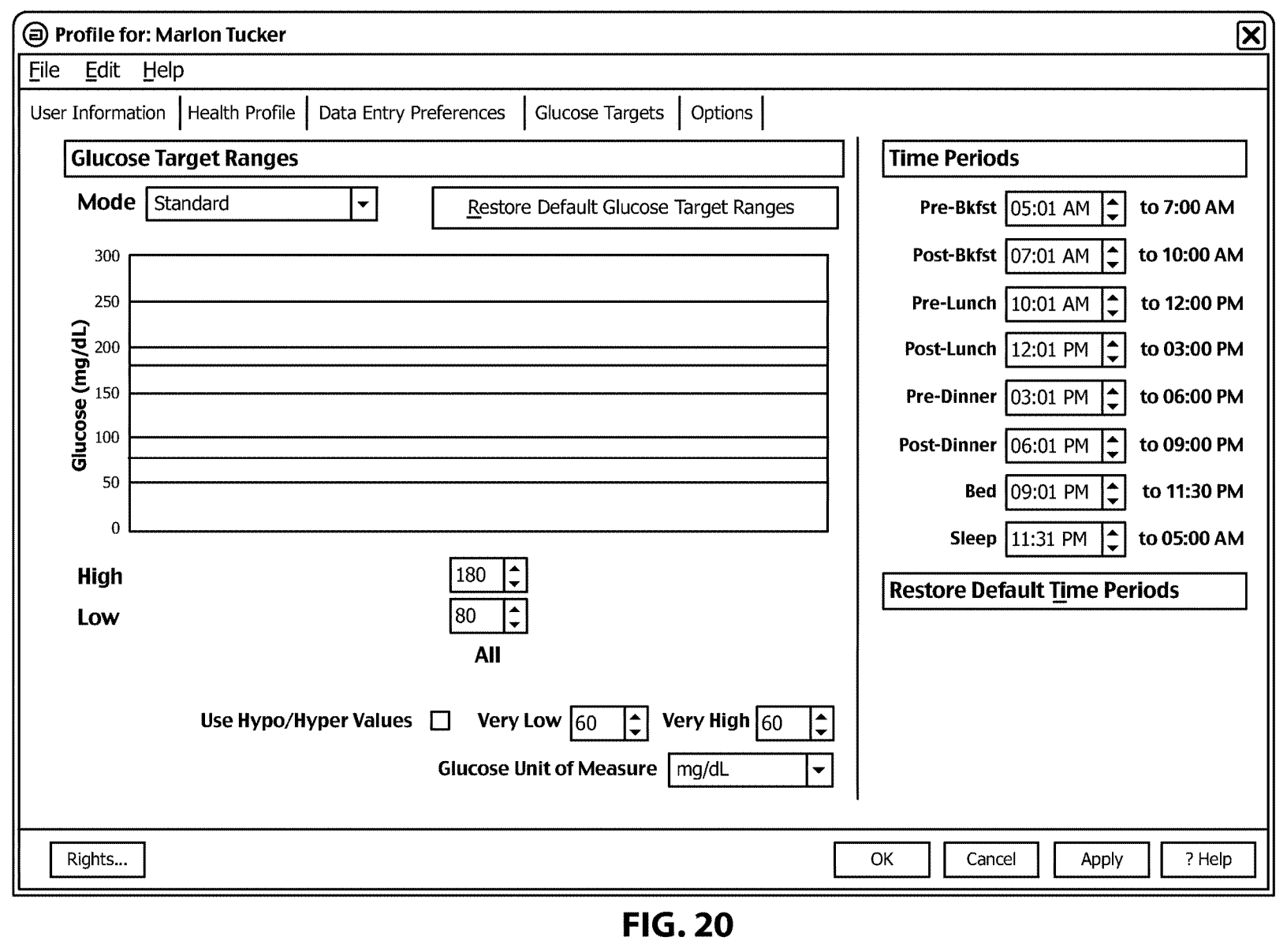

A user may select a Glucose Targets tab to enter target glucose ranges. If these are not known, the HCP can be contacted to help manage glucose levels. The target ranges that are set are displayed on a graph on the screen illustrated at FIG. 20, as well as in many other reports that can be generated by the System. The ranges may be displayed in signal colors for easy viewing.

Figure 21:
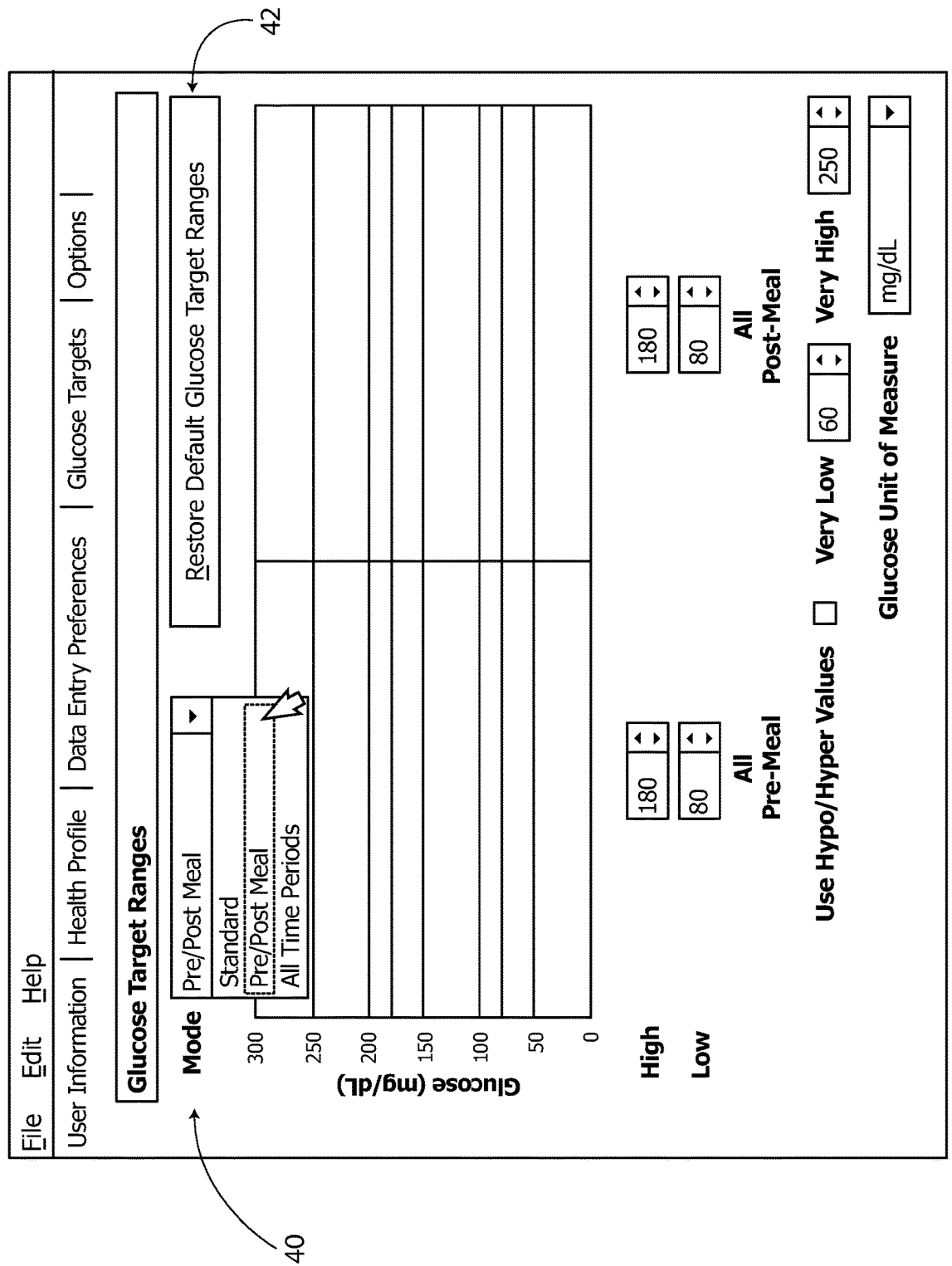
Figure 22A:
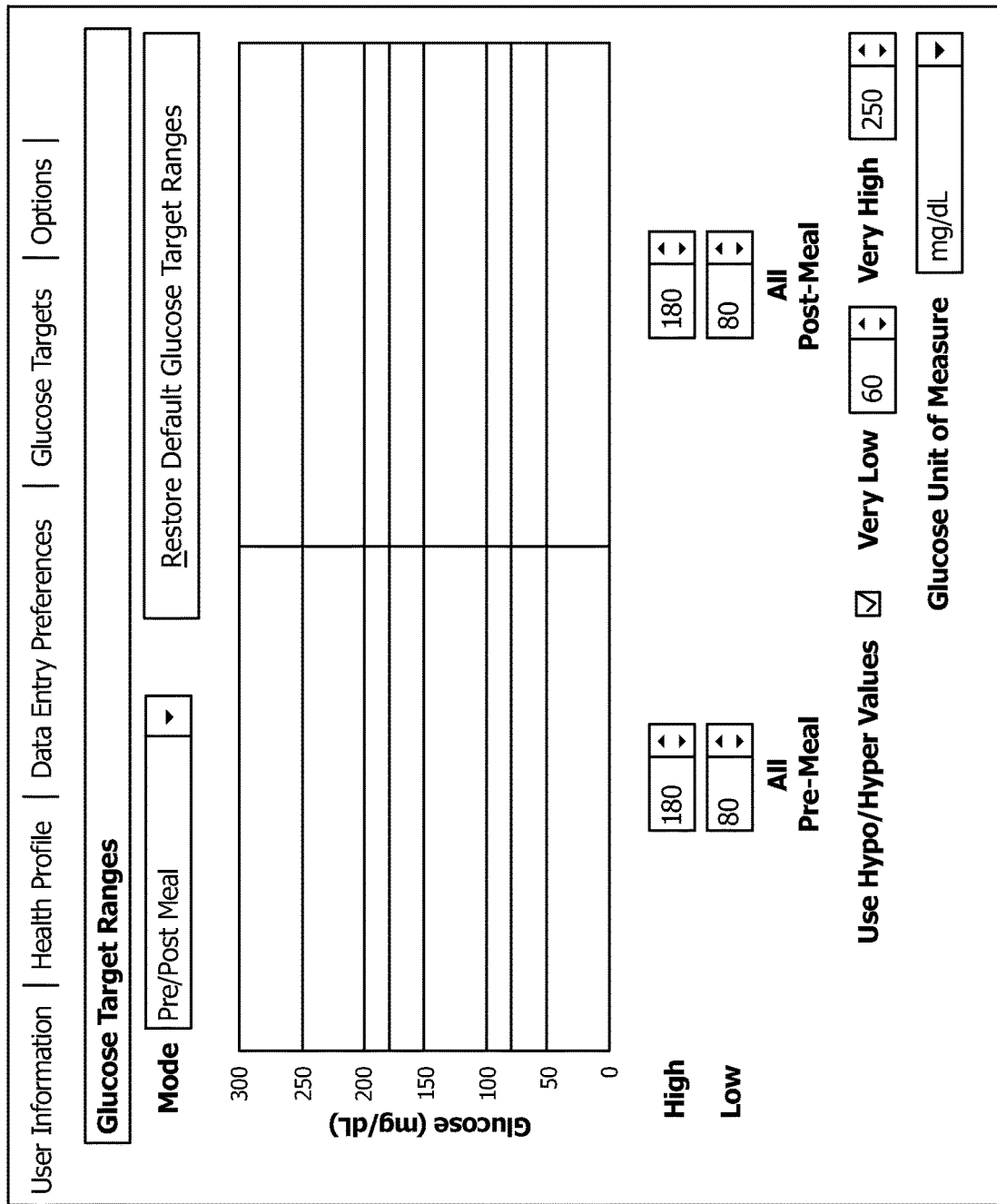

A graph can be viewed preferably in at least three modes. A desired mode may be selected from a Mode drop-down box 40, such as that illustrated at FIG. 21. Standard, Pre/Post Meal and All Time Periods modes may be selected. In Standard mode, glucose target ranges set apply to all glucose readings, regardless of when the glucose reading is taken. For example, target ranges will be the same for pre-meal readings as for post-meal readings or bedtime readings. In Pre/Post Meal mode, glucose target ranges set for pre-meal readings can be different from the target ranges for post-meal readings. In All Time Periods mode, glucose target ranges set can be different for each time period listed, for example, Pre-Bkfst, Post-Bkfst, Pre-Lunch, Post-Lunch, Pre-Dinner, Post-Dinner, Bed, and Sleep. FIG. 22A illustrates Pre/Post Meal Mode with Hypo/Hyper checked and FIG. 22B illustrates All Time Periods Mode.

Glucose targets may be set in all three modes to take advantage of different reports the System can create. A table of the reports that use glucose targets and the modes they use is provided further below. The glucose targets mode selected here will become the default and will display in the reports that use glucose targets. To change the mode, a different Mode can be selected by returning to the Glucose Targets screen illustrated at FIG. 21.

Figure 23:
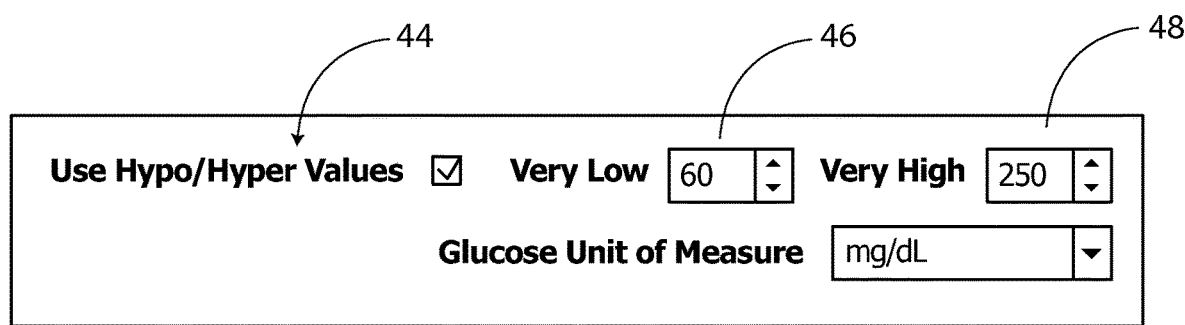

Clicking on up/down arrows for High and Low sets glucose targets. To automatically restore Glucose Target Ranges to the ranges shown in FIG. 20 (the defaults), a Restore Default Glucose Target Ranges button 42 can be clicked. Clicking Restore Default Glucose Target Ranges 42 preferably automatically also restores the mode to Standard Mode and unchecks a Use Hypo/Hyper Values box 44 illustrated at FIG. 23. Checking the Use Hypo/Hyper Values box 44 activates Very Low and Very High data fields 46 and 48. Clicking on up/down arrows for Very Low 46 and Very High 48 changes these values.

Figure 24:
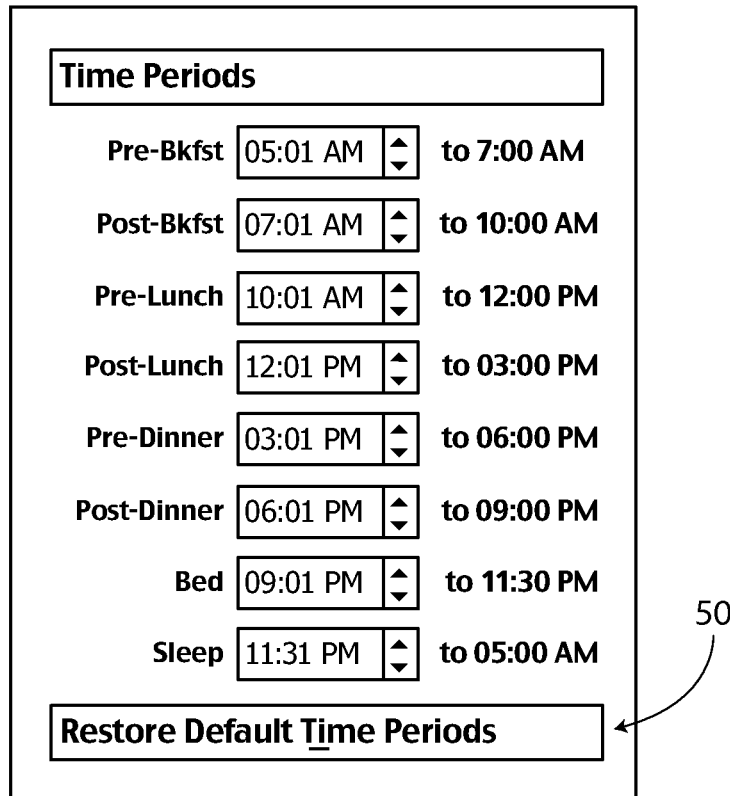
Figure 25:
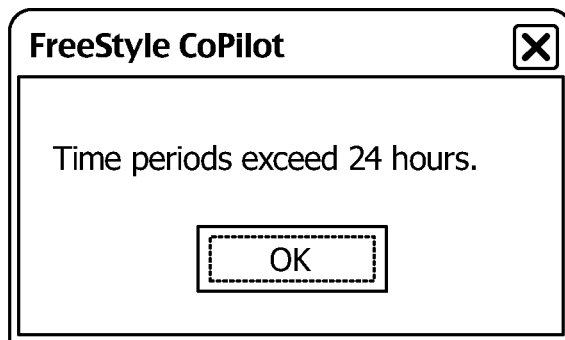
Figure 26:
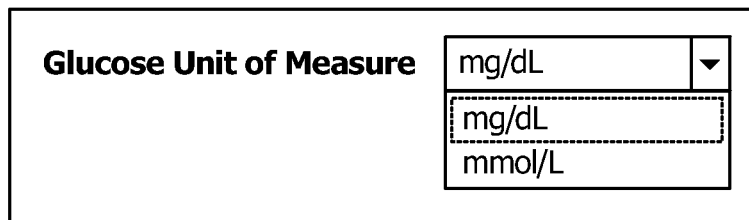

To customize Time Periods to a normal daily schedule, a user can click on up/down arrows next to a time period (for example, Pre-Bkfst, Post-Bkfst, Sleep, etc.) to change the time. To automatically restore all Time Periods to the times shown here as defaults, a user can click Restore Default Time Periods in the box illustrated at FIG. 24. The System will generally not allow a user to enter a normal daily schedule that exceeds 24 hours. If a user tries, he or she will receive an error message illustrated at FIG. 25, and the time periods will be readjusted to equal 24 hours. A user can select a Glucose Unit of Measure from the drop-down box illustrated at FIG. 26. The default is mg/dL; and another choice is mmol/L.

Figure 27:
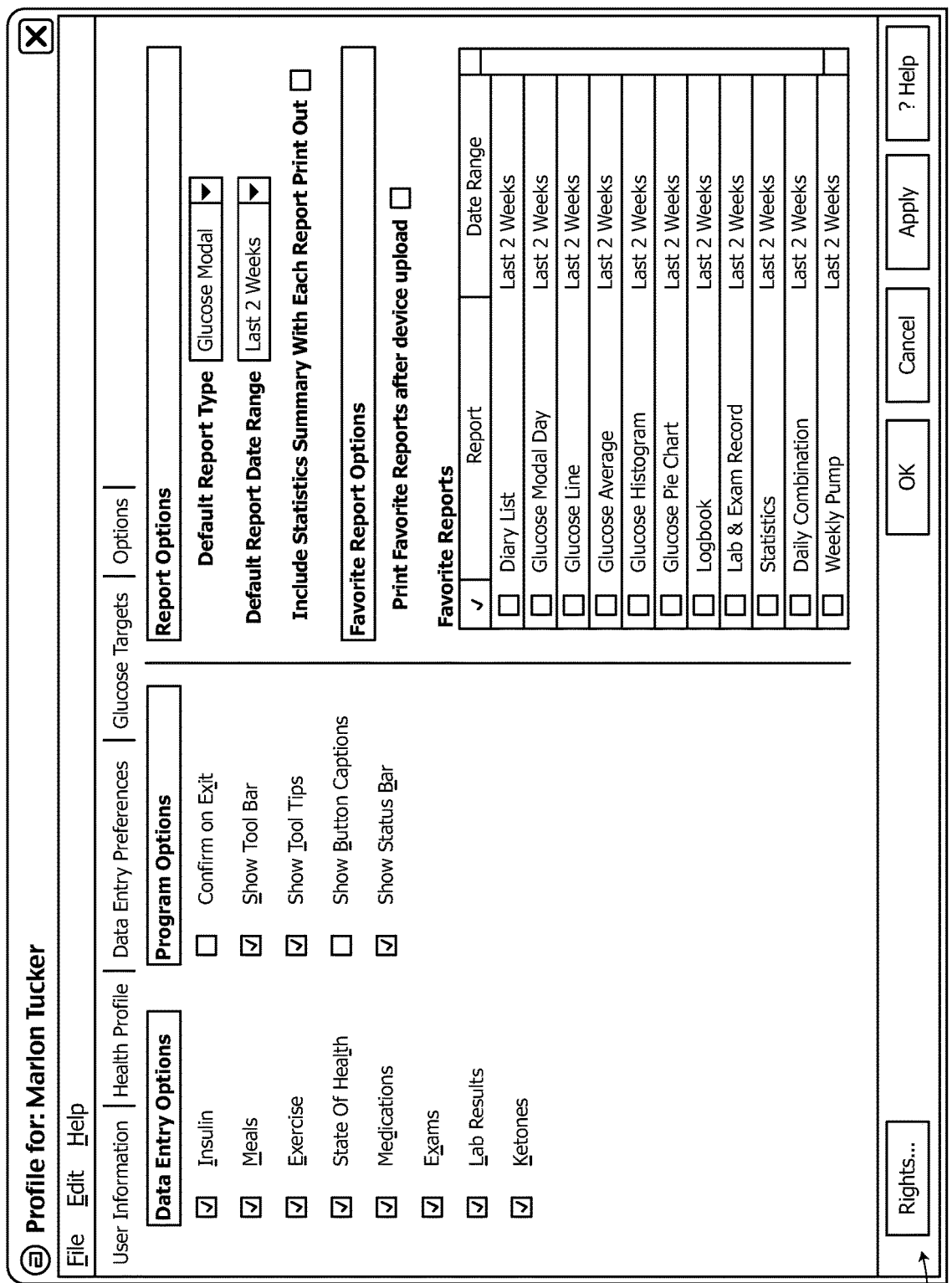

An option tab may be selected, and an options screen will appear such as that illustrated at FIG. 27. Under Program Options, boxes may be checked for the options a user wishes to use. A user may also select Data Entry and Report Options, and can select the options that apply to his or her diabetes management. This simplifies use, entry, and viewing of data/events.

Figure 28:
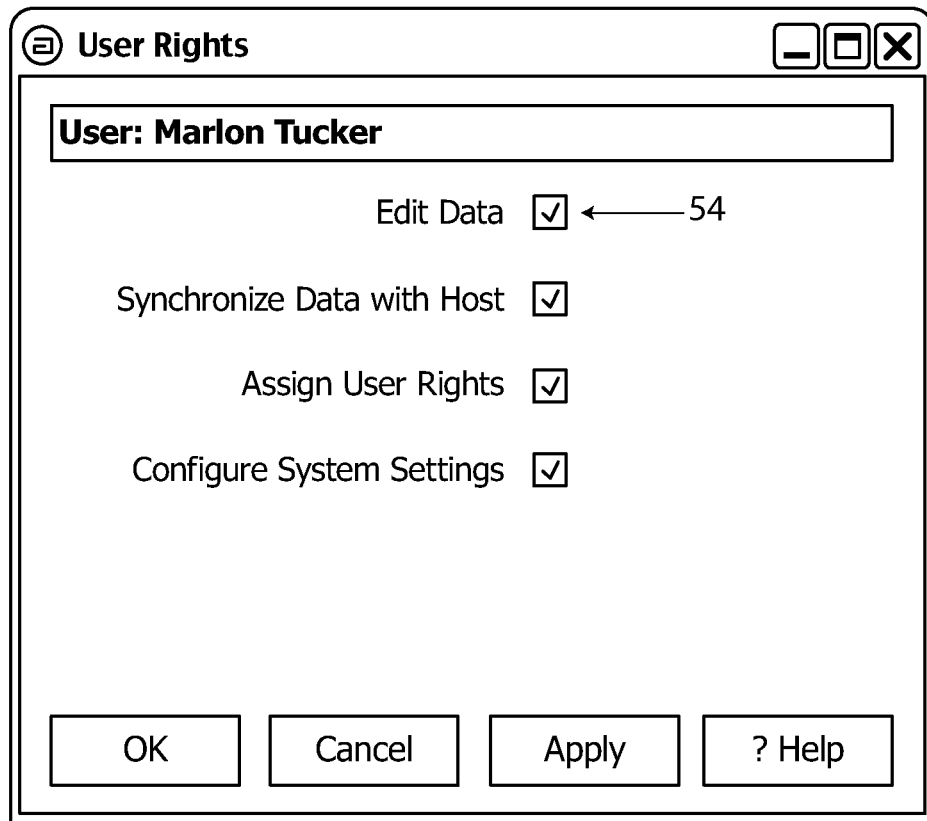

By selecting Rights 52 at the lower left of the Options screen illustrated at FIG. 27, a User Rights screen displays as illustrated at FIG. 28. A user may choose to control access for additional profiles that he or she may create. By checking the Edit Data box 54 allows the user to edit data/events and delete user accounts. For example, many households might have only one person using the System, but some households may have more than one.

Home User: Managing a User Profile

A user profile may be changed or updated. A user selects the tab he or she wants (e.g., User Information, Health Profile, etc.) and changes or adds information.

Figure 29:
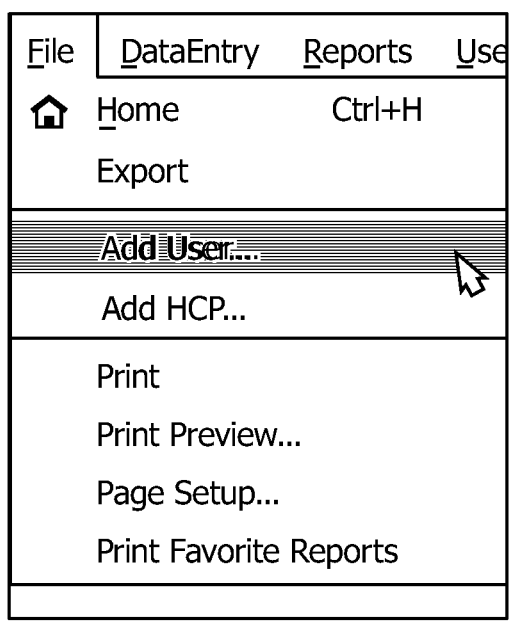

A User Profile may also be added by selecting Add User from a File drop-down box on the Home Page. FIG. 29 illustrates a File Drop-Down Box for Adding a User.

Figure 31:
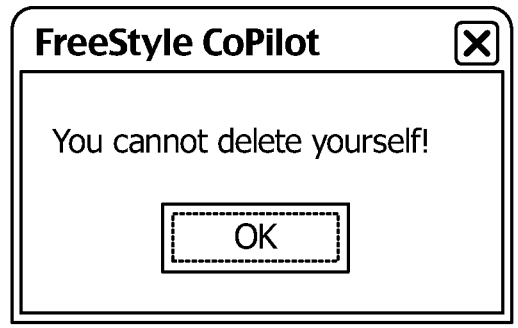

A user may also remove a User Profile at a User List screen such as that illustrated at FIG. 30. If a user tries to delete his or her own user profile, the System will display an error message such as that illustrated at FIG. 31.

Figure 32:
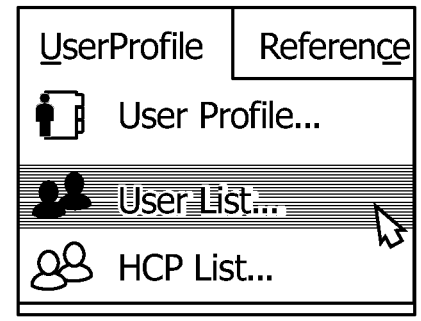
Figure 33:
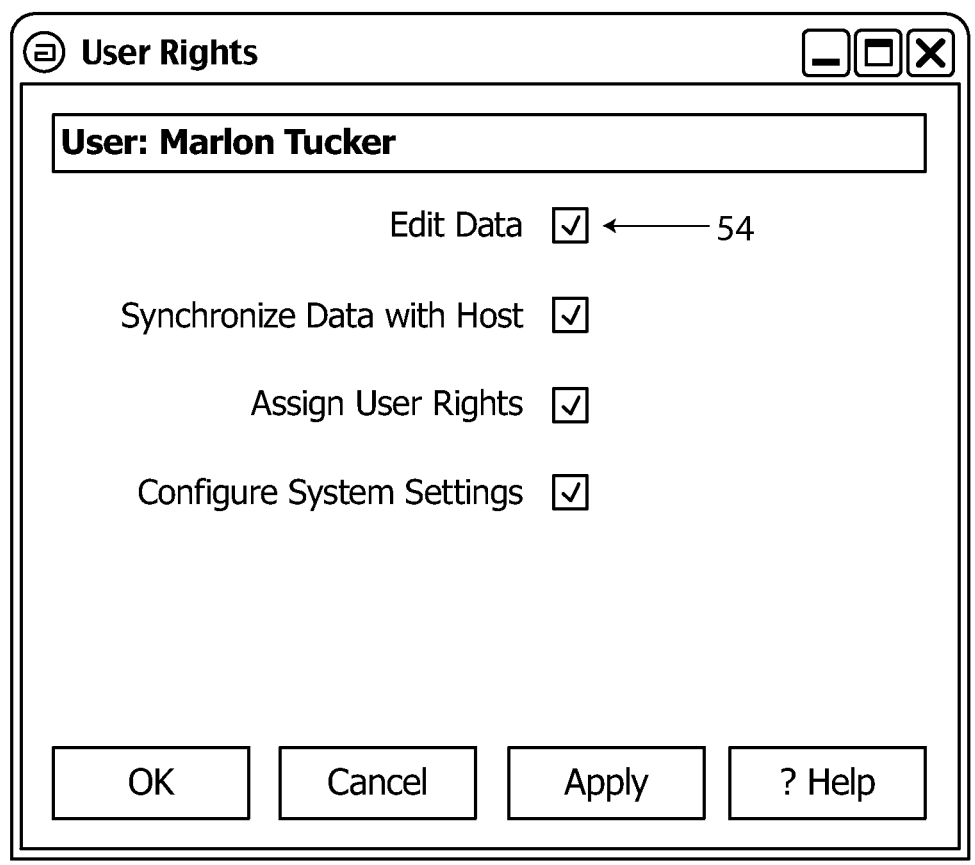

User rights may also be assigned. From the UserProfile drop-down box on the main menu bar 2 of the Home Page, User List may be selected as illustrated at FIG. 32. The User List screen displays (see FIG. 30). User rights may be changed by first highlighting the name of the user whose rights are to be changed. The User Rights screen will appear such as illustrated at FIG. 33, and rights can be selected or de-selected by checking or unchecking appropriate boxes. The Edit Data box 54 allows the user to edit data/events and/or delete user accounts.

Figure 34:
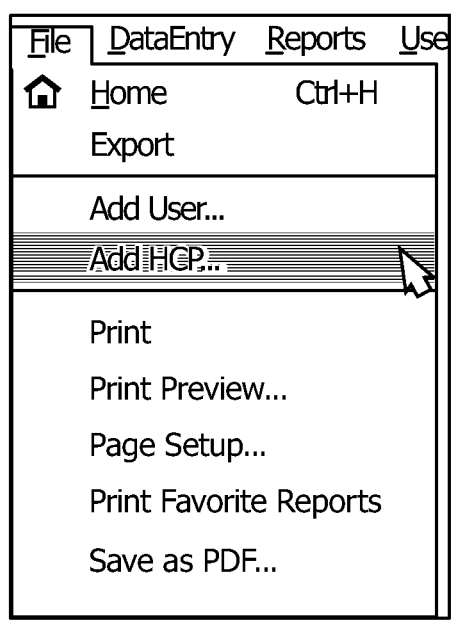
Figure 36:
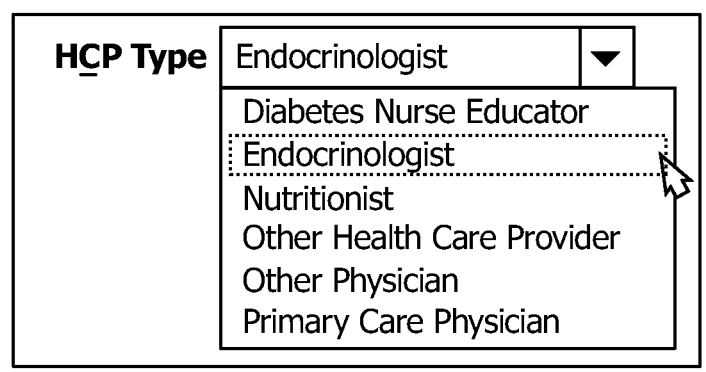

A HCP Profile may also be added. A user can create as many HCP profiles as is desired. This is often a good way to store names, addresses, and other information about doctors, clinics, etc. The HCPs added here will not have access to the user's System data unless the user invites them to share the data (described below). FIG. 34 illustrates a drop down box for adding a HCP. The Profile for screen displays as illustrated at FIG. 35. A user may select a description of the HCP from the HCP Type drop-down box illustrated at FIG. 36. If there is no selection for the one desired, then a user may type in a description.

Figure 37:
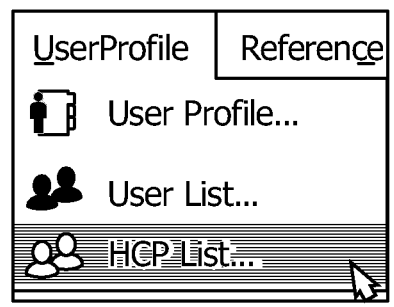
Figure 38:

A HCP Profile may be edited. From the UserProfile drop-down box illustrated at FIG. 37, which is accessible from the main menu bar 2 of the Home Page, HCP List is selected and the HCP list screen appears (see FIG. 38). The name of the HCP User is then highlighted. By selecting Edit HCP Profile from the File menu on the HCP List screen, or clicking a representative icon, the Profile for screen for the HCP user displays, and edits can be made on the screen.

A HCP Profile can be removed. From the UserProfile drop-down box on the main menu bar (see FIG. 37), a user can choose HCP List. By highlighting the name of the HCP User on the HCP List screen, and selecting Remove HCP from the File menu on the HCP List screen, the HCP can be removed. The System will ask the user to confirm.

HCP User: Setting up a User Profile

Figure 39:
Figure 40:
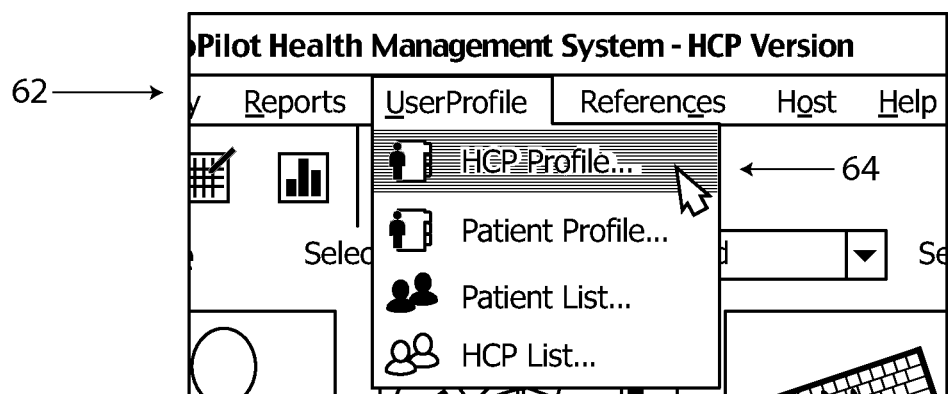
Figure 41:
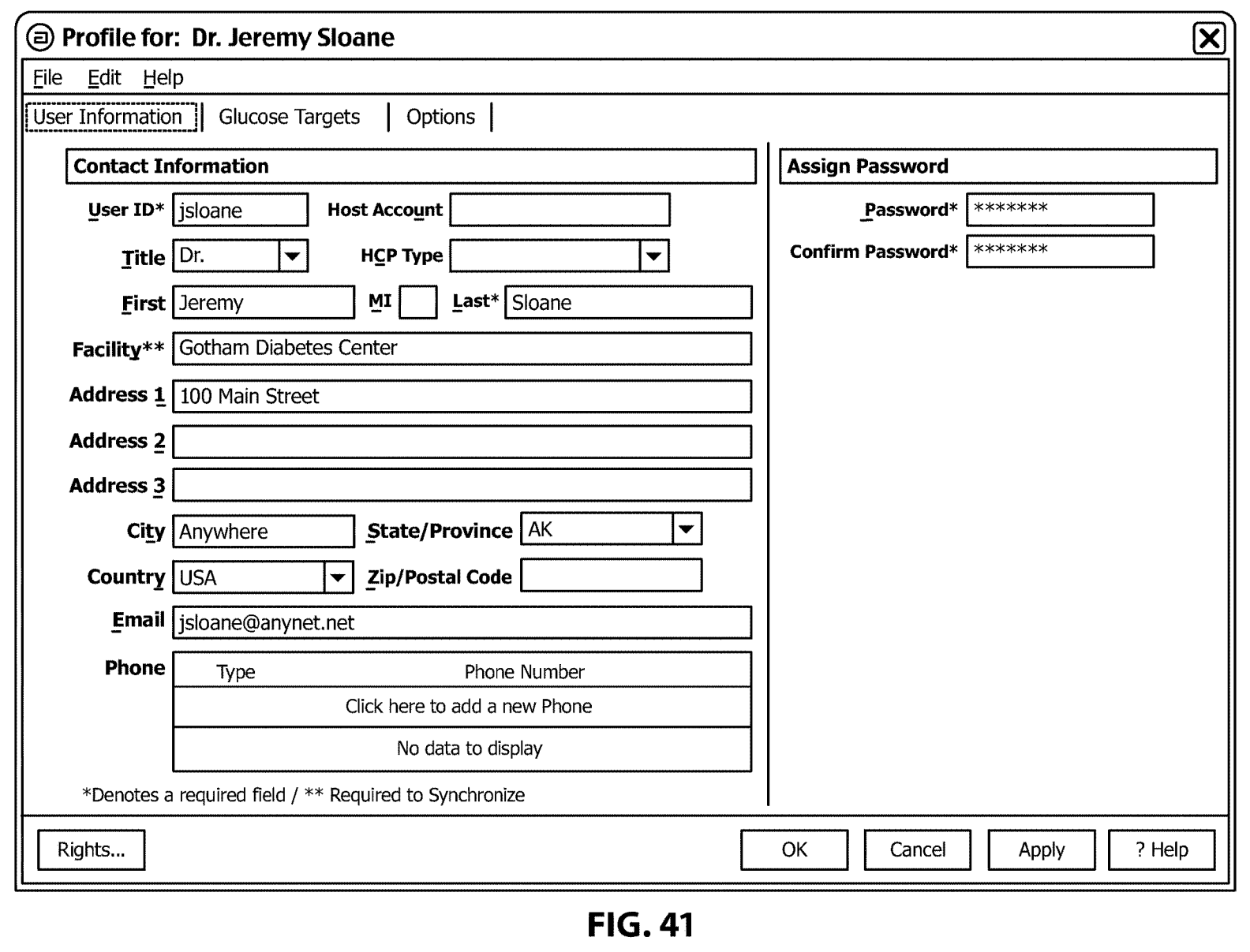

With a User ID and password, a user can use the System. But to take greater advantage of the System, a user may also set up a HCP Profile. This will allow a HCP user to view (and sometimes edit) data and reports to monitor trends in the patient's health or care. FIG. 39 illustrates a HCP Home Page. On the Home page, a user may select HCP Profile from the UserProfile drop-down box 64 on the main menu bar 62 as illustrated at FIG. 40. The HCP Profile for screen displays with the User Information tab selected as illustrated at FIG. 41. Information is filled in here. Information may be added by selecting items from drop-down boxes or by keying in words and numbers. If a desired HCP type is not found in the HCP Type drop-down box, a description can be entered at the keyboard.

Glucose Targets

Figure 42:
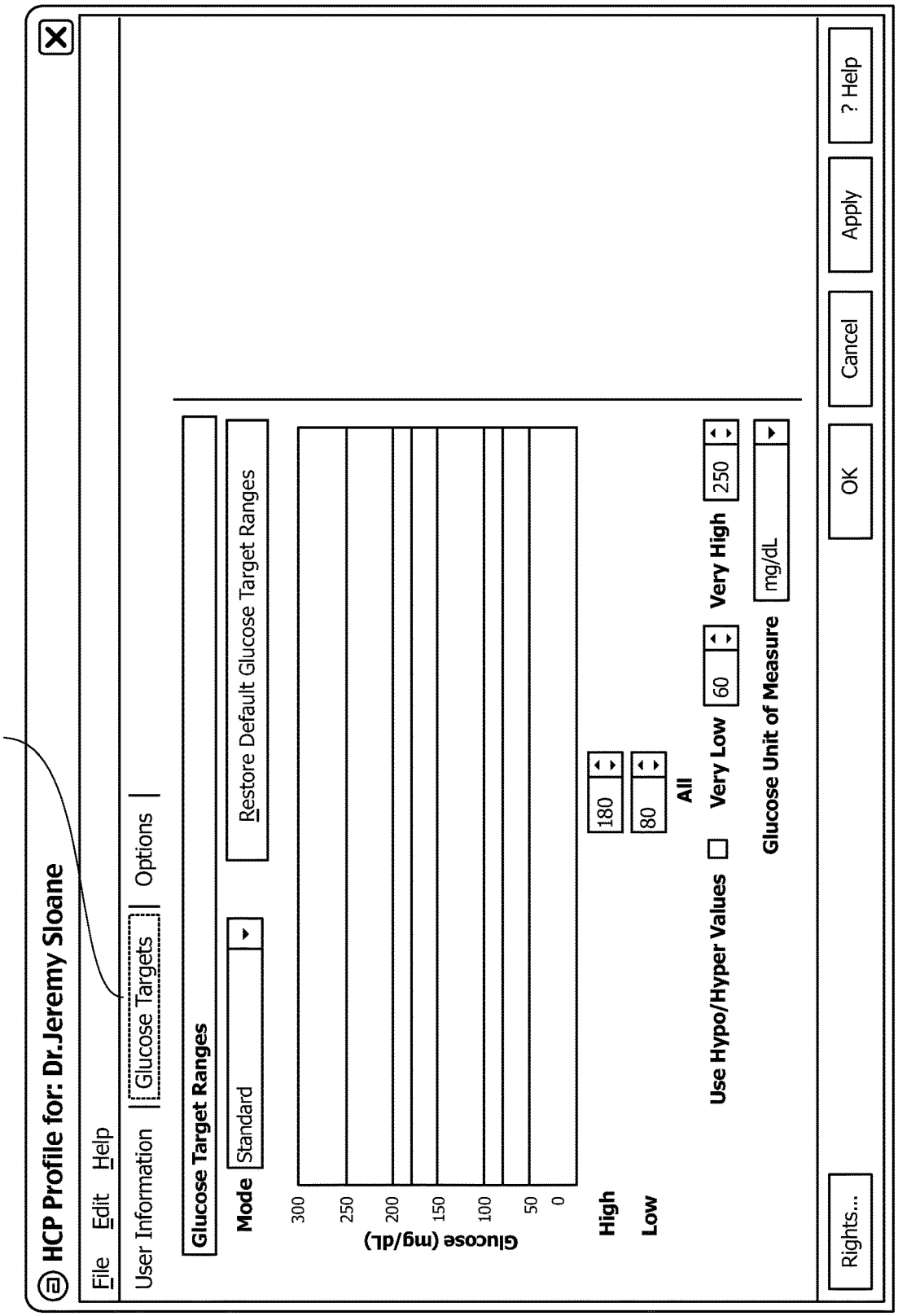
Figure 43:
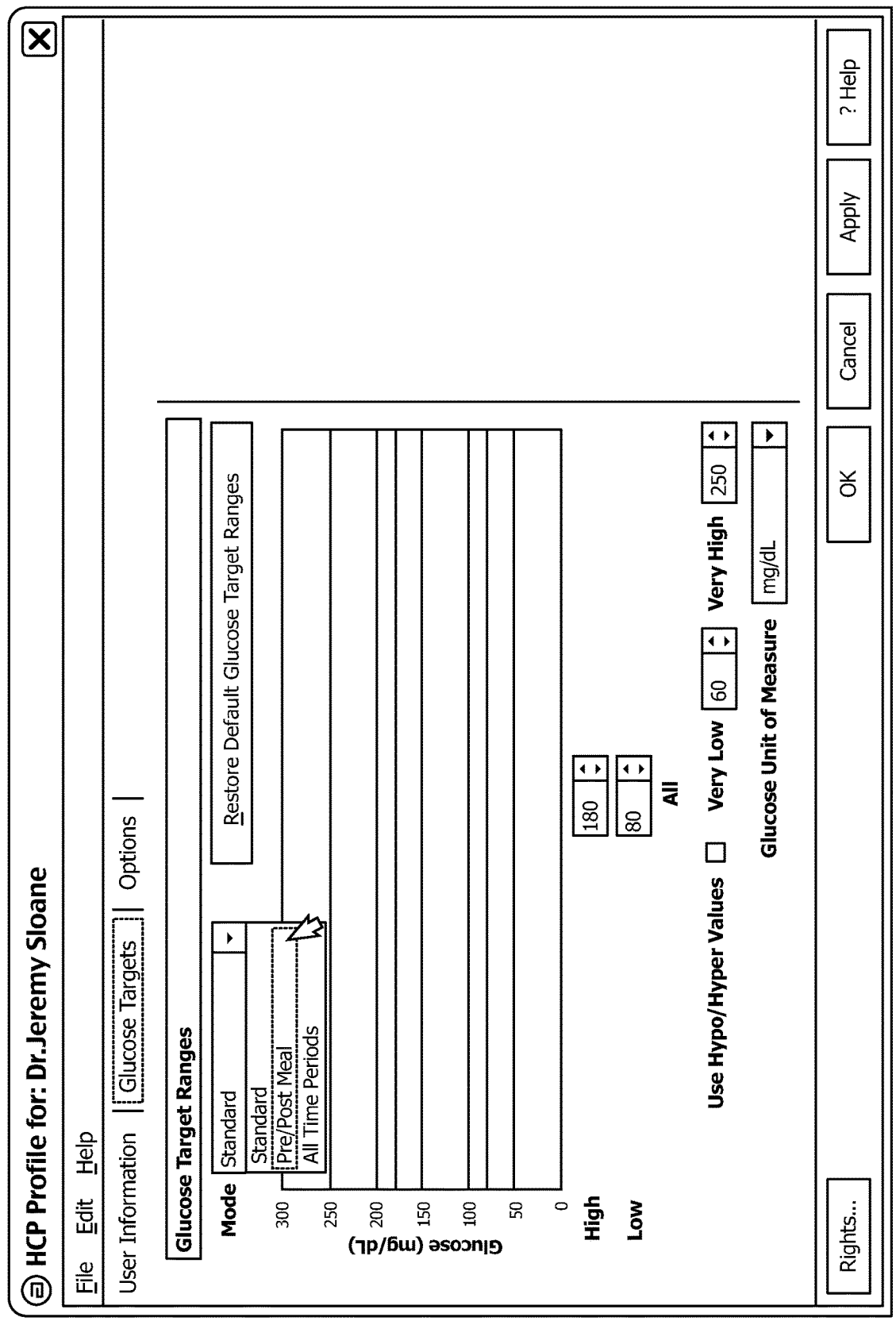
Figure 48:
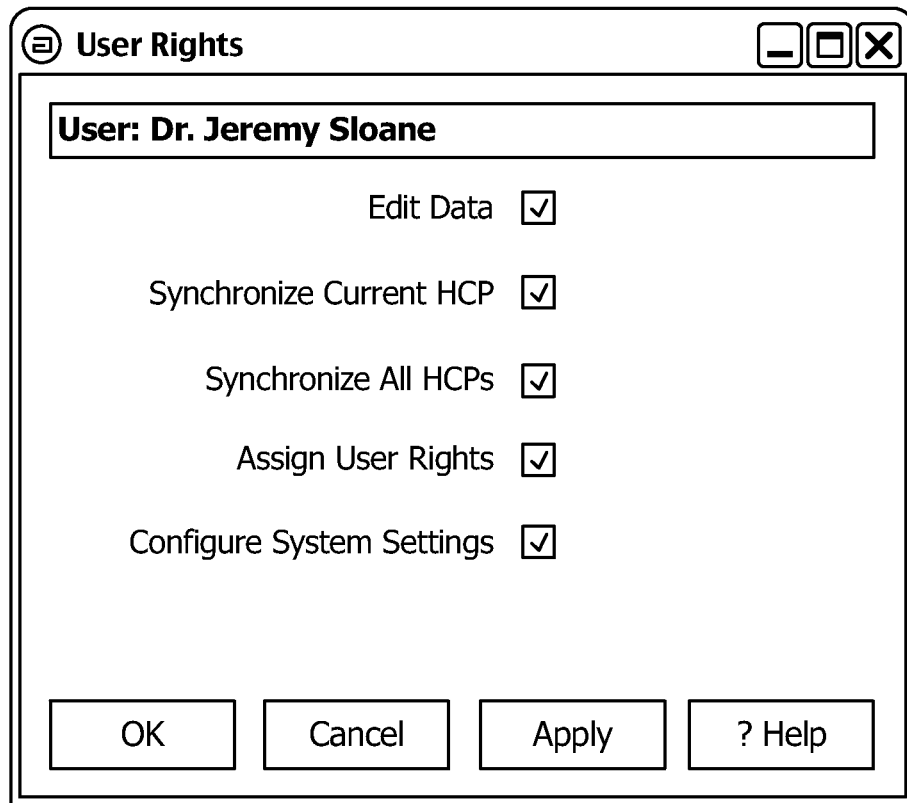
Figure 49:
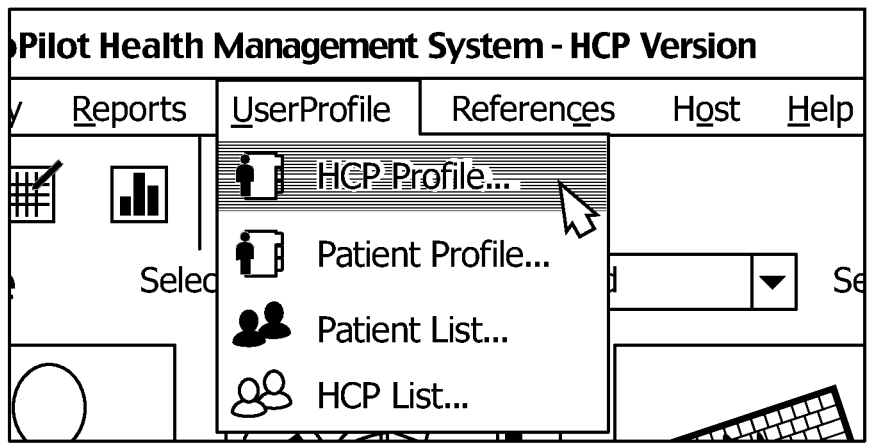
Figure 52:
Figure 53:
Figure 54:
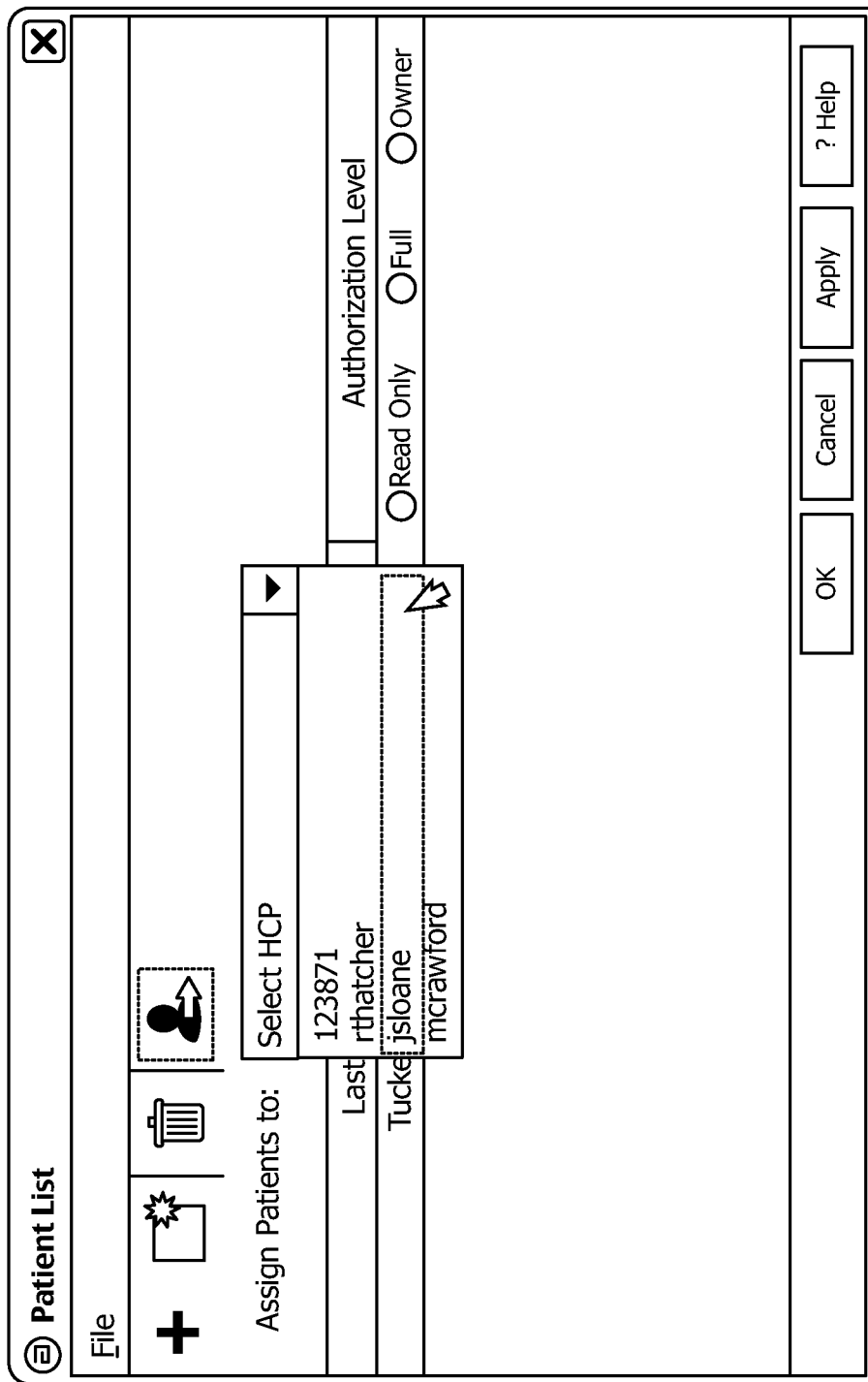

The Glucose Targets tab 66 can be selected from the HCP profile for screen illustrated at FIG. 42 to customize glucose target ranges. The glucose targets set here will apply to the reports viewed for the persons with diabetes the HCP user manages via the System. A HCP user may view the graph in three modes as illustrated in FIG. 43 by selecting the desired mode from the Mode drop-down box. The standard, Pre/Post Meal and All Time Periods modes were described above and not repeated here. In addition, setting target glucose ranges were described above and the descriptions of FIGS. 44, 45 and 46 are similar to those described above and thus not repeated here. FIGS. 47-48 illustrate an Options tab and User Rights screen also similar to described above for diabetic users and not repeated here. In addition, managing a HCP profile is similar to managing a diabetic user profile, and that description is not repeated here with reference to FIGS. 49-54.

Figures 55, 56:
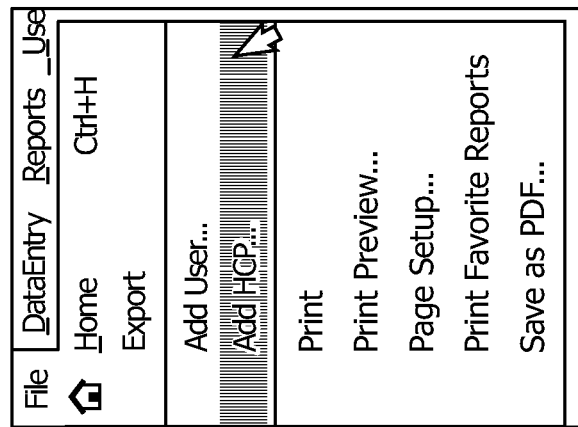
Figure 58:
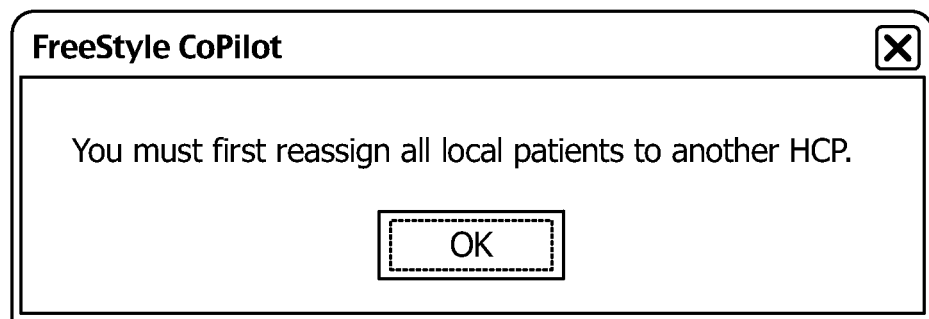
Figure 59:
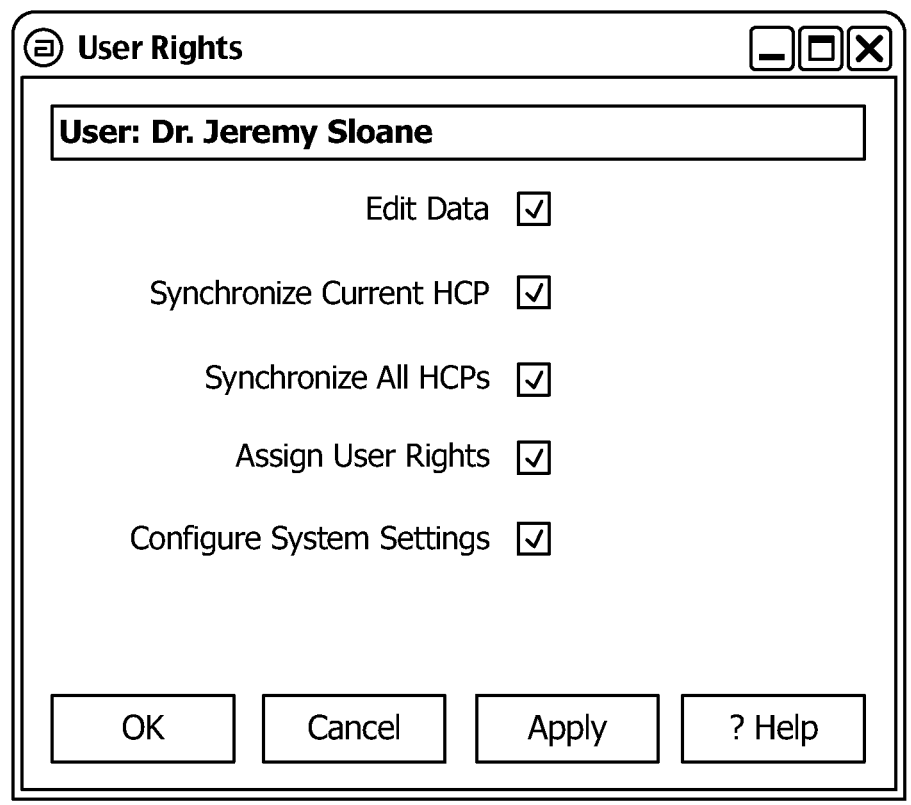

A user may set an Authorization Level (e.g., None, Read Only, Full, Owner) for the HCP by checking the desired level as illustrated at FIG. 55. Adding, Editing and Removing HCP profiles are similar to those described above and not repeated here with reference to FIGS. 55-57. However, if a HCP is to be removed, and if local patients are assigned to this HCP, the System then will prompt the user to reassign the patients to another HCP on the local computer as illustrated at FIG. 58. User rights may be assigned similar to above at a User Rights screen as illustrated at FIG. 59.

Data Entry

There are three ways to enter events (data) into the System in accordance with a preferred embodiment: upload from a device, manually enter data (e.g., from a keyboard, and import an existing file or database). The System can upload data from supported glucose monitoring devices (meters), such as FreeStyle Meter, Precision Xtra Meter, FreeStyle Flash Meter, FreeStyle Tracker System, and glucose meters of companies other than Abbott Diabetes Care Inc, as well as insulin pumps. At least the following data (event types) may be automatically uploaded to the System when uploading from a device: glucose readings, state of health, insulin doses, lab results, carbohydrates, medical exams, exercise, ketones (blood), medications and notes. Data previously uploaded from a device will not be overwritten when uploading again from that same device. Only the new data will be uploaded to the user's file. Meter functions, displays, and printed output assume a single glucose calibration type, either plasma or whole blood. When uploading glucose data from a device, the System does not differentiate between devices that are whole-blood or plasma calibrated. The System merely uploads the data with no calculations made. Because there are slight differences between the two calibrations, a user should not mix data from devices that use different calibration references. Uploading data into a user's account occurs if the device contains only that person's data. The System is preferably designed not to upload a specific portion of data from a device if data is intermixed with data from another person.

Connecting a Device to a Computer

Figure 60:
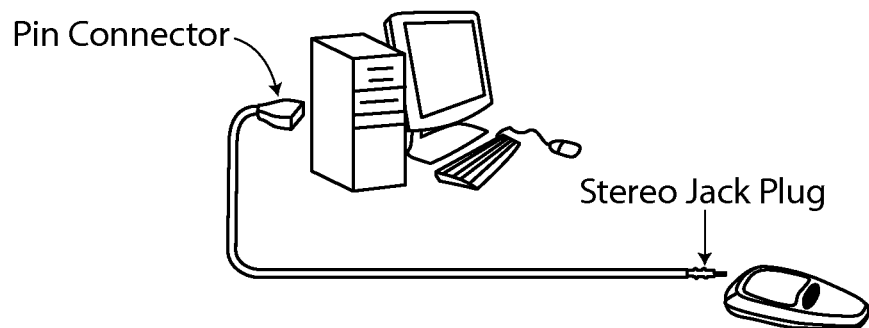
Figure 61:
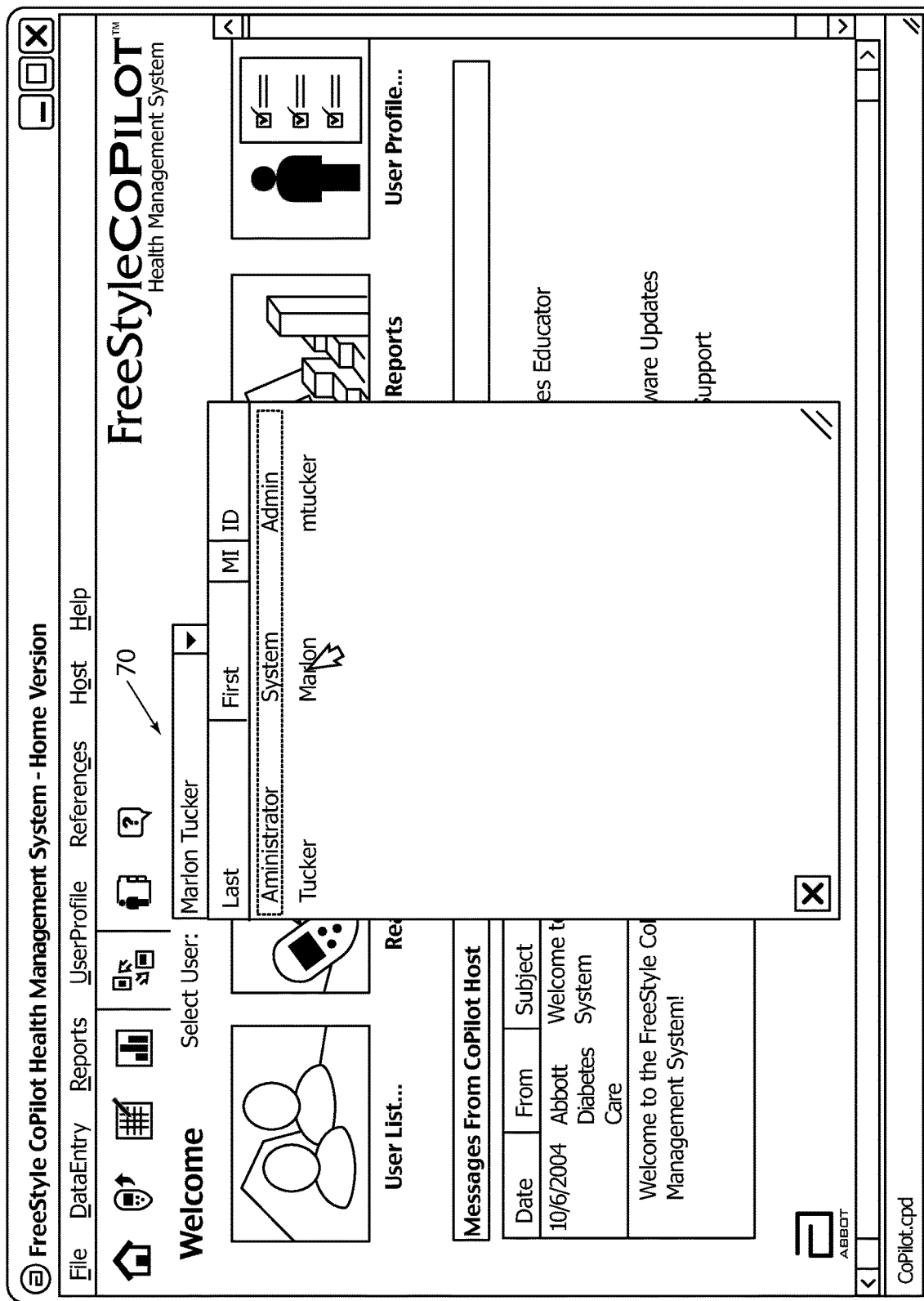
Figure 62:
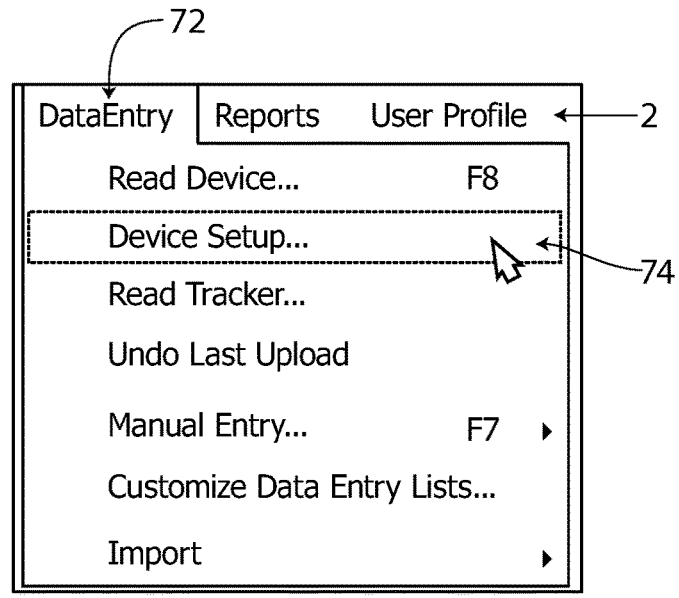

Before uploading, the device is connected to an available COM port on a PC or other computing appliance using an approved data cable for that device. An exemplary cable connection is illustrated at FIG. 60. To set up the device to the computing device, on the Home page, the user whose data is being uploaded from the device is selected, from the select user menu illustrated at the Home page of FIG. 61. Next, Data Entry 72 is selected on the main menu bar 2, as illustrated at FIG. 62; and then Device Setup 74 is chosen from the drop-down list.

Figure 63:
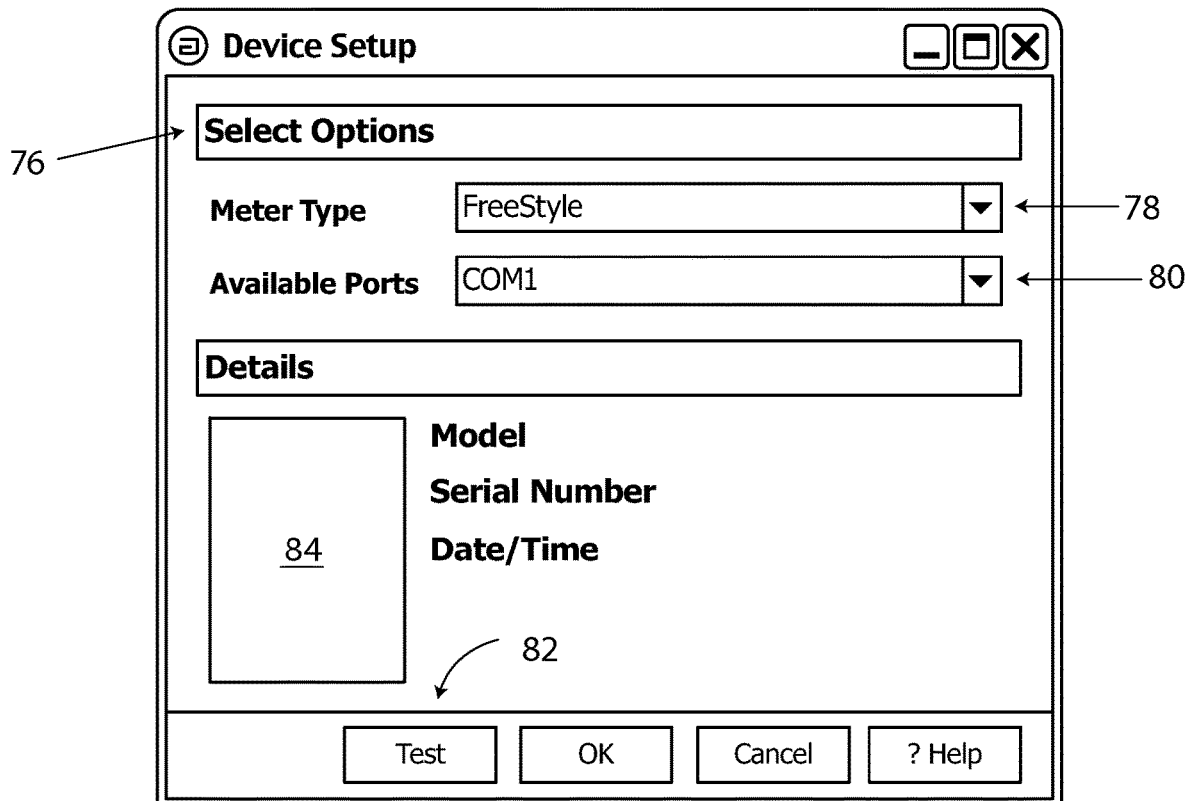
Figure 64:
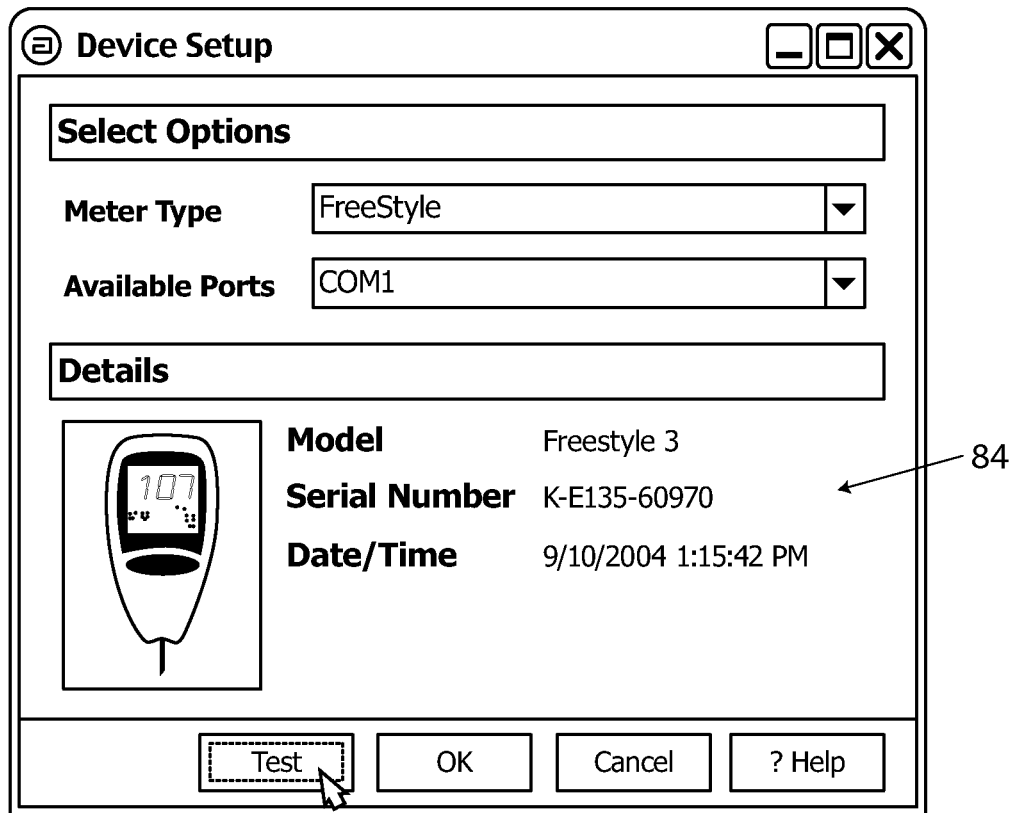

A Device Setup screen appears as illustrated at FIG. 63. Under Select Options 76, the device is selected from the Meter Type drop-down list 78. The communications port (COM1, COM2, etc.) is selected from the Available Ports drop-down list 80. The System stores Meter Type and Available Ports settings during Device Setup. The user will not have to select them the next time he or she uploads data from this meter as long as he or she connects the device to the same communications port. By clicking Test at the bottom of the Device Setup screen illustrated at FIG. 63, the device details are displayed in the Details box 84, and the System is ready to upload data from the meter. An illustration of the meter and details are preferably displayed as illustrated at FIG. 64.

Uploading Data from a Device

Figure 65:
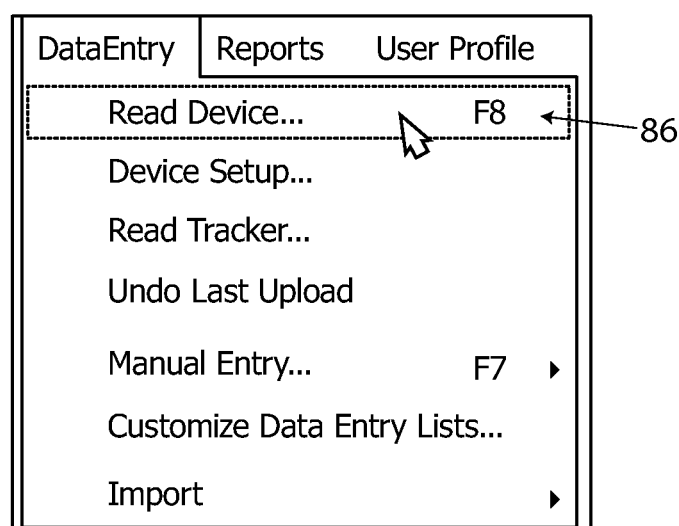
Figure 66:
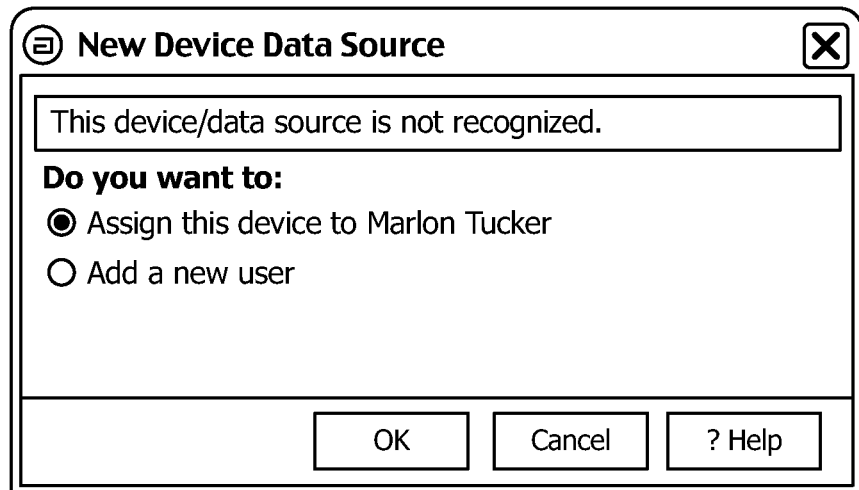
Figure 67:
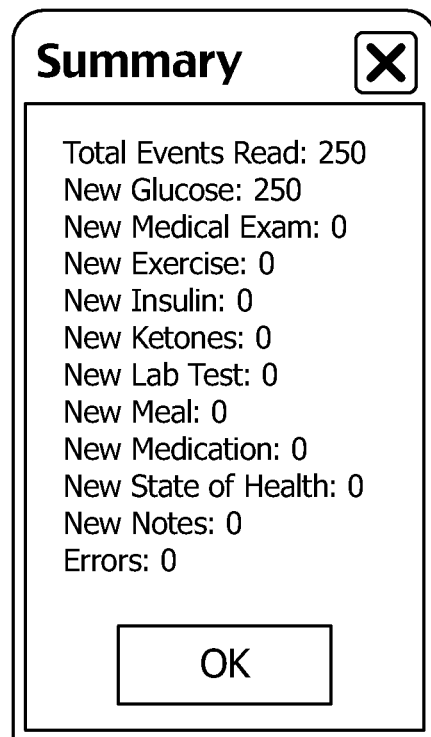

Once the device is connected to the computer and the device is set up, data may be uploaded to the System. On the home page the user whose data is being uploaded from the device is selected. As illustrated at FIG. 65, from DataEntry on the main menu bar; Read Device 86 is selected from the drop-down list. When a device has been detected but cannot be identified as belonging to a specific user, the System will prompt the user to assign the device to an existing user or to add a new user as illustrated at FIG. 66. The data from the device is then automatically uploaded to the PC. A progress bar indicates when the upload is complete. A summary of the upload then displays in a pop-up window as illustrated at FIG. 67.

Figure 68:
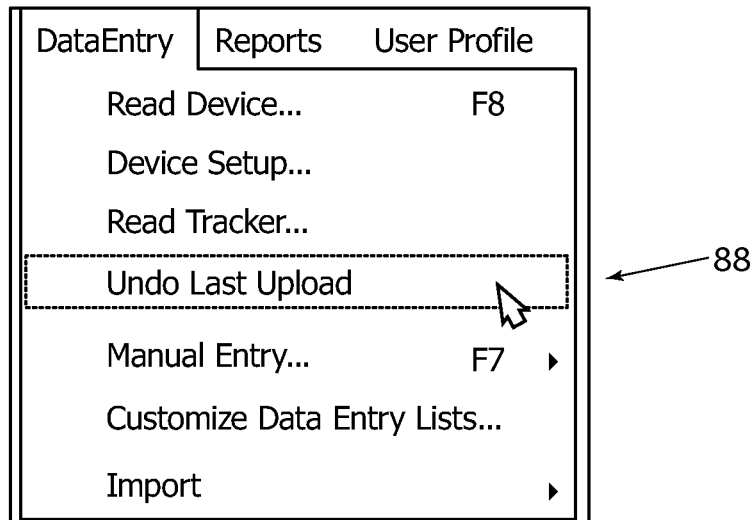

A device upload may be undone. That is, the data from the most recent device upload may be undone as long as no data has been manually entered since the device upload and another user has not been selected. DataEntry is selected on the main menu bar of the Home page; then Undo Last Upload 88 is chosen from the drop-down menu illustrated at FIG. 68. The System will then automatically undo the last upload.

Figure 69:
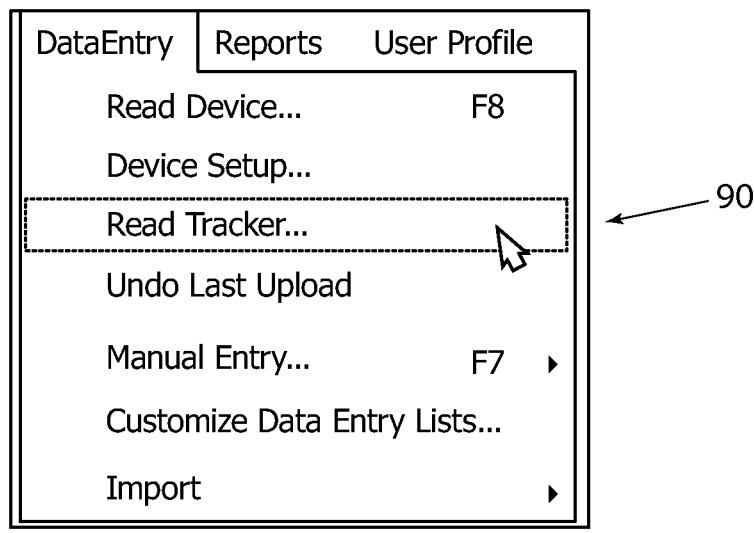
Figure 70:
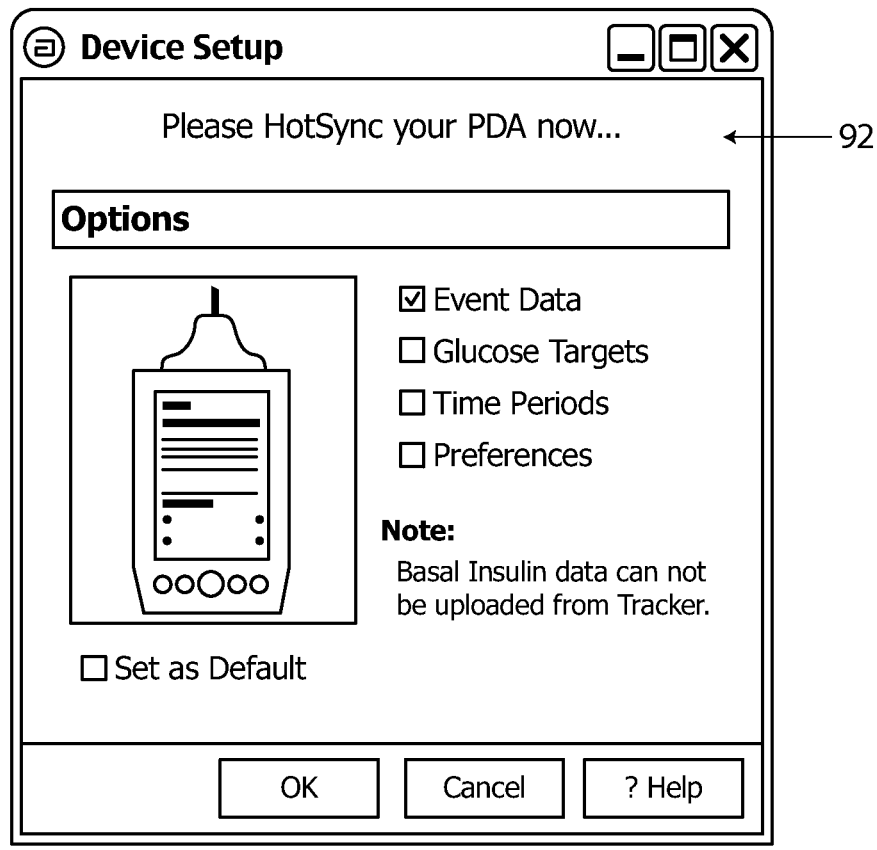
Figure 71:
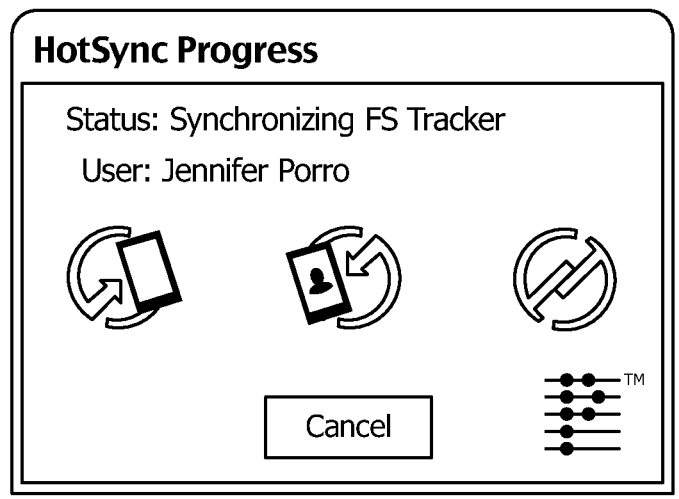

Uploading from a PDA-based system such as the FreeStyle Tracker System may be handled somewhat differently than uploads from other devices as follows. The PDA-based system is connected to the PC. DataEntry is selected from the main menu bar, and Read Tracker 90 or other PDA-based product is selected from the drop-down list as illustrated at FIG. 69. If the device is detected, the System prompts to HotSync 92 as illustrated at FIG. 70. As HotSync takes place, the HotSync Progress screen displays as illustrated at FIG. 71.

When HotSync completes, options may be selected for upload from the FreeStyle Tracker of other PDA-based device such as Event Data, Glucose Targets, Time Periods and Preferences, as illustrated at FIG. 70. Event Data will be generally automatically uploaded from the FreeStyle Tracker System. Glucose Targets may be selected to upload and overwrite the Glucose Targets data with data from the FreeStyle Tracker System. Time Periods may be selected to reset Time Periods data according to data from the FreeStyle Tracker System. Preferences may be selected to overwrite Preference Settings with settings from the FreeStyle Tracker System. Set as Default may be selected if a user wants to save these options as the defaults. If prompted to assign the device to a current user or to a new user, as illustrated at FIG. 72, then OK should be clicked after making a choice, keeping in mind that more than one device may be associated with a same user.

As data from the FreeStyle Tracker System is uploaded, the System displays the Profile Updated message illustrated at FIG. 73 if Preferences were checked on the Read Tracker screen of FIG. 70. When the upload is done, an Upload Summary screen displays (see FIG. 74). It shows a list of the type and number of events uploaded.

Manual Data Entry

Figure 75:
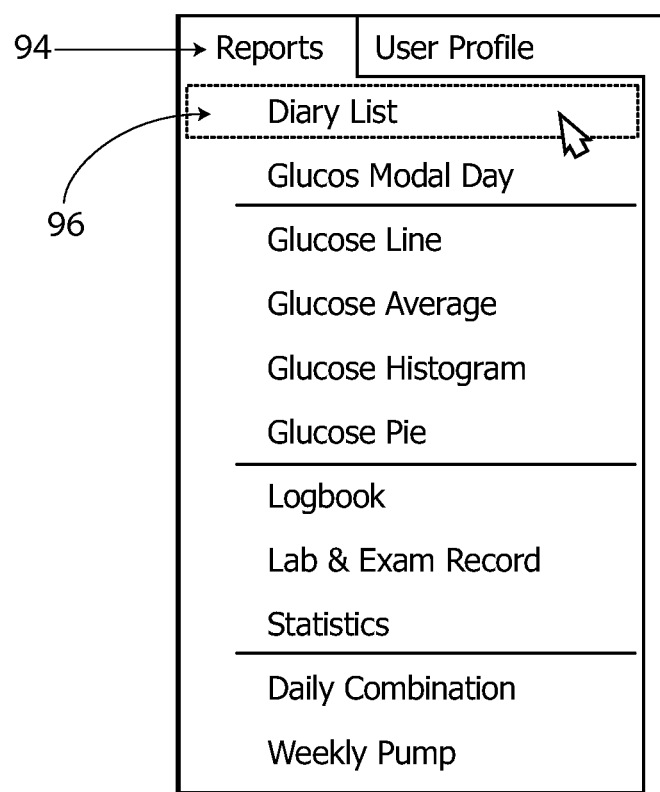

The System allows data to be added, edited, deleted, and recovered manually, e.g., from a keyboard. When manually recorded events are deleted, they are omitted from views and reports but are preferably not removed from the user's database. A complete list of a user's events (whether entered manually, uploaded, or imported) may be viewed by clicking on Reports 94 and selecting Diary List 96 as illustrated at FIG. 75.

Manually recordable events include the following categories: glucose readings, glucose control readings, insulin doses, meals (carbohydrates in grams, e.g.), exercise sessions, state of health/health conditions, medication doses, medical exams, lab results, ketone readings, or ketone control readings, or combinations thereof FIG. 76 illustrates a glucose reading data entry screen. If the date and time of the glucose reading are different from the current date and time, the Date, Time, and Time Period fields 98 at the top of the Glucose Reading screen should be adjusted using drop-down boxes and up/down arrows. The value of the manual glucose reading should be entered in the Glucose Value field 100. In the Sample Site field 102, the site may be selected from which the reading was taken (finger, forearm, etc.). In the Hours Since Last Meal field 104, the time of the last meal should be entered. A calibration code may be entered from the glucose monitor into the Calibration Code field 106. The control reading box 108 should be checked if this is a Control Solution reading from the user's glucose monitor. To add another event, the icon at the top of the Data Entry screen should be selected that applies, e.g., Insulin, Meal, Exercise, Health, Meds, Exam, Lab, Ketones, or Note.

Recording an Insulin Dose

Figure 77:
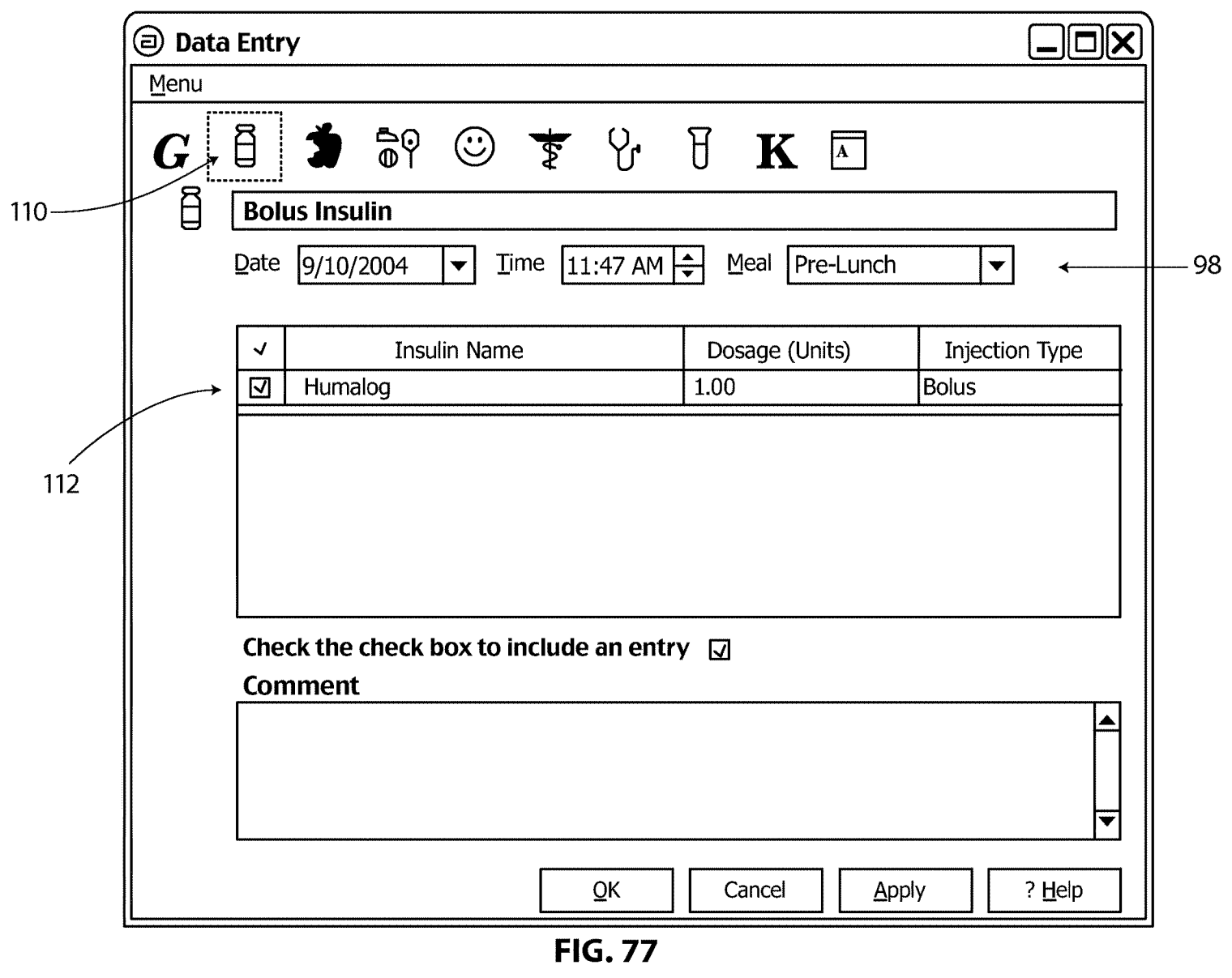

The insulin data screen illustrated at FIG. 77 will display when the insulin icon 110 is clicked on the Data Entry screen. An icon may be clicked at the Home page to get to the data entry screen as already described. The Date, Time, and Time Period fields can be set using the up/down arrows for the time of the injection that is being recorded. The field 112 directly under the Insulin Name header is for selecting the brand of insulin from the drop-down box. If the name of the insulin is not listed, it can be typed in. Dosage (Units) and injection type also are entered. Injection types generally include bolus, injection, meal, correction, combination, dual wave, and square wave.

Recording a Meal

Figure 78:
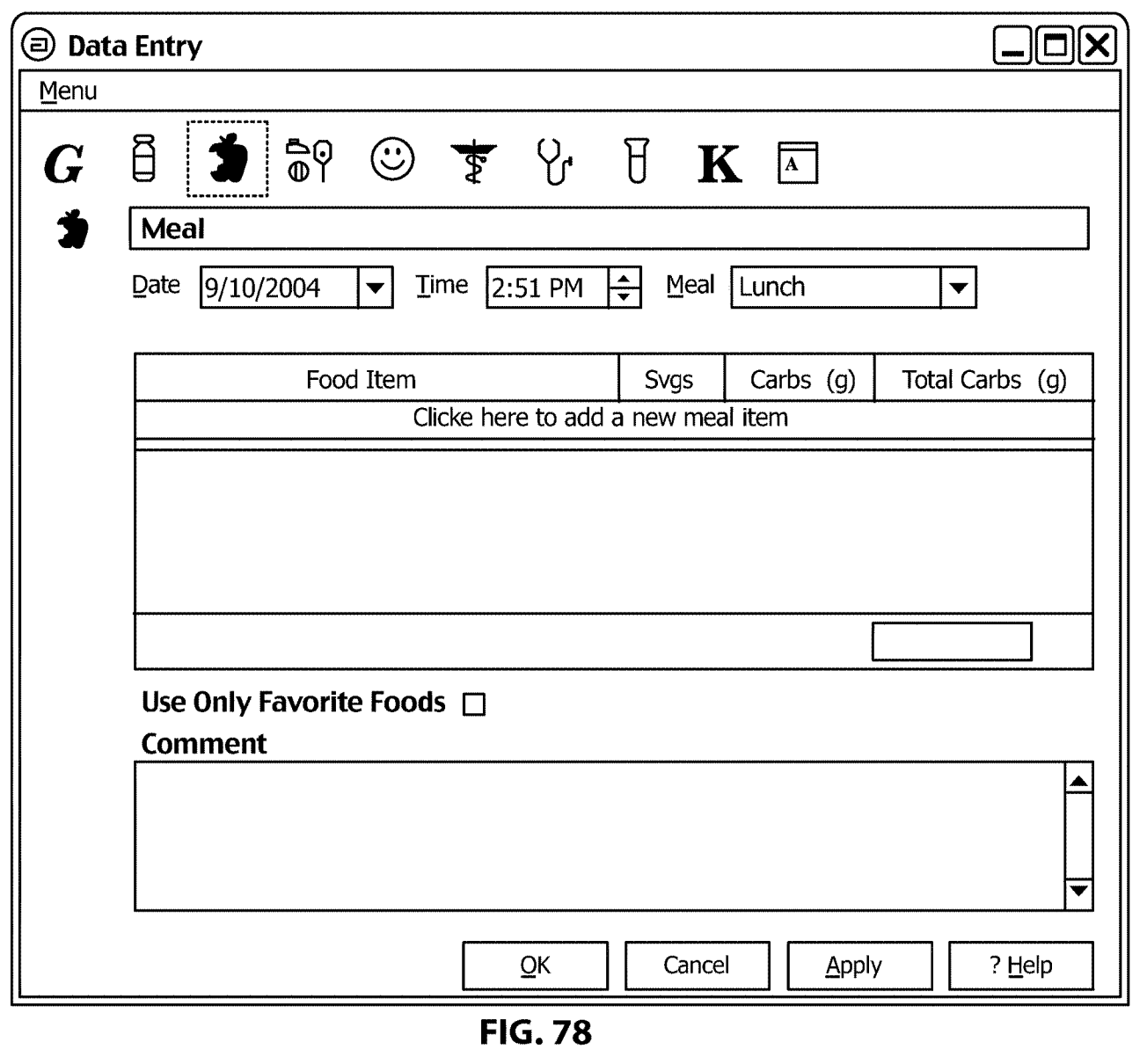

A meal may be recorded by selecting the Meal icon from the Data Entry screen to reveal a Meal data entry screen as illustrated at FIG. 78. Date, Time, and Meal fields may be adjusted for the meal being entered. Drop-down boxes may be used to describe the meal. The drop-down box displays a very extensive list of foods to choose from. If what was eaten is not listed, it may be typed in. Serving size and carbohydrates per serving should be entered with it. The number of servings should be selected, after which the grams of carbohydrates per serving and total carbs are automatically displayed.

Figure 81:
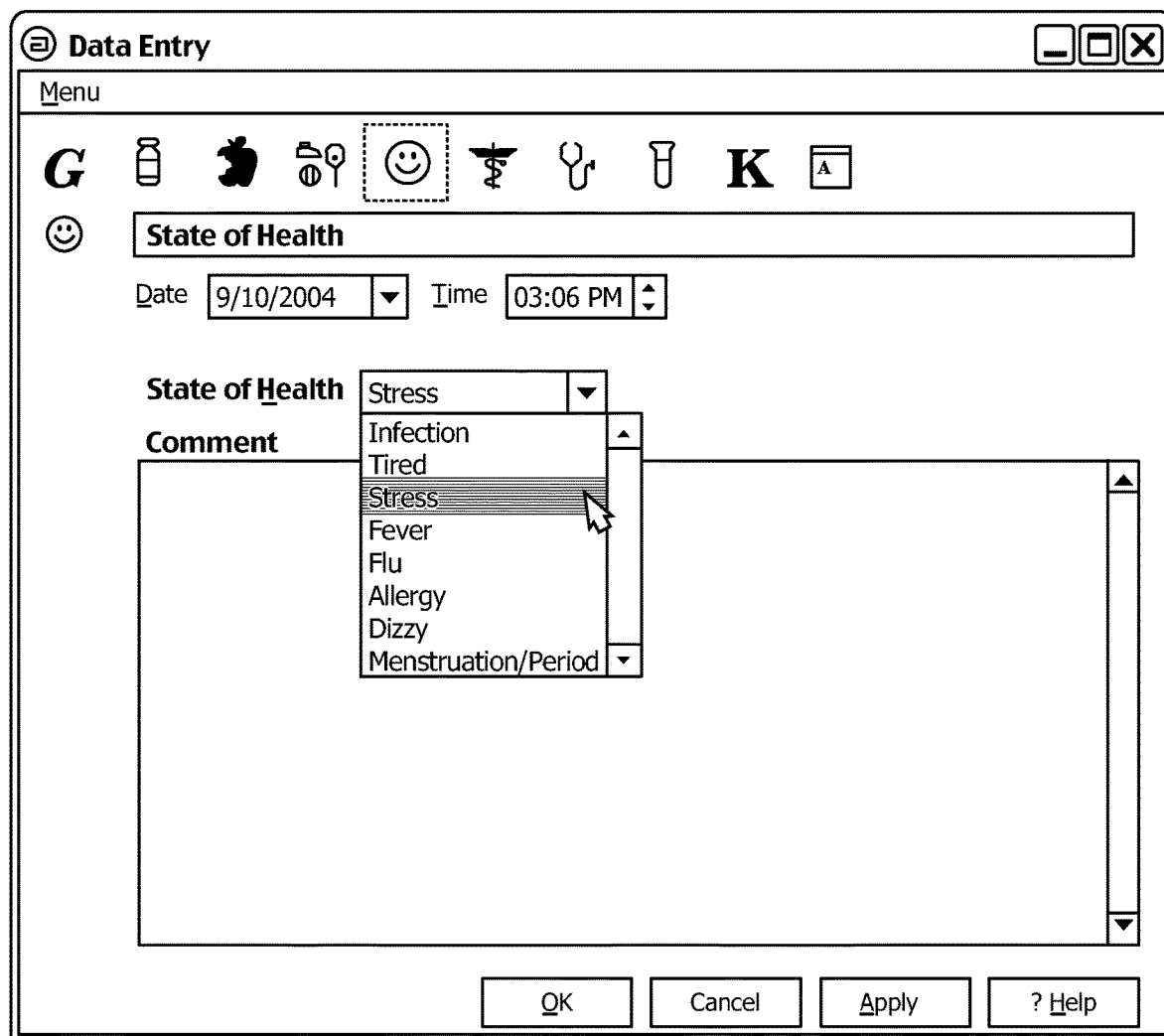
Figure 82:
Figure 83:
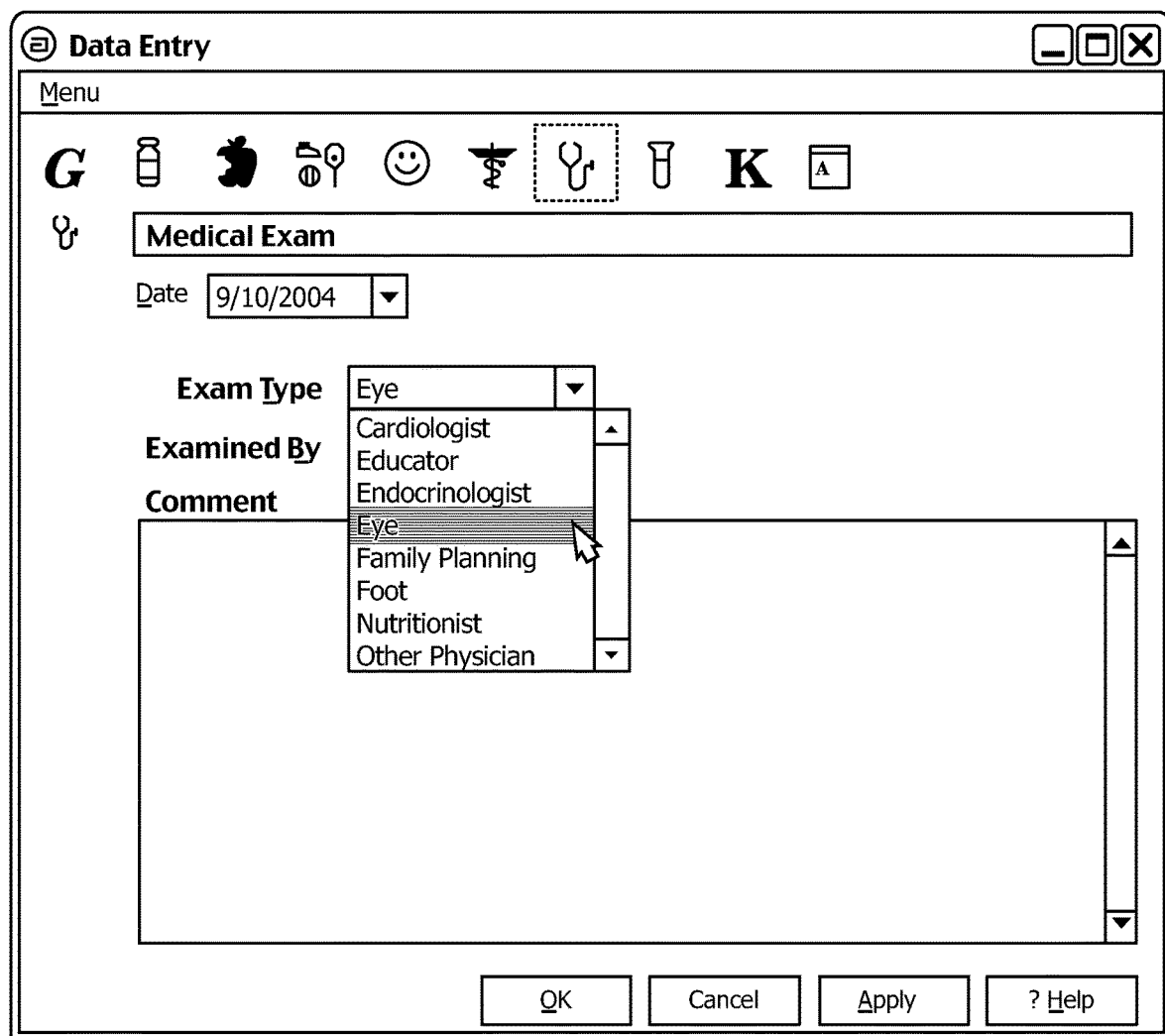
Figure 84:
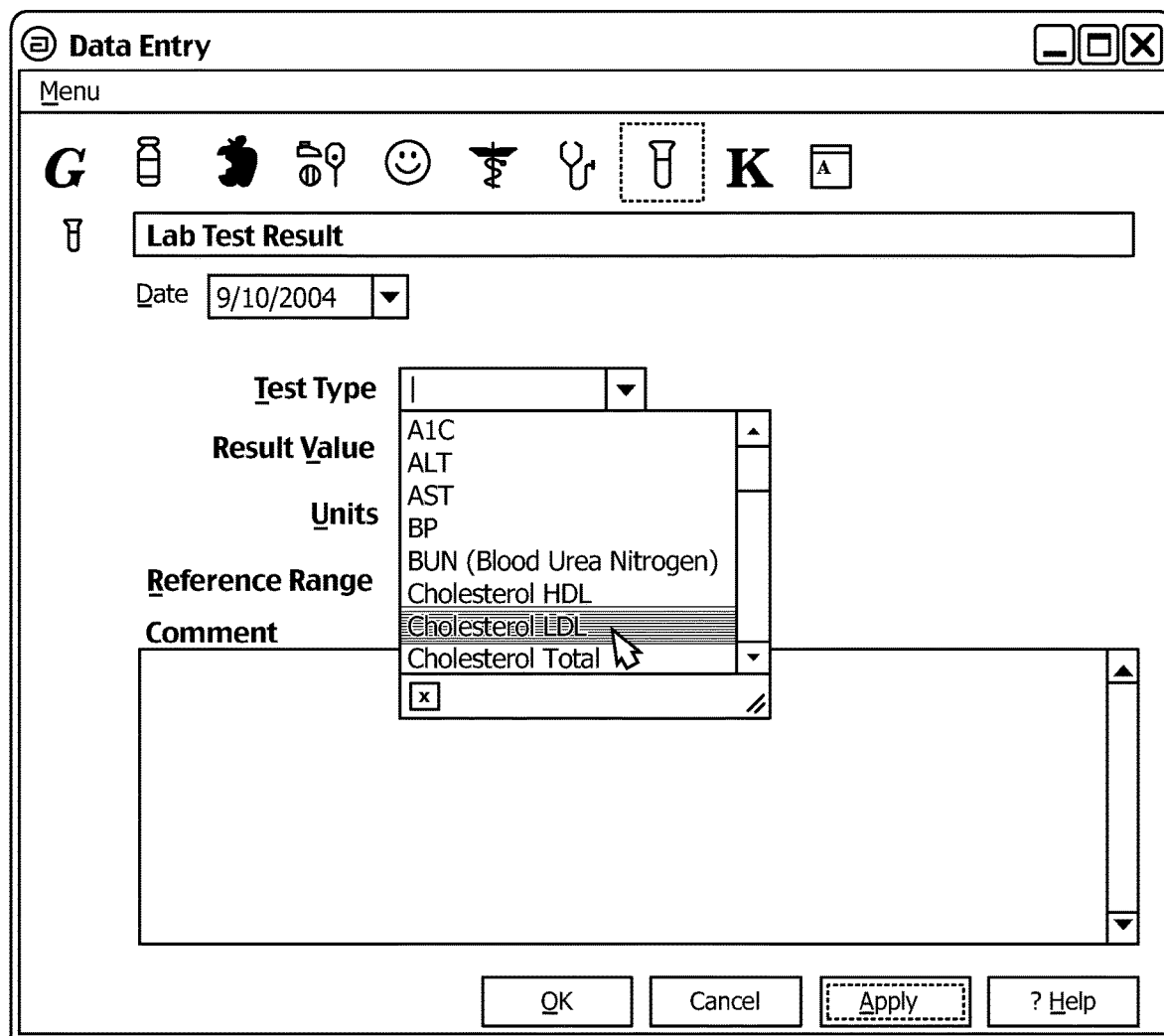
Figure 85:
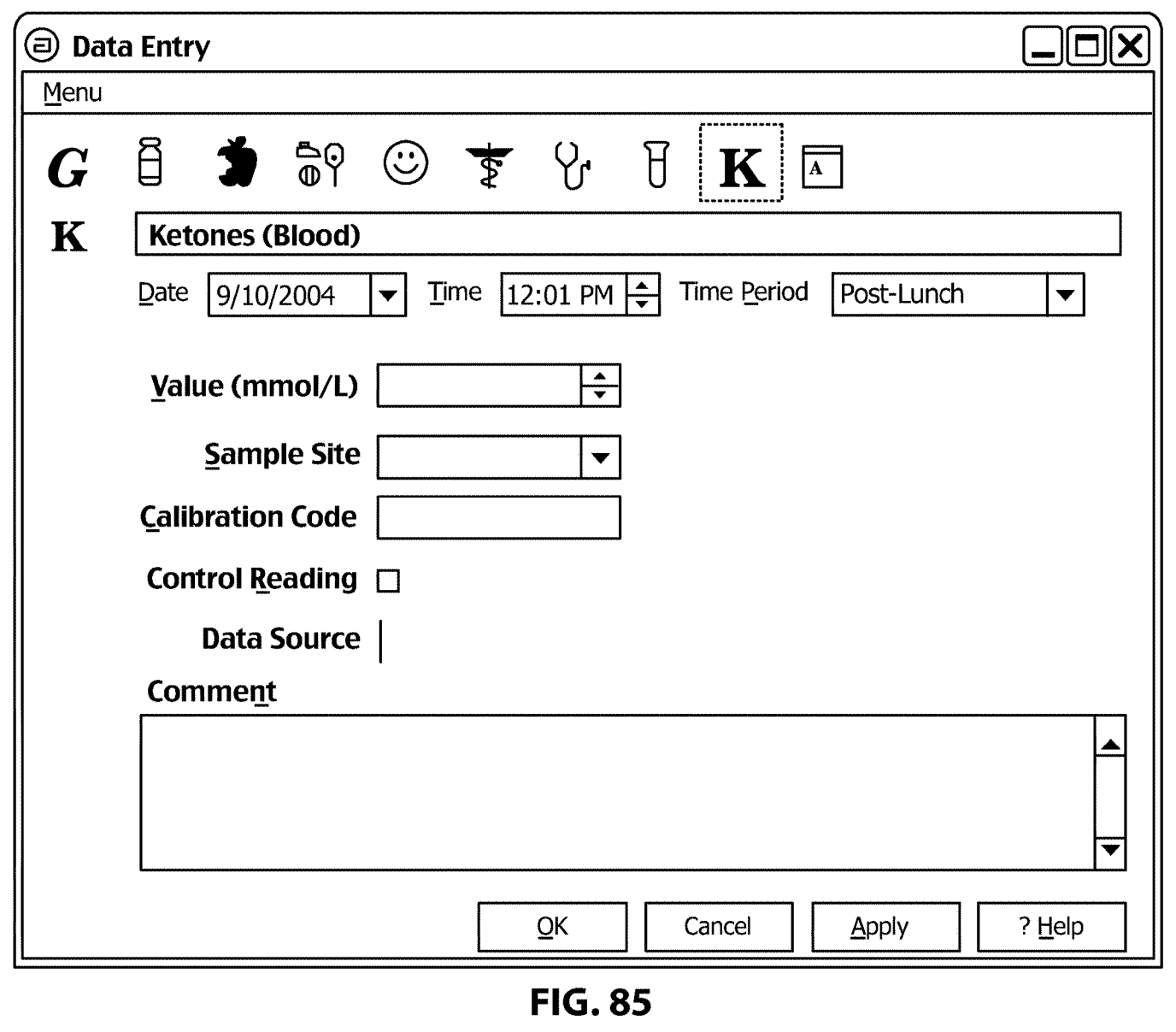
Figure 86:
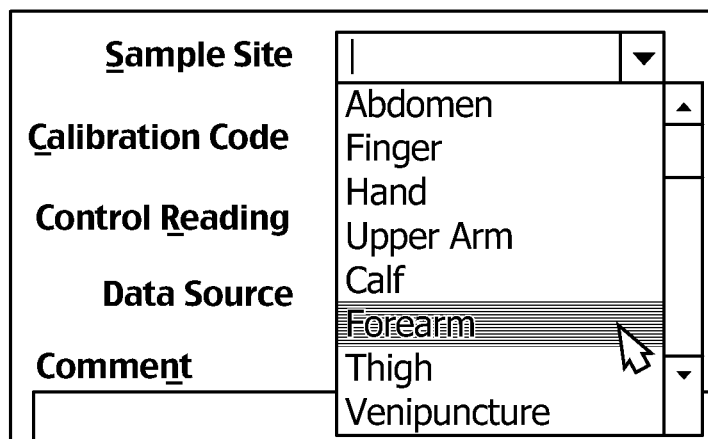
Figure 87:
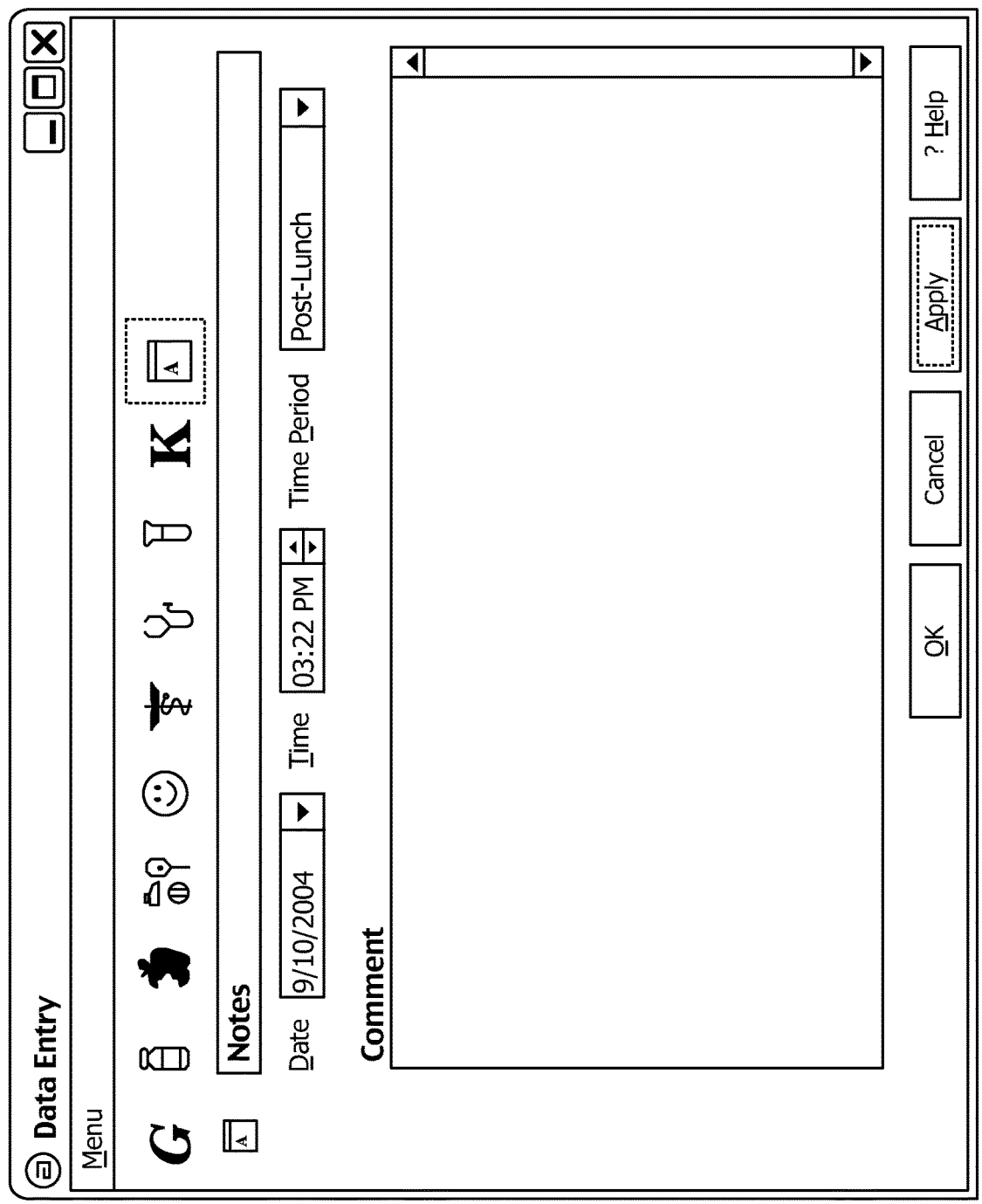

One meal may include more than one item (beverage, entree, fruit, etc.). To select several items to describe one meal, a food is selected in the Food Item list as well as the number of servings eaten. The Carbs and Total Carbs automatically display. The cursor is placed in the Total Carbs field to the right of the carbs displayed there. Then, another item is selected and so on. As items are added, the total carbs for the meal are shown as illustrated at FIG. 79. Other activities may be recorded including Exercise Activity (FIG. 80), State of Health (FIG. 81), a Medication event (FIG. 82), a Medical Exam (FIG. 83), a Lab Test Result (FIG. 84), a Ketone Reading (FIGS. 85 and 86) and notes (FIG. 87).

To make manual data entry faster and easier, a user can modify several of the drop-down lists by adding new entries or by hiding entries he or she does not use. The following lists may be modified.

| Exercise Types | Test Types |
| Food Items | Medications |
| Insulin Names | Exam Types |

Figure 88:
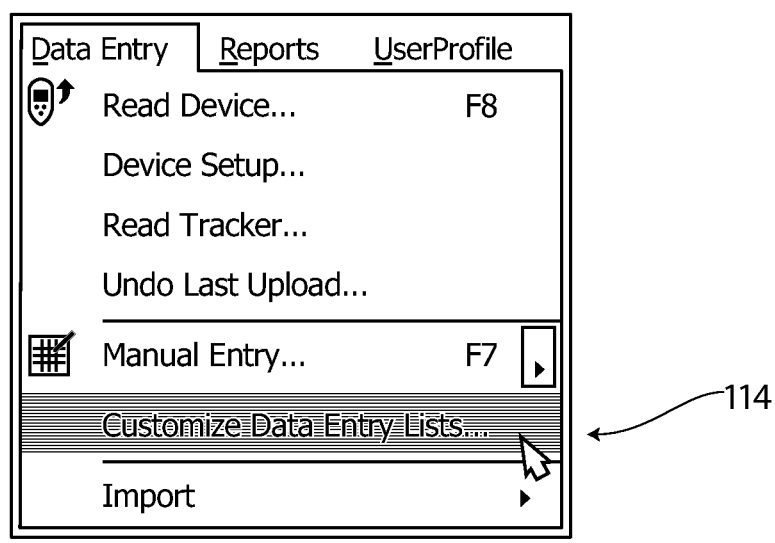
Figure 89:
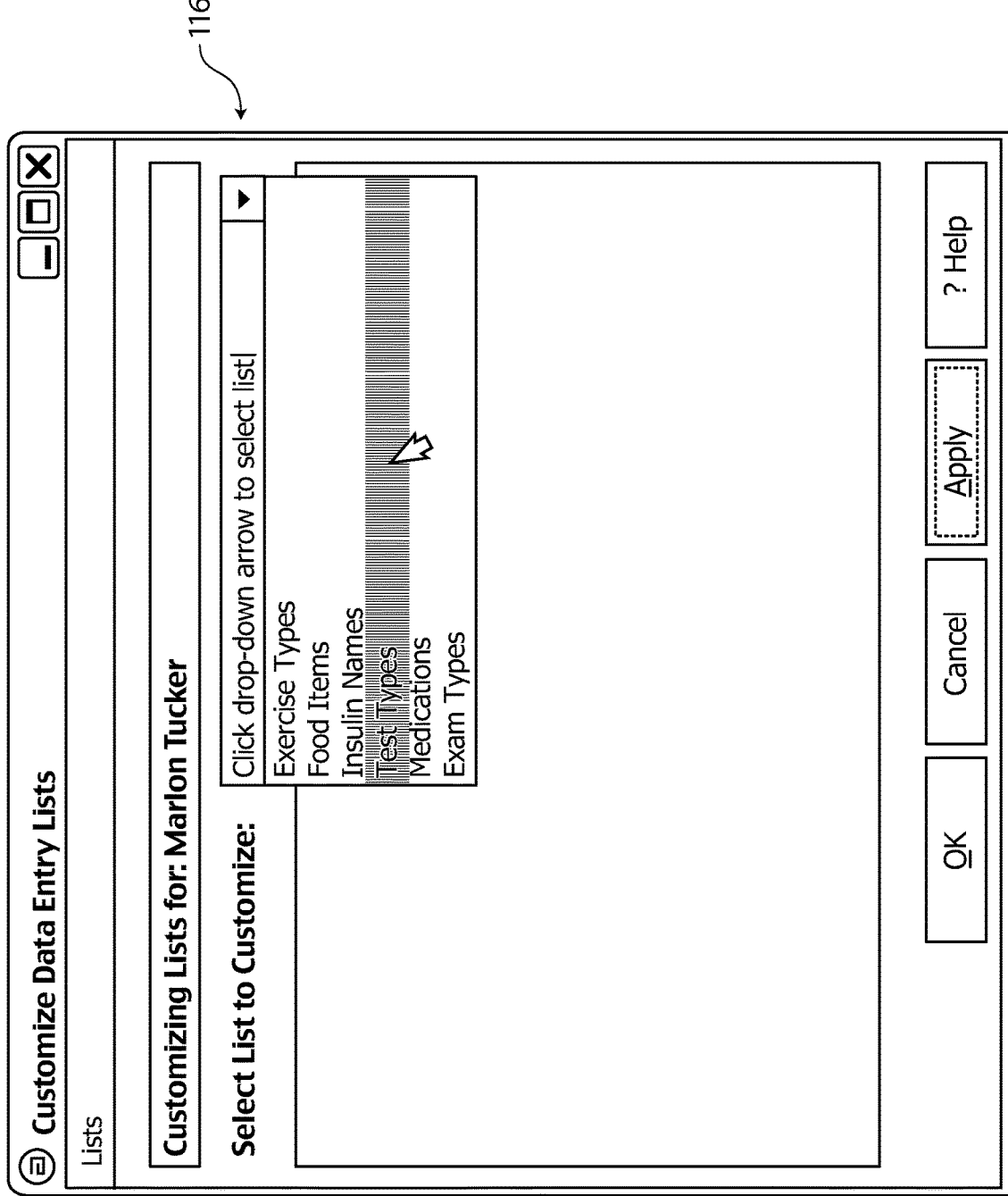
Figure 90:
Figure 91:
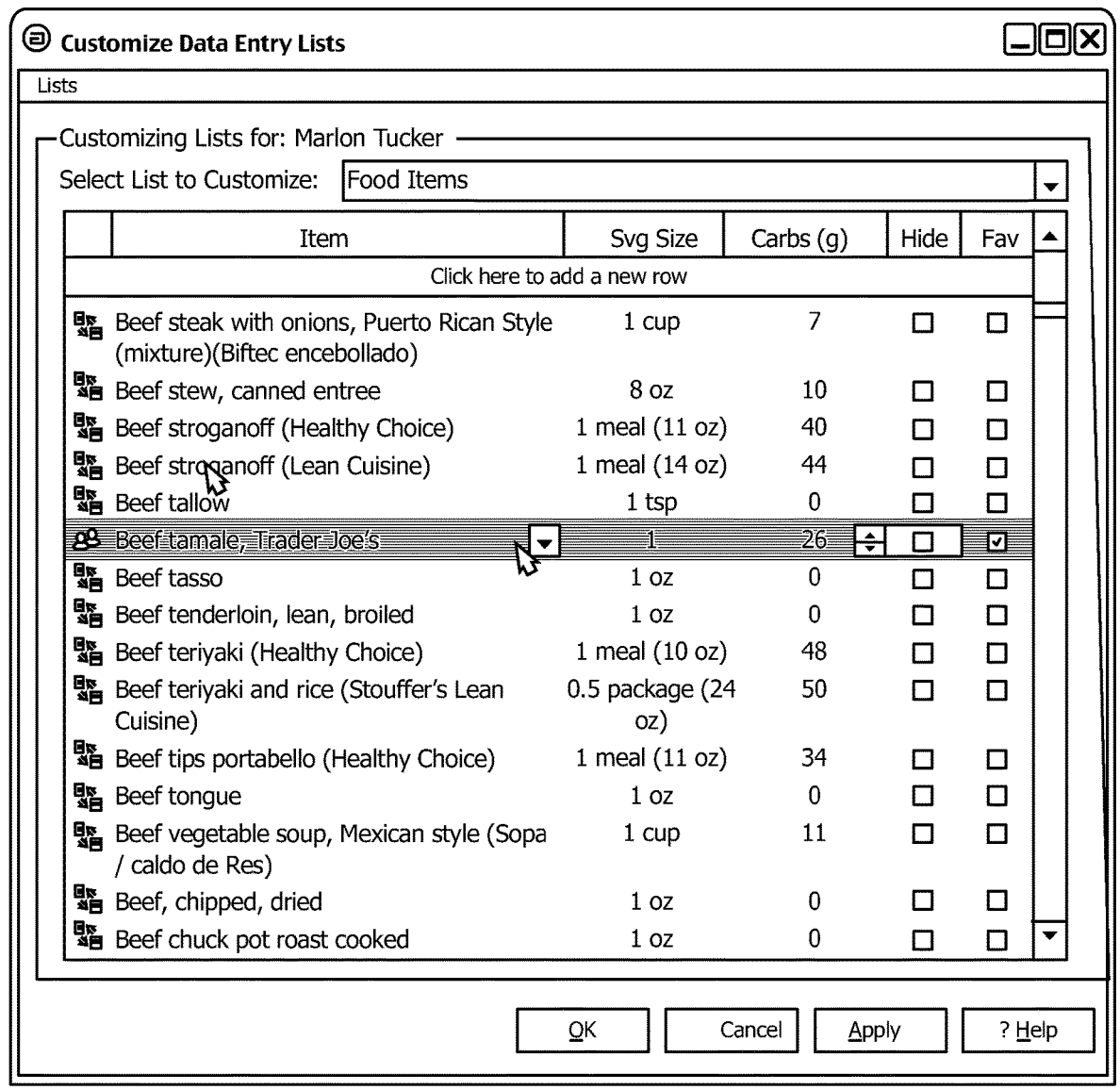
Figure 92:
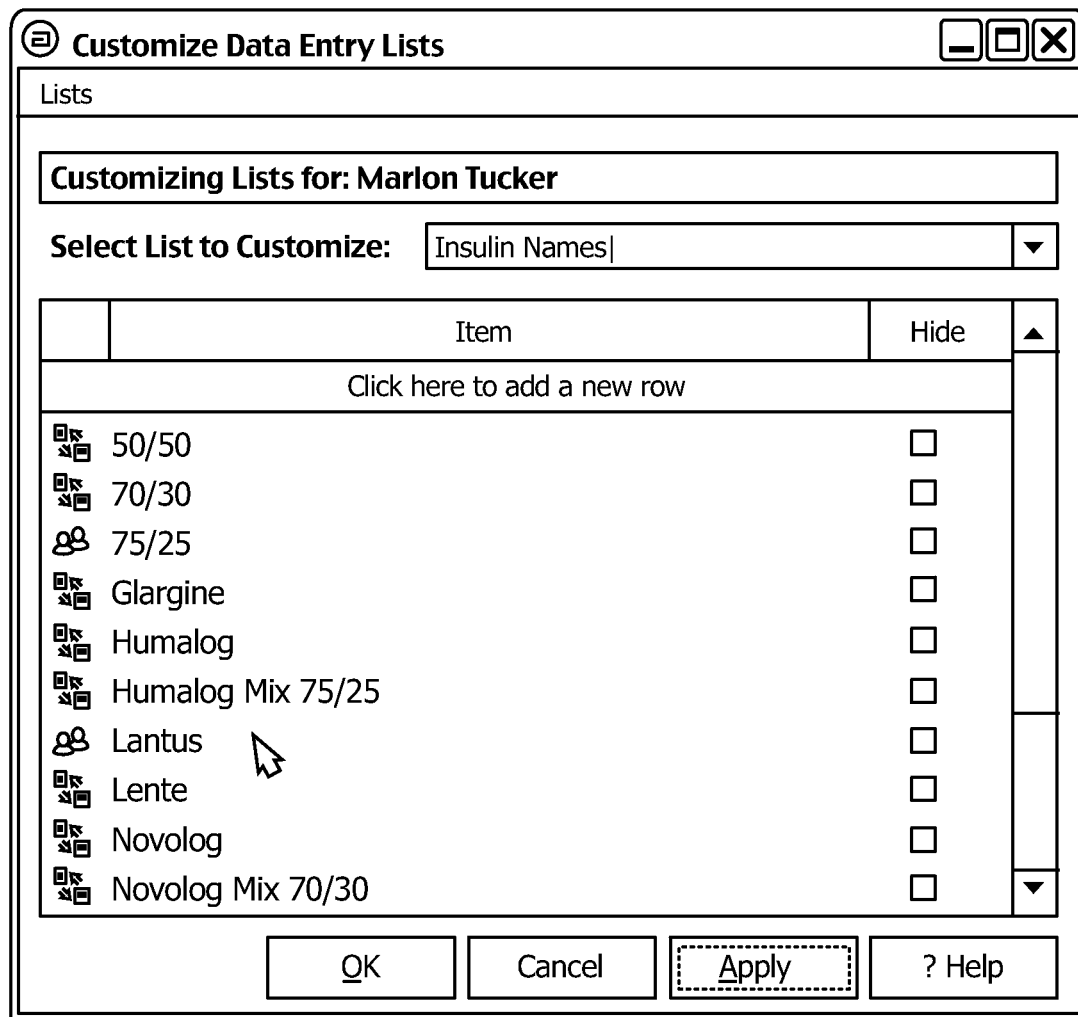
Figure 94:
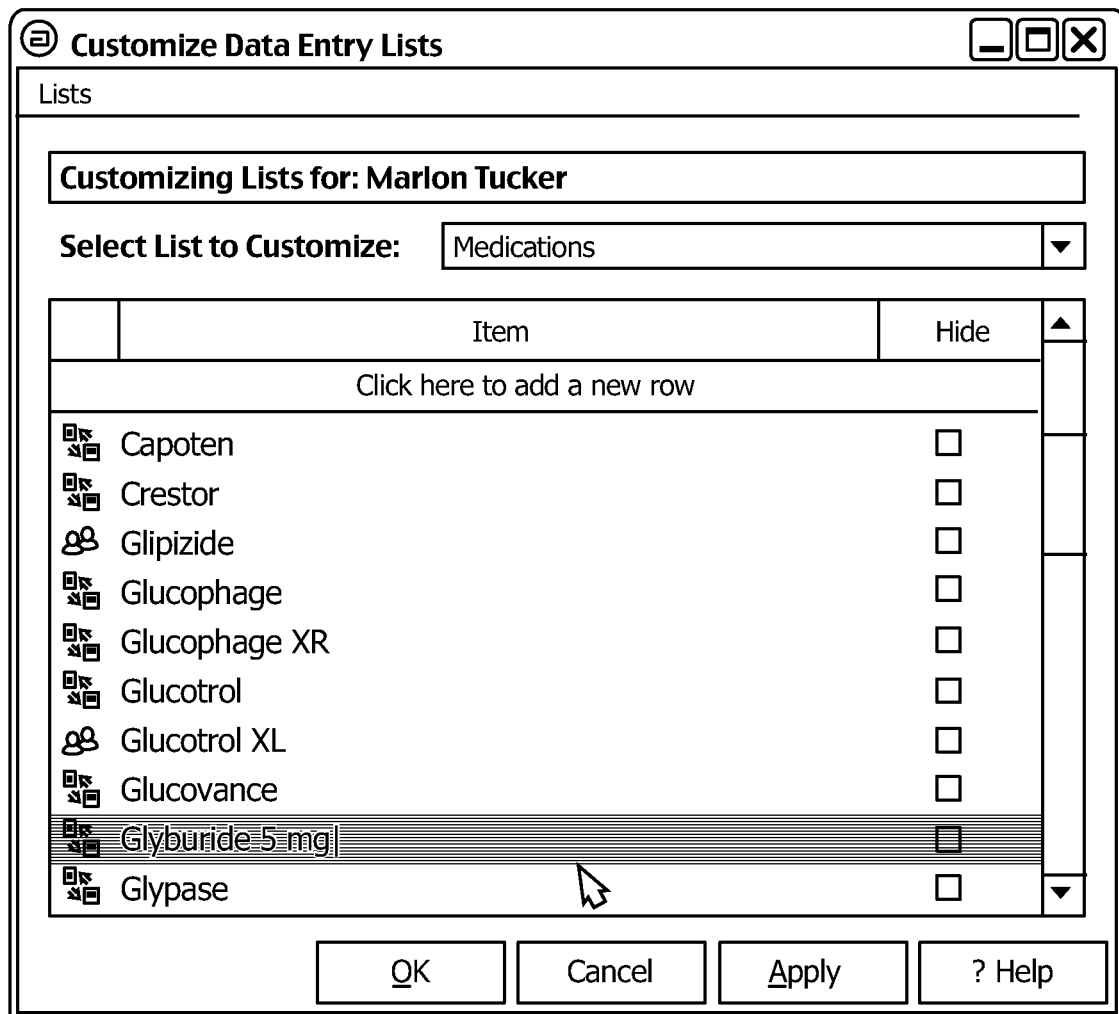

A list may be customized by selecting Customize Data Entry Lists 114 from the DataEntry drop-down box as illustrated at FIG. 88. The desired list is selected from the Select List to Customize drop-down list 116 illustrated at FIG. 89. FIGS. 90-95 illustrate different lists from the above table that may be customized.

Importing a Database

Figure 96:
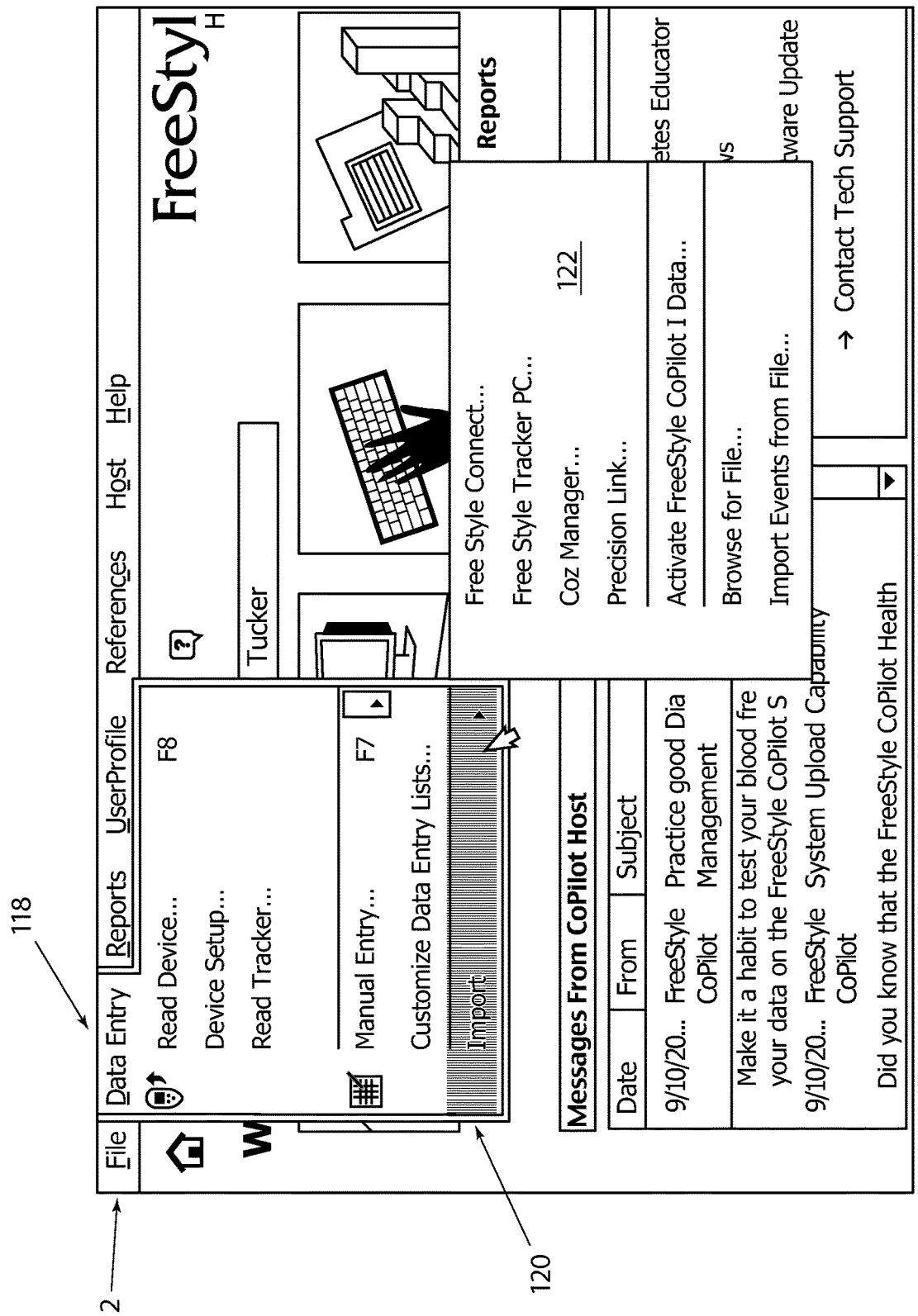
Figure 97:
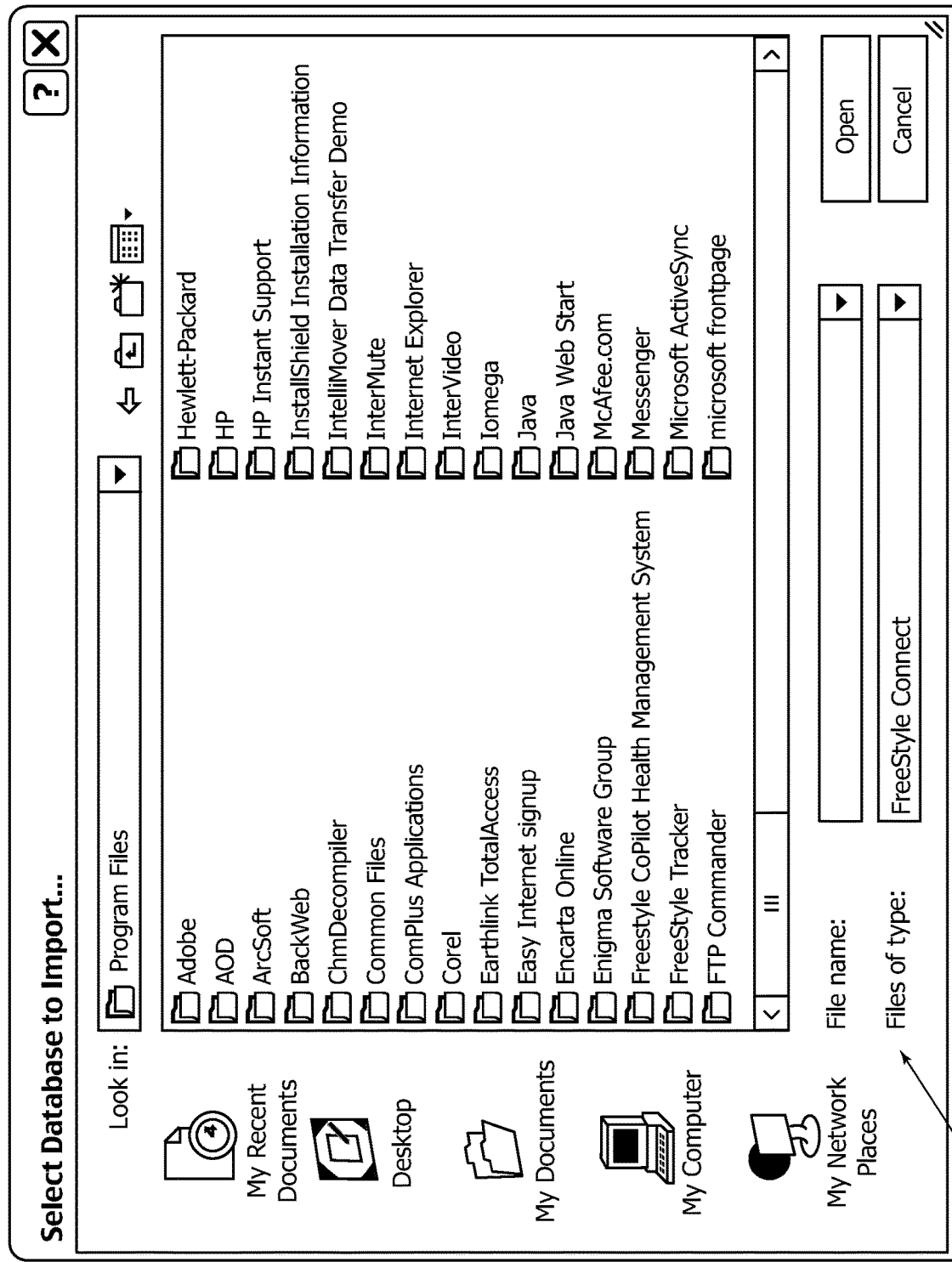
Figure 98:
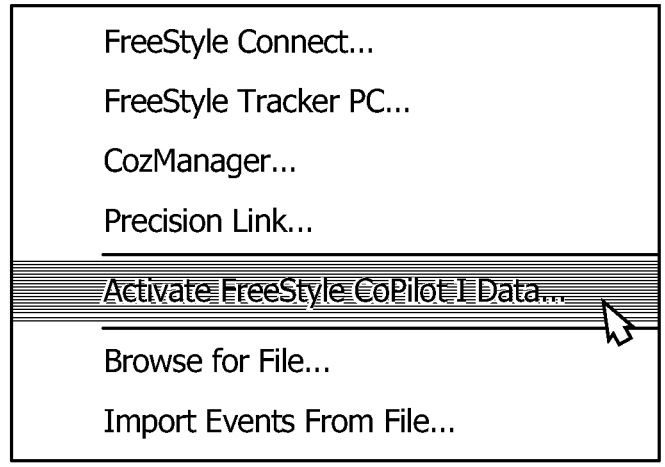
Figure 99:
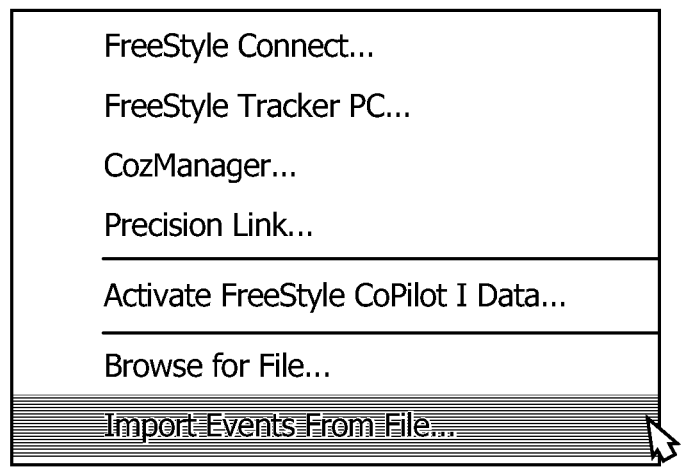
Figure 100:
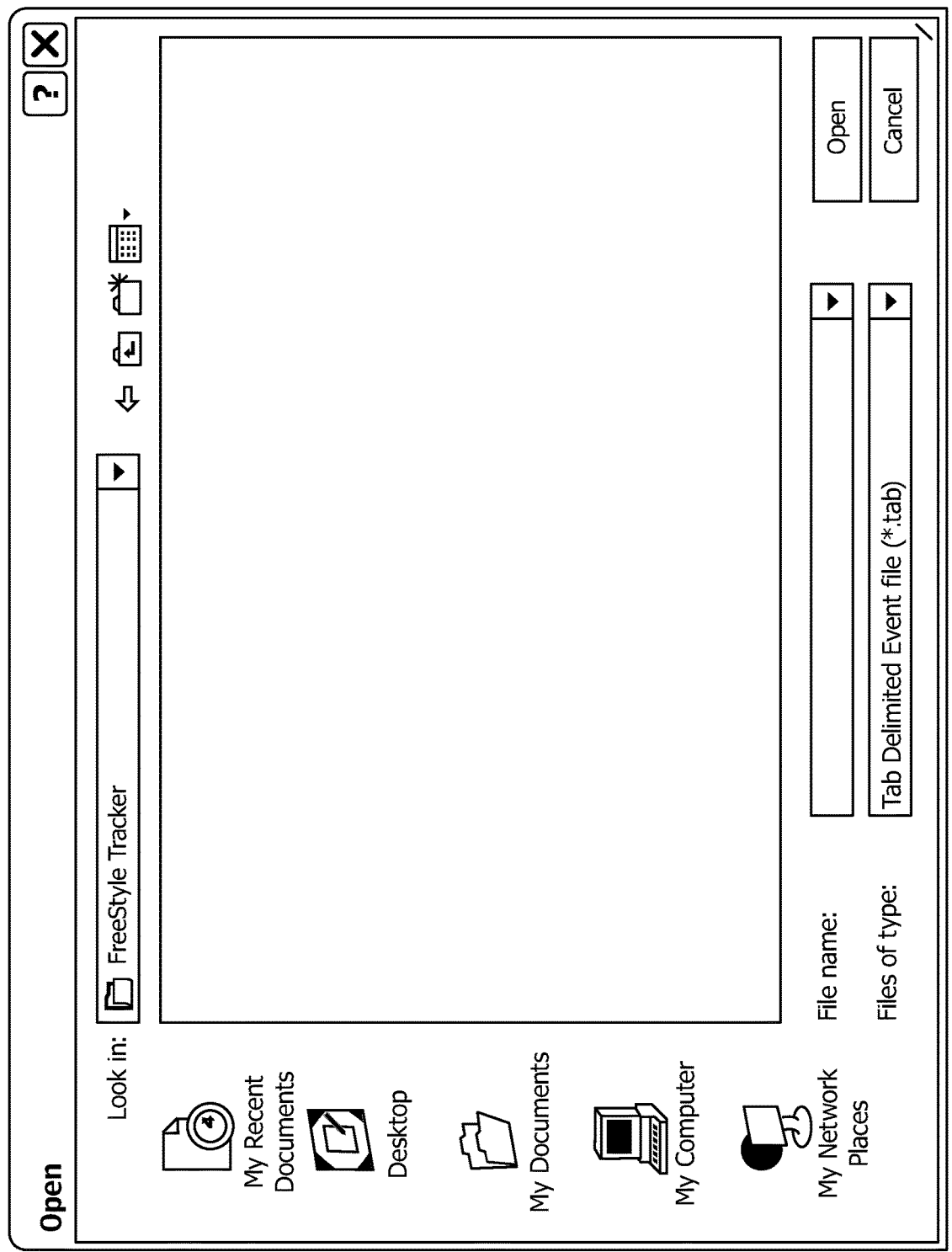

Some databases can be imported directly into the System. Databases from certain programs may be automatically detected by the System as long as the software for the programs that created them is installed on the user's PC. These programs are referred to as supported databases. To import a database, DataEntry 118 is selected on the main menu bar 2 of the Home page; and then Import 120 is selected from the drop-down box. From the Import drop-down box 122, the name of the device to upload the database from is selected as illustrated at FIG. 96. If the database is detected, the System will simply ask the user to confirm the import operation. If the database is not detected, the file browser opens as illustrated at FIG. 97. The user then browses to the directory where the file is located, selects the file type in the Files of Type window 124, and if the file is located in that directory, it will be displayed and can be opened. FIG. 98 illustrates an Import Drop-Down Box for Activating FreeStyle CoPilot I Data, and FIG. 99 illustrates an Import Drop-Down List for Importing Events From a File. FIG. 100 illustrates a File Browser Window for selecting a file type for automatic import according to file type.

Exporting Data

Figure 101:
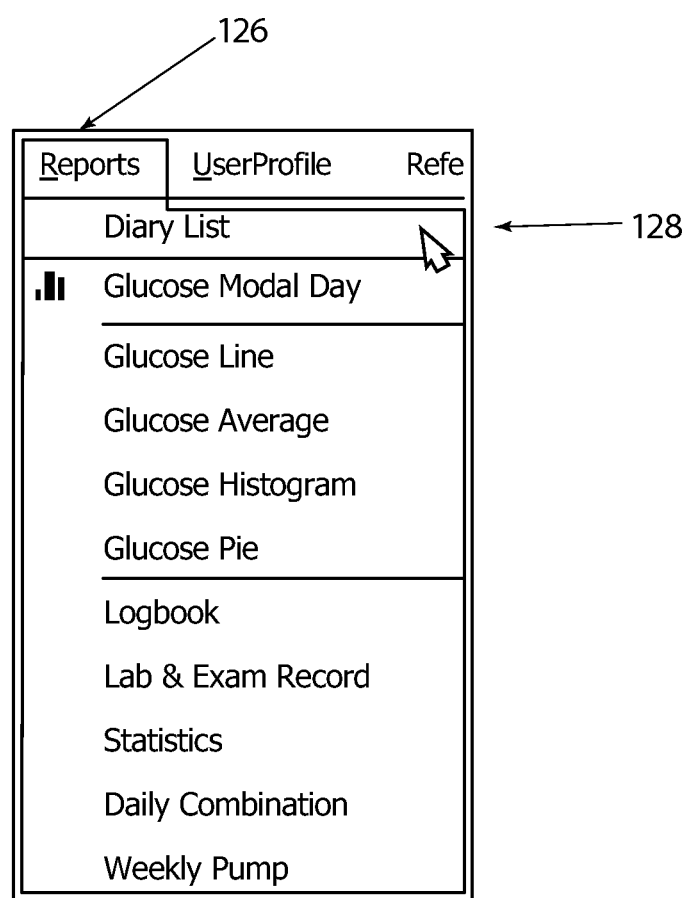
Figure 102:
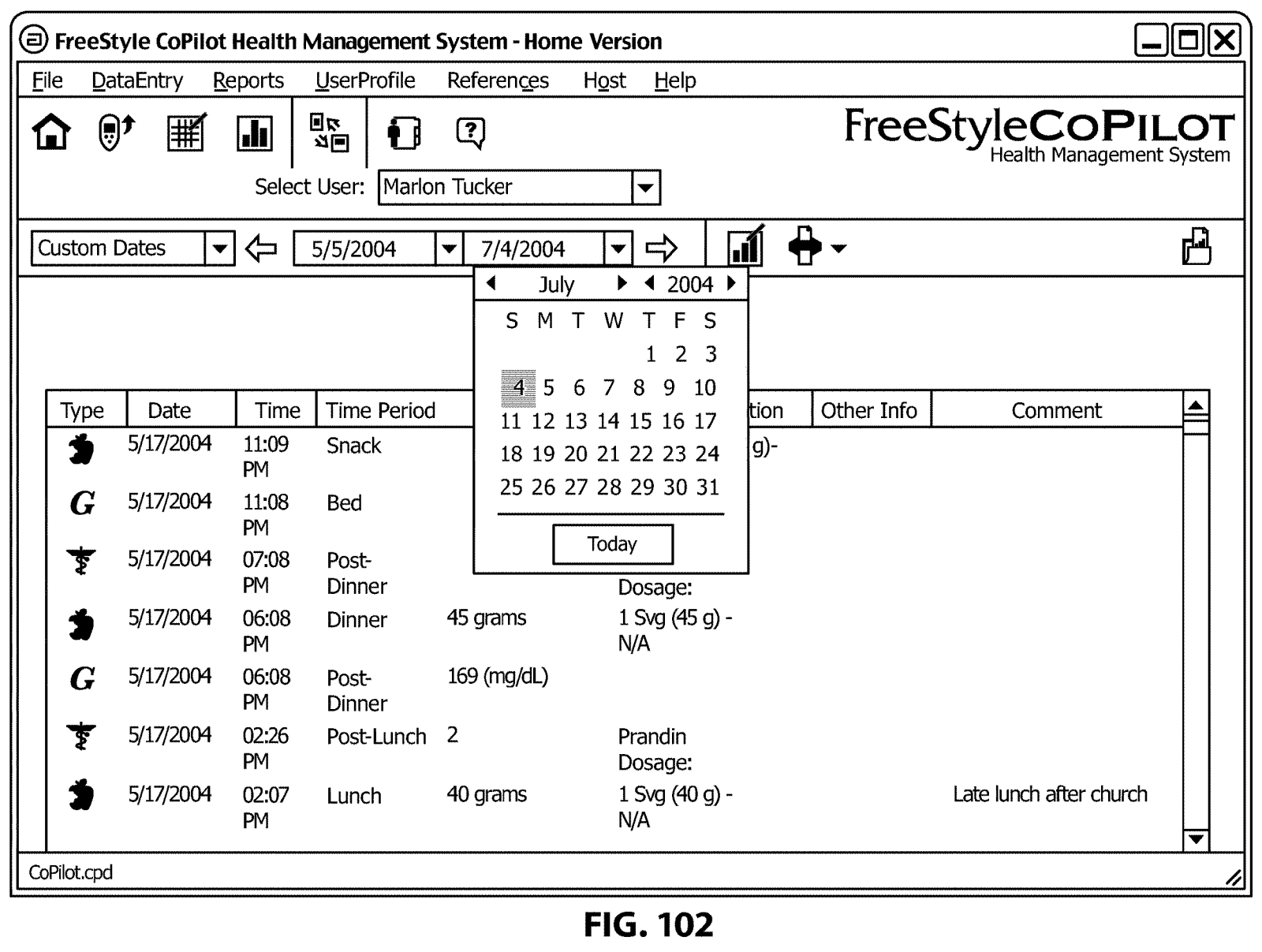
Figure 103:
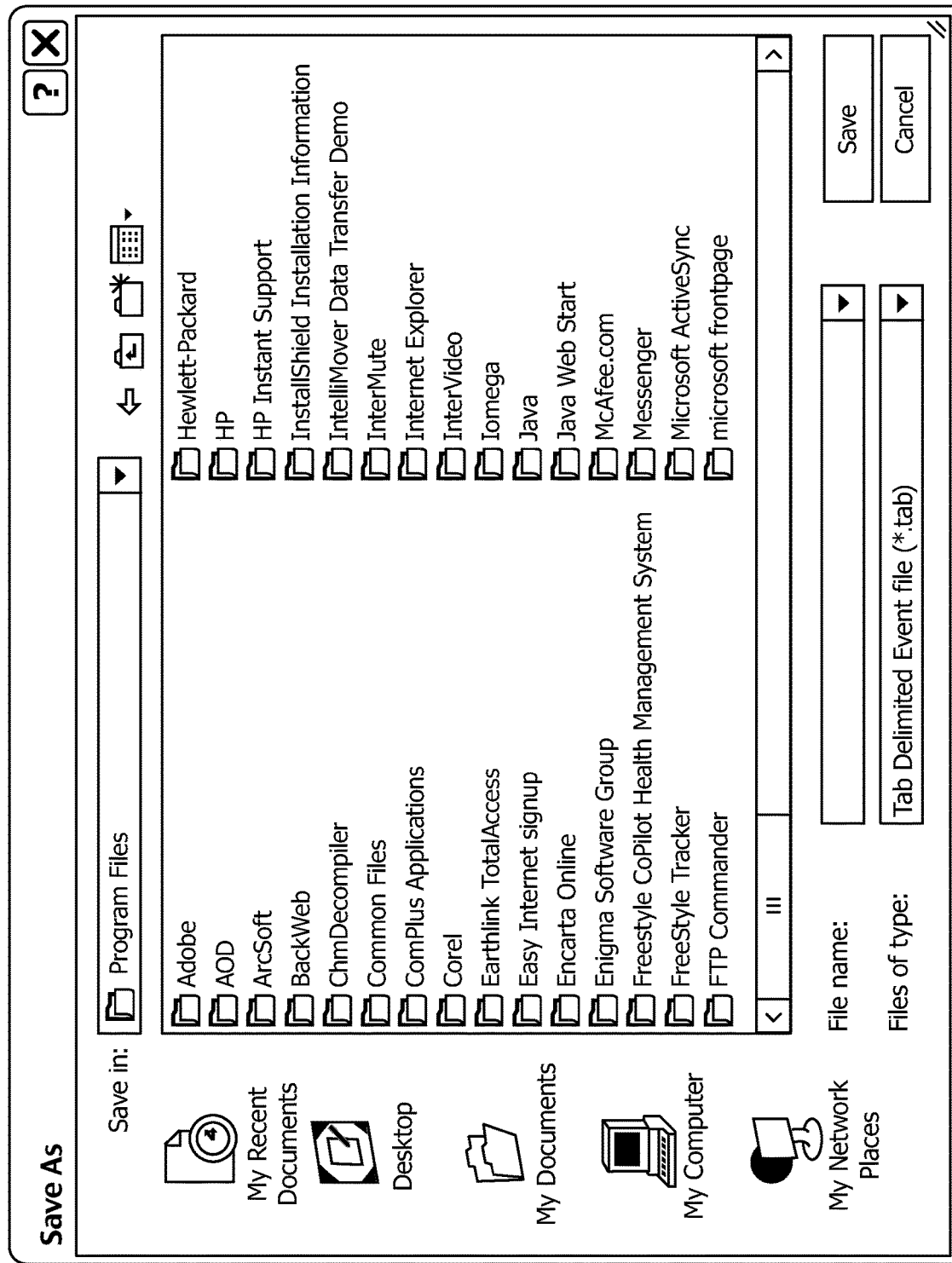

Exporting data is similar to archiving data (see below), except that exported data is not removed from the System's database. To export data, a user selects Reports 126 on the main menu bar; then chooses Diary List 128 from the drop-down box, as illustrated at FIG. 101. The Diary List displays, which is a log of the events that have been entered. The date may be adjusted to include the data desired to be exported, as illustrated at FIG. 102. A user selects Export from the File menu on the Home page. When file browser opens, a user can browse to the directory where the file is to be saved as illustrated at FIG. 103.

Reports

Figure 104:
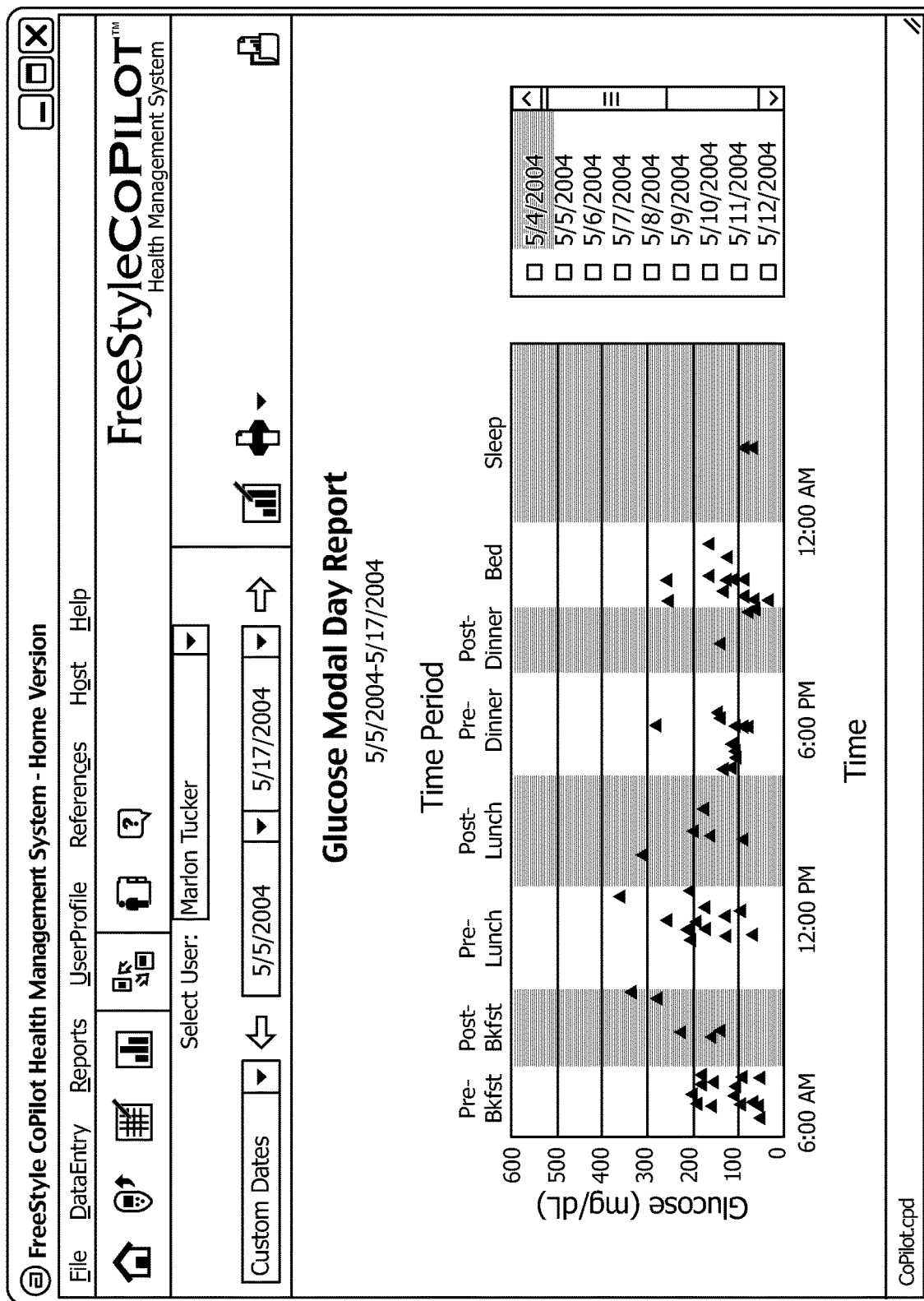

With the FreeStyle CoPilot System, data entered manually or uploaded from a device can be displayed on the screen in a variety of ways. Statistical and other calculations are automatically performed on the data, and the results are put into tables and graphs. A report is one or a set of these tables and/or graphs designed to present information helpful for health management. A reports window is illustrated at FIG. 104 as a Glucose Modal Day Report (Default Report).

A report can be customized to a user's preferences. Many variables can be adjusted in real time as the report is studied. Data preferably cannot be changed in reports except the Diary List. Corrections or additions can be made by accessing the Data Entry screen for the event. The changes display immediately on any affected report.

Once opened, a report remains open until it is closed by the user. Any number of reports can be open at the same time; while preferably only one is visible. Each open report shows as a tab at the top of the screen. Open reports apply an active date range, data filter options, and display features. In a preferred embodiment, changing these settings in one report changes them for one or more other open reports.

Opening a Report

Figure 105:
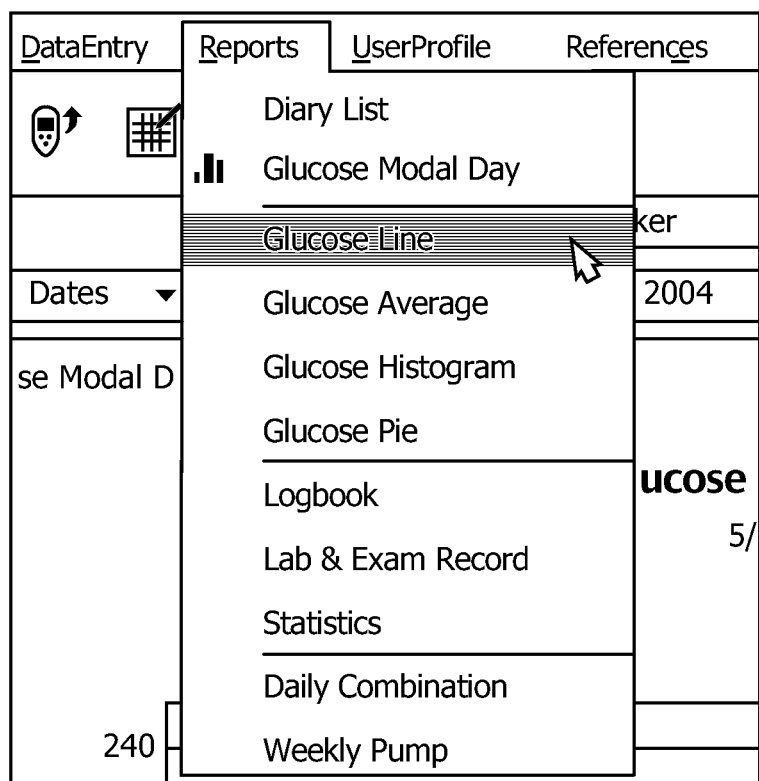
Figure 106:
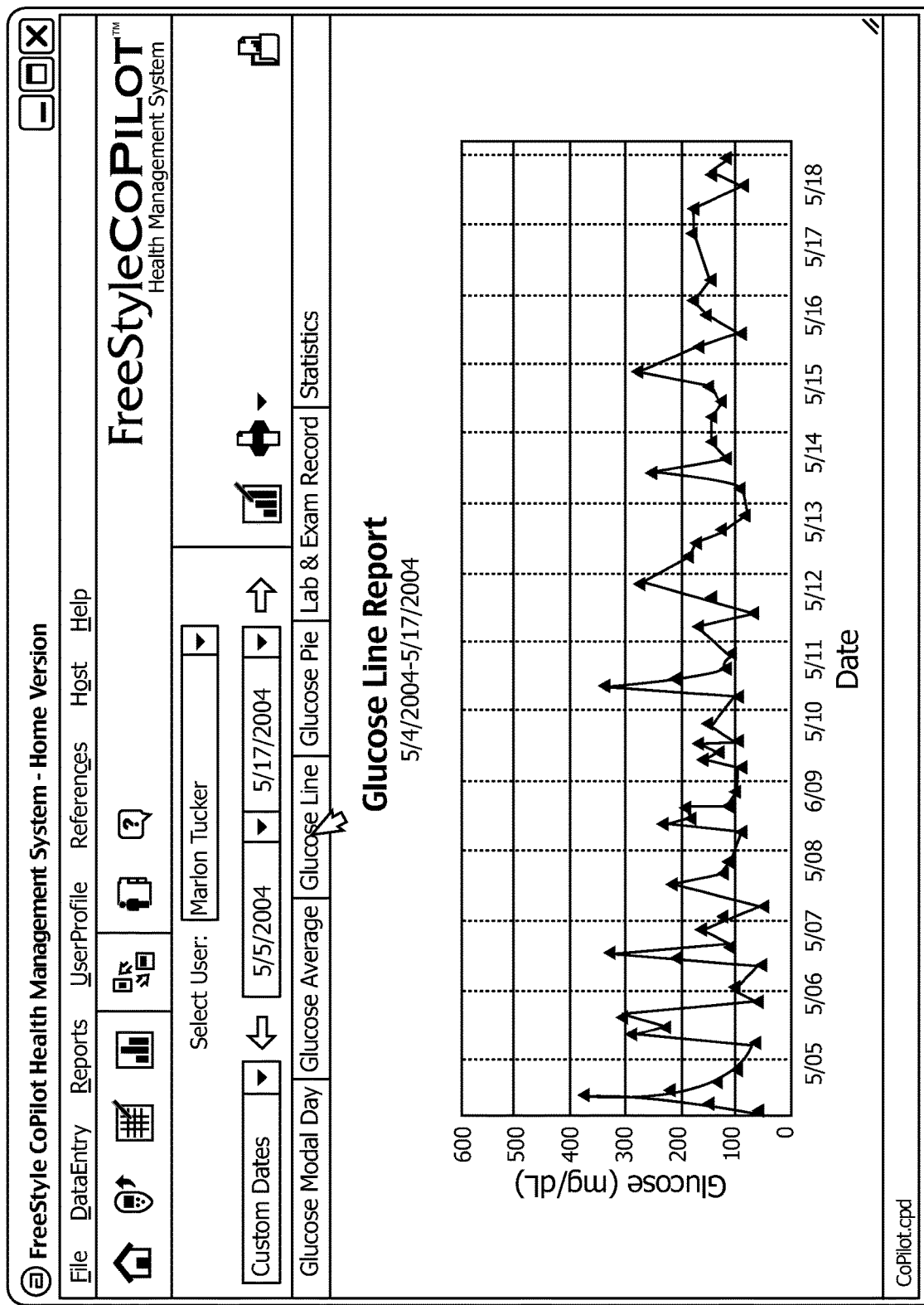

To call up a default report from the Home page, the View Reports large button is clicked. The user may select a default report and date range interval. To open another report, a name may be selected from a drop-down box under Reports on the main menu bar as illustrated at FIG. 105. The first report remains open but hidden, except for its tab (see FIG. 106). The new report displays with the same date range, active data filters, and display features. To redisplay a report, the user clicks its tab. To close an active report, the user clicks the Close Report icon on the Reports toolbar.

Navigating a Report

The reports screens offer numerous tools for navigation, including tools for setting the date range, interactive data elements, and signal colors that help users interpret reports at a glance. Displaying the legend will help a user understand the report.

Figure 107:
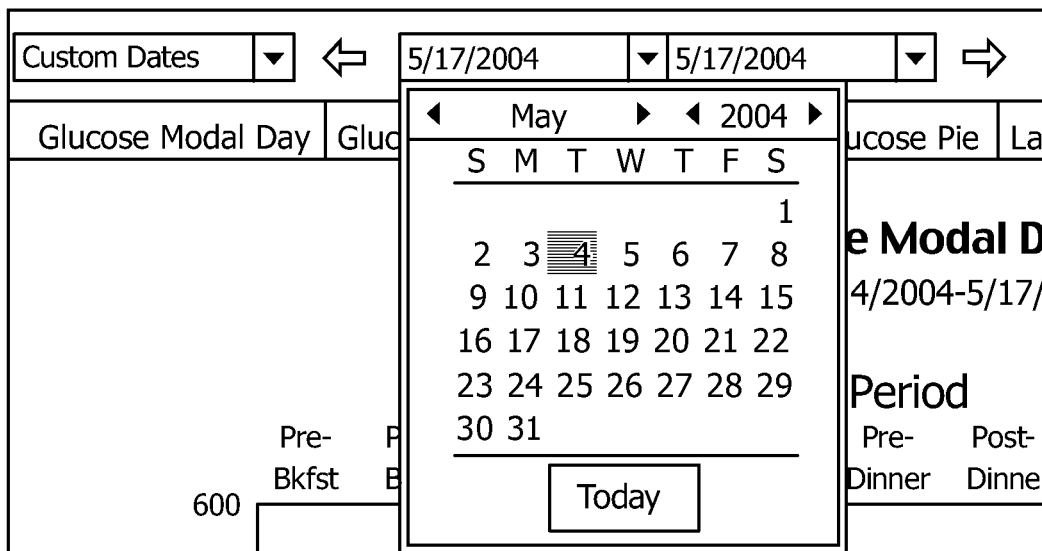

The data range may be adjusted to include any date and any date interval (see FIG. 107). To view entries over a date range ending on the current date (up to and including today's data), a user may select an interval of interest (for example, Last 2 Weeks, Current Month, etc.) from an Interval drop-down box on the Reports toolbar.

To move back in time in increments equal to the currently displayed date interval, the user clicks the Previous arrow (for example, if a 2-week date range is currently displayed, the user clicks the Previous arrow to display additional 2-week intervals). To move forward in time, the user may click the Next arrow. To select a specific date range (with beginning and ending dates specified), the user clicks or otherwise chooses the respective dates from the drop-down calendars.

Data Elements

The reports preferably have interactive data elements that link to related or more complete information. These elements can include data points on a graph, regions on a chart, and/or cells in a table. A pointer becomes the hand icon when it is hovering over an interactive data element. For example, by hovering the pointer over a triangle (glucose reading data element), a user can display the value, date, and time of the reading in a pop-up bubble. To go to the Glucose Reading event in the Diary List, the user can double-click the triangle. For example, carbohydrate events are represented by peach-colored circles; the size of each circle is proportional to the carbohydrate value. Insulin data is represented by dark green and dark red bars. Glucose readings are represented by circles (manual entries) or triangles (uploaded entries), which can be linked by a solid or dotted line.

Glucose readings are separated into target ranges, which are represented on graphs and tables either in signal colors or in distinctive patterns for black-and-white printing. A user can choose to display data in three ranges (High, Within, and Low) or five ranges (Very High, High, Within, Low, and Very Low). These choices can be changed at any time on the Miscellaneous tab of the Report Configuration form (see FIG. 111) by checking or unchecking the Show Hypo/Hyper box. Each target range is associated with a distinctive signal color: Very High (turquoise), High (purple), Within (green), Low (peachy-gold), and Very Low (pink). If a user selects to display glucose data in three ranges (the Show Hypo/Hyper box is not checked), Very High readings display as High readings (purple) and Very Low readings display as Low readings (peachy-gold).

Figure 108:
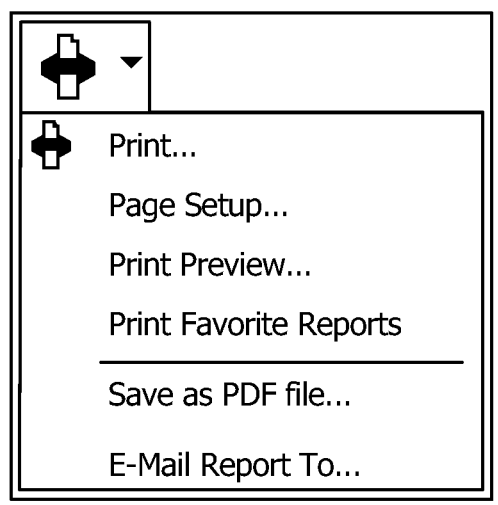

Reports may be printed (using a Print drop down box such as that illustrated at FIG. 108) and sent using standardized printing and email or fax architectures. A user may print one copy of each of his or her favorite reports on a default printer by clicking Print Favorite Reports. To save the open report in the Adobe Acrobat (PDF) file format, a user can click Save as PDF file. A user can select this option if the E-Mail Report to option (below) does not automatically create a *.pdf file. A user can select this option if there is a printing problem and then the report may be printed from Adobe Acrobat. To email a report as an attachment, a user can click E-Mail Report to, and the report will be attached to the e-mail message as a *.pdf file. (The user does not have to Save as PDF file before selecting E-Mail Report to). The E-Mail Report option is designed to automatically access a user's e-mail account and open a new e-mail message screen. The report is automatically attached to the message as a *.pdf file. If the e-mail account is not detected automatically, the user may e-mail the report manually.

Figure 109:
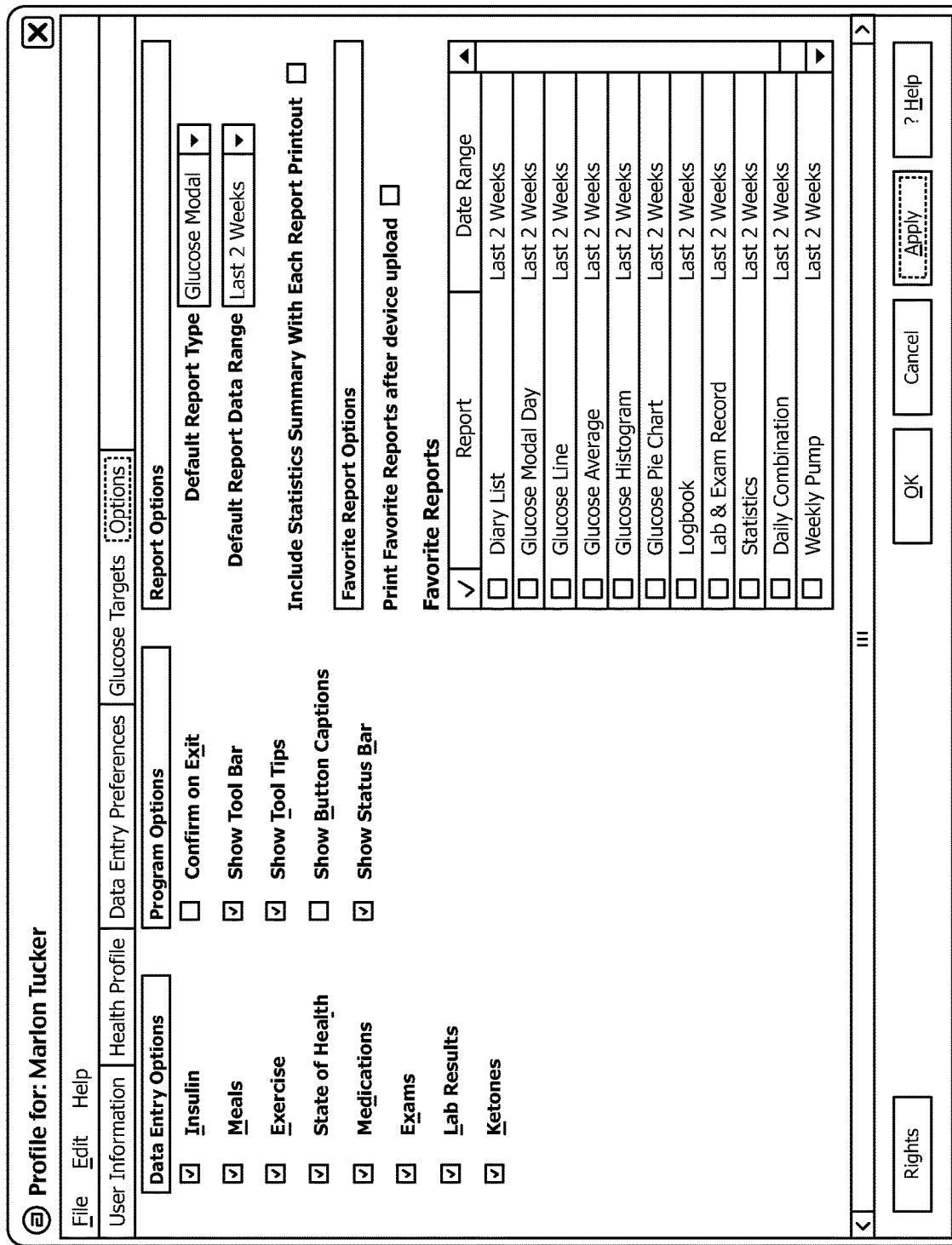

Reports can be personalized to a user's preferences by making choices for Report Options on the Profile for screen and by activating data filters and display features on the Report Configuration screen. FIG. 109 illustrates a User Profile Screen with Options Tab Active. Report options include default report type, default report data range, include statistics summary with each report printout, Print Favorite Reports After Device Upload, and Favorite Reports.

Data filters are tools for selecting the types of data a user wants to include in a report. A user selects the data filters desired by clicking a Report Configuration icon on the Reports toolbar and choosing items from the Event Types, Time Periods, and Week Days sections on the Data Filter tab (see FIG. 110). Data filters and display features (see below) preferably apply to all reports except the HCP Group Analysis Report. Changing data filter or display settings in a report changes them for other open reports. Not all filters are configurable in all reports. Several data filters can be applied together. For example, a user could uncheck Exercise events in the Event Types filter and check only Tuesday and Friday in the Week Days filter.

Figure 111:
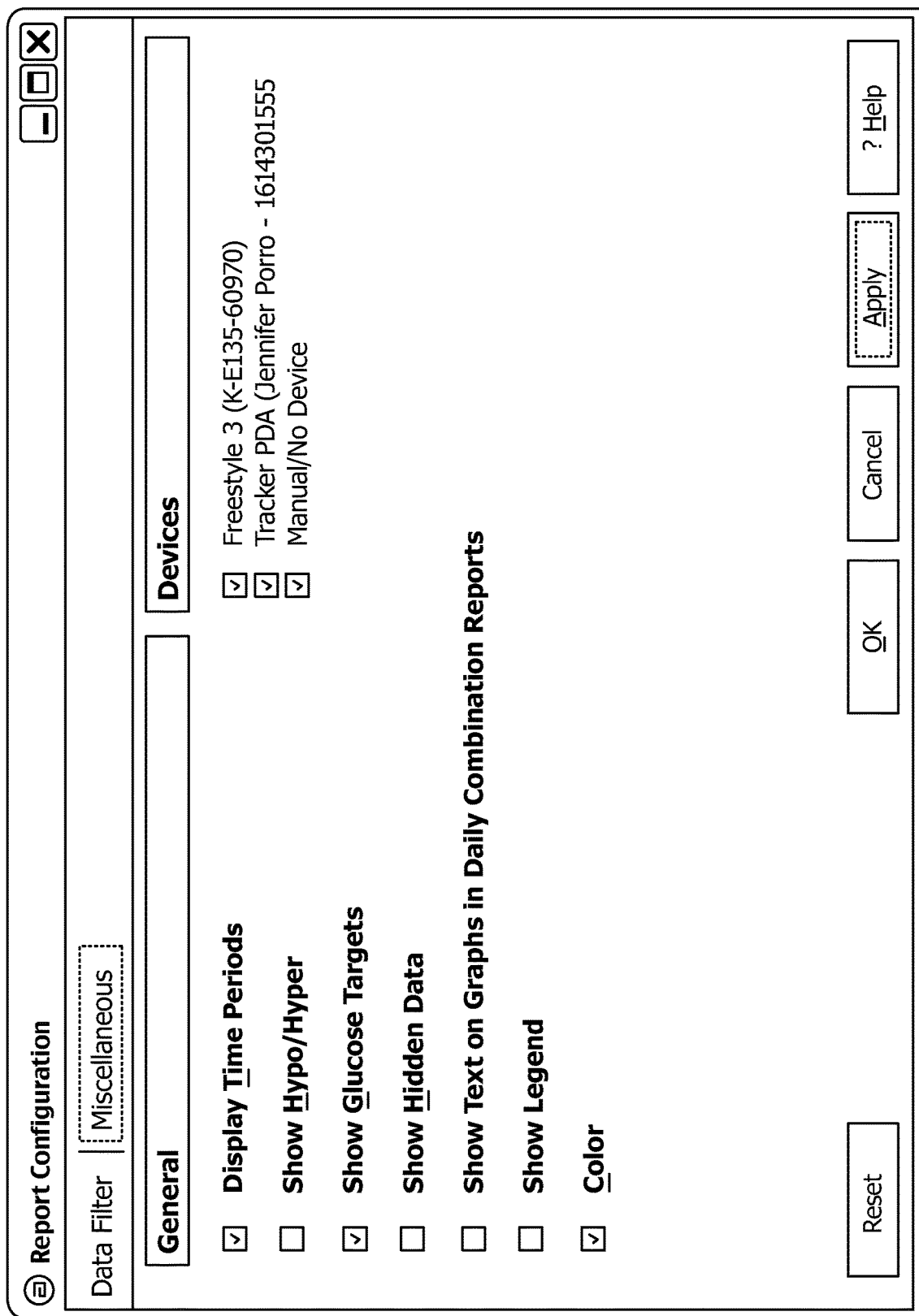
Figure 112:
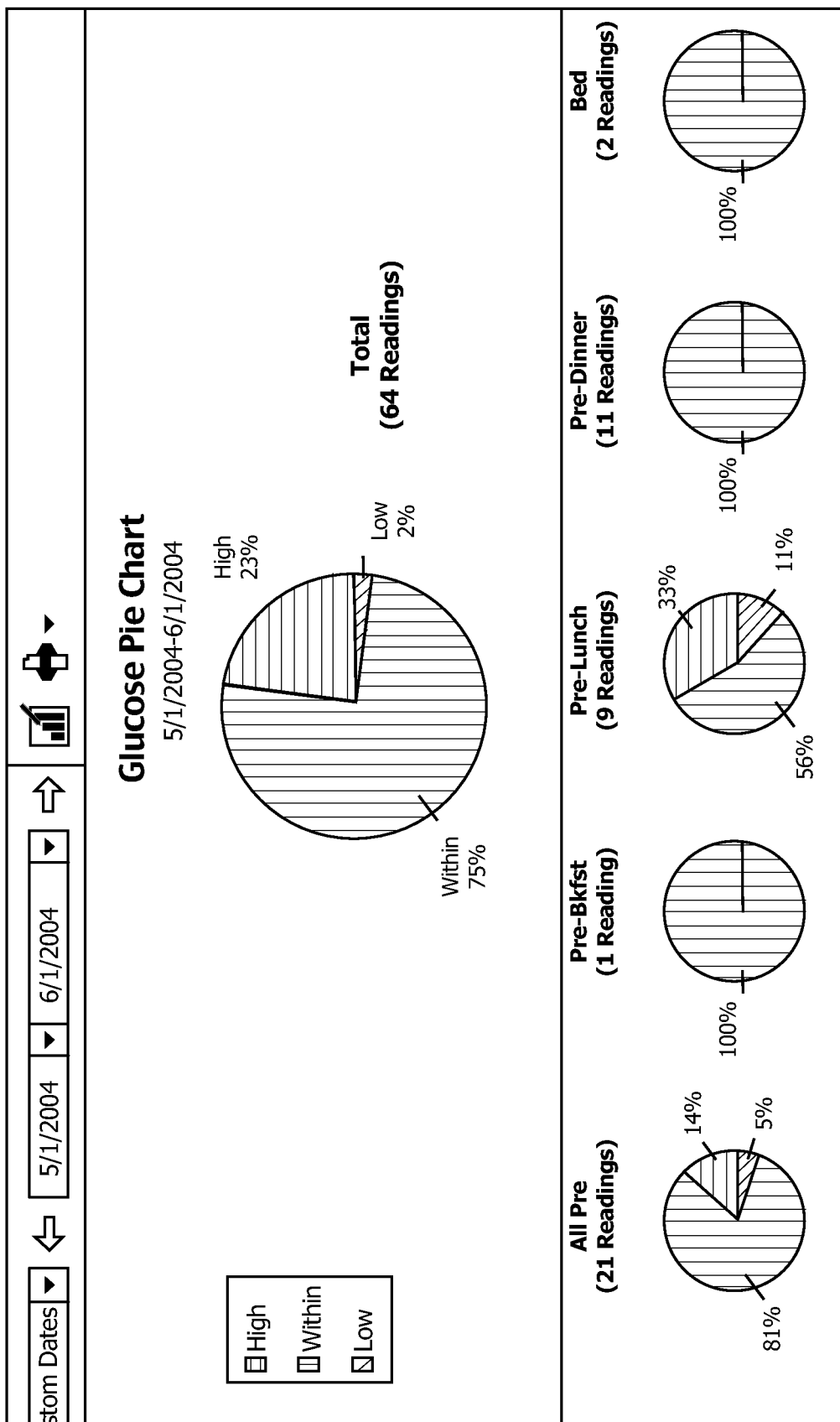

Some display features are configured on the Miscellaneous tab of the Report Configuration screen, as illustrated at FIG. 111. These include options to display time periods, show hypo/hyper, show glucose targets, show hidden data, show text on graphs in daily combination report, show legend and color. FIG. 112 illustrates a black-and-white display having distinctive patterns (screen detail).

Glucose Target Modes

The following is a table of reports that use glucose targets and the modes they use.

| Reports: Glucose Target Modes Used | | |
|---|---|---|
| Report | Home Version Glucose Target Mode | HCP Version Glucose Target Mode |
| Diary List | User's choice | HCP's choice |
| Glucose Modal Day | User's choice | HCP's choice |
| Glucose Line | Standard Mode | Standard Mode |
| Glucose Average | Standard Mode | Standard Mode |
| Glucose Histogram | Standard Mode | Standard Mode |
| Glucose Pie | User's choice | HCP's choice |
| Logbook | User's choice | HCP's choice |
| Lab & Exam Record | Not applicable | Not applicable |
| Statistics | User's choice | HCP's choice |
| Daily Combination View | User's choice | HCP's choice |
| Weekly Pump View | Standard Mode | Standard Mode |
| HCP Group Analysis | Not applicable | Standard Mode |

Definition of a Day

Depending on the report, a day (24 hours) is calculated from midnight to midnight or pre-breakfast to pre-breakfast. The various reports define a day as follows:

| Reports: Definition of a Day | |
|---|---|
| Report | Definition of a Day |
| Diary List | Midnight to Midnight |
| Glucose Modal Day | Pre-breakfast to Pre-breakfast |
| Glucose Line | Midnight to Midnight |
| Glucose Average | Pre-breakfast to Pre-breakfast |
| Glucose Histogram | Midnight to Midnight |
| Glucose Pie - Total Pie | Pre-breakfast to Pre-breakfast |

| Reports: Definition of a Day | |
|---|---|
| Report | Definition of a Day |
| Logbook | Pre-breakfast to Pre-breakfast |
| Lab & Exam Record | Midnight to Midnight |
| Statistics | Pre-breakfast to Pre-breakfast |
| Daily Combination View | Midnight to Midnight |
| Weekly Pump View | Midnight to Midnight |
| HCP Group Analysis | Midnight to Midnight |

Descriptions of Reports

The Diary List is a table of data entries made over the specified date range. Each row corresponds to one event. FIG. 113 illustrates a Diary List. A day (24 hours) is defined as midnight to midnight. The glucose target mode is user's choice. Columns are for data categories. The Value column displays the value in units appropriate to the event type. For Glucose Reading events, the Value cell is shaded with the signal color for the glucose target range. To call up the original Data Entry screen for a specific event, the user can double-click any cell in the row. Data that was entered manually can be edited. Uploads from devices cannot be edited.

Figure 114:
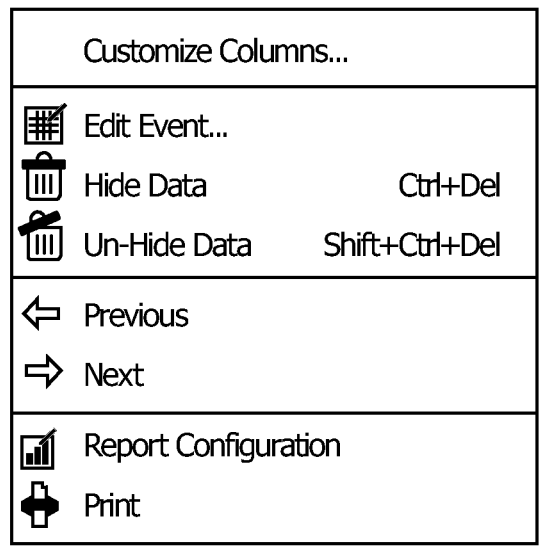

To Hide an event, a user can click any cell in the row, then right-click, and then Click Hide Data on the pop-up menu (see FIG. 114). To Un-Hide the event, the user can click on the Reports toolbar. On the Miscellaneous tab screen, the user can check the box to Show Hidden Data. The Diary List now displays with a Hidden column (far left). Hidden entries display in this column. The user can Right-click the hidden entry and select Un-Hide Data. The event is no longer hidden.

A user can customize columns in the Diary List by changing the order of events in a column, adding and removing columns, and resizing columns. To change the order of the events in the Diary List, the user can click any of the following column heads:

| | |
|---|---|
| Hidden | Hidden entries display at the top. Click to display hidden entries at the bottom. |
| Type | Events are grouped by Event Type. Click to reverse the order. |
| Date | Events display in ascending order (earliest date at the top) or descending order (latest date at the top). Click to reverse the order. |
| Time | The events display in chronological order. Click to group entries by time of day. |
| Time Period | Time periods are arranged in chronological order. Click to list the time periods in alphabetical order. |
| Value | Click to change the order. |
| Description | Events are displayed in ascending alphabetical order. Click to reverse the order. |
| Other Info | Click to reverse the order. |
| Comment | Events with Comments display in ascending alphabetical order. Events with no comments display first. Click to reverse the order. |

Figure 115:
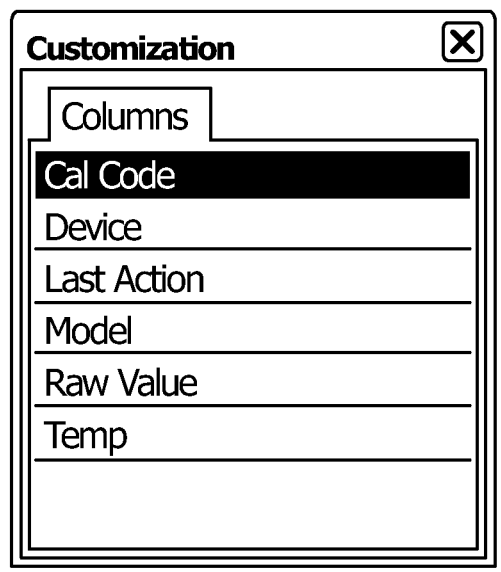

To remove a column from the report, the user can drag-and-drop the column head cell off the table. To add a column to the report, right-click anywhere on the table to call up the pop-up window (see FIG. 114). Select Customize Columns. The Customization list displays (see FIG. 115). From the list, select the column head you want to add. Then drag-and-drop it to the preferred position in the column-head row. Two green arrows display to help you position the column. To move columns left or right in the table, the user can drag-and-drop the column-head cell to the preferred position in the column head row. To adjust the width of any column, the user can use the sizing tool that becomes active when hovering the pointer over the right margin of the column-head cell.

Glucose Modal Day Report

Figure 116:
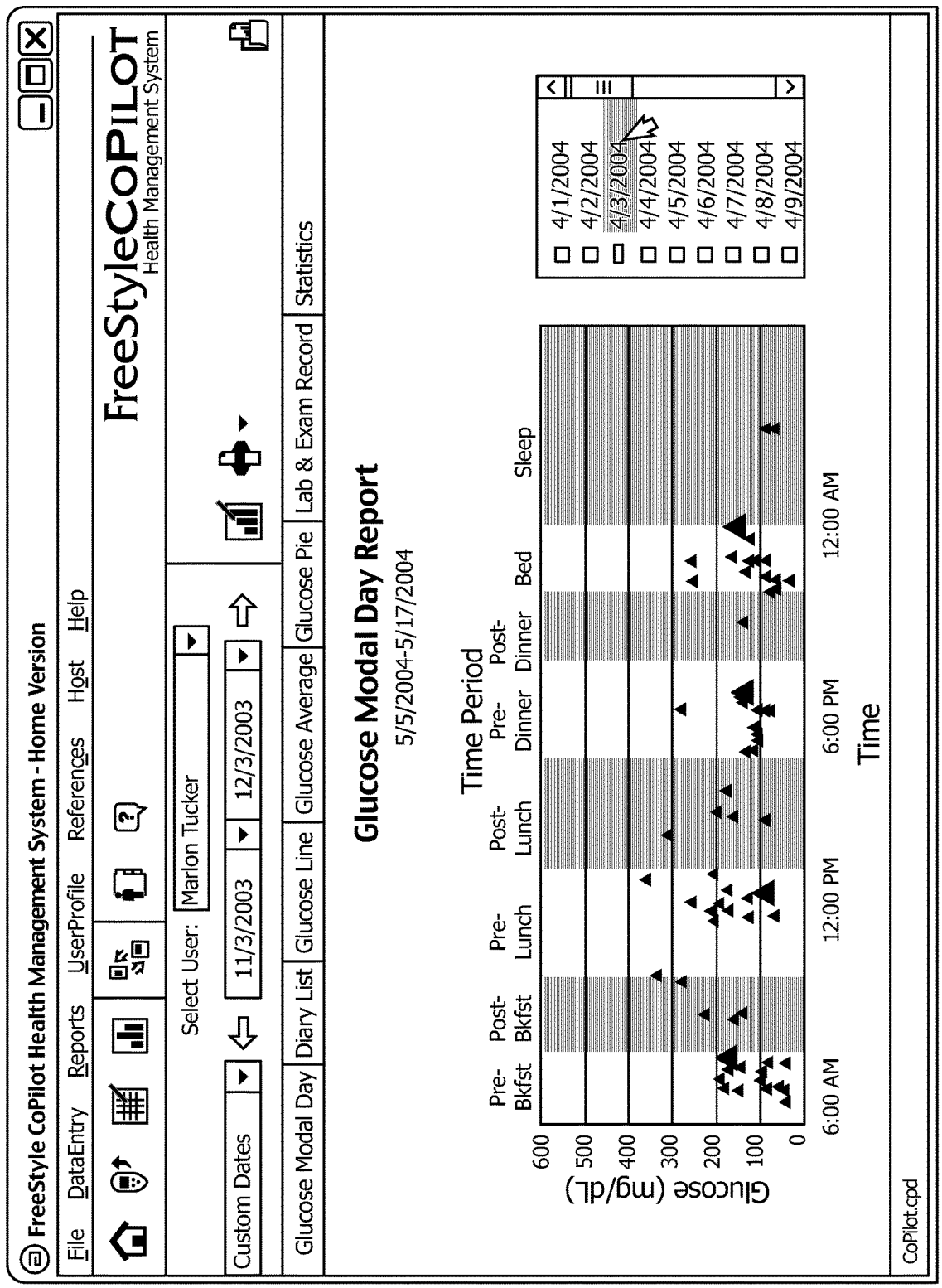

The Glucose Modal Day Report shows the daily pattern of glucose levels over the specified date range. A dotted line linking the readings for a specific date can be displayed or hidden. FIG. 116 illustrates a Glucose Modal Day Report (Dotted Line Linking Readings for Apr. 3, 2004). The horizontal axis is a 24-hour timeline. All readings for all dates display on the same timeline. The vertical axis plots the glucose level. A day (24 hours) is defined as pre-breakfast to pre-breakfast. The glucose target mode is user's choice. Each data element represents one glucose reading. For the date, time, and value of the reading, the pointer can be hovered over the triangle. HI/LO indicates a reading outside the working range of the meter. A list of all days in the date range displays to the right of the graph. To link all the readings for a single day with a dotted line, the user can click the date of interest in the list of all days in the date range (FIG. 116). All the data elements for that date change color and enlarge, and a dotted line is drawn linking them. By clicking on it, a triangle data element in the line can be cancelled.

To zoom in on (magnify) an area of the graph, a user can place the mouse in the upper left of the graph, press and hold the left mouse button, and drag to the lower right corner of the graph. The user can repeat this action to further magnify the area of interest. To return the graph to its original state, the user can place the mouse in the lower right of the graph, press and hold the left mouse button, and drag to the upper left corner. To go to the Glucose Reading entry in the Diary List, the user can double-click the data element.

Glucose Line Report

Figure 118:
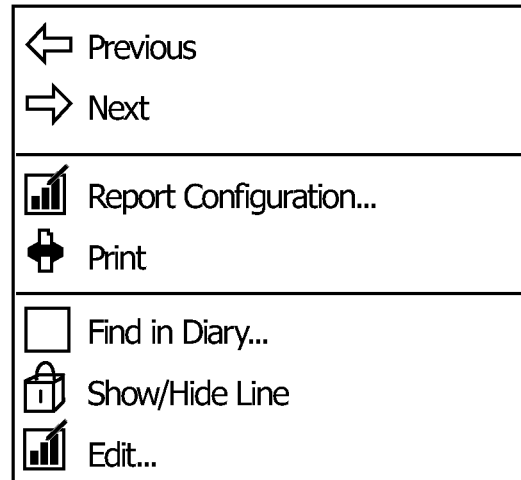
Figure 117:
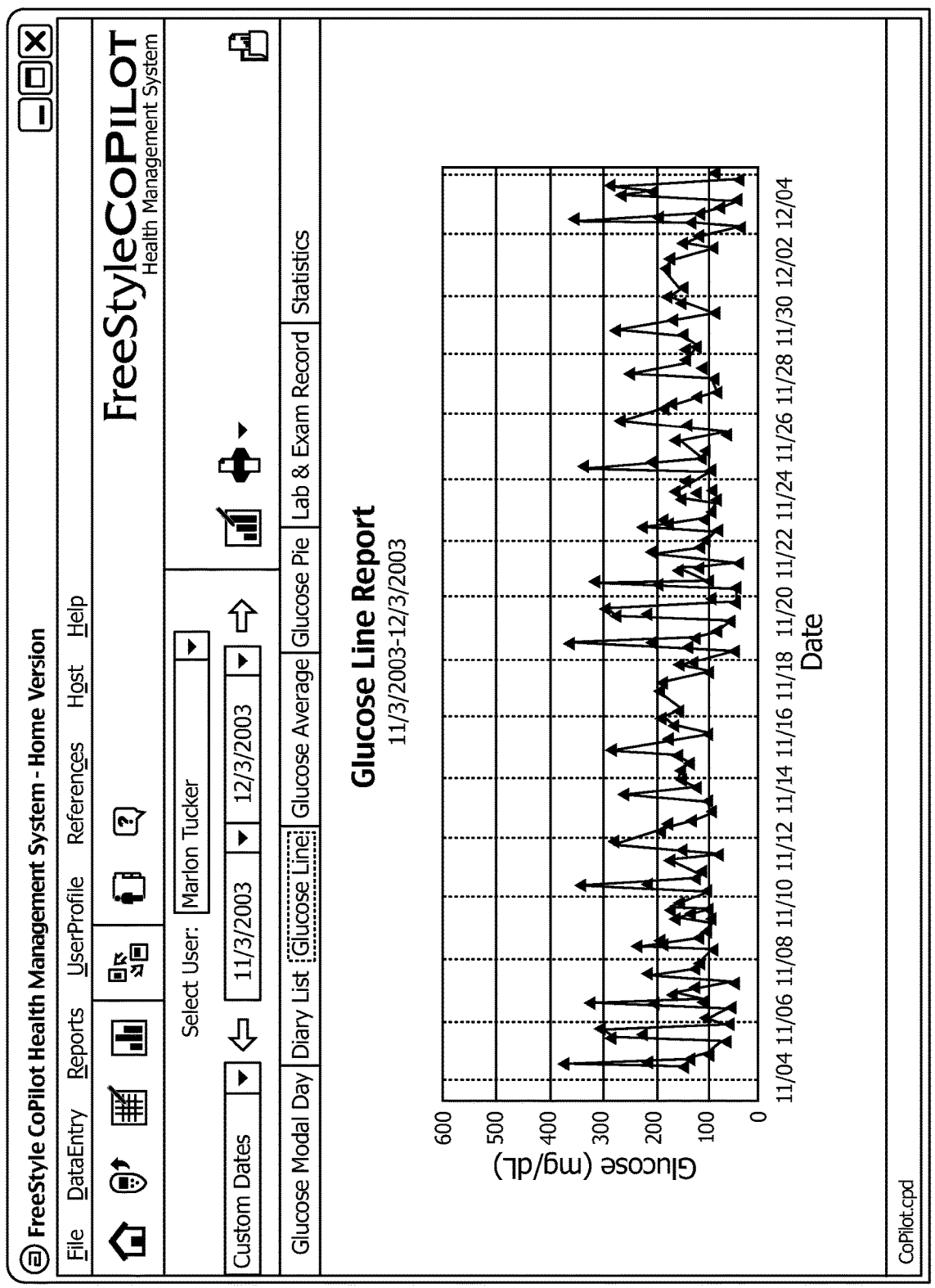

The Glucose Line Report is useful for seeing trends in glucose levels. It plots each glucose reading over the specified date range. FIG. 117 illustrates a Glucose Line Report (Show Line Is Activated). The horizontal axis is a timeline of the entire date range. The vertical axis plots the glucose level. A day (24 hours) is defined as midnight to midnight. The glucose target mode is Standard. Each data element represents one reading; a solid line connecting them can be displayed or hidden. To hide the line, point to any data element, then right-click. A user can click Show/Hide Line on the pop-up menu (see FIG. 118). For the date, time, and value of the glucose reading, the pointer can be hovered over the data element. To zoom in on (magnify) an area of the graph, the user can place the mouse in the upper left of the graph, press and hold the left mouse button, and drag to the lower right corner of the graph. The user can repeat this action to further magnify the area of interest. To return the graph to its original state, the user can place the mouse in the lower right of the graph, press and hold the left mouse button, and drag to the upper left corner. To go to the event data in the Diary List, the user can double-click the data element.

Glucose Average Report

Figure 119:
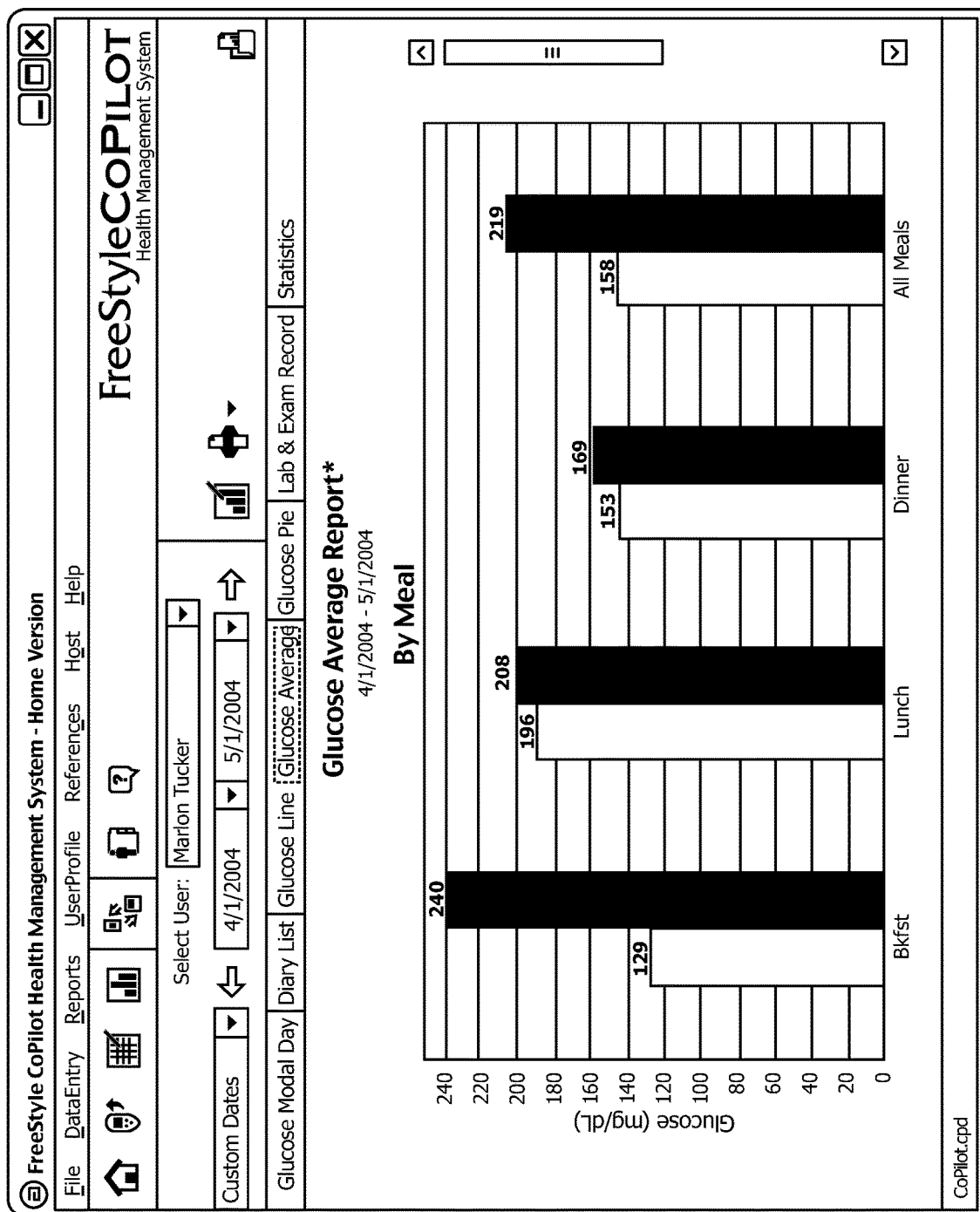
Figure 120:
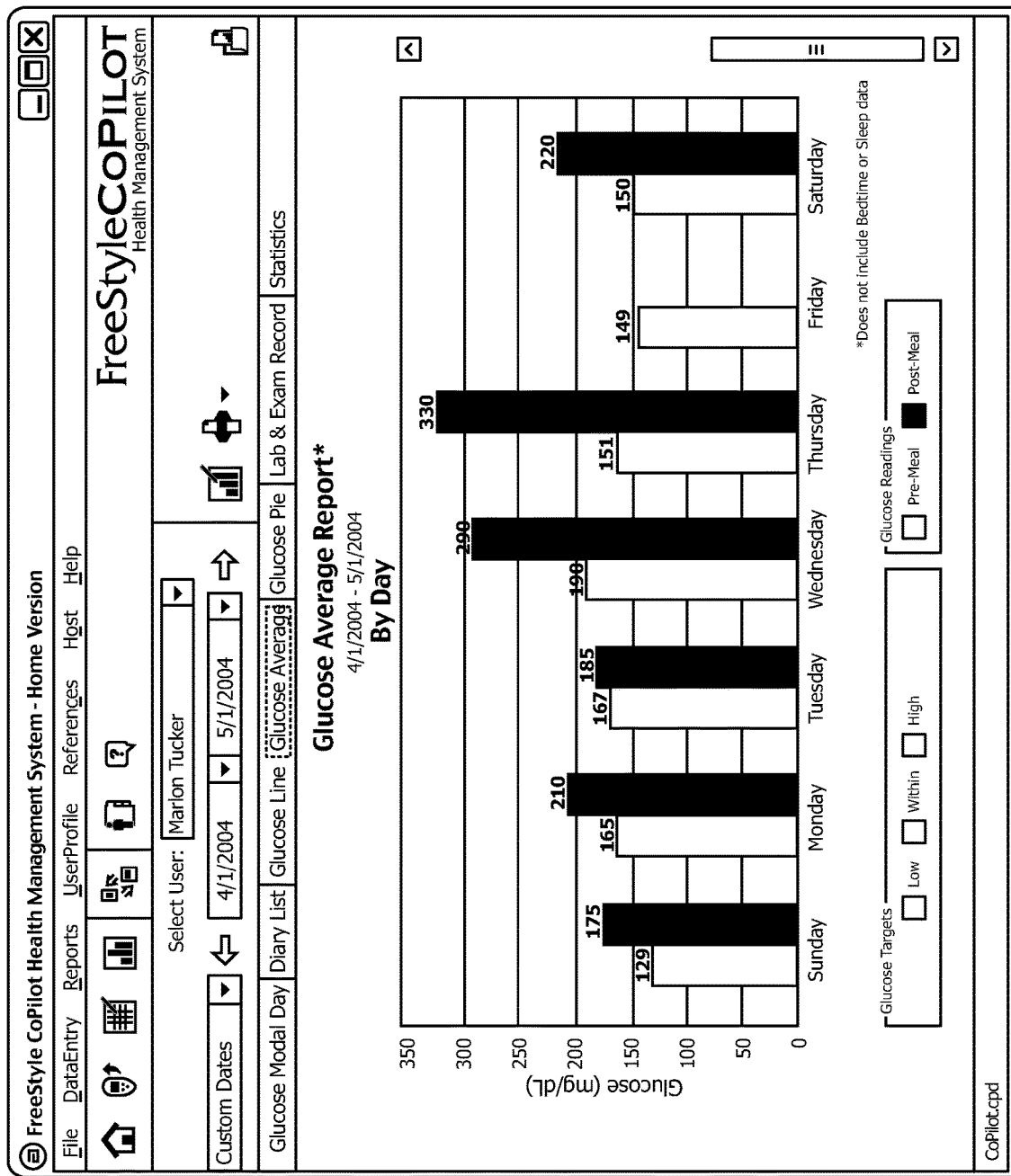

The Glucose Average Report may help identify times of the day that may need more testing or improved control. The report separates glucose readings over the specified date range into pre-meal (cream-colored bars) and post-meal (blue bars) groupings and averages the values for each group. For convenience, there are two graphs. One shows pre-meal and post-meal glucose averages over the date range by meal. The other shows overall pre-meal and post-meal averages by day over the date range. FIGS. 119-120 illustrate Glucose Average Reports by meal and by day, respectively. The horizontal axis is a timeline showing the time periods (pre-meal and post-meal) and the average for all meals. The vertical axis plots the glucose level. Each bar shows the average value of all glucose readings over the date range for the specific time period (for example, the average value of all pre-breakfast readings). A day (24 hours) is defined as pre-breakfast to pre-breakfast. A user can Double-click any bar to call up the Diary List entries for these events.

Glucose Histogram Report

Figure 121:
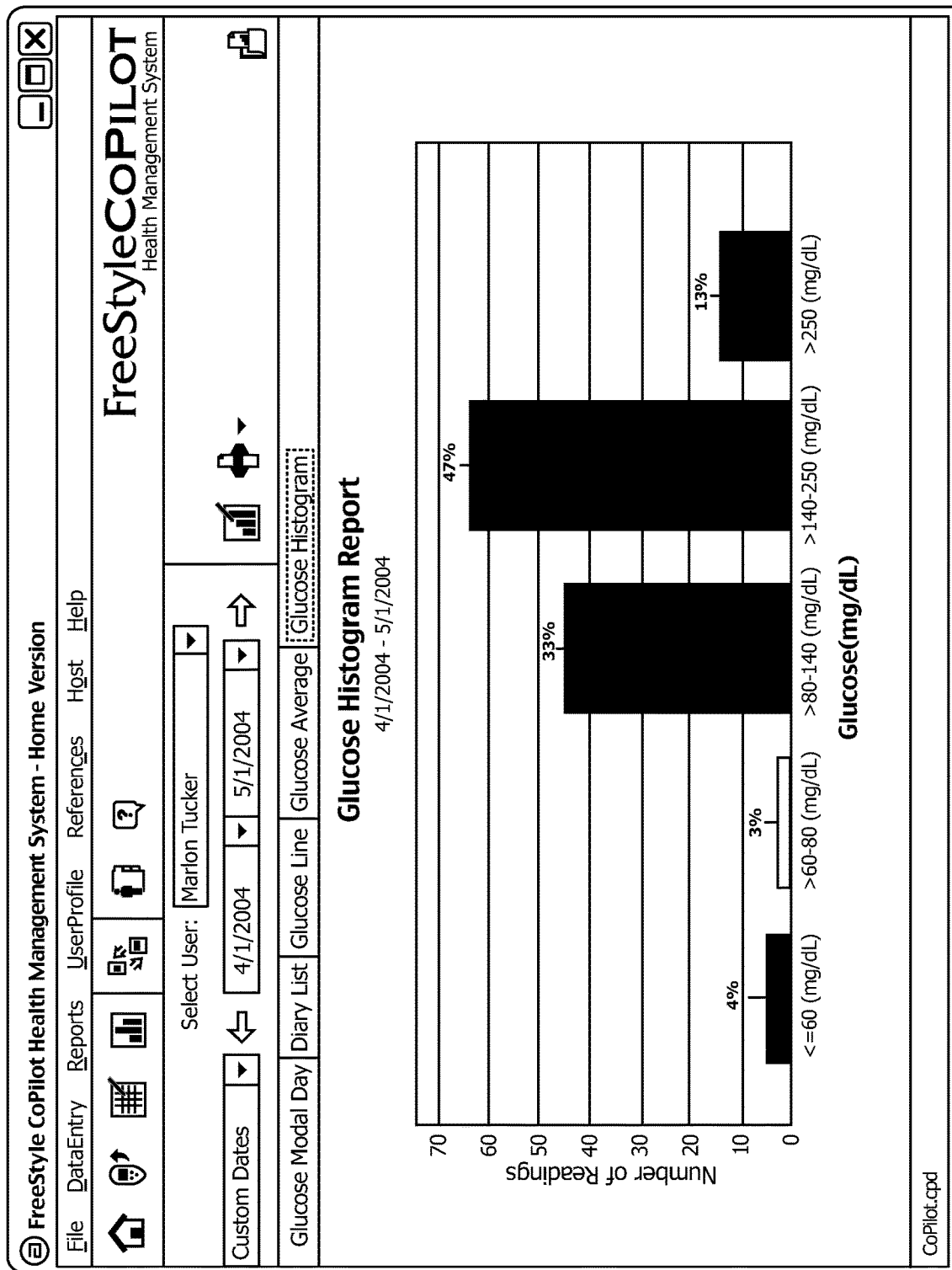

The Glucose Histogram Report separates glucose readings over the specified date range into the default target ranges and displays the data as a histogram (bar chart) with its bar height proportional to the number of readings in each glucose target range. FIG. 121 illustrates a Glucose Histogram Report. The horizontal axis shows the default glucose target ranges (not the user-defined glucose target ranges). The vertical axis plots the glucose level. A day (24 hours) is defined as midnight to midnight. The color of the bar corresponds to the signal color for the glucose target range. The height of the bar is proportional to the number of readings in that range; that is, the bar for a range in which there are 20 readings is twice as high as the bar for a range with 10 readings. The percentage of readings in the range is shown at the top of the bar. The user can double-click the bar to call up the Diary List entries that make up that bar.

Glucose Pie Chart

Figure 122:
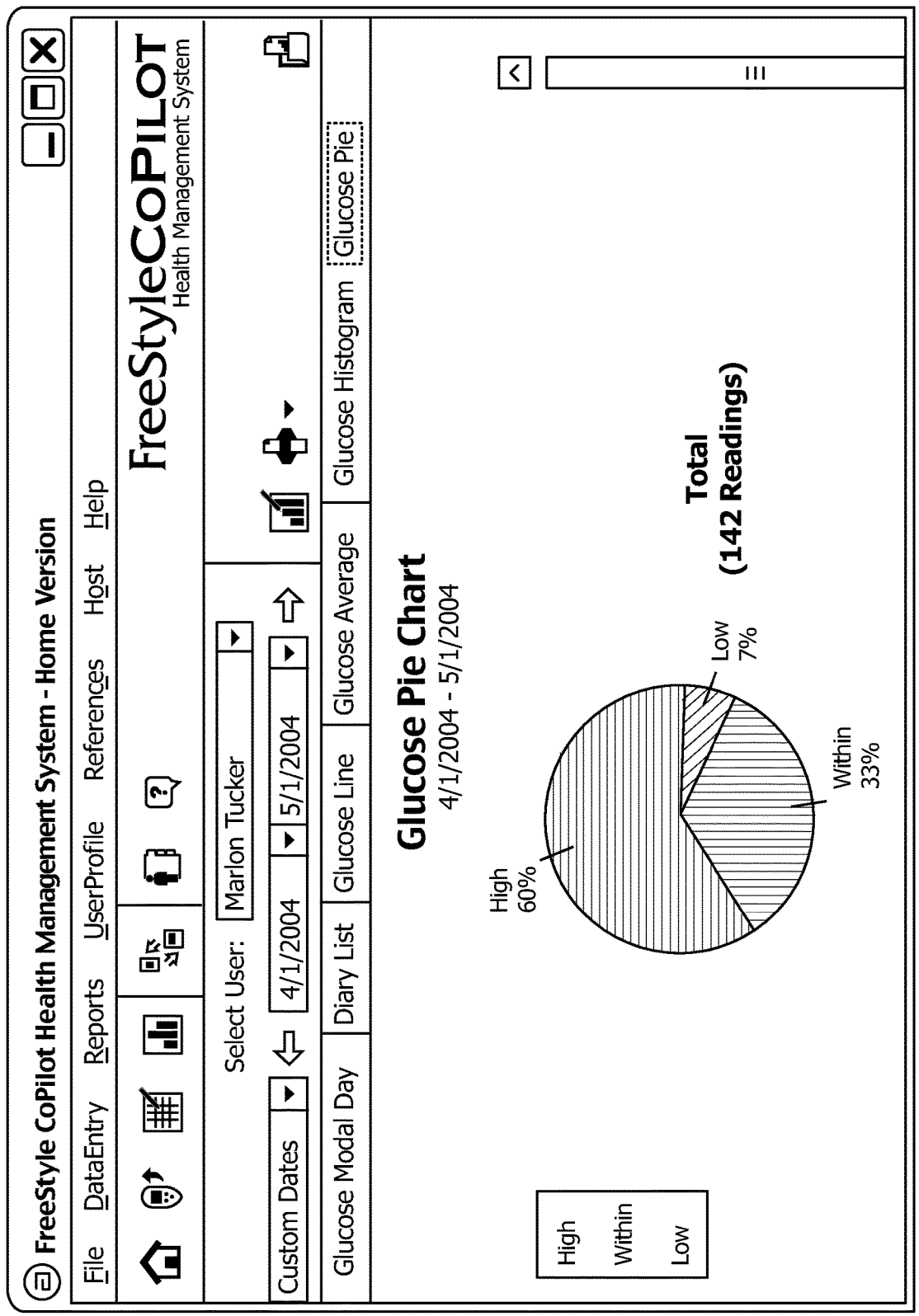
Figure 123:
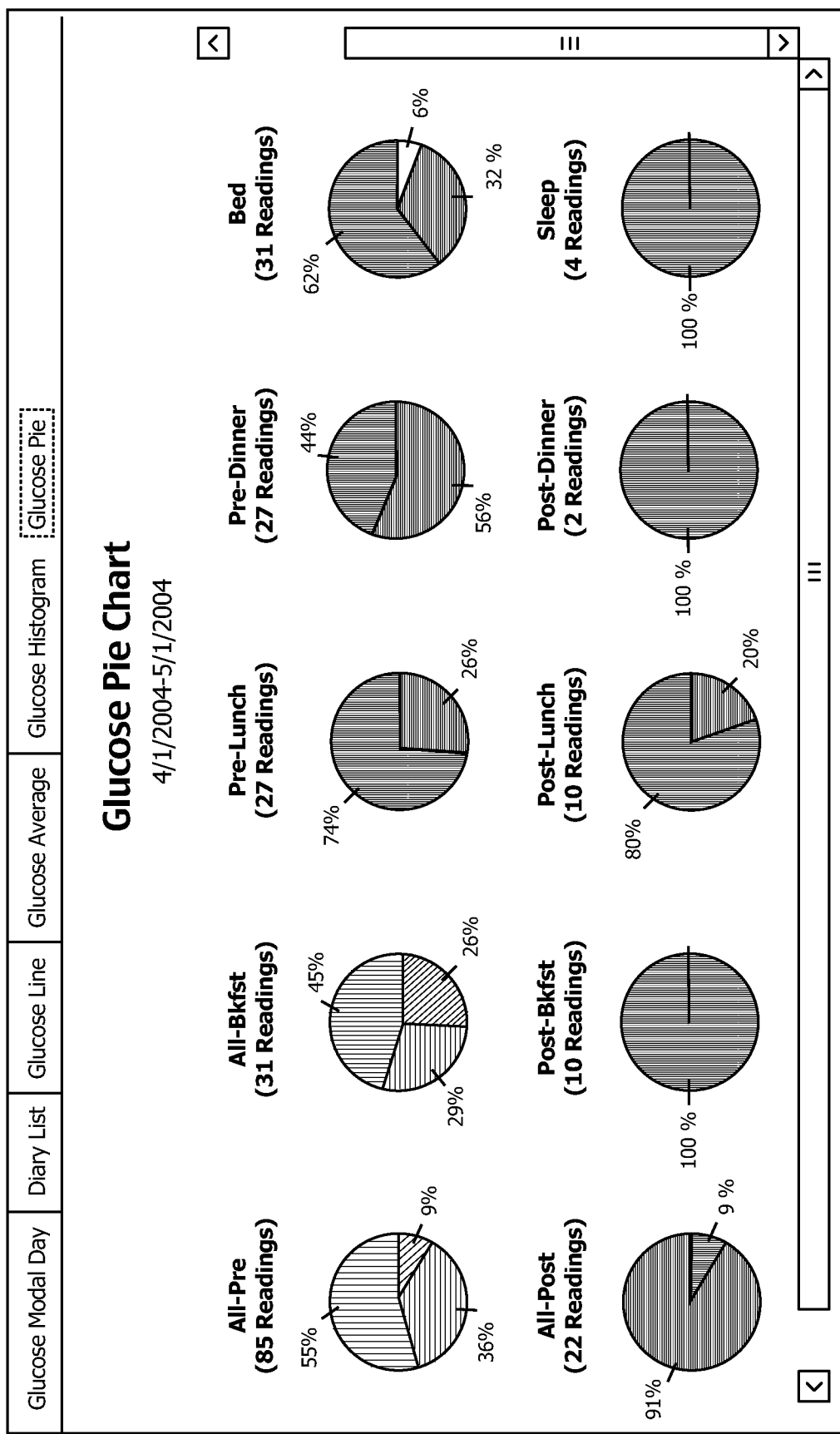

The Glucose Pie Chart separates glucose readings over the date range into the default glucose target ranges and averages the values within each range. These averages are displayed in a series of pie charts. Each segment (wedge) displays in the signal color of its glucose target range. FIG. 122 illustrates a Glucose Pie Chart Report: Total Readings Pie Chart, and FIG. 123 illustrates a Glucose Pie Chart Report: Ten Summary Pie Charts. A maximum of 10 individual pie charts (2 rows of 5) and 1 total pie chart summarizing the glucose readings for all configured time periods over the date range are displayed. A day (24 hours) is defined as pre-breakfast to pre-breakfast on Total Readings pie chart (see FIG. 122). The glucose target mode is user's choice. A user can double-click a wedge on any of the pie charts to call up the Diary List entries that make up that wedge.

Logbook Report

The Logbook Report is a table of glucose, carbohydrate, and insulin values associated with each time period over the specified date range. FIG. 124 illustrates a Logbook Report. Insulin, carbohydrate, and pre-meal, post-meal, bedtime, and sleep glucose reading values are displayed in columns under each time period (Breakfast, Lunch, Dinner, Bed and Sleep) for each day over the date range. A day (24 hours) is defined as pre-breakfast to pre-breakfast. The glucose target mode is user's choice. To call up the entry in the Diary List, a user can double-click any cell in the row.

Lab and Exam Record Report

Figure 127:
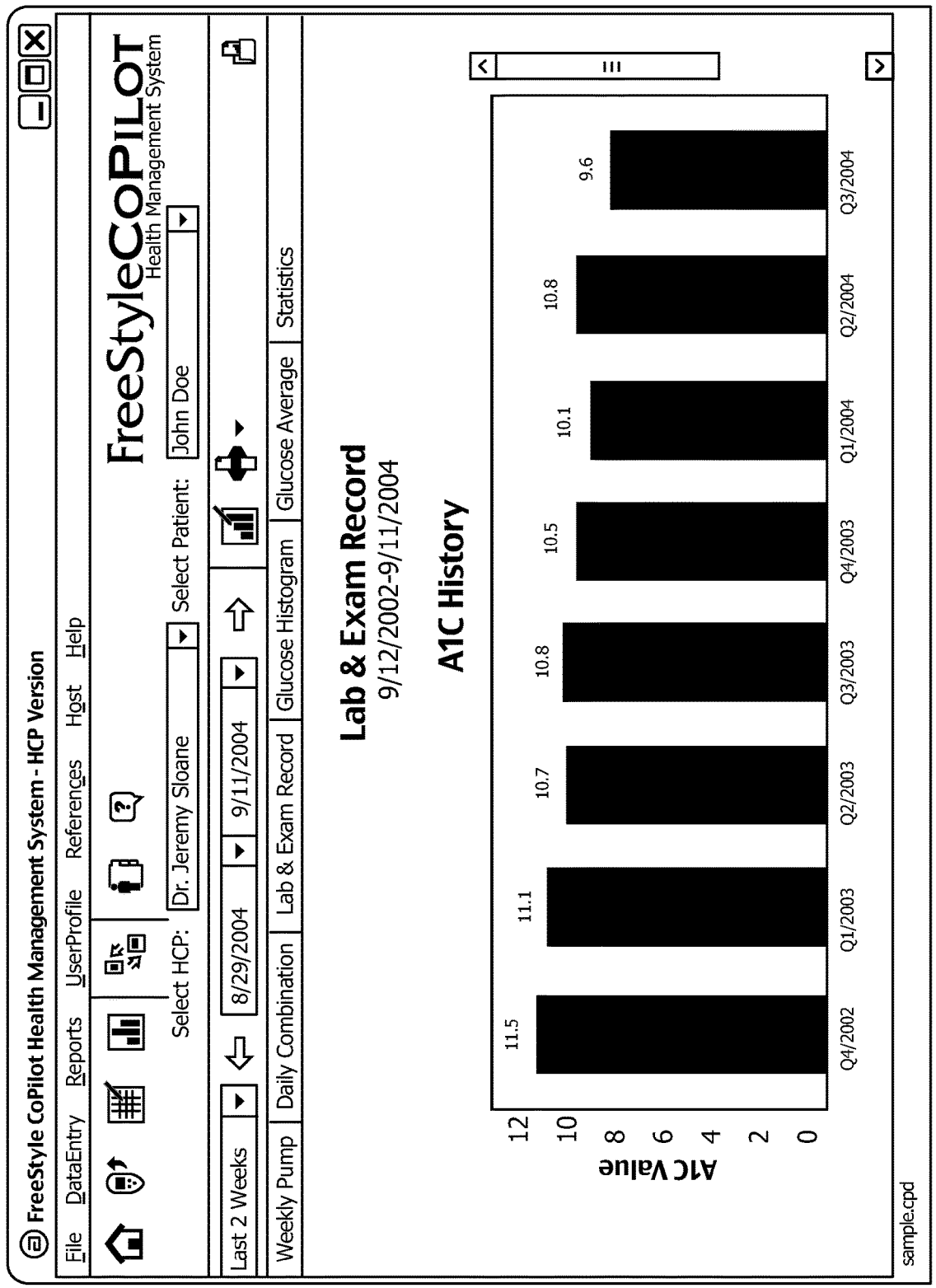

The Lab and Exam Record Report is a table of data from all Medical Exam and Lab Test Result data entry screens over the specified date range. FIGS. 125-127 illustrate Lab & Exam Record Reports: Lab Record, Exam Record, and A1C History, respectively. The screen shows a table of lab test data on the top (FIG. 125) and the exam data below (FIG. 126). Each event is shown in one row. Below the table is a graph showing A1C test results for the current year and the previous year (FIG. 127). A day (24 hours) is defined as midnight to midnight. A user can double-click any cell in a row to go to the Diary List entry for the event. The user can double-click any bar on the graph to go to the Diary List entry for the A1C test event.

Statistics Report

The Statistics Report provides an overview of glucose, carbohydrate, and insulin data (including insulin pump data) over the date range and displays it in a series of tables. A user can attach the Statistics Report to any other report by default. FIG. 128 illustrates a Statistics Report: Glucose Statistics. A day (24 hours) is defined as pre-breakfast to pre-breakfast. The glucose target mode is user's choice. A user can double-click any cell to see the entries from the Diary List that are included in the data set for a particular statistical calculation.

Glucose Statistics

The Glucose Statistics table (see FIG. 128) shows data regarding the number of readings per day, the values of the highest and lowest readings in each time period, and the results of some automatic calculations (averages and standard deviation) within and across time periods.

| | |
|---|---|
| # Readings | By Time Period: Reports the number of readings recorded during the Time Period specified for each day of the selected Date Range.<br>Total/Summary: Reports the number of readings recorded during the selected Date Range. |
| # Days W/Readings | By Time Period: Reports the number of days within the selected Date Range where one or more readings are recorded during the specified Time Period.<br>Total/Summary: Reports the number of days within the selected Date Range where one or more readings are recorded. |
| Avg Readings/Day | By Time Period: Reports the number of readings recorded during the Time Period specified for each day of the selected Date Range divided by the number of days in the selected Date Range regardless of whether a glucose reading was recorded or not.<br>Total/Summary: Reports the number of readings recorded during the selected Date Range divided by the number of days in the selected Date Range regardless of whether a glucose reading was recorded or not. |
| Highest | By Time Period: Reports the highest reading recorded during the Time Period specified within the selected Date Range.<br>Total/Summary: Reports the highest reading recorded during the selected Date Range. |
| Lowest | By Time Period: Reports the lowest reading recorded during the Time Period specified within the selected Date Range.<br>Total/Summary: Reports the lowest reading recorded during the selected Date Range. |

-continued

| | |
|---|---|
| Average | By Time Period: Reports the sum of the readings recorded during the selected Date Range that fall within the specified Time Period divided by the number of readings recorded during the selected Date Range that fall within the specified Time Period.<br>Total/Summary: Reports the sum of the readings recorded during the selected Date Range divided by the number of readings recorded during the selected Date Range. |
| Standard Deviation | By Time Period: Reports the mean* of the readings recorded during the Time Period specified within the selected Date Range.<br>Total/Summary: Reports the mean* of the readings recorded during the selected Date Range.<br>Note: N/A is displayed where fewer than three readings are recorded. |
| Above % | By Time Period: Reports the number of readings recorded above the patient's defined normal glucose limits during the Time Period specified within the selected Date Range divided by the total number of readings recorded during the Time Period specified within the selected Date Range.<br>Total/Summary: Reports the total number of readings recorded above the patient's defined normal glucose limits during the selected Date Range divided by the total number of readings recorded during the selected Date Range. |
| Within % | By Time Period: Reports the number of readings recorded within the patient's defined normal glucose limits during the Time Period specified within the selected Date Range divided by the total number of readings recorded during the Time Period specified within the selected Date Range.<br>Total/Summary: Reports the total number of readings recorded within the patient's defined normal glucose limits during the selected Date Range divided by the total number of readings recorded during the selected Date Range. |
| Below % | By Time Period: Reports the number of readings recorded below the patient's defined normal glucose limits during the Time Period specified within the selected Date Range divided by the total number of readings recorded during the Time Period specified within the selected Date Range.<br>Total/Summary: Reports the total number of readings recorded below the patient's defined normal glucose limits during the selected Date Range divided by the total number of readings recorded during the selected Date Range. |
| Very High % | By Time Period: Reports the number of readings recorded as hyper events during the Time Period specified within the selected Date Range divided by the total number of readings recorded during the Time Period specified within the selected Date Range.*<br>Total/Summary: Reports the total number of readings recorded as hyper events during the selected Date Range divided by the total number of readings recorded during the selected Date Range.* |
| High % | By Time Period: Reports the number of readings recorded above the patient's defined normal glucose limits and below the limits of a hyper event during the Time Period specified within the selected Date Range divided by the total number of readings recorded during the Time Period specified within the selected Date Range.*<br>Total/Summary: Reports the total number of readings recorded above the patient's defined normal glucose limits and below the limits of a hyper event during the selected Date Range divided by the total number of readings recorded during the selected Date Range.* |
| Low % | By Time Period: Reports the number of readings recorded below the patient's defined normal glucose limits and above the limits of a hypo event during the Time Period specified within the selected Date Range divided by the total number of readings recorded during the Time Period specified within the selected Date Range.*<br>Total/Summary: Reports the total number of readings recorded below the patient's defined normal glucose limits and above the limits of a hypo event during the selected Date Range divided by the total number of readings recorded during the selected Date Range.* |
| Very Low % | By Time Period: Reports the number of readings recorded as hypo events during the Time Period specified within the selected Date Range divided by the total number of readings recorded during the Time Period specified within the selected Date Range.*<br>Total/Summary: Reports the total number of readings recorded as hypo events during the selected Date Range divided by the total number of readings recorded during the selected Date Range.* |

*The mean of the recorded readings is related to the patient's average glucose level. For example, a small number (less than half the average) indicates that most of the glucose readings during the day are close to the average value and that the patient is maintaining glucose levels near that value. A large number (more than half the average) indicates that many glucose levels during the day vary considerably from the average and that the patient is not maintaining glucose levels near the average value.
**Available when three target zones are being reported: Show Hypo/Hyper not selected.
***Available when five target zones are being reported: Show Hypo/Hyper selected.

Insulin Statistics

The Insulin Statistics table (see FIG. 129) shows average insulin dosages over the date range (calculated from insulin data). FIG. 129 illustrates a Statistics Report: Insulin and Carbs Statistics Tables.

| | |
|---|---|
| Avg per Day (insulin name) | By Time Period: Reports the sum of the units of Insulin delivered during the Time Period specified for the selected Date Range divided by the number of days in the selected Date Range where that particular type of Insulin was recorded during that Time Period.<br>Total/Summary: Reports the sum of the units of Insulin delivered during the selected Date Range divided by the number of days in the selected Date Range where that particular type of Insulin was recorded.<br>Note: Separate entries exist for each type of Insulin recorded. |
| Avg Total Insulin per Day | By Time Period: Reports the sum of the units of all Insulin delivered during the Time Period specified for the selected Date Range divided by the number of days in the selected Date Range where any type of Insulin was recorded during that Time Period.<br>Total/Summary: Reports the sum of the units of all Insulin delivered during the selected Date Range divided by the number of days in the selected Date Range where any type of Insulin was recorded. |

These entries are calculated using all types of insulin recorded.

Pump Statistics

If the insulin is administered by pump, the table (FIG. 129) will say Pump Statistics (instead of Insulin Statistics) and display the following information:

| | |
|---|---|
| Avg General Bolus per Day | By Time Period: Reports the sum of all Meal Bolus* Insulin recorded during the specified Time Period for the selected Date Range divided by the number of days in the selected Date Range where Meal Bolus* Insulin entries were recorded during that Time Period.<br>Total/Summary: Reports the sum of all Meal Bolus* Insulin recorded during the selected Date Range divided by the number of days in the selected Date Range where Meal Bolus* Insulin entries were recorded. |
| Avg Correction Bolus per Day | Bolus per Day By Time Period: Reports the sum of all Correction Bolus Insulin recorded during the specified Time Period for the selected Date Range divided by the number of days in the selected bate Range where Correction Bolus Insulin entries were recorded during that Time Period.<br>Total/Summary: Reports the sum of all Correction Bolus Insulin recorded during the selected Date Range divided by the number of days in the selected Date Range where Correction Bolus Insulin entries were recorded. |
| Total Avg Bolus per Day | By Time Period: Reports the sum of all Meal and Correction Bolus Insulin entries recorded during the specified Time Period for the selected Date Range divided by the number of days in the selected Date Range where Meal and Correction Bolus Insulin entries were recorded during that Time Period.<br>Total/Summary: Reports the sum of all Meal and Correction Bolus Insulin entries recorded during the selected Date Range divided by the number of days in the selected Date Range where Meal and Correction Bolus Insulin entries were recorded. |
| Avg Basal per Day | By Time Period: Reports the sum of the Basal Insulin delivered during the Time Period specified for the selected Date Range divided by the number of days in the selected Date Range where Basal Insulin was recorded for that Time Period.<br>Total/Summary: Reports the sum of the Basal Insulin delivered during the selected Date Range divided by the number of days in the selected Date Range where Basal Insulin was recorded. |
| Avg Total Insulin per Day | By Time Period: Reports the sum of the Total Bolus and Basal Insulin doses delivered during the Time Period specified for the selected Date Range divided by the number of days in the selected Date Range where Insulin entries were recorded for that Time Period.<br>Total/Summary: Reports the sum of the Total Bolus and Basal Insulin doses delivered during the selected Date Range divided by the number of days in the selected Date Range where Insulin entries were recorded. |

*Meal Bolus is defined as the sum of all insulin entries (from pump uploads and manual entries) of the following injection types: Injection, Bolus, Meal Bolus, Combination Bolus, Dual Wave Bolus, and Square Wave Bolus.

Carbohydrate Statistics

The Carbs Statistics table (see FIG. 129) shows average carbohydrates over the date range (calculated from carbohydrates data).

| | |
|---|---|
| Average per Day Carbs | By Time Period: Reports the sum of the meal Carbohydrate intake for the Time Period specified during the selected Date Range divided by the number of days within the selected Date Range where meal Carbohydrate entries were recorded during the Time Period specified.<br>Total/Summary: Reports the sum of the meal Carbohydrate intake during the selected Date Range divided by the number of days within the selected Date Range where meal Carbohydrate entries were recorded. |

Daily Combination View Report

Figure 130:
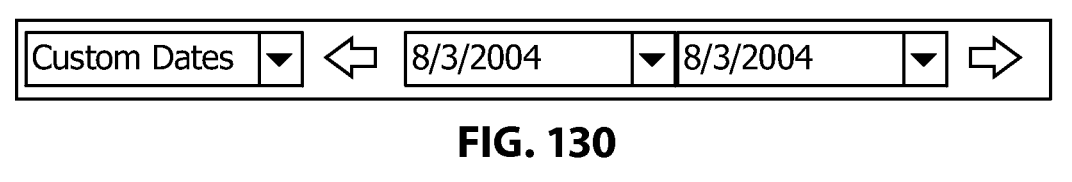
Figure 131:
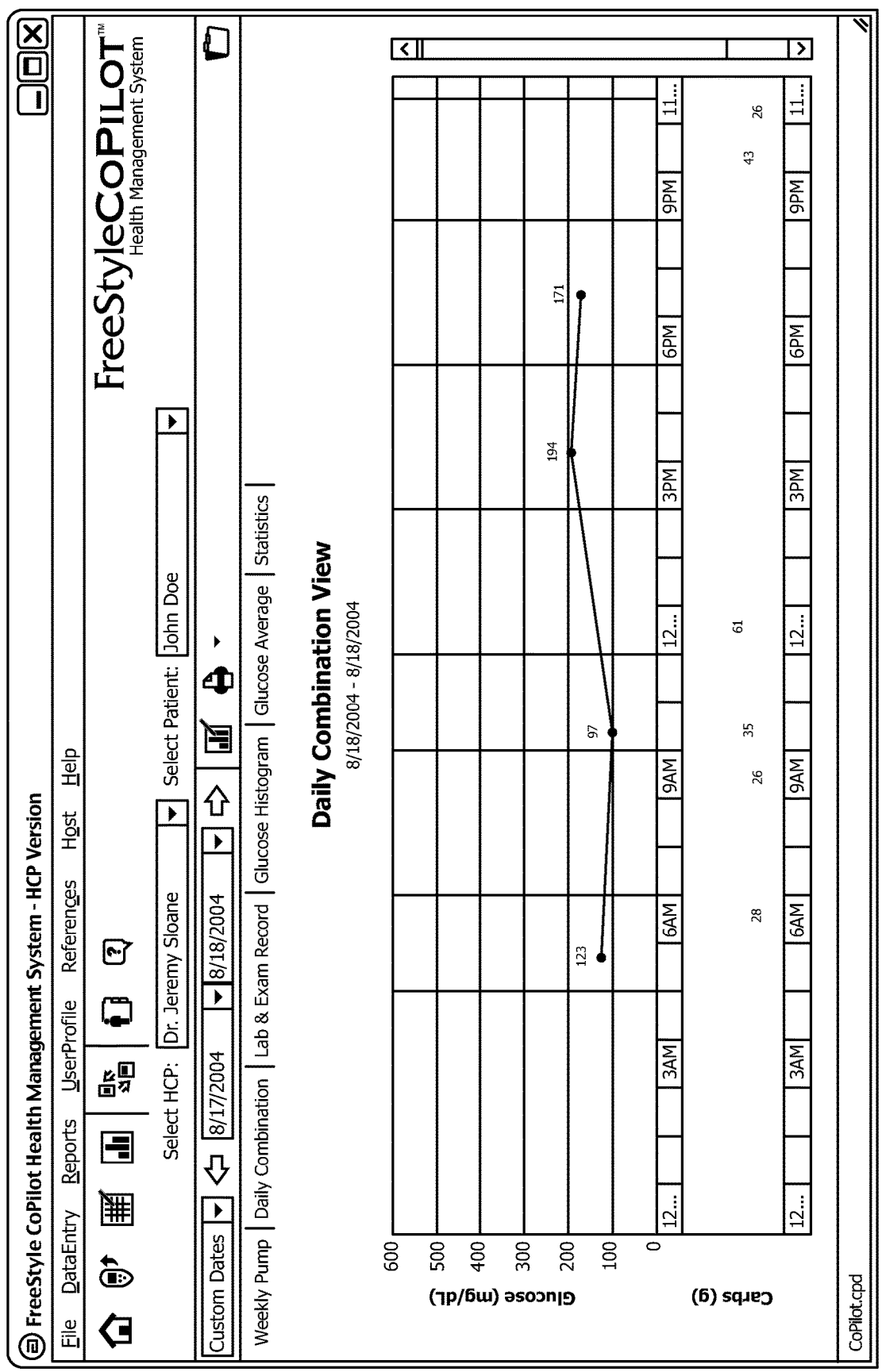

The Daily Combination View Report summarizes glucose, carbohydrate, and insulin data (including pump data) for a single day and displays it in both graphic and table formats. To select the day for the data you want to see, a user can use the date field on the right (see FIG. 130). Also, the user can set the date field on the left to the same date. FIG. 130 illustrates a Date Field for Selecting Date. FIG. 131 illustrates a Daily Combination View Report: Glucose Line and Carbohydrates Graphs.

Glucose Line Graph

This graph (see FIG. 131) plots glucose readings by hour of day. The horizontal axis is a 24-hour timeline. The vertical axis plots the glucose level. Each data element represents one reading. The user can hover the cursor over the data element to see the glucose value, date, and time of that reading. The user can double-click a data element to view this entry in the Diary List. To display or hide the solid line connecting the data elements, the user can right-click a data element, then select Toggle Glucose Line from the pop-up list.

Carbohydrates Graph

This graph (see FIG. 131) plots carbohydrate events by hour of day. The carbohydrate data element represents one carbohydrate event. The size of the circle is proportional to the carbohydrate value. Its position along the horizontal axis corresponds to the time (hour) of the meal. The user can double-click an icon to view this entry in the Diary List.

Insulin Summary

Figure 132:
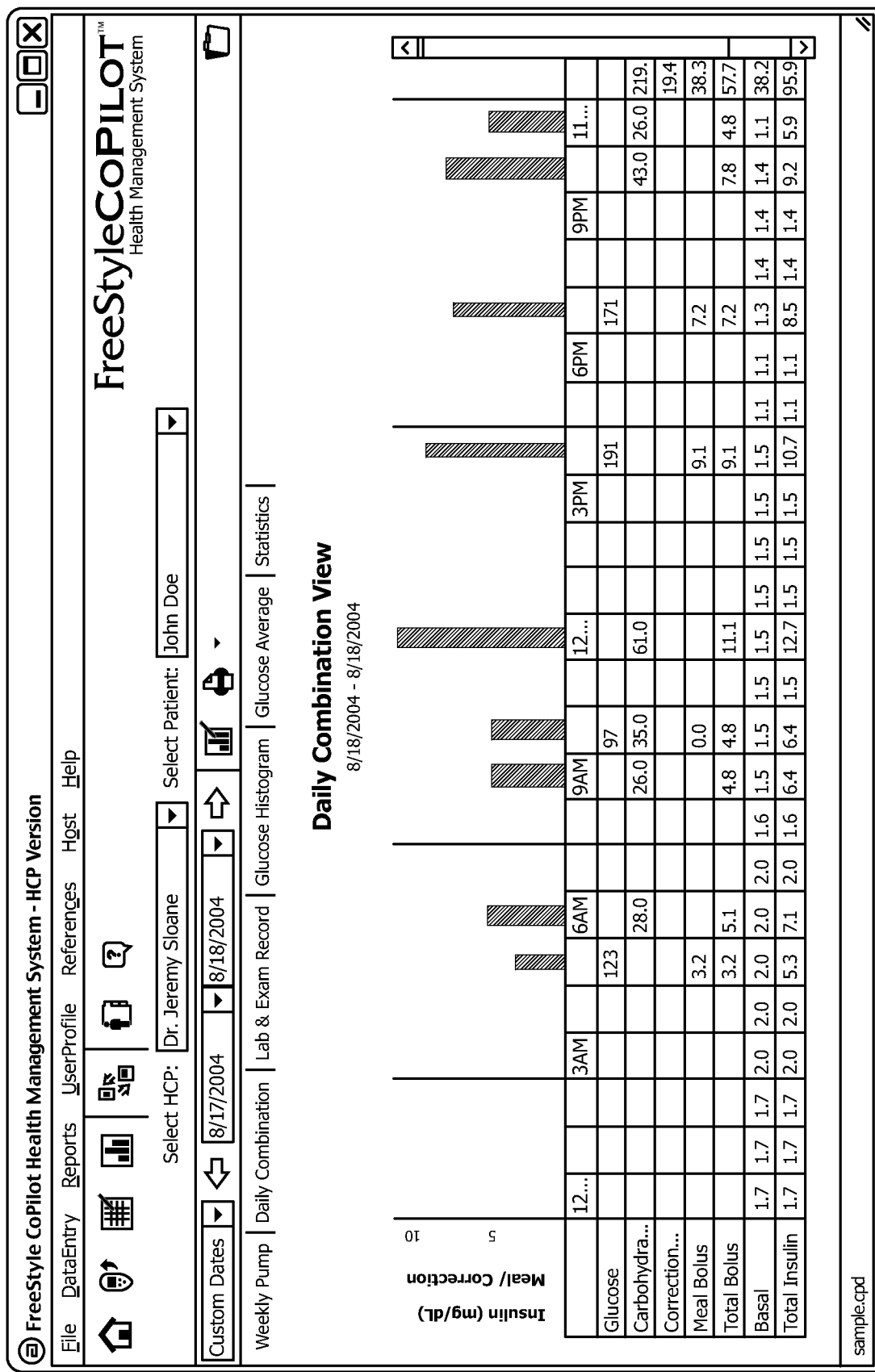

FIG. 132 illustrates a Daily Combination View Report: Insulin Summary and Data Table. This graph (FIG. 132) plots insulin events by hour of day. The horizontal axis is a 24-hour timeline. The vertical axis is units of insulin. Basal insulin data (light green shaded area) can be uploaded to the System. Each dark green bar represents one meal bolus insulin event. Its position along the horizontal axis corresponds to the time (hour) of the insulin event. Its height correlates with dosage. A user can double-click to view this entry in the Diary List. Each red bar represents one correction bolus insulin event. Its position along the horizontal axis corresponds to the time (hour) of the insulin event. Its height correlates with dosage. A user can double-click to view this entry in the Diary List. A meal bolus may be an extended, square wave, or combination bolus. The scale is indicated on the left.

Data Table

This table (see FIG. 132) tracks glucose, carbohydrates, and insulin values hourly. Each column represents 1 hour. Each event type is one row. Each event is one cell. The value associated with the event displays in the cell. A user can double-click the cell to view this event in the Diary List.

Weekly Pump View Report

Figure 133:
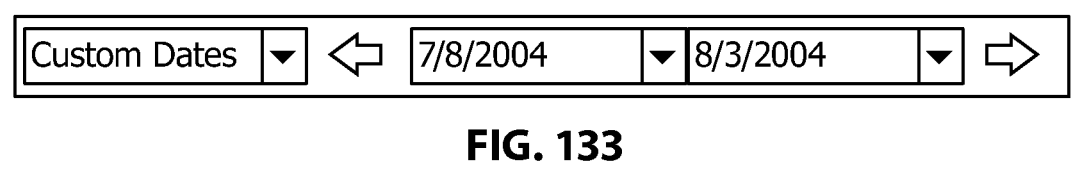
Figure 134:
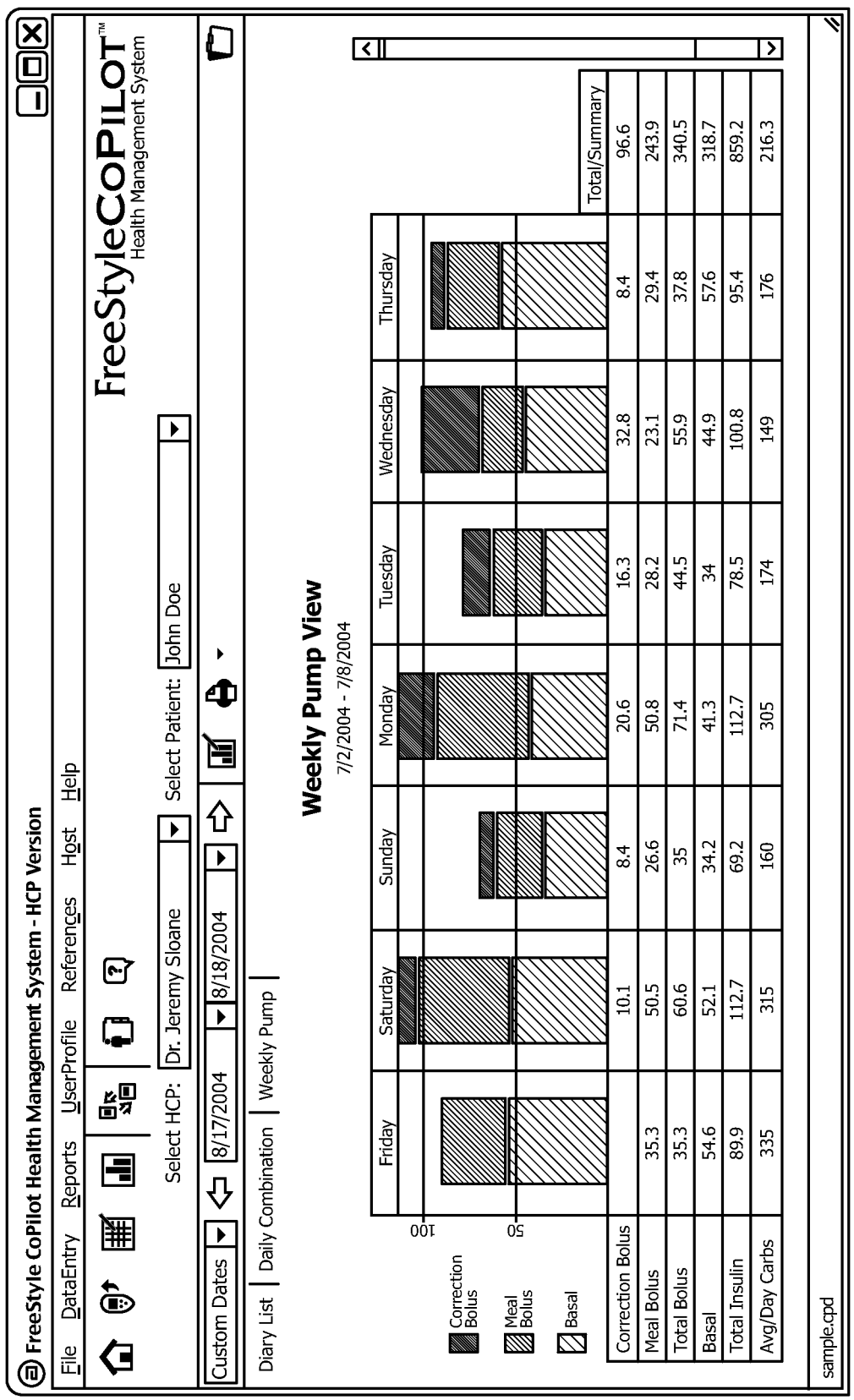
Figure 135:
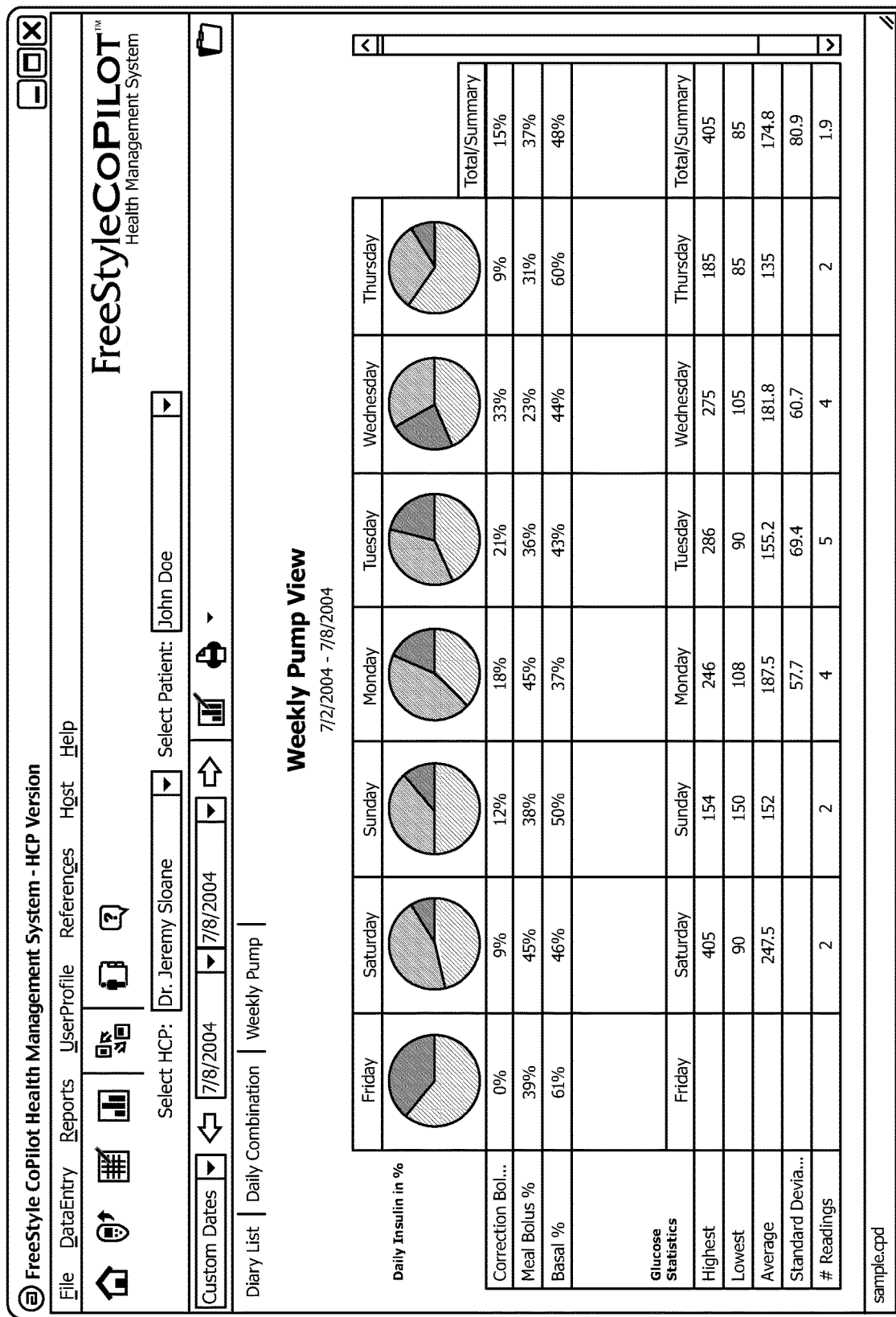

The Weekly Pump View Report shows the components of insulin doses for each day in a seven-day period in bar graph (FIG. 134) and pie chart (FIG. 135) formats. To select the week (7 days) for the data a user wants to view, using the date field on the right (see FIG. 133), the user can select the last date in the week the user wants to see (Aug. 3, 2004, for example). The user can set the date field on the left to the first day of that week (Jul. 28, 2004, for example). FIG. 133 illustrates a Date Field for Selecting a Date. FIGS. 134-135 illustrate Weekly Pump View Reports: Bar Graph and Pie Charts and Glucose Statistics Table, respectively. A Glucose Statistics table (see FIG. 135) summarizes the glucose readings for the week displayed.

HCP Group Analysis Report

Figure 136:
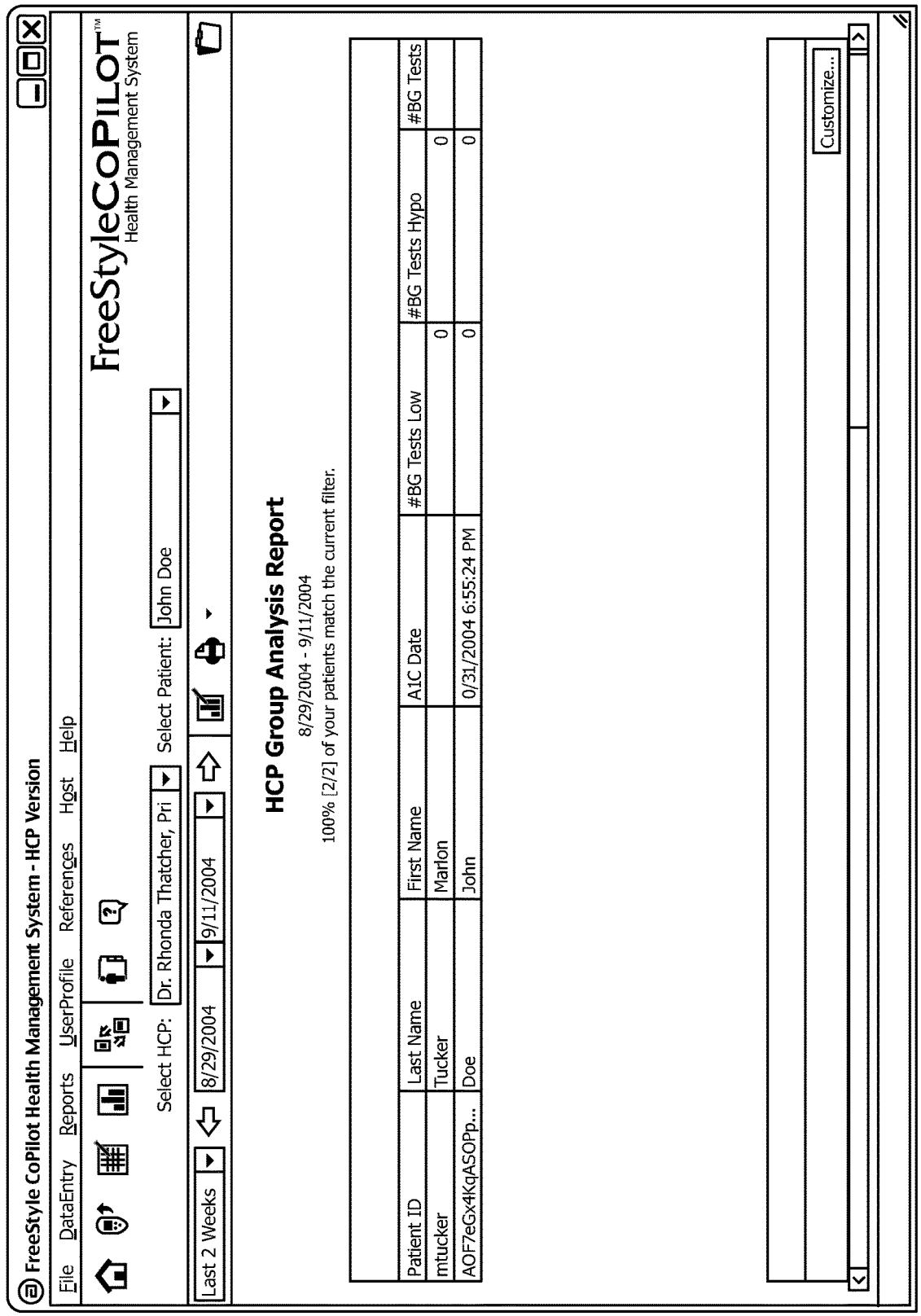

The HCP Group Analysis Report is available to HCP users only. This report is a user-configurable view of all FreeStyle CoPilot System data for all patients of the HCP. The HCP can display data for any patient he/she manages. This includes all device data uploaded at the clinic during a patient visit, all data entered manually at the clinic, and all data imported into the HCP's database through information sharing (see Chapter 7, Host). This report facilitates viewing and comparing of data for all patients of the HCP or clinic. FIG. 136 illustrates a HCP Group Analysis Report. By default, the report displays with column heads for Patient ID, Last Name, First Name, and for a number of event-related data fields. Data for each patient displays in one row. Each glucose value displays in a cell shaded the signal color of its target range. The glucose target mode is Standard. A day (24 hours) is defined as midnight to midnight.

A user can customize the columns in the HCP Group Analysis Report by changing the order of events in a column, adding and removing columns, and resizing columns. To save the custom changes, the user can click Customize (bottom right of screen). The Filter Builder screen displays (see FIG. 139). The user can then select Save As, enter a filename, and click Save.

Figure 137:
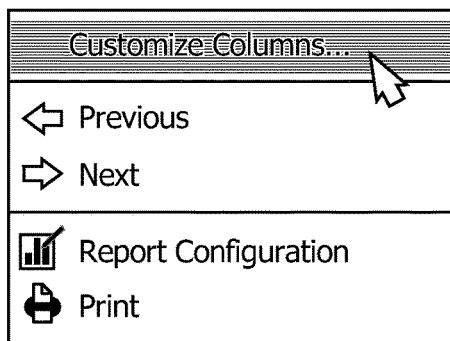
Figure 138:
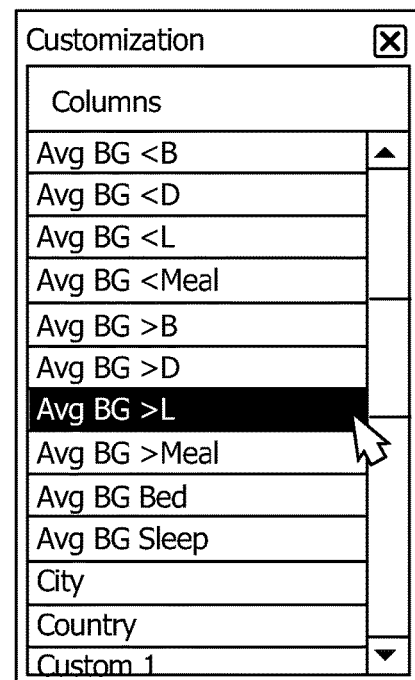

To reverse the order of items in any column, the user can click on the column heading, then click on the little arrow that appears to the right of the heading. The user can do the same to change the order back to its original sequence. To remove a column from the report, the user can drag-and-drop the column head cell off the table. To add a column to the report, the user can right-click anywhere on the table to call up a pop-up window (see FIG. 137), and select Customize Columns. The Customization list displays (see FIG. 138). From the list, the user can select the column head you want to add. Then the user can drag-and-drop it to the preferred position in the column-head row. Two green arrows display to help the user position the column. FIG. 138 illustrates a Customization List. To move columns left or right in the table, the user can drag-and-drop the column-head cell to the preferred position in the column head row. To adjust the width of any column, the user can use the sizing tool that becomes active when he or she hovers the pointer over the right margin of the column-head cell.

Data Filter

Figure 139:
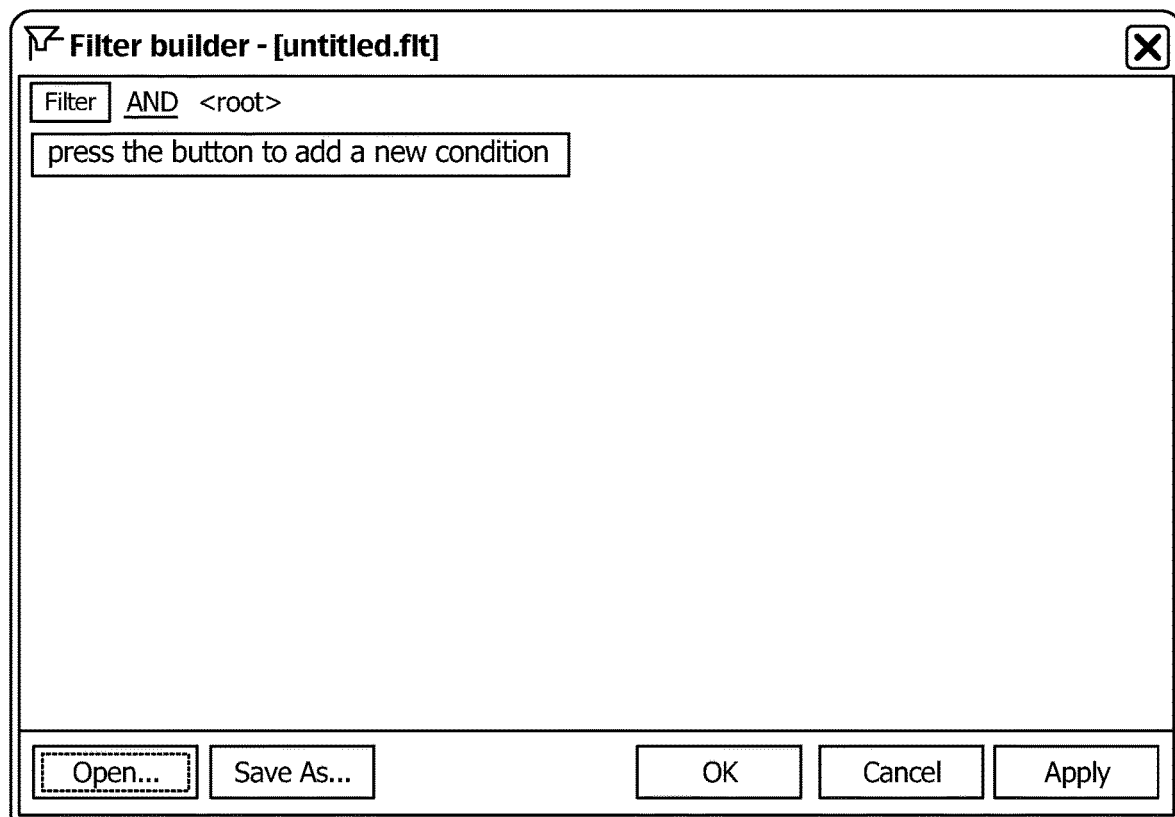

For any column-head in the table, a user can configure a data filter using the selection list. To display the selection list for any column, the user can click the down-arrow at the right. To display data for all patients, with any or no entry in the corresponding data field, the user can click All. To customize the data filter, the user can click Customize, and complete the dialog box. FIG. 139 illustrates a Filter Builder Screen. To display data for any patient with a particular value in the corresponding data field, the user can click the value of interest. To save the data filter changes, the user can click Customize (bottom right of screen). The Filter Builder screen displays (see FIG. 139). The user can select Save As, enter a filename, and click Save.

Insulin Management Tools

Figures 140, 141:
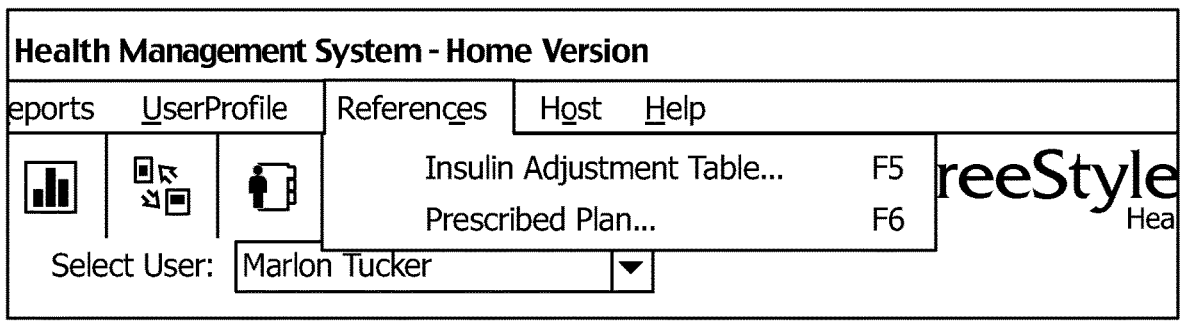

The System of the preferred embodiment incorporates insulin management tools to make health management easier for Home and HCP users. The System provides additional insulin management tools to support the Home User's healthcare. An Insulin Adjustment Table is used to determine insulin dose adjustment based on a user's current blood glucose level. All values entered in this table should be determined by the HCP. A Prescribed Plan table is used to store and review healthcare guidelines established by the HCP. FIG. 140 illustrates a References Drop-Down Box.

Insulin Adjustment Table

The HCP first sets up the values in this table (see FIG. 141). Insulin adjustment may not be necessary for every Home user. The Glucose Start Value (mg/dL) in the table is the blood glucose level at which the insulin dose should be increased. Beginning with this value, consecutive blood glucose ranges are provided for each increase in insulin. These ranges are determined by the value entered as the patient's Insulin Sensitivity. The Insulin Dosage Amount is the amount of insulin above the patient's normal dose that should be taken when the patient's blood glucose level falls within the range specified. The Insulin Adjustment Table is provided as a convenient reference, and entries made in this table are generally not used by other application features.

Defining Insulin Adjustment

On the Home page, a user can select References on the main menu bar (see FIG. 140). A user can select Insulin Adjustment Table from the drop-down list, and the Insulin Adjustment Table displays. FIG. 141 illustrates an Insulin Adjustment Table. The user can set the Glucose Start Value (mg/dL) to the value determined by his or her HCP. The Glucose Start Value is used to set the lowest glucose value on the Insulin Adjustment Table and indicates when to start adjusting the insulin dose. The user can set the value of Insulin Sensitivity to the value determined by the user's HCP. The Insulin Sensitivity value is used to set the increase in value between each of the consecutive blood glucose ranges displayed.

Prescribed Plan

The Prescribed Plan is a table Home users can use to store and review guidelines from their HCP for Insulin type, dosage, and time of day, insulin sensitivity, medication type, dosage, and time of day, carbohydrates for each individual meal time, and/or ratio of amount of insulin per grams of carbohydrate. FIG. 142 illustrates a Prescribed Plan. Data for each of these items can be individually entered for breakfast, lunch, dinner, bedtime, and a snack. Comments can also be added. Once the Prescribed Plan is entered, a user can view the plan by returning to this screen. A user can also print it out by clicking Print at the bottom of the screen.

Defining a Prescribed Plan

On the Home page, a user can select References on the main menu bar (see FIG. 140). The user can select Prescribed Plan from the drop-down list. The Prescribed Plan screen (see FIG. 142) then displays. The user can select an entry type from the Type drop-down list: Insulin or Medication. The user can select Insulin to record an insulin type and dose for each meal field. The user can select Medication to record a medication type and dose for each meal field where it is taken. The user can enter the name of the Insulin or the Medication and the dosage in the Item field. The user can select Ratio to record the optimum meal-based insulin-to-carbohydrate ratio. The user can select Carbohydrates to record the optimum carbohydrate intake. The user can enter the desired number of grams of carbohydrate for each meal field. The user can select Sensitivity and enter the Insulin Sensitivity factor his or her HCP calculated for the user. The user can enter any comments in the Comments field (optional). By clicking OK, the plan is saved and the Prescribed Plan window closes. (Or, to clear all data entered into the plan, the user can click Reset.)

Insulin Sensitivity

Individuals with low insulin sensitivity usually need a higher insulin dose to lower their glucose levels to acceptable levels than people with higher insulin sensitivity. The user's insulin sensitivity is determined by his or her HCP. The insulin-to-carbohydrate ratio is used to determine how much insulin to administer per grams of carbohydrates eaten. A user's insulin-to-carbohydrate ratio is determined by his or her HCP.

Host

The Host System of the preferred embodiment resides on an Internet server. The Host database stores data that has been synchronized with the System data on a user's PC. Data stored on the Host can be shared with other users. A Home user can choose to share data with his or her HCP or several HCPs. HCP users can share data with other HCPs. In either case, the user "invites" the other party to share data. The user sets up a Host Account if he or she wishes to use the Host's capabilities. A Host Account defines access, privileges, and functions associated with a particular user.

Synchronization

Synchronization is the process whereby the System application on a user's PC connects to the Internet and transmits data and other information between the user's program and the Host server. Synchronization matches and updates the data between the System application installed on the user's computer and the Host System. Following synchronization, new and modified data is reflected in both the local System database and the database on the Host server.

Host Account Setup

The first time a user synchronizes with the Host, the Synchronize window opens. The user can follow the steps on the screen, a Host account will be created and a confirmation e-mail will be sent to the user. The user can verify his or her Host account number by looking on the User Profile screen. If a user selects an item from the Host drop-down menu, the System will try to open an Internet connection automatically. If the Internet connection cannot be opened this way, it can be opened manually before selecting items on the Host menu.

The user can click the Synchronize icon or select Host on the main menu bar and choose Synchronize from the drop-down box (Home version) or Synchronize Current HCP (HCP version).

FIG. 143 illustrates a Home User: Host Drop-Down Box (left), and HCP User: Host Drop-Down Box (right). The End-User Agreement Screen will display. The user can review the End-User Agreement (see FIG. 144), and click Next to continue.

Figure 144:
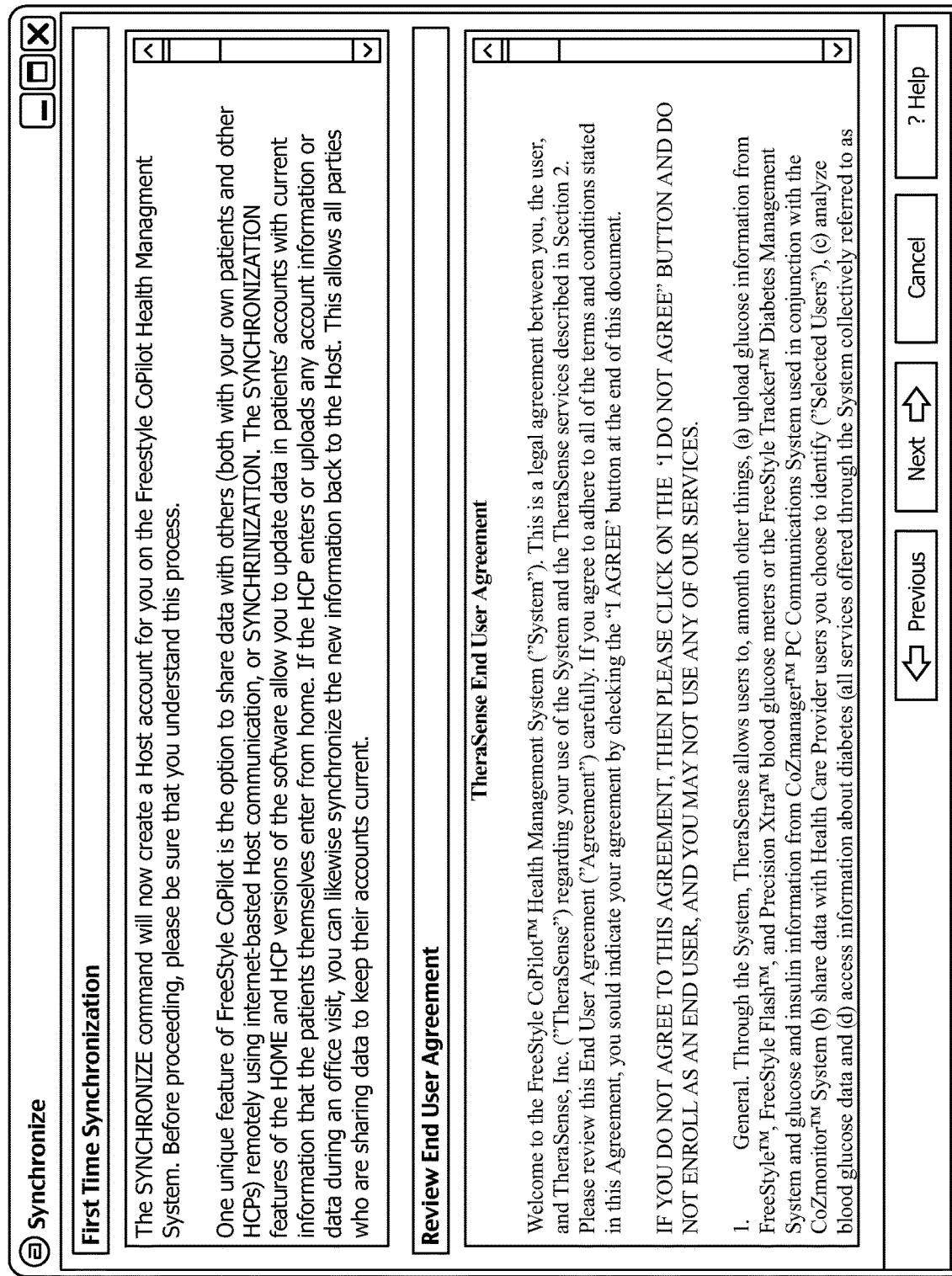

FIG. 144 illustrates a-First Time Synchronization Screen. The user proceeds through the setup process on the screen. A password is established and a Host Account number is assigned to the user (which now appears on his or her user Profile screen).

Figure 145:
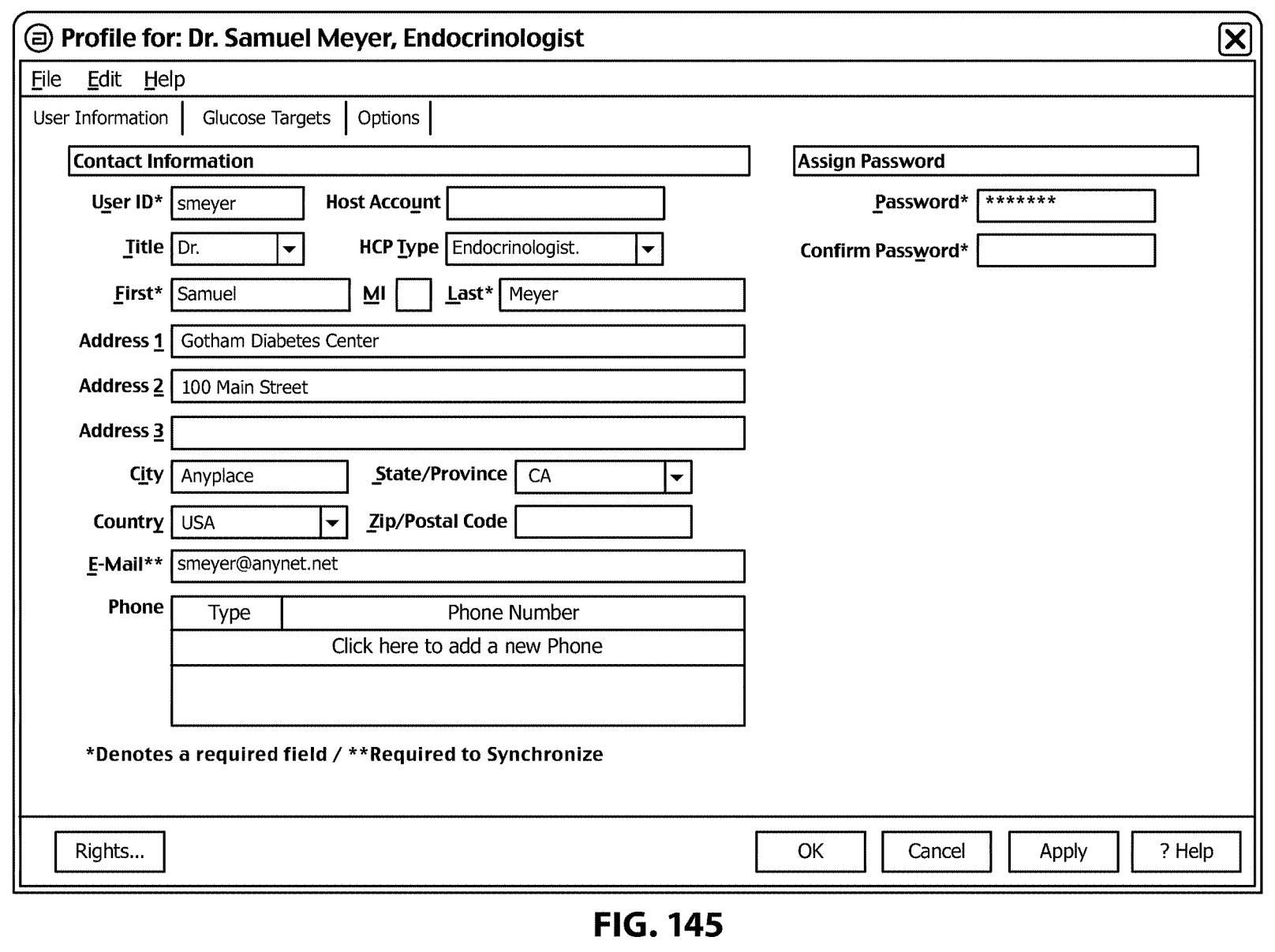

FIG. 145 illustrates a Host Account Number. The System then synchronizes the user's account, and a summary of the synchronized data automatically displays.

Figure 146:
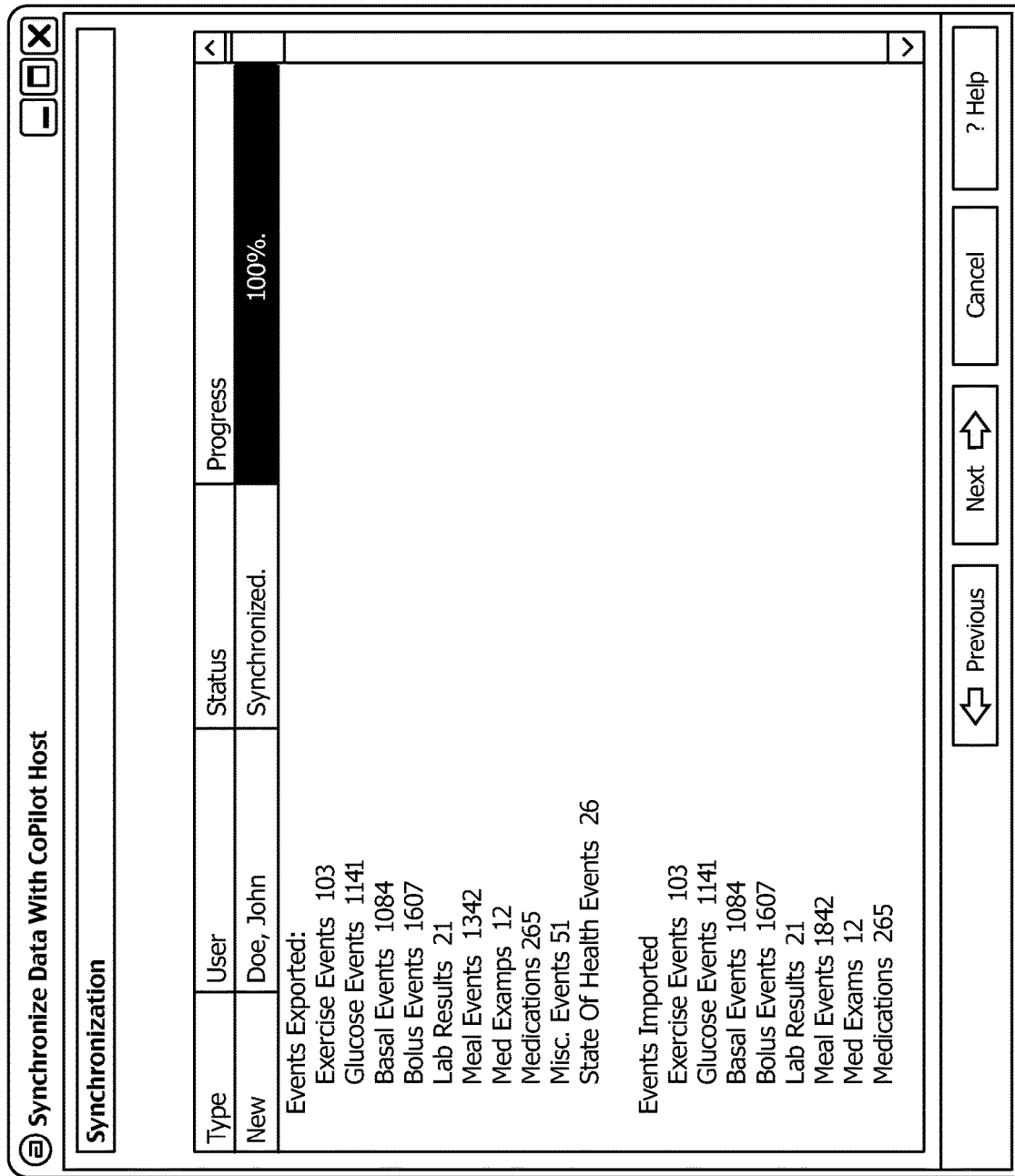
Figure 147:
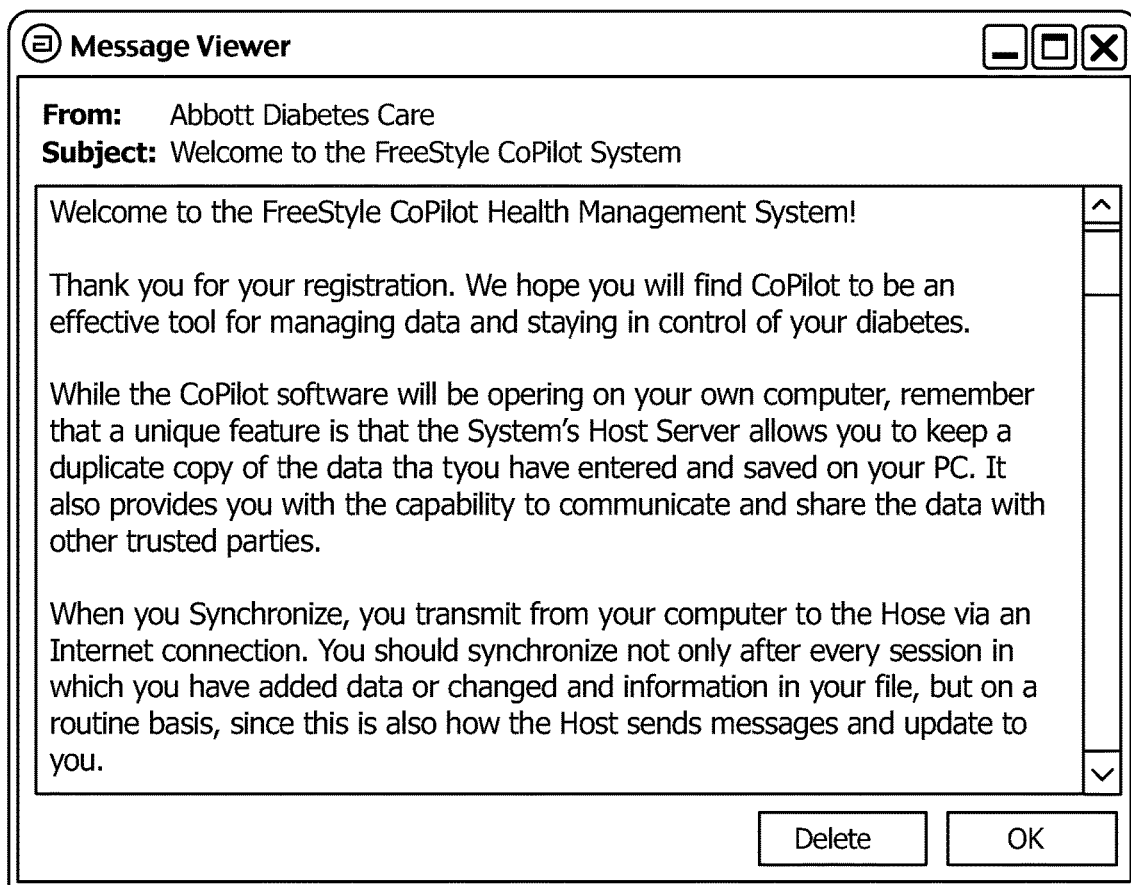

FIG. 146 illustrates a Synchronization Summary Screen. A confirmation message is sent to the user from the Host and to the user's e-mail address. FIG. 147 illustrates a Confirmation Message From the Host.

Synchronizing with the Host

If the user has previously logged in and set up an account, he or she can synchronize with the Host as follows. The user can click the icon or select Host on the main menu bar and choose Synchronize from the drop-down box (Home version) or Synchronize Current HCP (HCP version) (see FIG. 143). The System then automatically synchronizes the user's local and Host accounts (including all event and profile data). A summary of the synchronized data automatically displays (see FIG. 146).

Synchronize All (Home Version)

In a single household, there may be more than one person with diabetes that manages their diabetes using the System. For convenience, a Home user may synchronize the data for all the Home users using the System in the household with a single click of the mouse. The user can select Host on the main menu bar and choose Synchronize All from the Home user Host drop-down box (see FIG. 143). The System displays a list of all the Home users on the PC. Synchronization starts automatically. A blue progress bar indicates when synchronization is complete for each Home user's data.

Synchronize All HCP Users (HCP Version)

In a clinic, for example, there may be several HCPs using the same System. For convenience, a HCP may synchronize the patient data for all the HCPs using the System with a single click of the mouse. The user can select Host on the main menu bar and choose Synchronize All HCPs from the drop-down box (see FIG. 143). The System displays a list of all the HCPs on the local system and the patients they manage. Synchronization starts automatically. A blue progress bar indicates when synchronization is complete for each HCP's and patient's data.

Invitation to Share Data

Once the user (Home or HCP) sets up a Host Account, he or she can authorize one or more HCPs to have access to the data. To do this, the user can initiate an "invitation" to the HCP to share data via the Host. This notifies the Host that the user will allow the selected HCP to view (and in some cases, edit) their data.

There are several ways to invite an HCP to share data. The HCP may have a Host Account: Once a user is logged in to the Host, he or she can search for the HCP using the HCP's State/Province or Host Account number. The HCP may not have a Host Account: In this case, the HCP's e-mail address is discovered and used. If the HCP fails to accept or decline the invitation within 30 days, the invitation to share data expires. A user then can send another invitation to the same HCP after 30 days.

Invitation to Share Data: HCP has a Host Account

Figure 148:
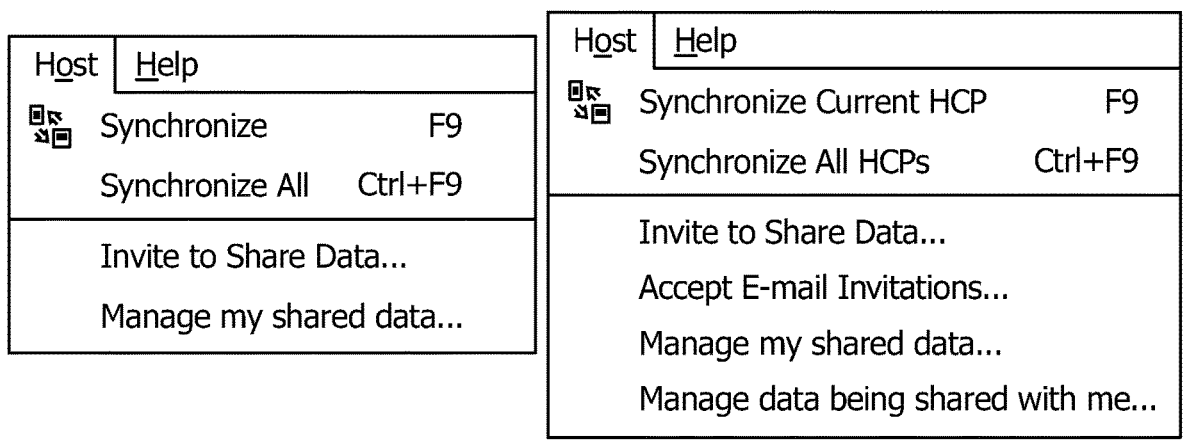

From the Host menu on the main menu bar, the user can choose Invite to Share Data. FIG. 148 illustrates an Invite to Share Data (Home User Screen, left; HCP User Screen, right). An Internet connection to the Host server will be opened and the screen illustrated at FIG. 149 will display. The user can select the appropriate option. If the user does not know the HCP's Host Account number, he or she can select Search Host HCP database to find an HCP from the list of existing accounts, and then click next. On the next screen, the user can select the state/province where the HCP is located.

FIG. 150 illustrates a Find HCP from Existing Accounts Screen. The user can then click Search. HCPs from the selected state with a Host Account will be displayed. The user can then highlight the HCP he or she wants and click Next. The screen for selecting Access Level displays.

FIG. 151 illustrates an Assign Access Level Screen. The user can select Read-Only Access or Full Access (Read and Enter Data), and then click Submit. The Host then displays the Process Complete screen and sends an invitation to share data to the HCP.

Figure 152:
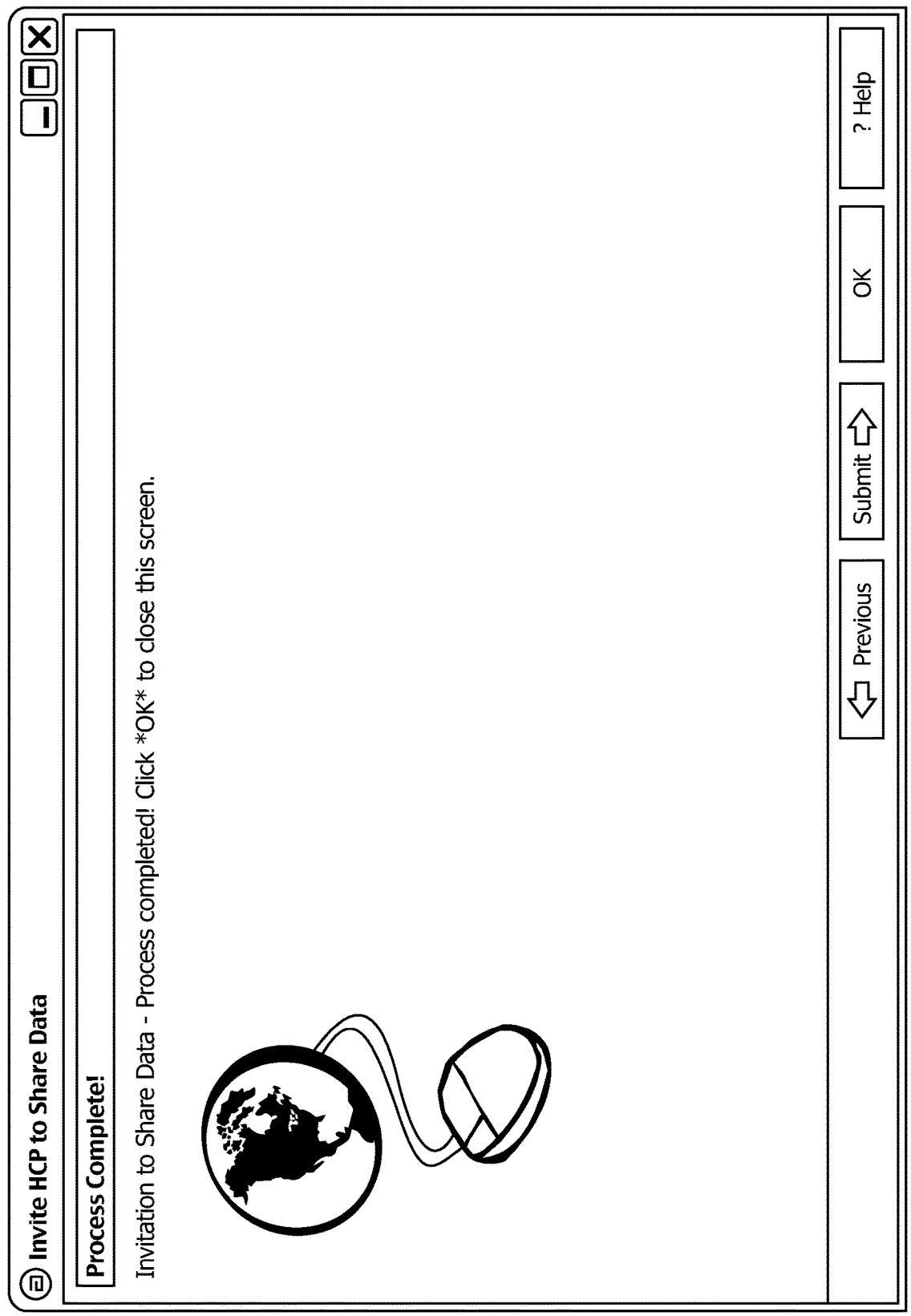

FIG. 152 illustrates a Process Complete Screen. If you know the HCP's Host Account Number, he or she can select enter the Host HCP Account Number provided by the HCP.

FIG. 153 illustrates an Invite HCP to Share Data Screen. The user can click Next. On the next screen, the user enters the Host HCP Account Number.

FIG. 154 illustrates an Enter Host HCP Account Number Screen. The user can click Search. The HCP is displayed as the search result. If this is the HCP the user is looking for, the user can click Next. The screen for selecting Access Level displays. The user can select Read-Only Access or Full Access (Read and Enter Data), and click Submit.

Figure 156:
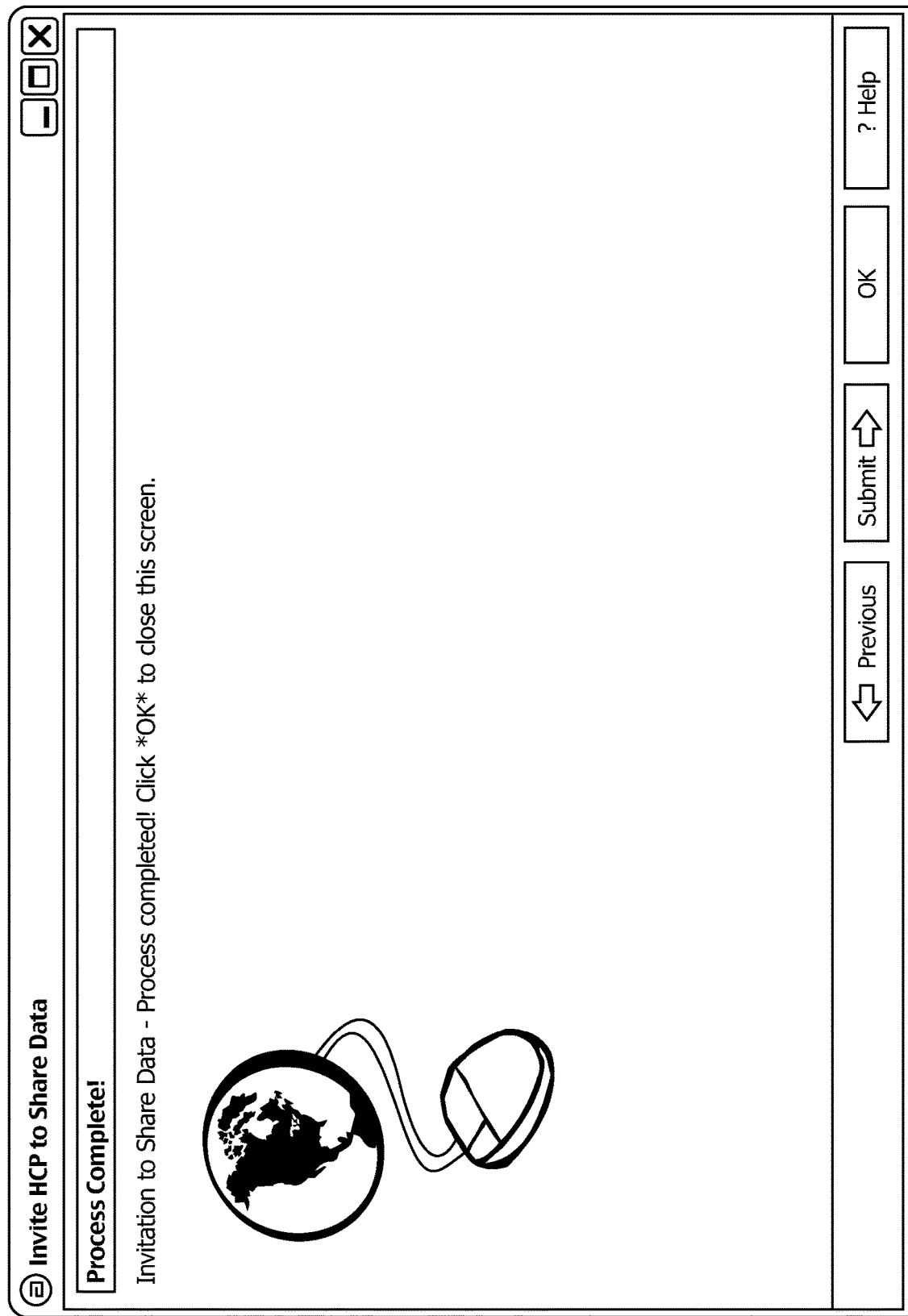

FIG. 155 illustrates an Assign Access Level Screen. The Host then displays the Process Complete screen and sends an invitation to share data to the HCP. FIG. 156 illustrates a Process Complete Screen.

Accepting an Invitation from the Host to Share Data: HCPs Only

Figure 158:

If a patient user issues an invitation to share their data with a user, the user will see a message in the Messages From CoPilot Host window as illustrated at FIG. 157. If the user fails to accept or decline the invitation within 30 days, the invitation to share data expires. The user can double-click the message header to display the invitation to share data. FIG. 158 illustrates an Invitation to Share Data (from Host). To accept the invitation, a user can click Accept Invitation (bottom of screen). The Host will then synchronize with the user's system, and the patient's data will be uploaded to Host computer. A summary of the synchronized data then automatically displays. The user can then click Close to exit. At this point, the user has successfully accepted the invitation and received the patient's data.

Invitation to Share Data: HCP does not have a Host Account

If the HCP does not have a Host Account, a user can send an e-mail invitation to the HCP to share data if the HCP's Internet address (example: jsloane@aol.com) is known. From the Host menu on the main menu bar, the user can choose Invite to Share Data. An Internet connection to the Host server will open and the screen illustrated at FIG. 159 will display. The user can select send an e-mail invitation to an HCP who does not have an existing account, and click next. When the next screen opens, the user can enter the Name and E-mail Address of the HCP he or she wishes to invite.

FIG. 160 illustrates an E-mail Invitation to HCP with No Host Account. The screen for selecting Access Level displays. The user can select Read-Only Access or Full Access (Read and Enter Data), and click Submit.

Figure 162:
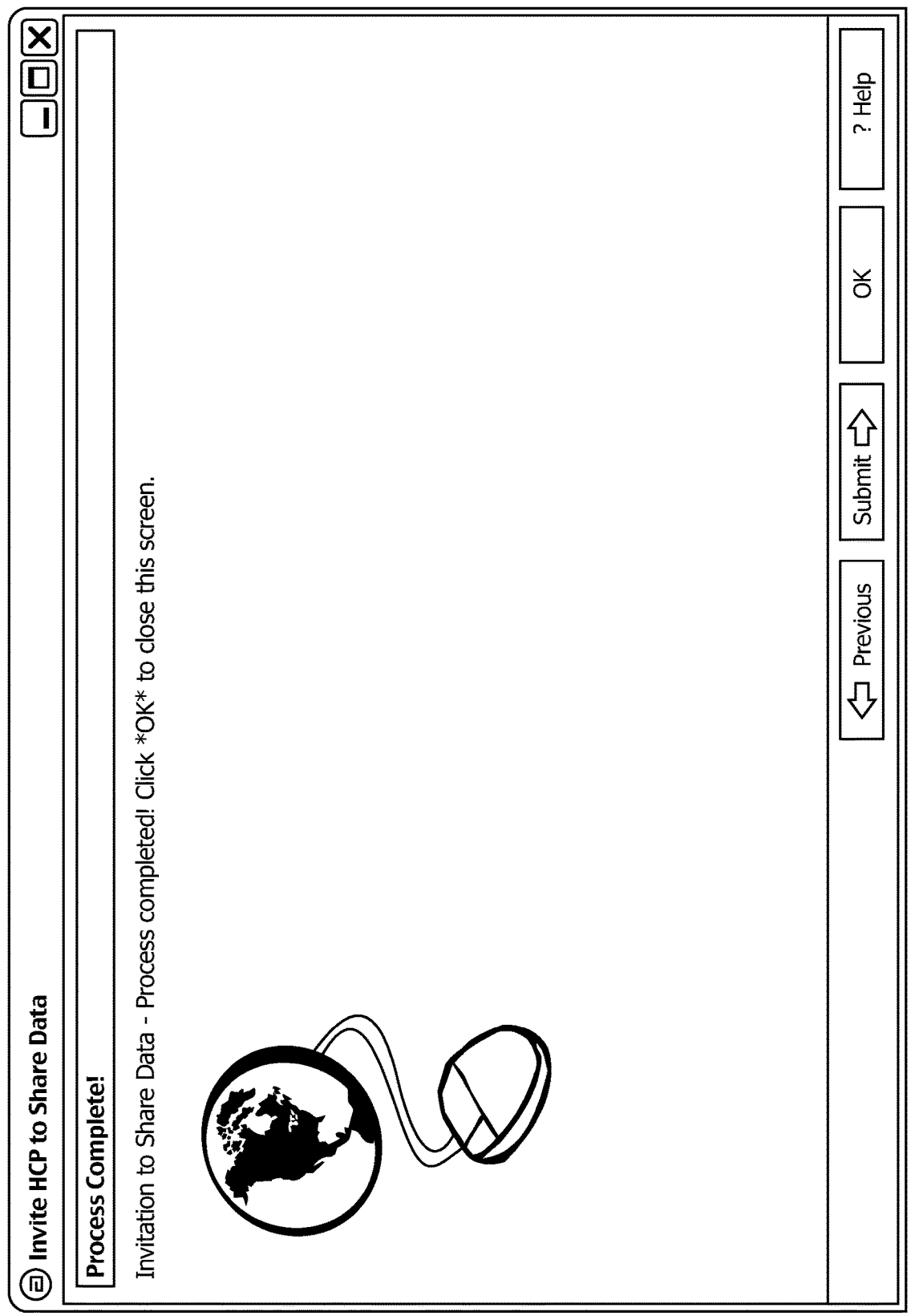

FIG. 161 illustrates an Assign Access Level screen. When the user clicks next, the Host then displays the Process Complete screen. FIG. 162 illustrates a process Complete Screen. The Host will send the HCP an e-mail inviting him/her to have access to the data. The message instructs the HCP to download the Management System, install the software and set up a user profile, and synchronize with the Host and set up a Host Account. The user then makes note of the Invitation Code included near the end of the e-mail. The Host will notify the user when the HCP has accepted the invitation to share data. If the user does not receive this message within a reasonable period of time, the HCP should be contacted directly.

Accepting an E-Mail Invitation to Share Data (HCPs Only)

Figure 163:
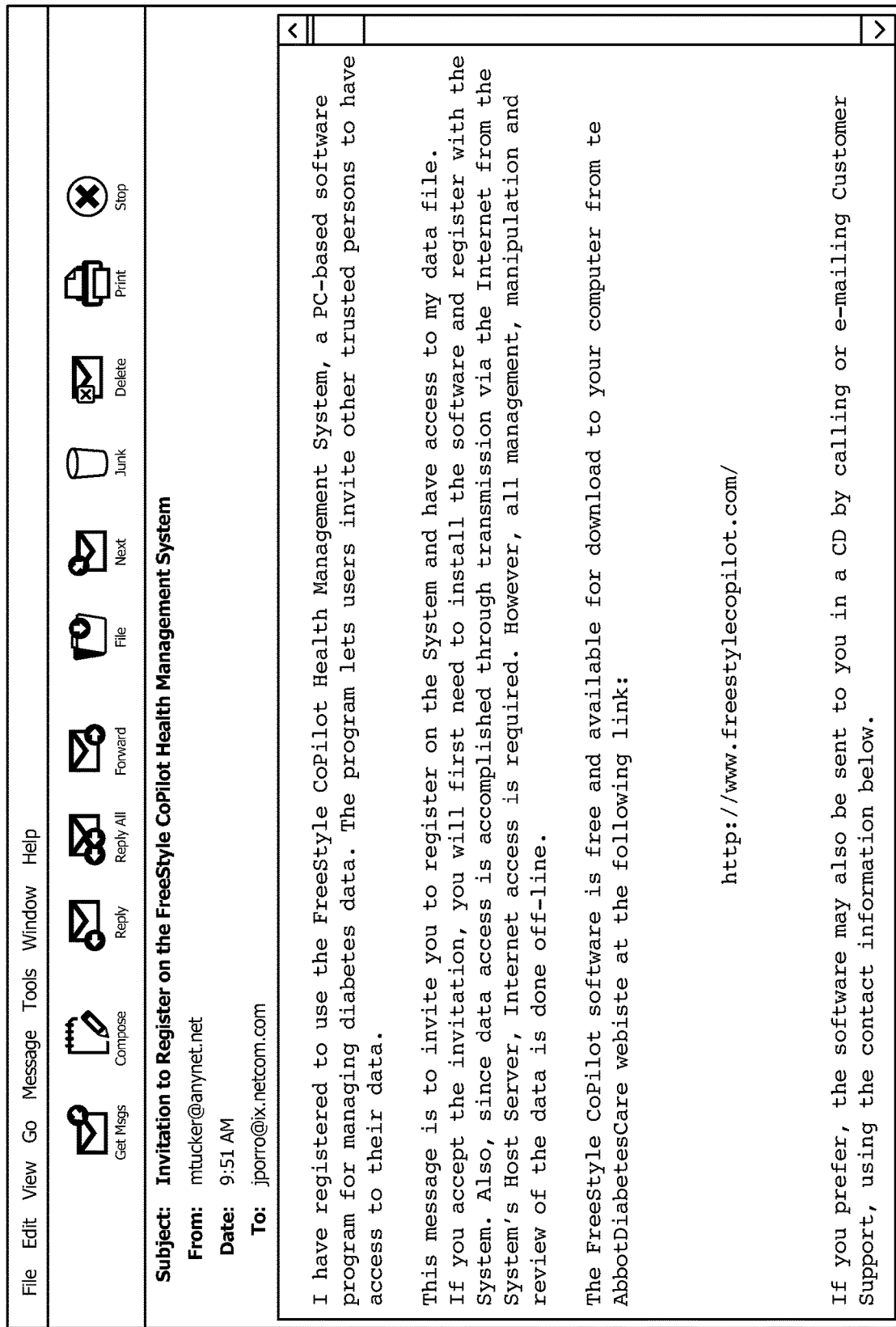

When a user receives an e-mail invitation to share data, the message will instruct the user to download the Health Management System from the Internet (e.g., by just clicking on the hyperlink in blue), install the software and set up a user profile, and synchronize with the Host and set up a Host Account. The user then makes note of the Invitation Code included near the end of the e-mail (see FIG. 164). FIG. 163 illustrates an E-mail Invitation to Register and Share Data. An invitation code may look like that illustrated in FIG. 164.

Figures 164, 165:
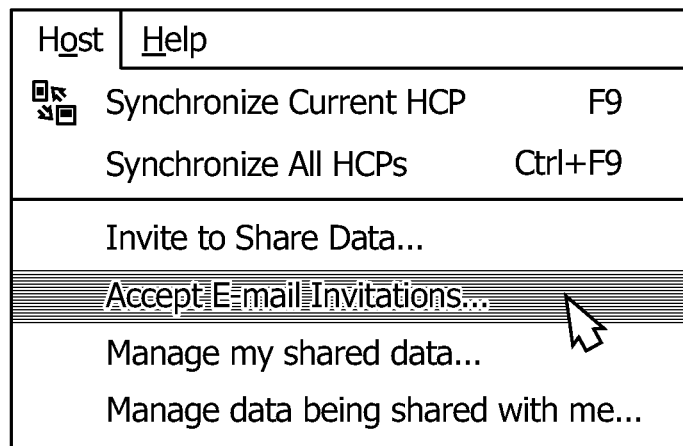
Figure 166:
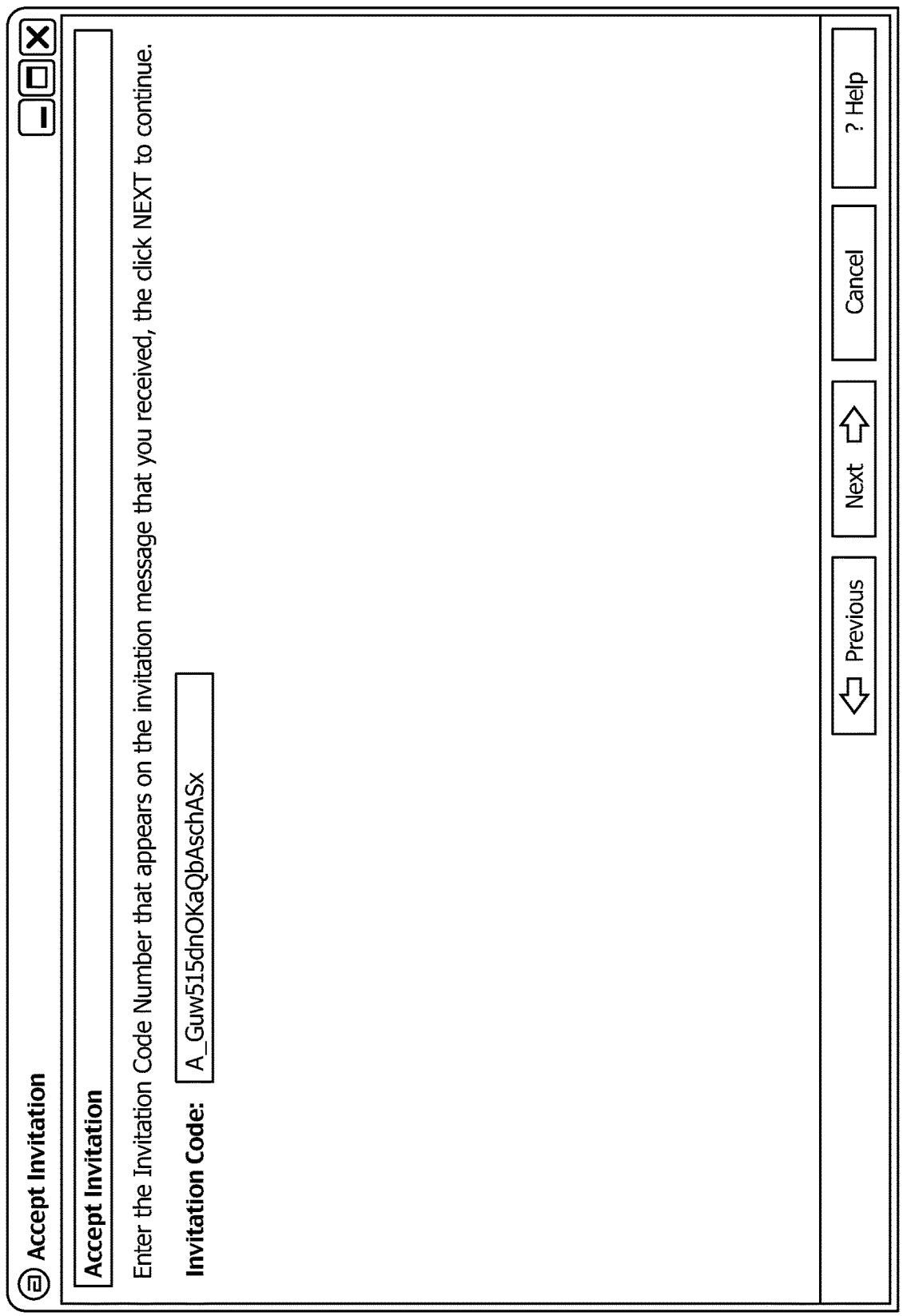
Figure 167:
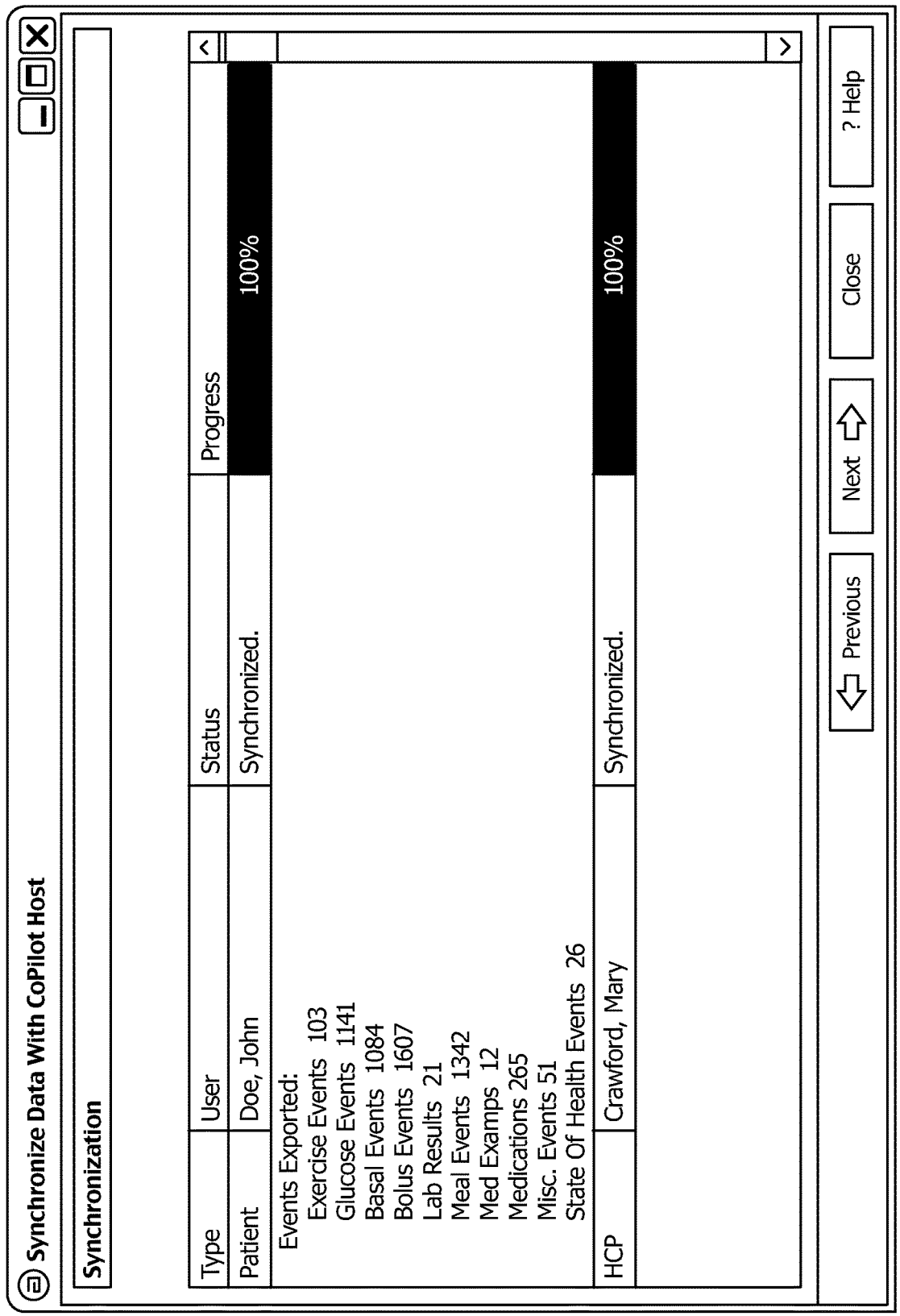

After the user has downloaded and installed the software, he or she can set up a user profile and register with the Host. From the Host drop-down box on the main menu bar, the user can choose Accept E-Mail Invitation. FIG. 165 illustrates a HCP: Host Drop-Down List. The System connects to the Host server and the screen illustrated at FIG. 166 displays. The user can enter the Invitation Code in the box provided and click Next. The Host then synchronizes with the user's System, and the patient's data is downloaded. A summary of the synchronized data then automatically displays. A synchronization screen is illustrated at FIG. 167.

Managing Shared Data: Home User

A user can limit, expand, or deny an HCP access to his or her data on the Host using a Manage Shared Data function.

Defining or Changing HCP Access to Data

Figure 168:
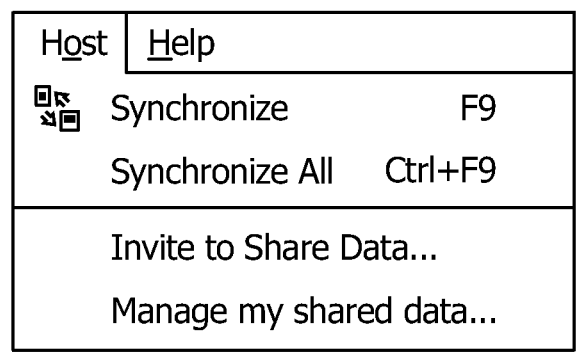

From the Host drop-down box (see FIG. 168) on the main menu bar, the user can choose Manage my shared data. The next screen shows a list of each authorized HCP along with the level of access granted to them. FIG. 169 illustrates a Manage My Shared Data Screen. The user can highlight the HCP whose access he or she wishes to change and choose to Grant NO Access which removes all access to the user's data by the listed HCP, Grant Read-Only Access, which restricts the HCP to viewing the user's data, or Grant Full Access, which allows the HCP to view and edit the data, including event data, glucose targets, the user's prescribed plan, etc. The user can click Close to exit, and the Host the sends a message to the HCP about the changed access level.

Managing Shared Data: HCP User

Figure 170:
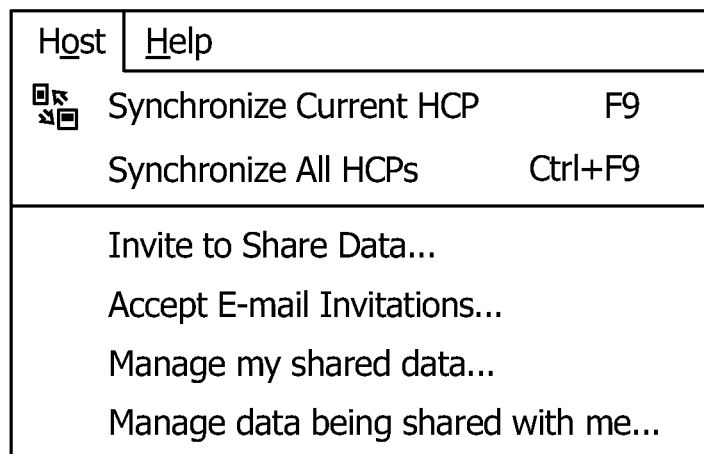
Figure 171:
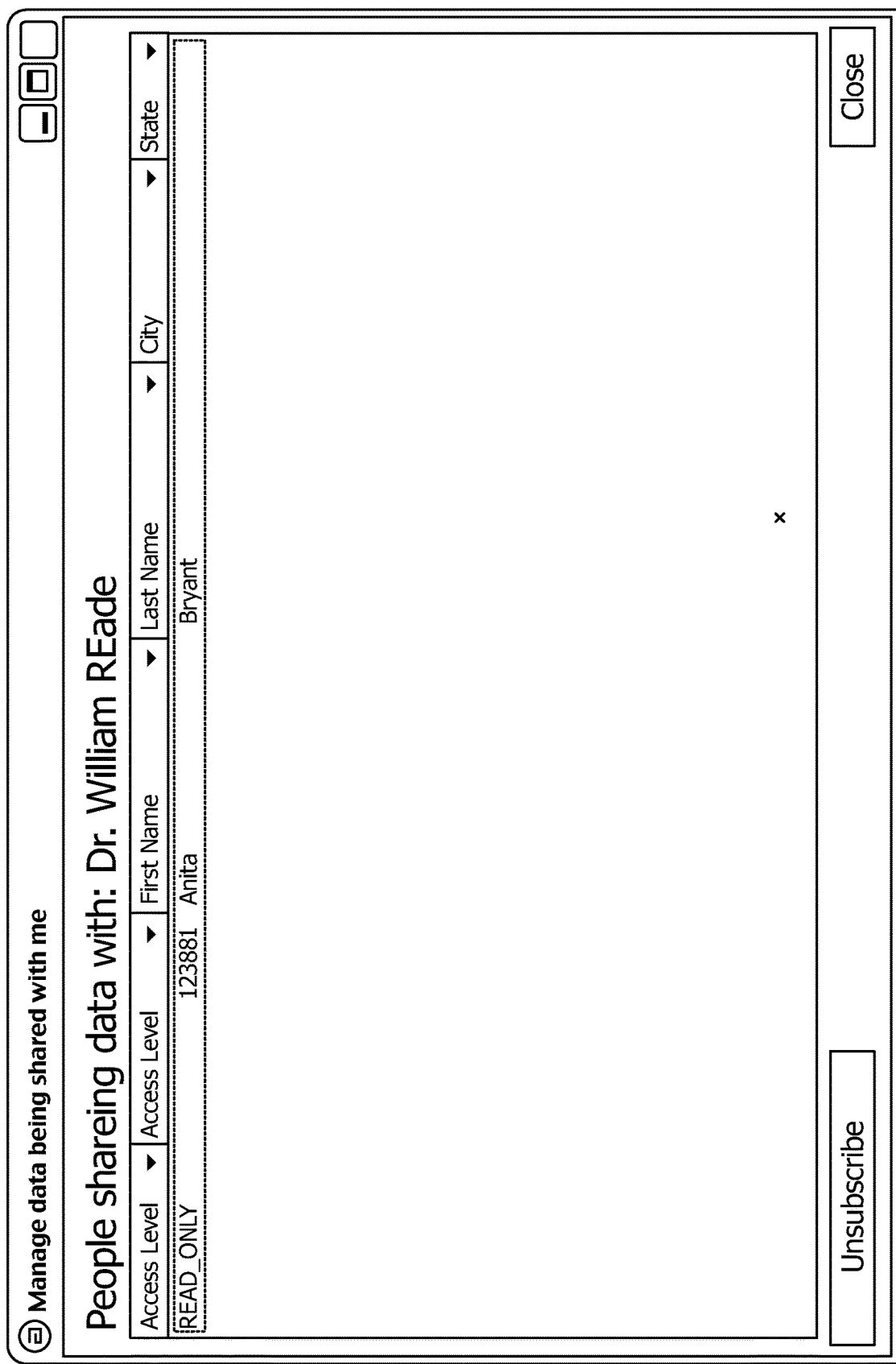
Figure 172:
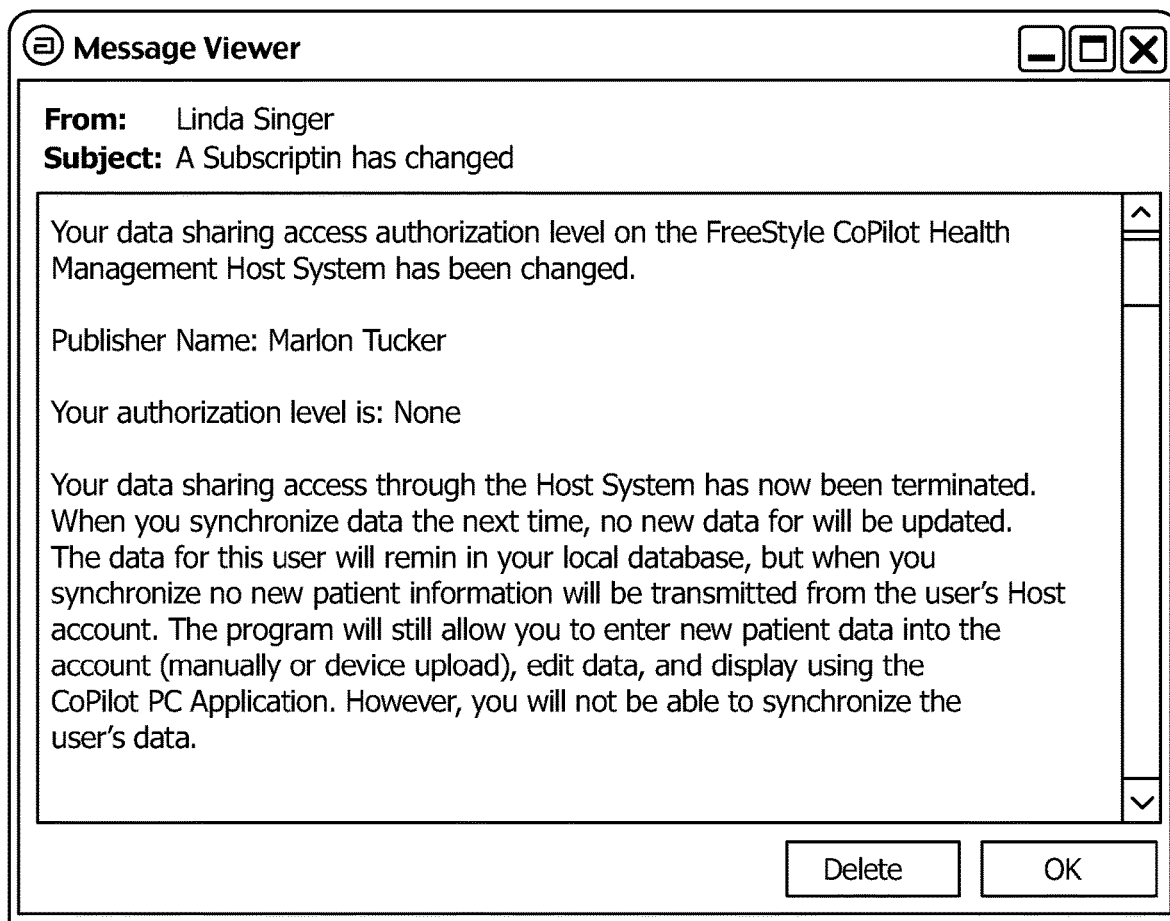

A HCP user can view a list of the patients with whom he or she shares data. The HCP user can also unsubscribe patients, which means the HCP user will no longer have access to their data. From the Host drop-down box (see FIG. 170) on the main menu bar, the HCP user can choose Manage data being shared with me (see FIG. 171). The next screen shows a list of the patients who share data with the HCP user. The HCP user can then highlight the patient that he or she wants to unsubscribe. Then, the HCP user can click the Unsubscribe button (lower left of screen). The Access Level for this patient will change to NONE. The Host will send a message confirming the changed Access Level. The next time the patient or the HCP who assigned the patient to synchronize with the Host, the Access Level on their Manage My Shared Data screen will be NONE. FIG. 172 illustrates a Changed Access Level Message.

Database Management

To ensure that information remains accurate, the System provides the user with the capability to perform database maintenance. The Database Maintenance feature includes the ability to, archive data, backup data and restore data from the last backup. More than one database can be created and maintained by the System application. The last database selected will be opened by each successive execution of the software until another database is selected by the user.

Archiving Data

Figure 173:
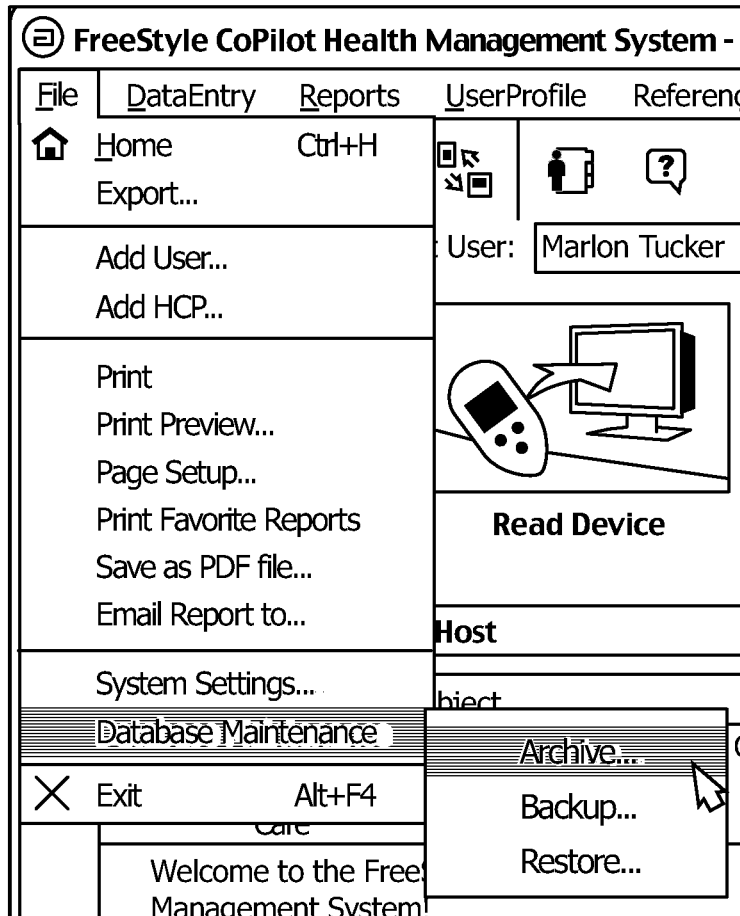
Figure 174:
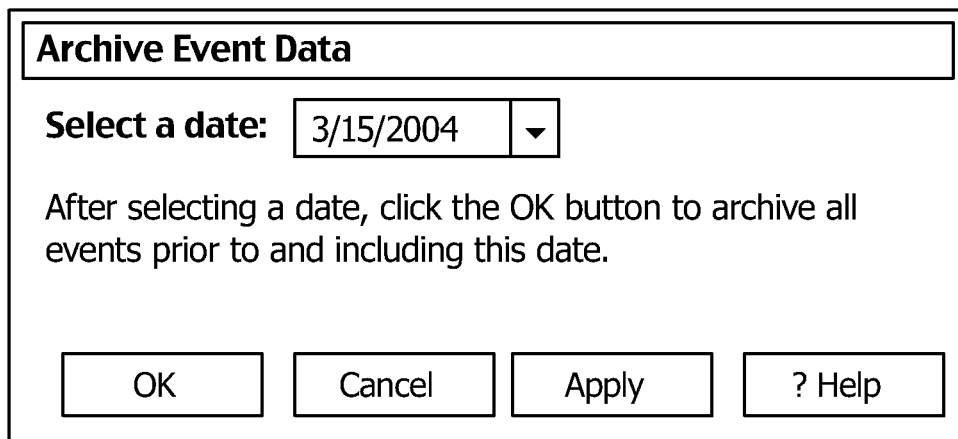
Figure 175:
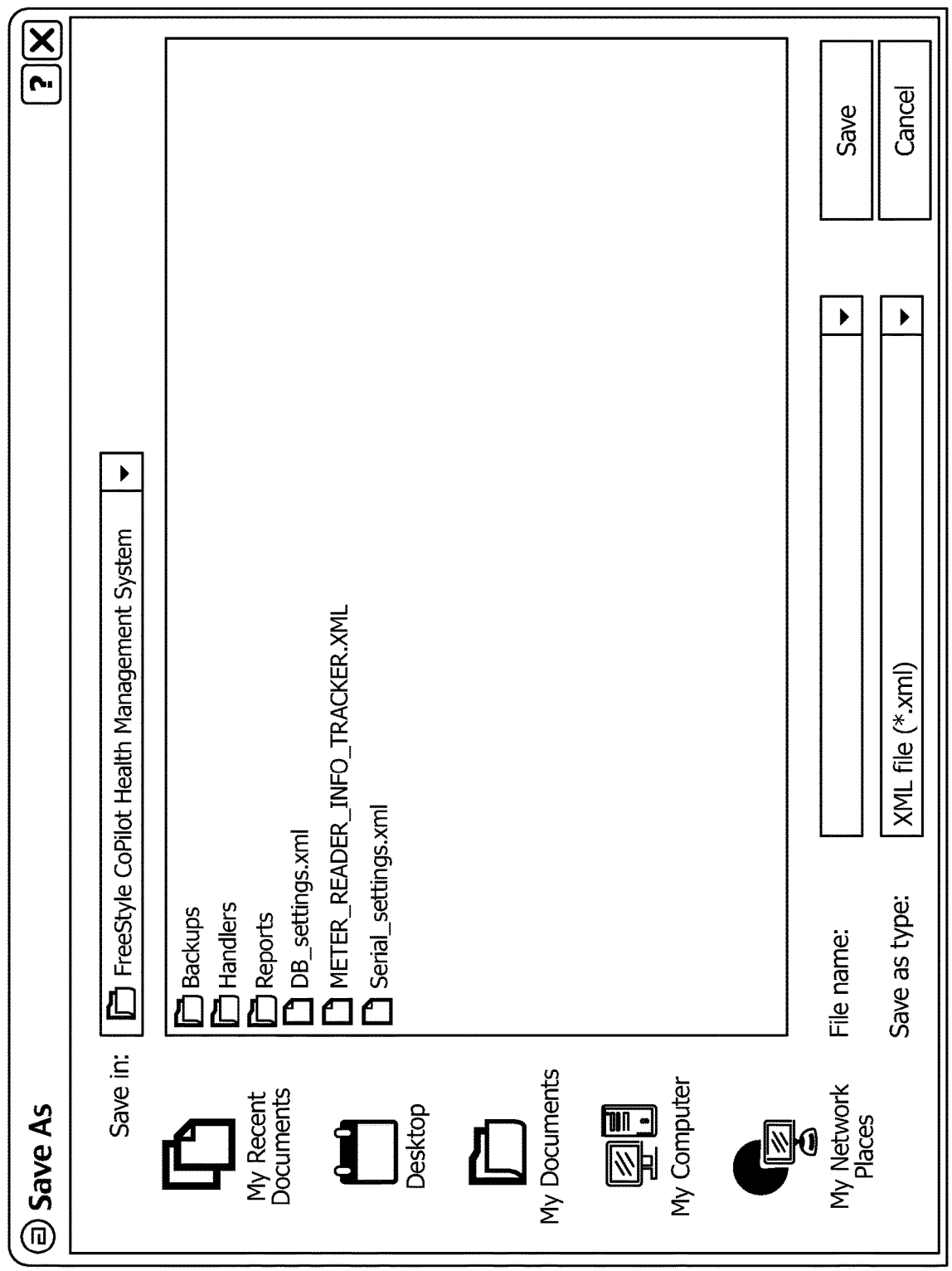

When a user chooses to archive data, the data being archived will be removed from the System database. The user can restore the data by importing it. On the Home page, the user can select Database Maintenance from the File drop-down box (see FIG. 173). The user can select the Archive option from the menu. A window will open, allowing the user to specify a date. The user can select the last date of the data to be included in the archive, and click OK. FIG. 174 illustrates an Archive Event Data Screen. A file browser will open. The user can browse to the directory where the file is to be saved. The user should make sure XML file (*.xml) is displayed in the Save as Type window. FIG. 175 illustrates a File Browser Window: Save Archive Data. The user can enter the name of the file in the File Name window and click Save. The file is saved as an .xml file in the directory specified.

Viewing Archived Data

Figure 176:
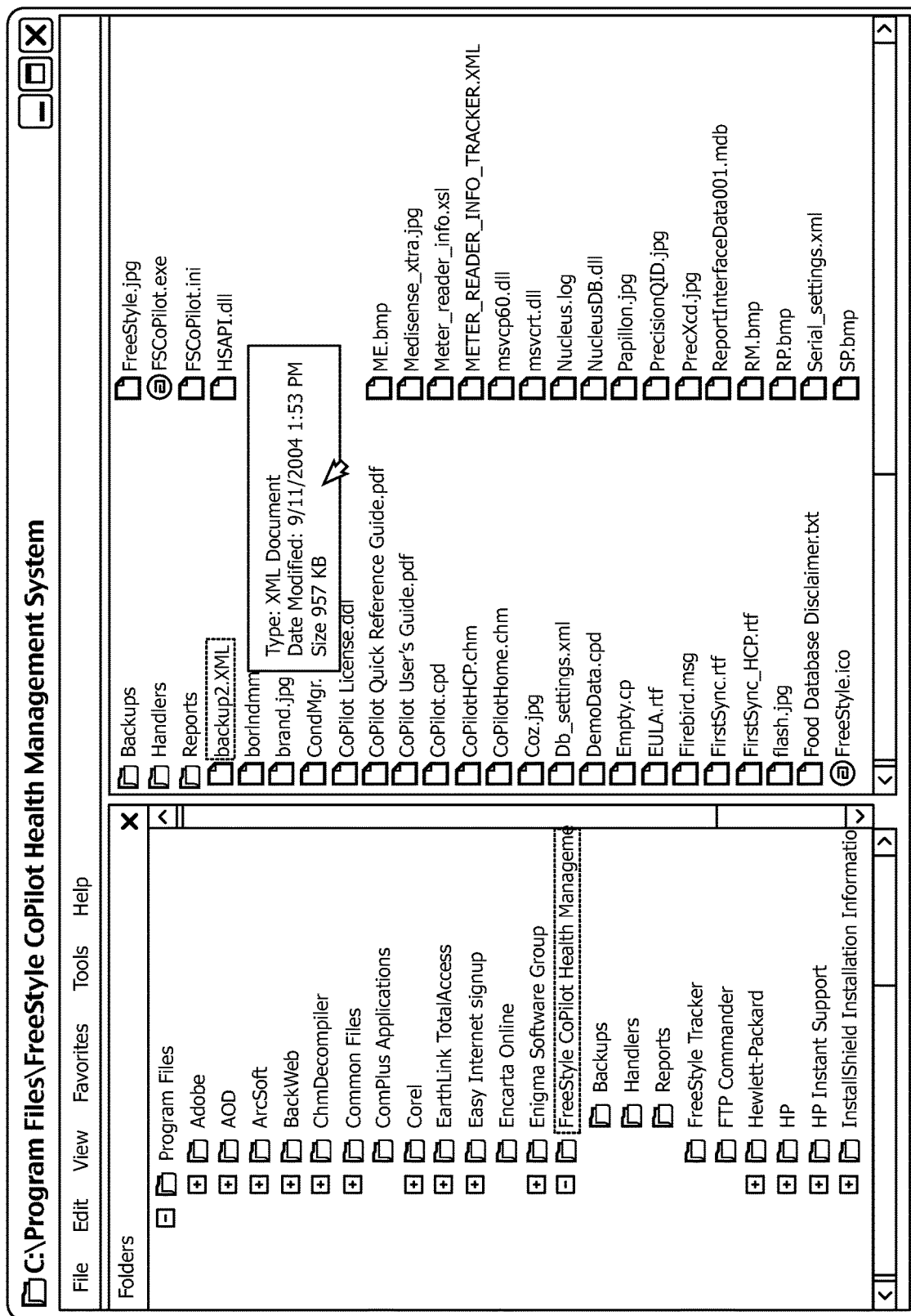

The user can close or minimize the system application. The user opens the file browser and browses to the folder where he or she saved the archived *.xml file. FIG. 176 illustrates a File Browser: Location of Archived Data File (*.xml). To open an *.xml file, a Web browser (for example, Internet Explorer, Netscape, etc.) is used that is installed on your PC. The user can highlight the archive file and click Open.

Restoring Archived Data

Figure 177:
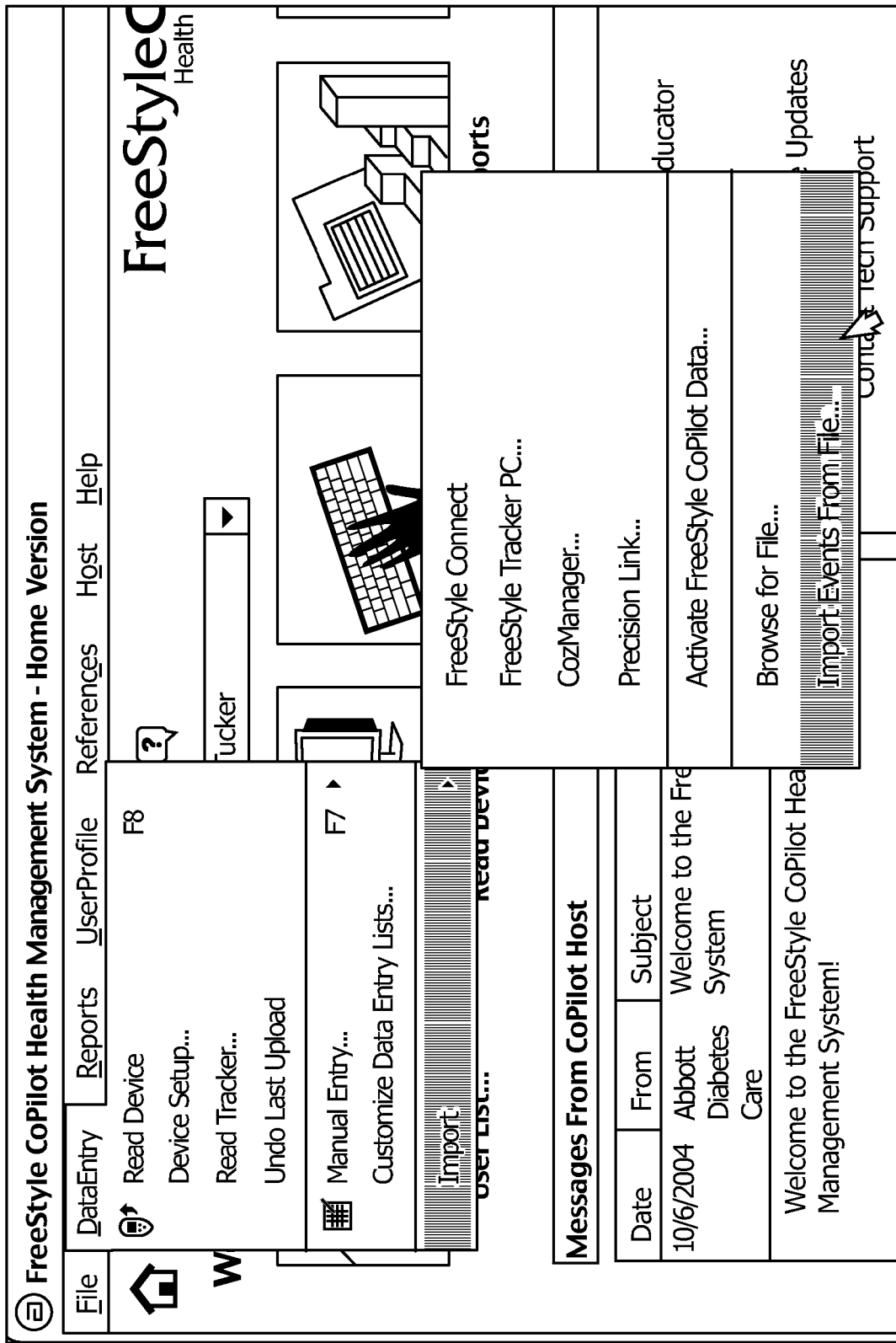
Figure 178:
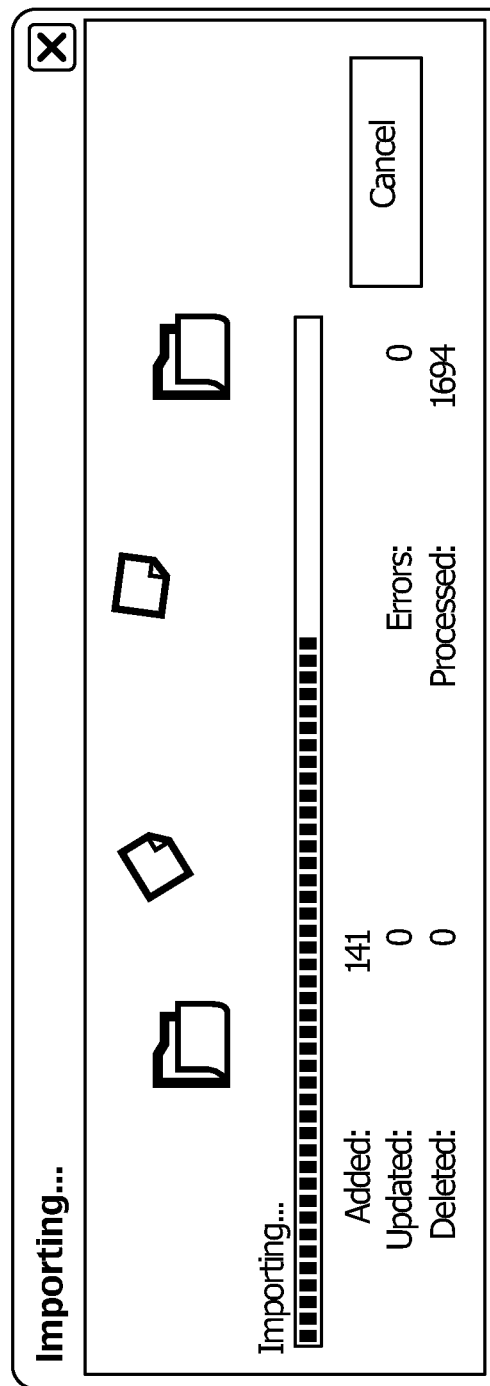

Archived data can be reloaded into the System as follows. On the Home page, a user can select Import from the DataEntry drop-down box (see FIG. 177). The user can choose Import Events from File from the Import submenu. A file browser opens. The user can browse to the directory where the file is located. The user can select the file type (*.xml or *.tab) in the Files of Type window. The user can Highlight the file and click Open. Importing will automatically begin. The Importing progress screen (see FIG. 178) displays the progress of the import procedure. The Importing screen closes when data import is finished.

Backing up the Database

Figure 179:
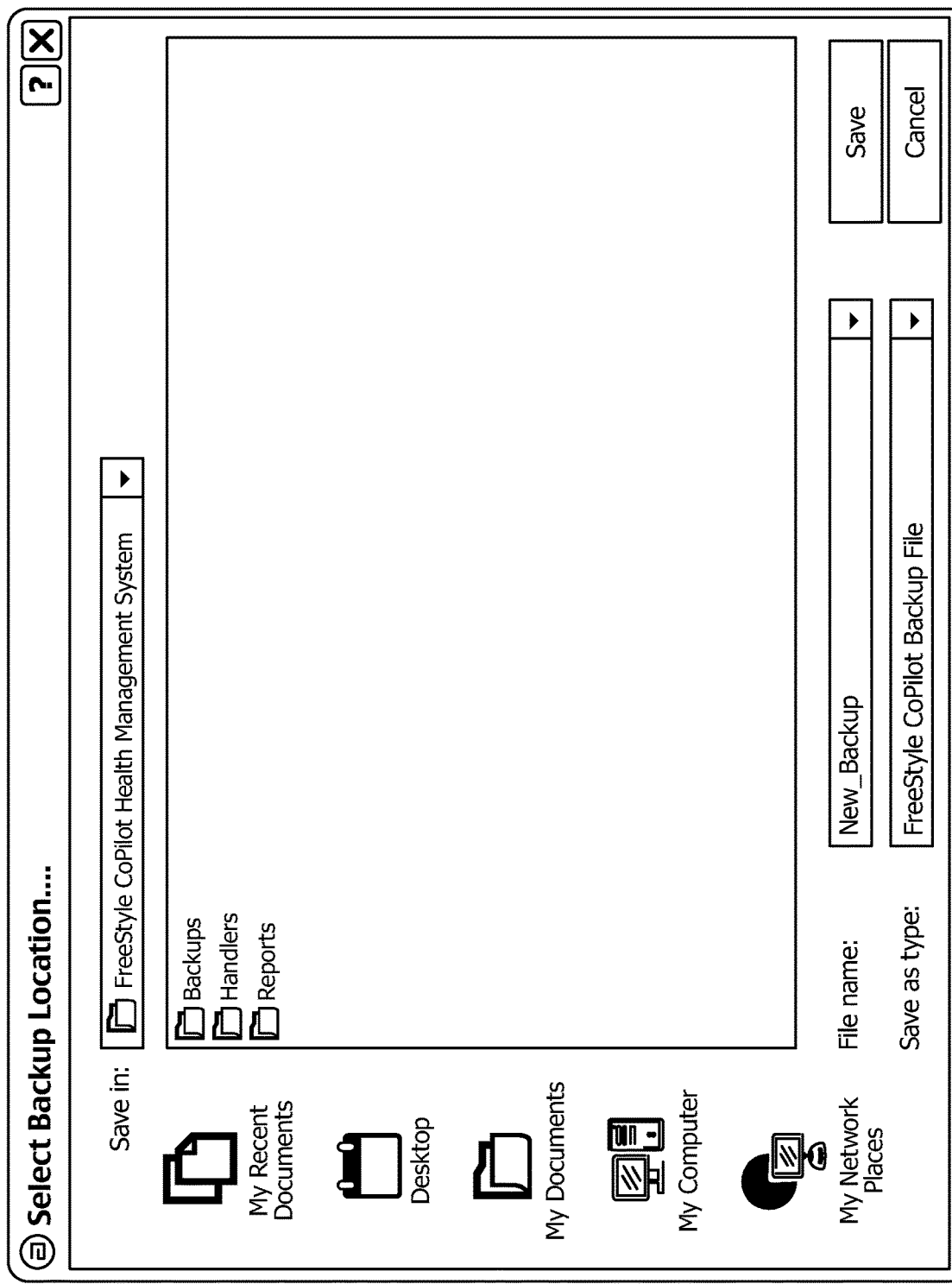

A backup of the database is performed automatically each time the user exits (closes) the application. The user can also create a backup of his or her database at any time and save it in any directory. The user can backup the database as follows. On the Home page, the user can select Database Maintenance from the File drop-down box (see FIG. 173). The user can choose Backup from the Database Maintenance submenu. A file browser opens. The user can browse to the directory where he or she wants the file to be located. FIG. 179 illustrates a File Browser: Select Backup Location. The user makes sure that the words System (or other designated name such as FreeStyle CoPilot) Backup File are displayed in the Save as Type window. The user can then enter the name of the file in the File Name window and click Save.

Restoring a Backed Up Database

Figure 180:
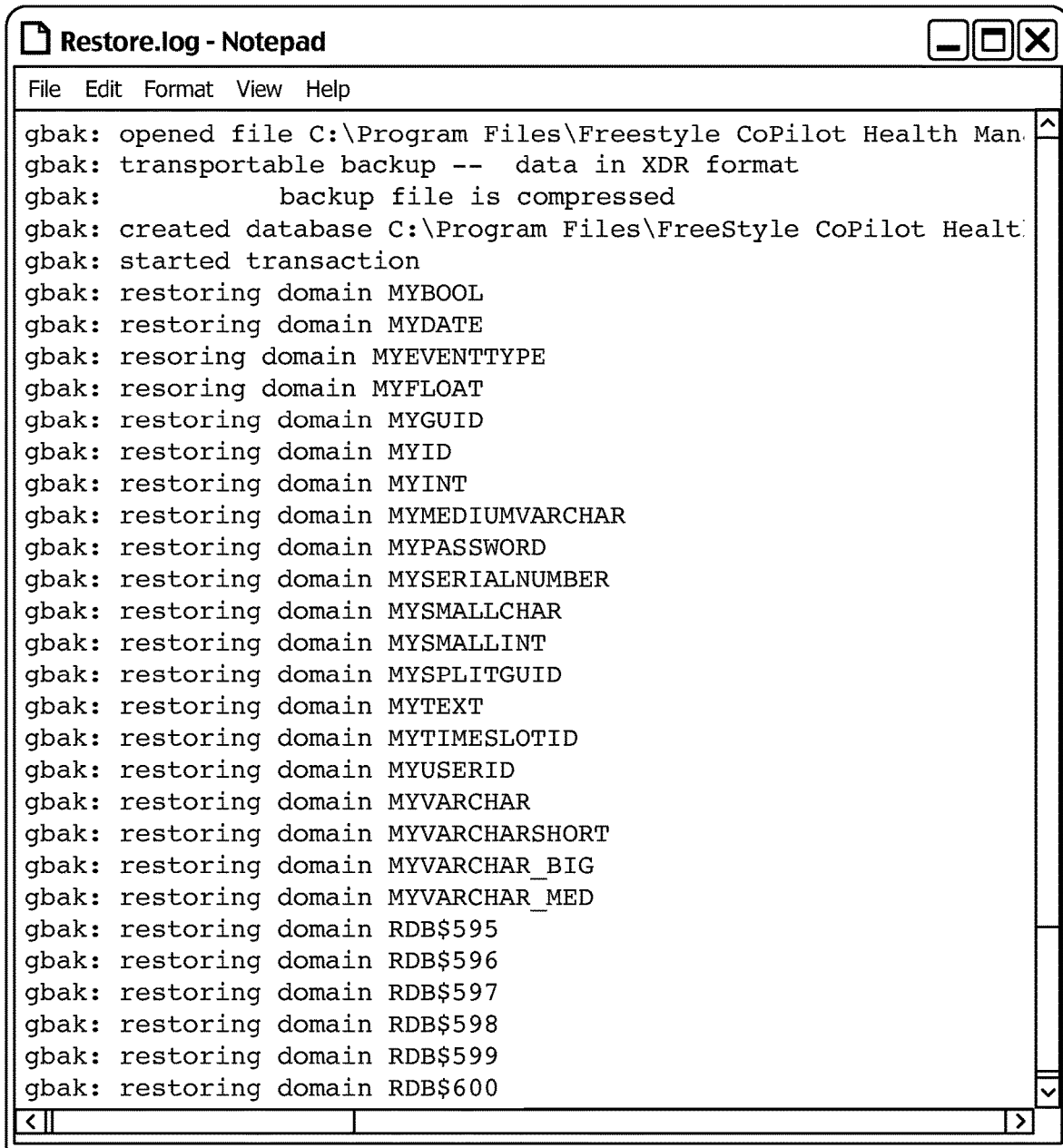

The System database is automatically restored if a system integrity check fails. A user can also restore a database whenever desired, as follows. On the Home page, the user can select Database Maintenance from the File drop-down box (see FIG. 173). The user can choose Restore from the Database Maintenance submenu. A file browser opens. The user can browse to the directory where the database was saved. The checks to make sure the words System or FreeStyle CoPilot Backup are displayed in the File of Type window. The user enters the name of the file in the File Name window and clicks Open. The Restore Log then displays as illustrated at FIG. 180, showing the restored transactions.

Viewing the Restore Log

Figure 181:
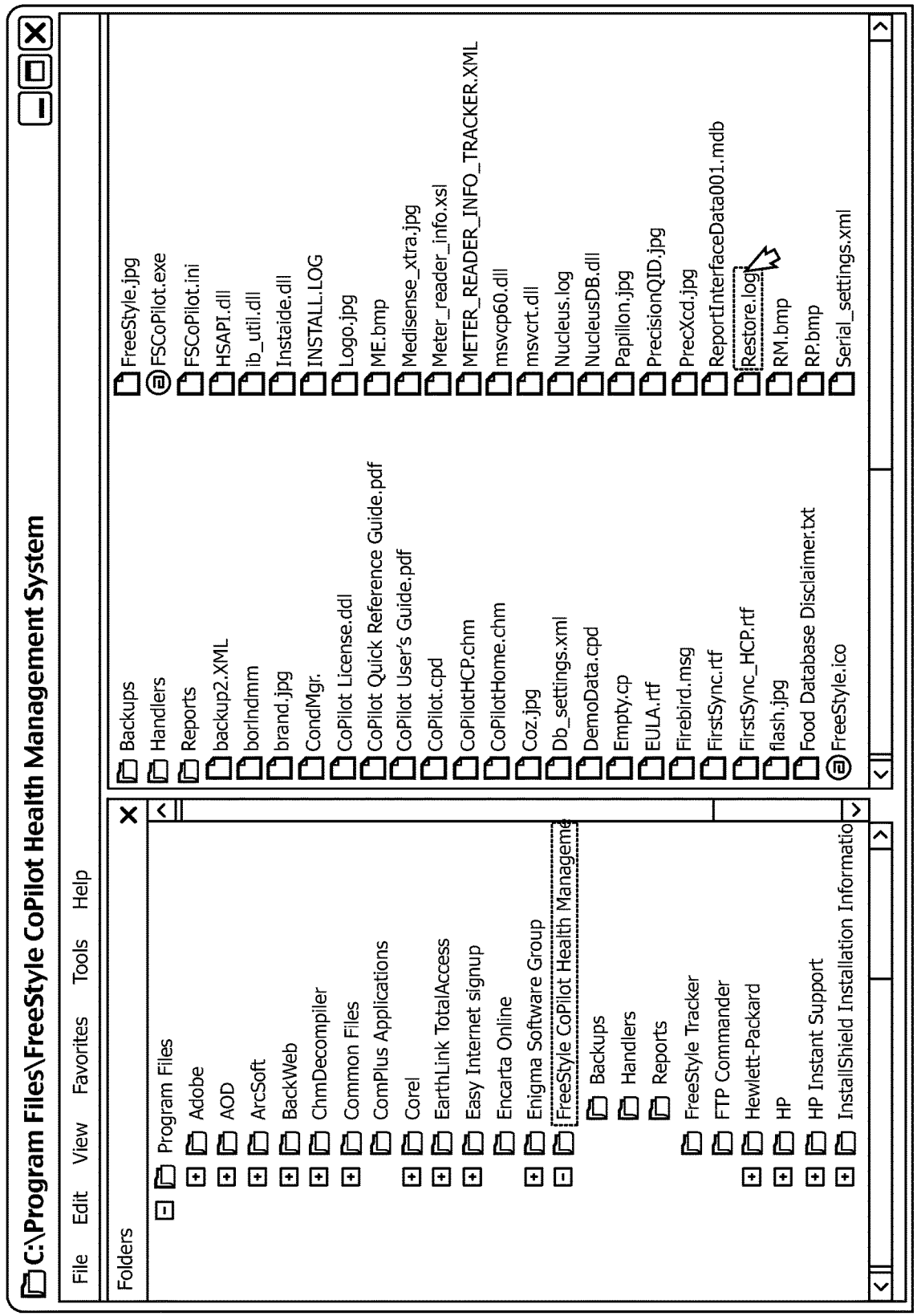

The user can view the Restore Log at any time, as follows. The user can close or minimize the System application. The user can open the file browser and find the Health Management System folder. This is the folder where the application was installed. FIG. 181 illustrates a File Browser: Restore Log. The user can highlight the file named Restore Log and click Open to view the log.

Help

For answers to questions about how to do something within the System, a user can consult the User's Guide or take advantage of the System's built-in onscreen Help. The user can access Help from any screen in the System that displays the main menu bar. The user can get context-sensitive Help on most screens. For example, if the user is viewing the Diary List and has a question, he or she can click WY. The Help screen will automatically open to the Help text that describes the Diary List.

Accessing on-Screen Help

Figure 182:
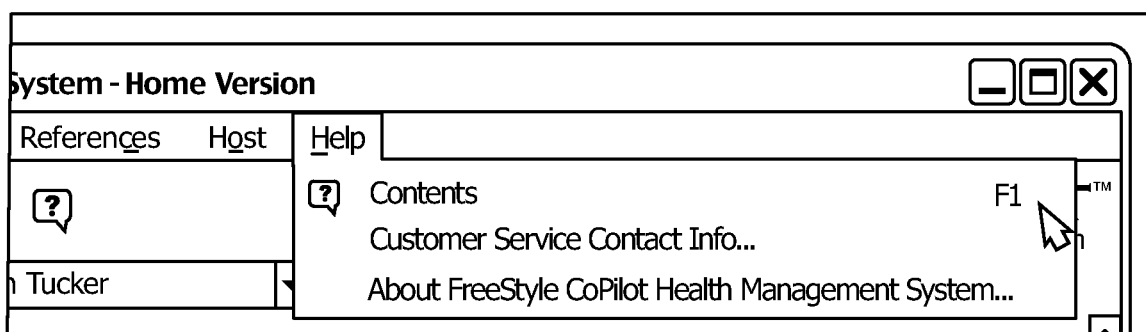
Figure 183:
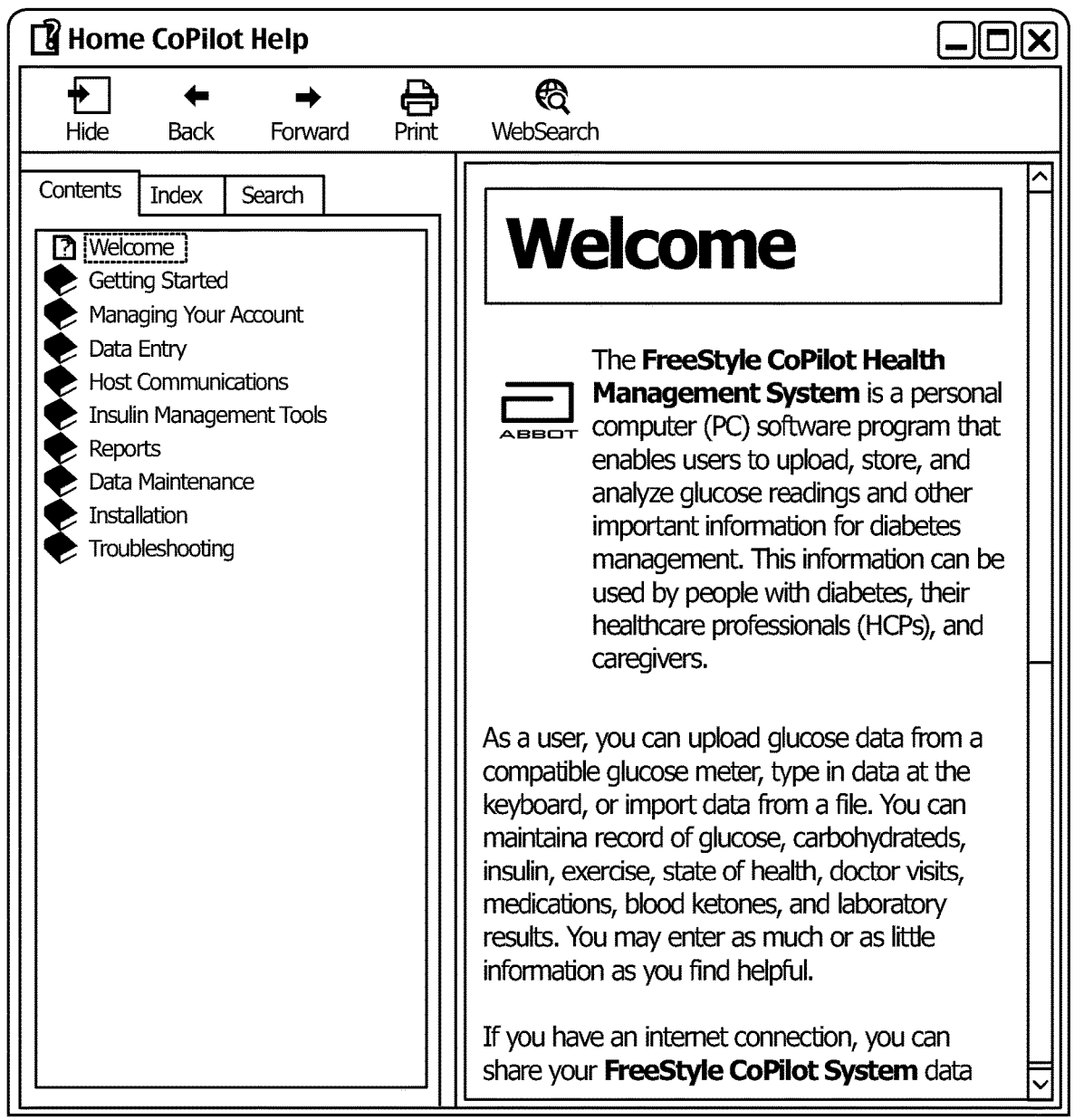

On the Home page, a user can click an icon, or select Help on the main menu bar and then select Contents from the drop-down list (see FIG. 182). FIG. 183 illustrates a Help Screen that would then display.

Help Screen

Help text is displayed in the large window on the Help screen. The Contents, Index, and Search tabs at the left offer three ways to find the Help topic the user is looking for. When the user selects a topic, the Help text appears in the large window on the right. Some text may contain links to more detailed information about a topic. These links appear as blue text followed by three dots (for example, Local Home User Account . . . ). If it is a link, the cursor will change from an arrow to a hand when passed over the link. The user can click the link to see the additional text. Green text may be underlined and in italics. If it is a link, the cursor will change from an arrow to a hand when passed over the link. The user can click the link to see the additional text.

Help Screen Icons

The user can click to hide the column with the Contents, Index, and Search tabs from displaying on screen. The user can click to show the column with the Contents, Index, and Search tabs. The user can click to see the previous page in the Help text. The user can click to see the next page in the Help text, and can click to print the Help page being viewed.

Contents Tab

Contents is the first tab displayed when the user opens the Help screen (see FIG. 183). This is the table of contents for the Help file. The Help information is arranged by topic here. The user can double-click on a topic listed (for example, Getting Started) and subsections will display. Some of the subsections have further subsections.

Index Tab

Figure 184:
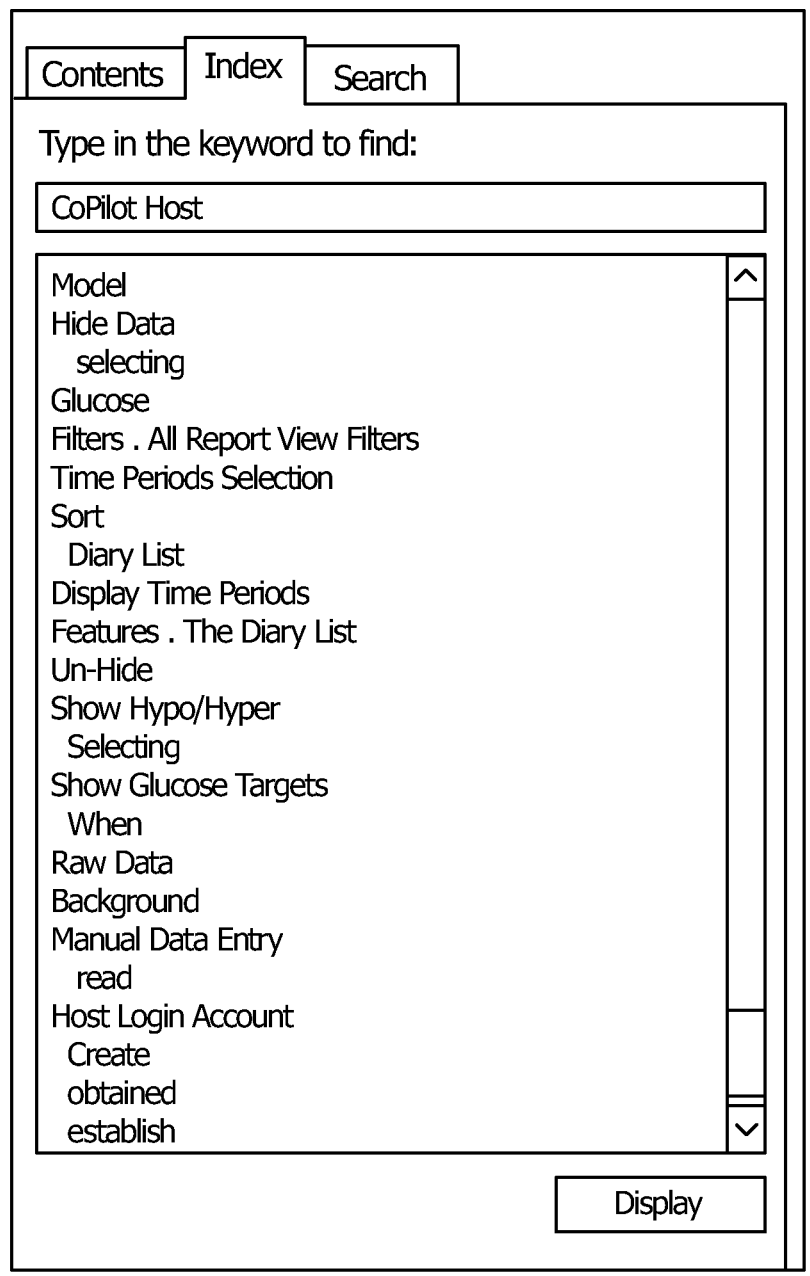

The user can click on the Index tab to display an alphabetical list of all topics covered in the Help file. The user can select a topic from the list and double-click. The text displays in the big window (see FIG. 183). FIG. 184 illustrates a Help: Index Tab. Alternatively, a user can type a keyword into the Type in the keyword to find: field. Then click the icon at the bottom of the screen. A list of Help topics matching the keyword displays. The user can select a topic and double-click. The text displays in the big window.

Search Tab

Figure 185:
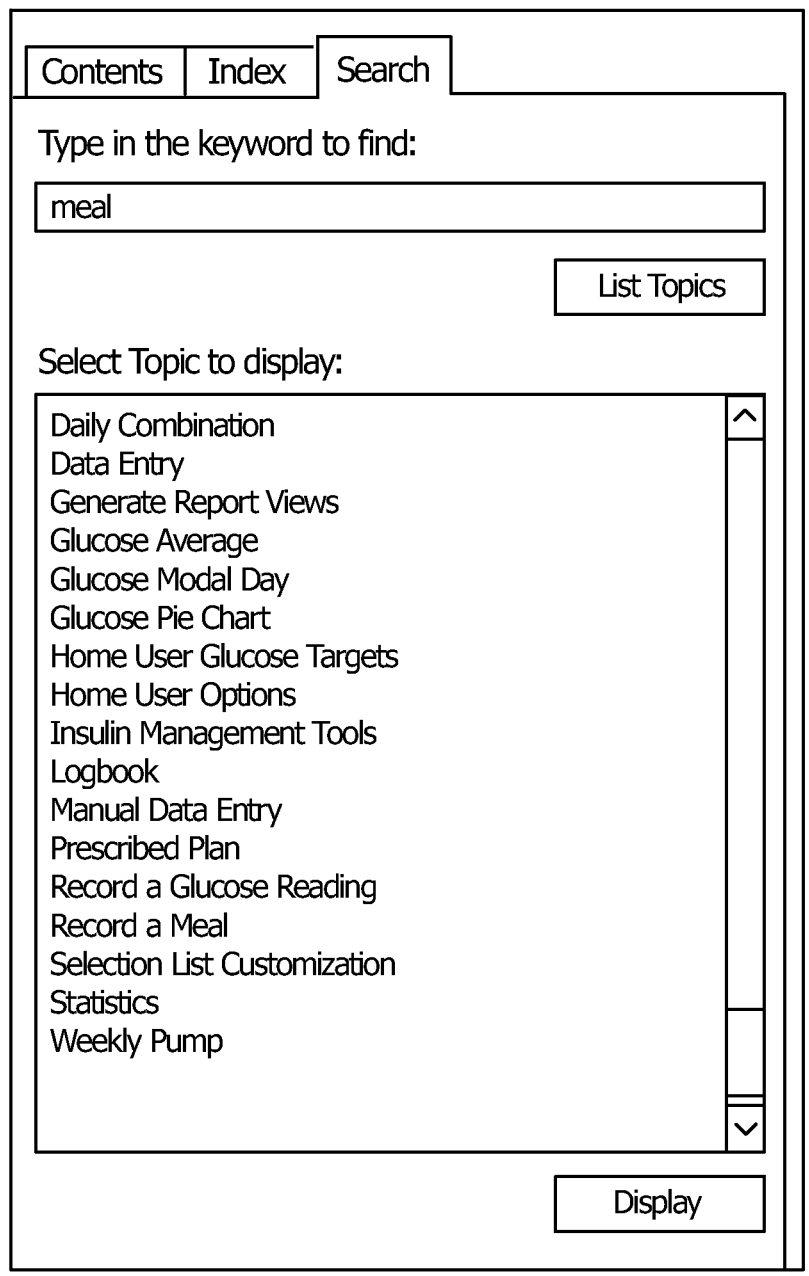
Figure 186:
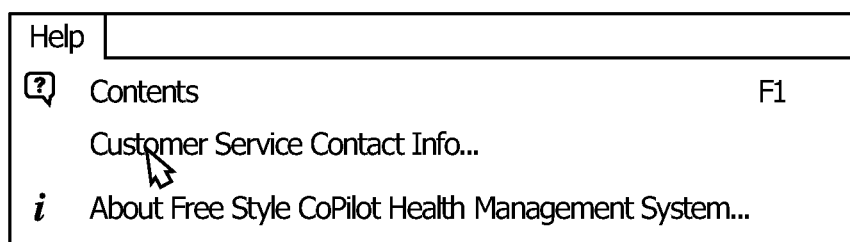
Figure 187:
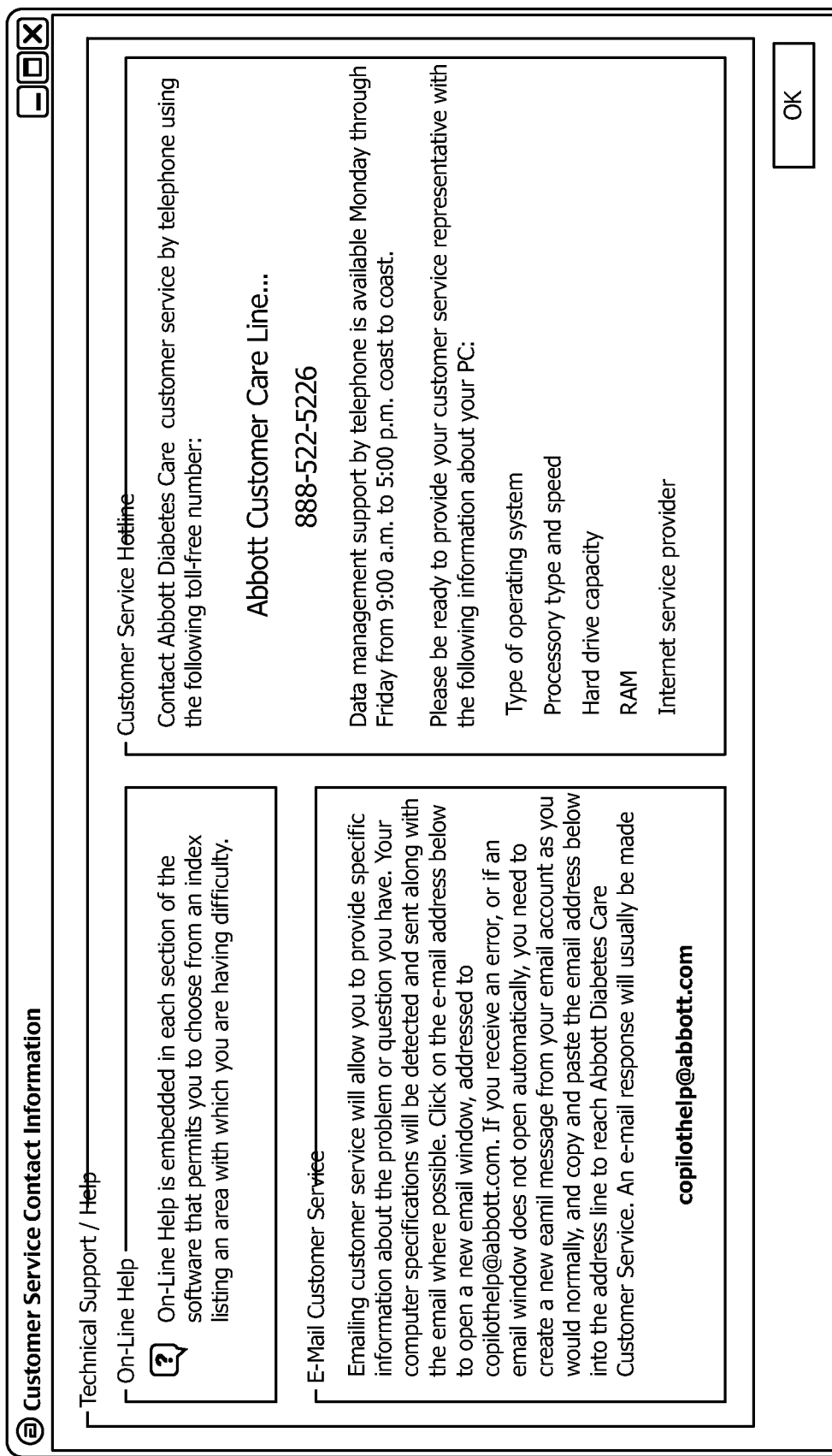

The user can click on the Search tab if he or she wants to use keywords to find Help text. FIG. 185 illustrates a Help: Search Tab. To search, the user can type a keyword into the Type in the keyword to find: field. Then click the icon. A list of topics related to the user's keyword displays in the Select Topic to Display window. The user can select a topic and double-click (or select a topic and click the icon). The text displays in the large window. The user can also contact Technical Support and Service (see FIG. 186 which illustrates a Help Drop-Down Box). A Customer Service Contact Information screen displays (see FIG. 187). The screen shows the ways a user can get help if he or she has questions about using the System, such as On-Line Help, E-Mail Customer Service, and Customer Service Hotline. FIG. 187 illustrates a Customer Service Contact Information Screen.

The present invention is not limited to the embodiments described above herein, which may be amended or modified without departing from the scope of the present invention as set forth in the appended claims, and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, the following references, in addition to the summary of the invention section, are hereby incorporated by reference into the detailed description of the preferred embodiments as disclosing alternative embodiments:

U.S. Pat. Nos. 5,307,263, 5,899,855, 6,186,145, 5,918, 603, 5,913,310, 5,678,571, 5,822,715, 5,956,501, 6,167,362, 6,233,301, 6,379,301, 5,997,476, 6,101,478, 6,168,563, 6,248,065, 6,368,273, 6,381,577, 5,897,493, 5,933,136, 6,151,586, 5,960,403, 6,330,426, 5,951,300, 6,375,469, 6,240,393, 6,270,455, and 6,161,095;

United States published Application Nos. 2001/0011224, 2003/0163351, now U.S. Pat. No. 8,626,521, and 2003/0069753, now U.S. Pat. No. 7,970,620;

U.S. Patent Application Nos. 60/577,064 and 10/112,671, now U.S. Pat. No. 7,041,468; and Internet web sites: www.freestylecopilot.com, www.abbottdiabetescare.com, www.lifescan.com/care, www.bddiabetes.com, www.roche-diagnostics.com, www.healthhero.com, and www.minimed.com.

We claim:

1. A system for managing diabetes care data, comprising:
a host configured to receive data associated with glucose levels from a plurality of client devices, the host comprising:
a database for storing the received data associated with glucose levels;
one or more servers accessible over a computer network for handling client interactions with the system;
one or more processors; and
memory operably coupled to the one or more processors, wherein the memory includes instructions stored therein that, when executed by the one or more processors, cause the one or more processors to interact with graphical user interfaces (GUIs) on the plurality of client devices, each of the GUIs including:
a report generation component configured to generate a set of reports based on selected data associated with glucose levels, wherein the set of reports includes:
a plurality of data elements configured in a daily pattern of glucose levels for a plurality of time periods; and a glucose histogram associated with at least three predetermined glucose ranges, wherein the glucose histogram comprises one or more bars, wherein a length of each of the one or more bars corresponds with a percentage of time in which the glucose levels were within one of the at least three predetermined glucose ranges during a specified time period; and a security component adapted to enable a patient to authorize a health care professional (HCP) to have access to diabetes care data relating to the patient, wherein the security component is adapted to prompt the HCP to enter manually, with an input of a computing device, an invitation code provided by the patient, and wherein the invitation code is configured to expire if not accepted within a predetermined amount of time.

2. The system of claim 1, wherein each of the GUIs further includes a health care professional (HCP) selection component adapted to permit reviewing of data relating to a particular HCP of multiple HCPs.

3. The system of claim 1, wherein each of the GUIs further comprises a device selection component permitting reviewing of data from a particular device model of multiple device models.

4. The system of claim 1, wherein each of the GUIs further includes a pattern recognition component configured to determine whether patterns of interest exist within the received data associated with glucose levels, and to indicate one or more of a recognized pattern of glucose data above a predetermined range, a recognized pattern of glucose data below the predetermined range, and a recognized pattern of glucose data within the predetermined range.

5. The system of claim 1, wherein the set of reports further includes a table displaying statistics corresponding to the glucose levels, wherein the table displaying statistics further includes a displayed average carbohydrate intake per day.

6. The system of claim 5, wherein the table displaying statistics corresponds to a one month period of time.

* * * * *